US007183273B2

(12) United States Patent
Bridger et al.

(10) Patent No.: US 7,183,273 B2
(45) Date of Patent: Feb. 27, 2007

(54) CHEMOKINE RECEPTOR BINDING HETEROCYCLIC COMPOUNDS

(75) Inventors: Gary J. Bridger, Bellingham, WA (US); Renato Skerlj, Vancouver (CA); Al Kaller, Vancouver (CA); Curtis Harwig, Vancouver (CA); David Bogucki, Surrey (CA); Trevor R. Wilson, Langley (CA); Jason Crawford, British Columbia (CA); Ernest J. McEachern, White Rock (CA); Bem Atsma, Abbotsford (CA); Siqiao Nan, Richmond (CA); Yuanxi Zhou, Surrey (CA); Dominique Schols, Herent (BE)

(73) Assignee: AnorMED, Inc., Langley (CA)

( * ) Notice: Subject to any disclaimer, the term of this patent is extended or adjusted under 35 U.S.C. 154(b) by 0 days.

(21) Appl. No.: 10/837,467

(22) Filed: Apr. 30, 2004

(65) Prior Publication Data

US 2004/0235823 A1 Nov. 25, 2004

Related U.S. Application Data

(62) Division of application No. 09/535,314, filed on Mar. 24, 2000, now Pat. No. 6,750,348.

(60) Provisional application No. 60/125,823, filed on Mar. 24, 1999.

(51) Int. Cl.
*A61K 31/55* (2006.01)
*A61K 31/47* (2006.01)
*A61K 31/445* (2006.01)
*A61P 19/02* (2006.01)
*A61P 31/18* (2006.01)

(52) U.S. Cl. ............... 514/218; 514/221; 514/282; 514/286; 514/299; 546/139; 546/152; 544/180; 544/183; 544/194; 544/235; 544/236; 544/256; 544/279; 544/349; 544/353

(58) Field of Classification Search ............... 514/218, 514/221, 282.12, 286, 299, 282
See application file for complete search history.

(56) References Cited

U.S. PATENT DOCUMENTS

| 5,563,151 A | 10/1996 | Bowles et al. ............ 546/118 |
| 5,583,131 A | 12/1996 | Bridger et al. ............ 514/183 |
| 5,698,546 A | 12/1997 | Bridger et al. ............ 514/183 |
| 5,817,807 A | 10/1998 | Bridger et al. ............ 540/474 |

FOREIGN PATENT DOCUMENTS

| EP | 0 434 385 A | 6/1991 |
| WO | WO 99/04794 A | 2/1999 |
| WO | WO 99/32100 | 7/1999 |

OTHER PUBLICATIONS

Baggiolini et al. Immunology Today 21(9) 418-420,2000.*
Kedzierska et al. Antivir. Chem. Chemother. 12(3): 133-50.*
Carroll R., et al. (1997). *Science* 276:273-276.
Casella L., et al. (1996). *Inorganic Chem* 35:7516-7525.
Donzella G., et al. (1998). *Nature Medicine* 4:72-77.
Ghosh D., et al. (1998). *Inorganic Chem* 37:6597-6605.
Gultneh Y., et al. (1995). *Inorganic Chem* 34:3633-3645.
Gupta S., et al. (1998). *J Biol Chem* 7:4282-4287.
Kanda W., et al. (1995). *Angew Chem Int Ed Engl* 34:588-590.
Miedema F., et al. (1994). *Immune Rev* 140:35-72.
Peled A., et al. (1998). *Science* 283:845-848.
Ponath P. (1998). *Exp Opin Invest Drugs* 7:1-18.
Schols D., et al. (1997). *J Exp Med* 186:1383-1388.
Schols D., et al. (1997). *Antiviral Research* 35:147-156.
Tachibana K., et al. (1998). *Nature* 393:591-594.
Wyatt R., et al. (1998). *Science* 280:1884-1888.
Biard-Piechaczyk et al., 1999 "Role of CXCR4 in HIV-1-induced Apoptosis of Cells with a CD4+, CXCR4+ Phenotype" Immunology Letters 70 (1999) 1-3.
Blanco, et al. , 2000 "The CXCR4 Antagonist AMD3100 Efficiently Inhibits Cell-Surface-Expressed Human Immunodeficiency Virus Type 1 Envelop-Induced Apoptosis" American Society for Microbiology, Jan. 2000, p. 51-56.
Fedyk, et al. "Maturation Decreases Responsiveness of Human Bone Marrow B Lineage Cells to Stromal-Derived Factor 1 (SDF-1)", Journal of Leukocyic Biology, 66, p. 667.
Herbein et al., 1998 "Apoptosis of CD8+ T cells is Mediated by Macrophages Through Interaction of HIV gp 120 with Chemokine Receptor CXCR4" Nature 395, 1998, pp. 189-193.
Hesselgesser et al., 1997 "CD4-Independent Association Between HIV-1 gp 120 and CXCR4: Functional Chemokine Receptors are Expressed in Human Neurons", Current Biology, 7(2), pp. 112-121.
Hesselgesser et al. 1998 "Neuronal Apoptosis Induced by HIV-1 gp 120 and the Chemokine SDF-1α is Mediated by the Chemokine Receptor CXCR4" Current Biology , 8 (10), pp. 595-598.
Lee et al., 1999 "Coreceptor/Chemokine Receptor Expression on Human Hematopoietic Cells: Biological Implications for Human Immunodeficiency Virus-Type 1 Infection" Blood, 93(4), pp. 1145-1156.
Nikolic et al., 1998 "The p35/Cdk5 Kinase Is a Neuron-Specific Rac Effector That Inhibits Pak1 Activity", Nature 395, 194.

(Continued)

Primary Examiner—Venkataraman Balasubramanian
(74) Attorney, Agent, or Firm—Morrison & Foerster LLP

(57) ABSTRACT

Heterocyclic compounds that bind chemokine receptors and inhibit the binding of their natural ligands are disclosed. The invention compounds are protective against infection by HIV and exert effects characteristic of antagonists to the CXCR4 receptor.

10 Claims, 54 Drawing Sheets

OTHER PUBLICATIONS

Ohagen et al., 1999 "Apoptosis Induced by Infection of Primary Brain Cultures with Diverse Human Immunodeficiency Virus Type 1 Isolates: Evidence for a Role of the Envelop" Journal of Virology, 73(2), pp. 897-906.

Schramm et al., 2000 "Viral Entry through CXCR4 Is a Pathogenic Factor and Therapeutic Target in Human Immunodeficiency Virus Type 1 Disease", Journal of Virology, Jan. 2000, p. 184-192.

* cited by examiner

| AMD# | Structures | Formula | Observed (M+H)+ |
|---|---|---|---|
| 7129 | 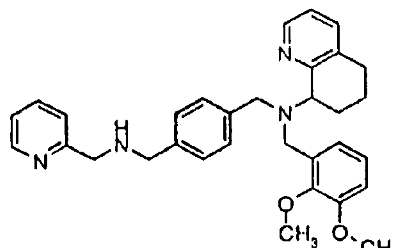 | $C_{32}H_{36}N_4O_2$ | 509.4 |
| 7130 | 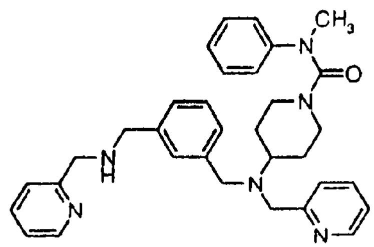 | $C_{33}H_{38}N_6O$ | 535.4 |
| 7131 | 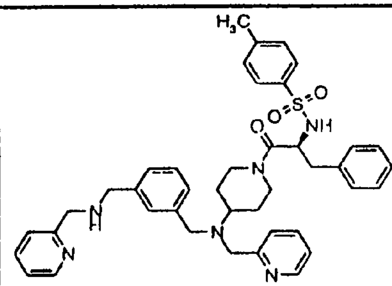 | $C_{41}H_{46}N_6O_3S$ | 703.2 |

| | | | |
|---|---|---|---|
| 7136 | [structure] | $C_{38}H_{37}ClN_6O_2$ | 639.6 (+NH$_4$) |
| 7138 | [structure] | $C_{31}H_{34}N_4O$ | 479.4 |
| 7140 | [structure] | $C_{32}H_{33}N_5$ | 488.1 |
| 7141 | [structure] | $C_{31}H_{31}N_5$ | 474.3 |

Figure 1 B

| AMD# | Structures | Formula | Observed (M+H)+ |
|---|---|---|---|
| 7142 | 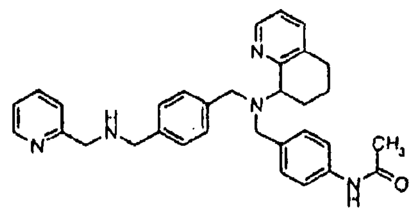 | $C_{32}H_{35}N_5O$ | 506.7 |
| 7145 | 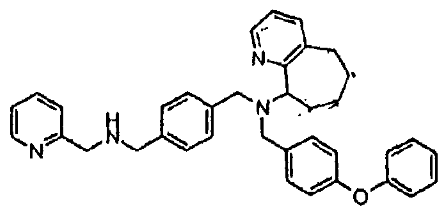 | $C_{37}H_{38}N_4O$ | 555 |
| 7147 | 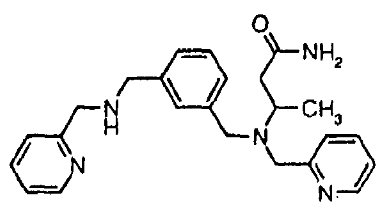 | $C_{24}H_{29}N_5O$ | 404.6 |
| 7151 | 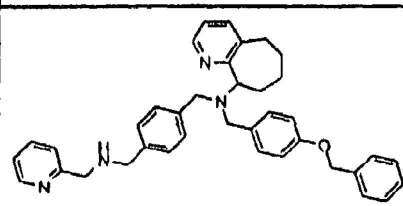 | $C_{38}H_{40}N_4O$ | 569.4 |

Figure 1 C

| AMD# | Structures | Formula | Observed (M+H)+ |
|---|---|---|---|
| 7166 | 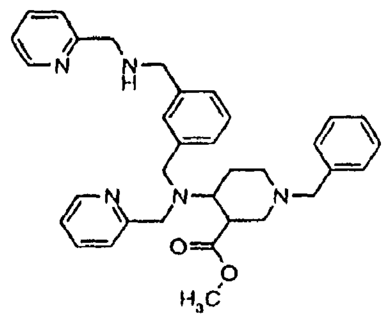 | C34H39N5O2 | 550.2 |
| 7167 | 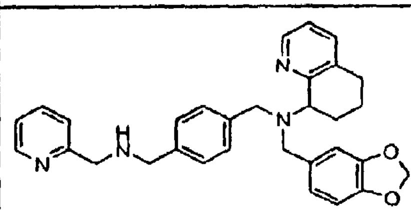 | C31H32N4O2 | 493.5 |
| 7168 | 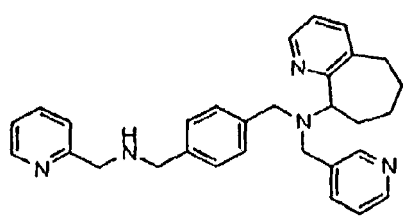 | C30H33N5 | 464.4 |

Figure 1 F

| AMD# | Structures | Formula | Observed (M+H)+ |
|---|---|---|---|
| 7180 | 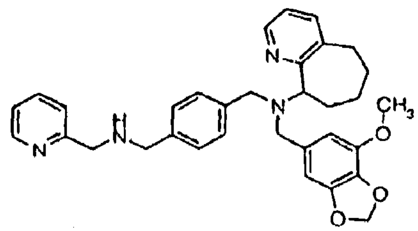 | $C_{33}H_{36}N_4O_3$ | 537.3 |
| 7182 | 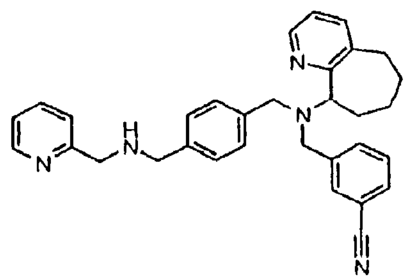 | $C_{32}H_{33}N_5$ | 488.4 |
| 7184 | 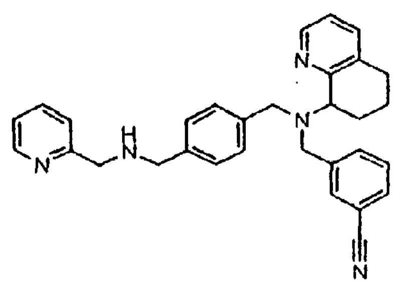 | $C_{31}H_{31}N_5$ | 474.3 |

Figure 1 I

| | | | |
|---|---|---|---|
| 7185 | [structure] | C₃₁H₃₆N₄S | 497.4 |
| 7186 | [structure] | C₃₀H₃₄N₄S | 483.3 |
| 7187 | [structure] | C₃₁H₃₂F₂N₄ | 499.5 |
| 7188 | [structure] | C₃₀H₃₀F₂N₄ | 485.4 |

Figure 1 J

| AMD# | Structures | Formula | Observed (M+H)+ |
|---|---|---|---|
| 7189 | 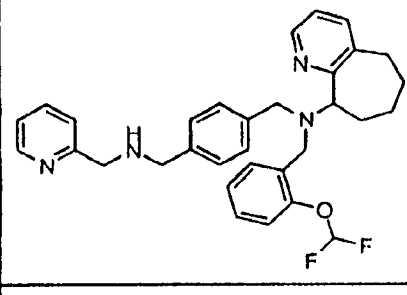 | $C_{32}H_{34}F_2N_4O$ | 529.2 |
| 7195 | 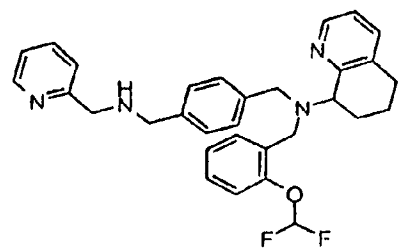 | $C_{31}H_{32}F_2N_4O$ | 515.4 |
| 7196 | 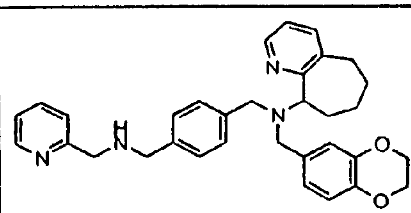 | $C_{33}H_{36}N_4O_2$ | 521.4 |

| AMD# | Structures | Formula | Observed (M+H)+ |
|---|---|---|---|
| 7201 | 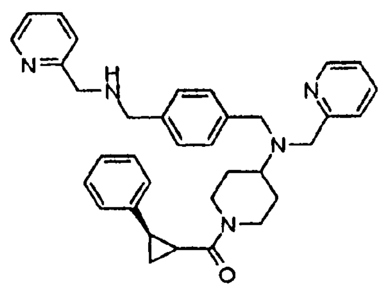 | $C_{35}H_{39}N_5O$ | 546.2 |
| 7202 | 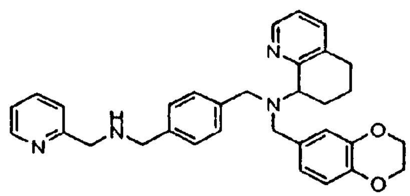 | $C_{32}H_{34}N_4O_2$ | 507.6 |
| 7203 | 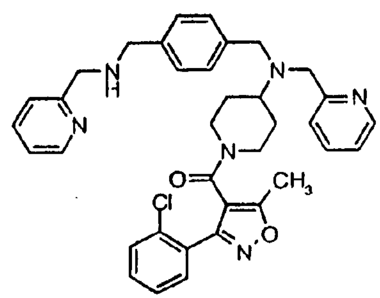 | $C_{36}H_{37}ClN_6O_2$ | 621.4 |

| | | |
|---|---|---|
| 7204 |  $C_{32}H_{36}N_6OS$ | 553.2 |
| 7207 |  $C_{30}H_{30}F_2N_4$ | 485.4 |
| 7208 |  $C_{29}H_{33}N_5$ | 452.3 |

| AMD# | Structures | Formula | Observed (M+H)+ |
|---|---|---|---|
| 7216 | 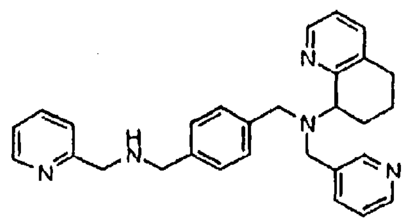 | $C_{29}H_{31}N_5$ | 450.2 |
| 7217 | 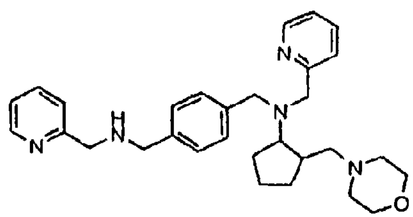 | $C_{30}H_{39}N_5O$ | 486.4 |
| 7220 | 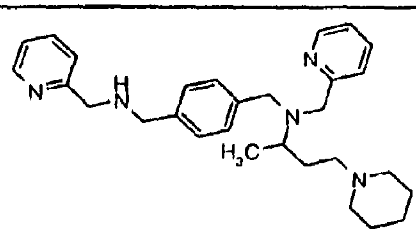 | $C_{29}H_{39}N_5$ | 458.3 |

Figure 1 Q

| | | |
|---|---|---|
| 7222 |  | C$_{32}$H$_{34}$N$_6$ | 503.3 |
| 7223 |  | C$_{31}$H$_{35}$N$_5$ | 478.4 |
| 7228 |  | C$_{33}$H$_{39}$N$_5$O | 522.5 |

| AMD# | Structures | Formula | Observed (M+H)+ |
|---|---|---|---|
| 7230 | 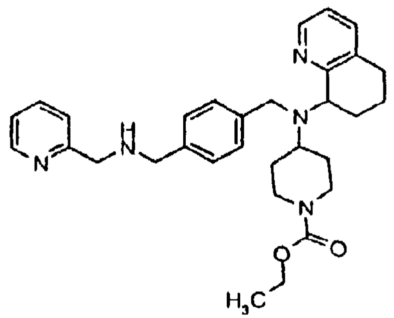 | $C_{31}H_{39}N_5O_2$ | 514.4 |
| 7231 | 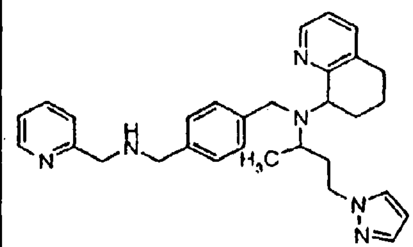 | $C_{30}H_{36}N_6$ | 481.4 |
| 7235 | 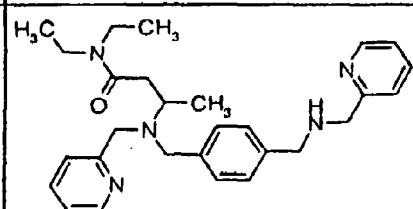 | $C_{28}H_{37}N_5O$ | 460.4 |

Figure 1 T

| | | | |
|---|---|---|---|
| | 541.4 | 527.3 | 554.4 | 544.4 |
| | $C_{32}H_{36}N_4O_2S$ | $C_{31}H_{31}ClN_4O_2$ | $C_{33}H_{36}ClN_5O$ | $C_{35}H_{37}N_5O$ |
| | | | | |
| 7236 | 7238 | 7239 | 7241 |

Figure 1 U

| AMD# | Structures | Formula | Observed (M+H)+ |
|---|---|---|---|
| 7242 | 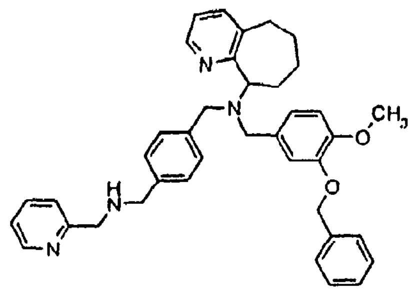 | $C_{39}H_{42}N_4O_2$ | 599.7 |
| 7244 | 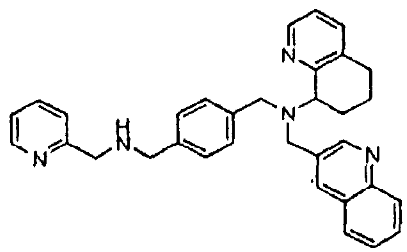 | $C_{33}H_{33}N_5$ | 500.3 |
| 7245 | 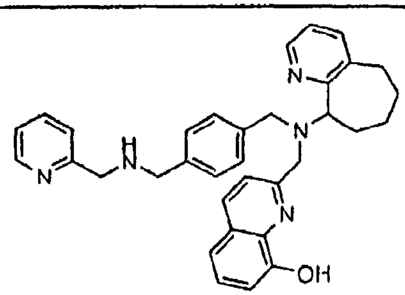 | $C_{34}H_{35}N_5O$ | 530.3 |

| | | | |
|---|---|---|---|
| 7247 | (structure) | $C_{34}H_{35}N_5$ | 514.4 |
| 7249 | (structure) | $C_{33}H_{37}N_5O$ | 520.7 |
| 7250 | (structure) | $C_{24}H_{26}N_6$ | 399.5 |

Figure 1 W

| AMD# | Structures | Formula | Observed (M+H)+ |
|---|---|---|---|
| 7253 | 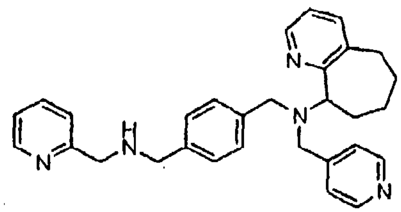 | $C_{30}H_{33}N_5$ | 464.6 |
| 7254 | 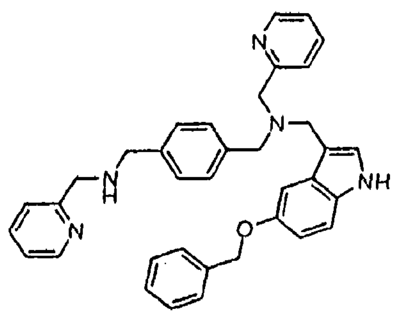 | $C_{36}H_{35}N_5O$ | 554.4 |
| 7256 | 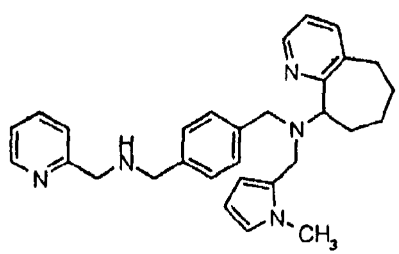 | $C_{30}H_{35}N_5$ | 466.4 |

Figure 1 Y

| AMD# | Structures | Formula | Observed (M+H)+ |
|---|---|---|---|
| 7262 | 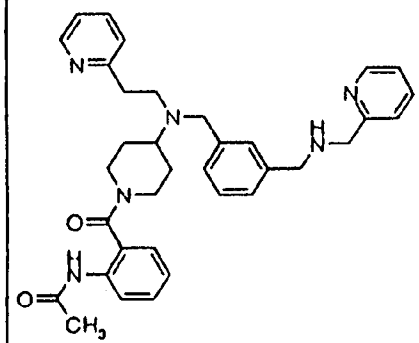 | $C_{35}H_{40}N_6O_2$ | 577.5 |
| 7270 | 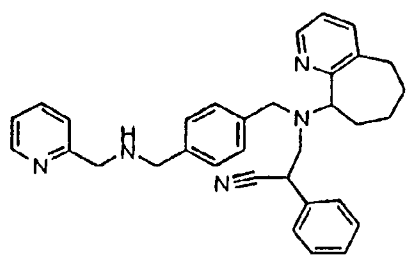 | $C_{33}H_{35}N_5$ | 502.4 |
| 7272 | 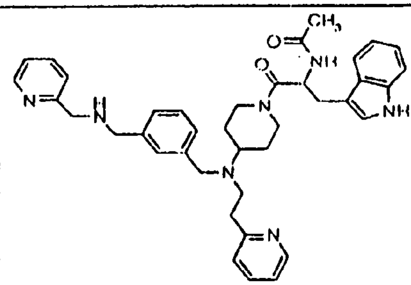 | $C_{39}H_{45}N_7O_2$ | 644.4 |

Figure 1 BB

| AMD# | Structures | Formula | Observed (M+H)+ |
|---|---|---|---|
| 7277 | 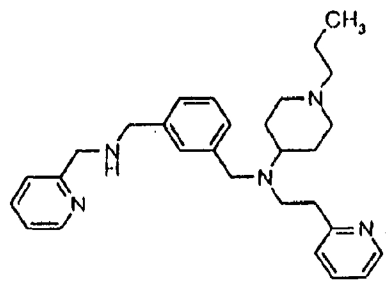 | $C_{29}H_{39}N_5$ | 458.4 |
| 7278 | 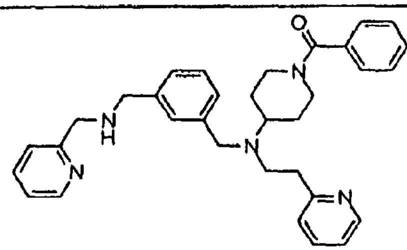 | $C_{33}H_{37}N_5O$ | 520.4 |
| 7290 | 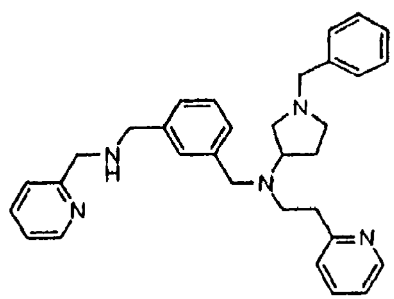 | $C_{32}H_{37}N_5$ | 492.5 |

| | | | |
|---|---|---|---|
| 7309 |  | $C_{31}H_{33}N_5$ | 476.6 |
| 7311 |  | $C_{25}H_{28}N_6$ | 413.2 |
| 7359 |  | $C_{33}H_{39}N_5$ | 506.6 |
| 7374 |  | $C_{30}H_{32}N_6$ | 477.2 |

| AMD# | Structures | Formula | Observed (M+H)+ |
|---|---|---|---|
| 7379 | 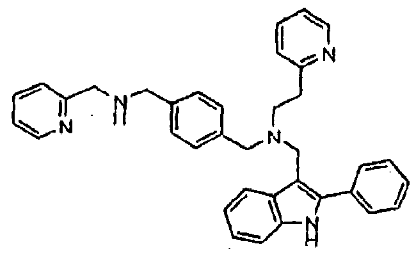 | $C_{36}H_{35}N_5$ | 538.4 |
| 9025 | 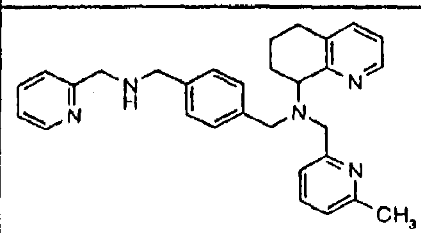 | $C_{30}H_{33}N_5$ | 464.4 |
| 9031 | 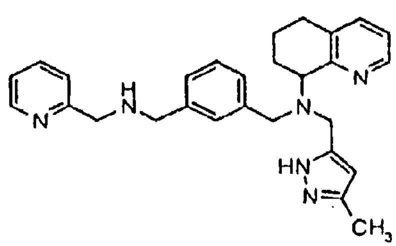 | $C_{28}H_{32}N_6$ | 453 |

| | | | |
|---|---|---|---|
| 9032 |  | $C_{31}H_{34}N_4O$ | 479.4 |
| 9039 |  | $C_{33}H_{38}N_4O$ | 507.6 |
| 9045 |  | $C_{32}H_{36}N_4O$ | 493.2 |

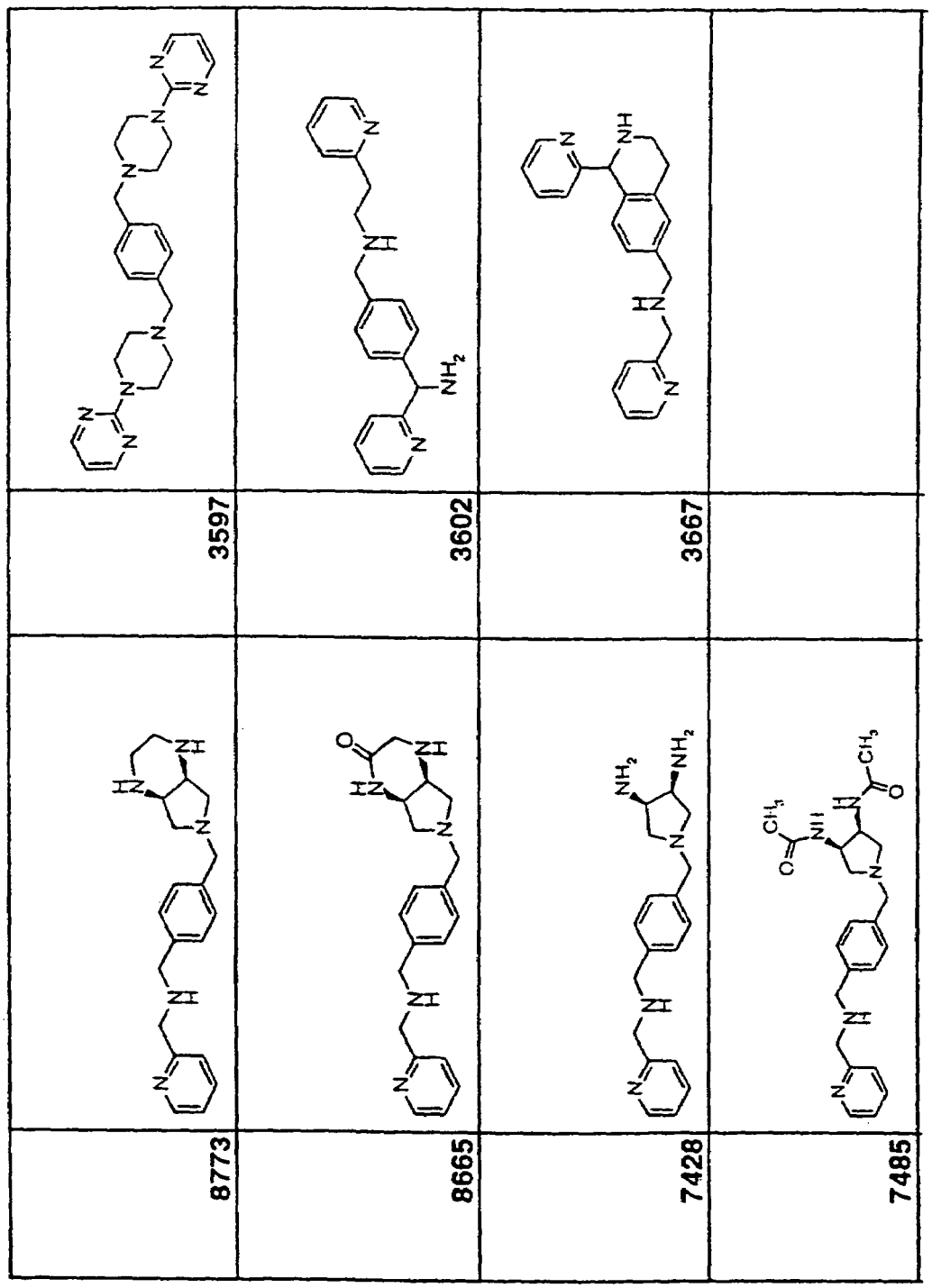
Figure 1 AAA

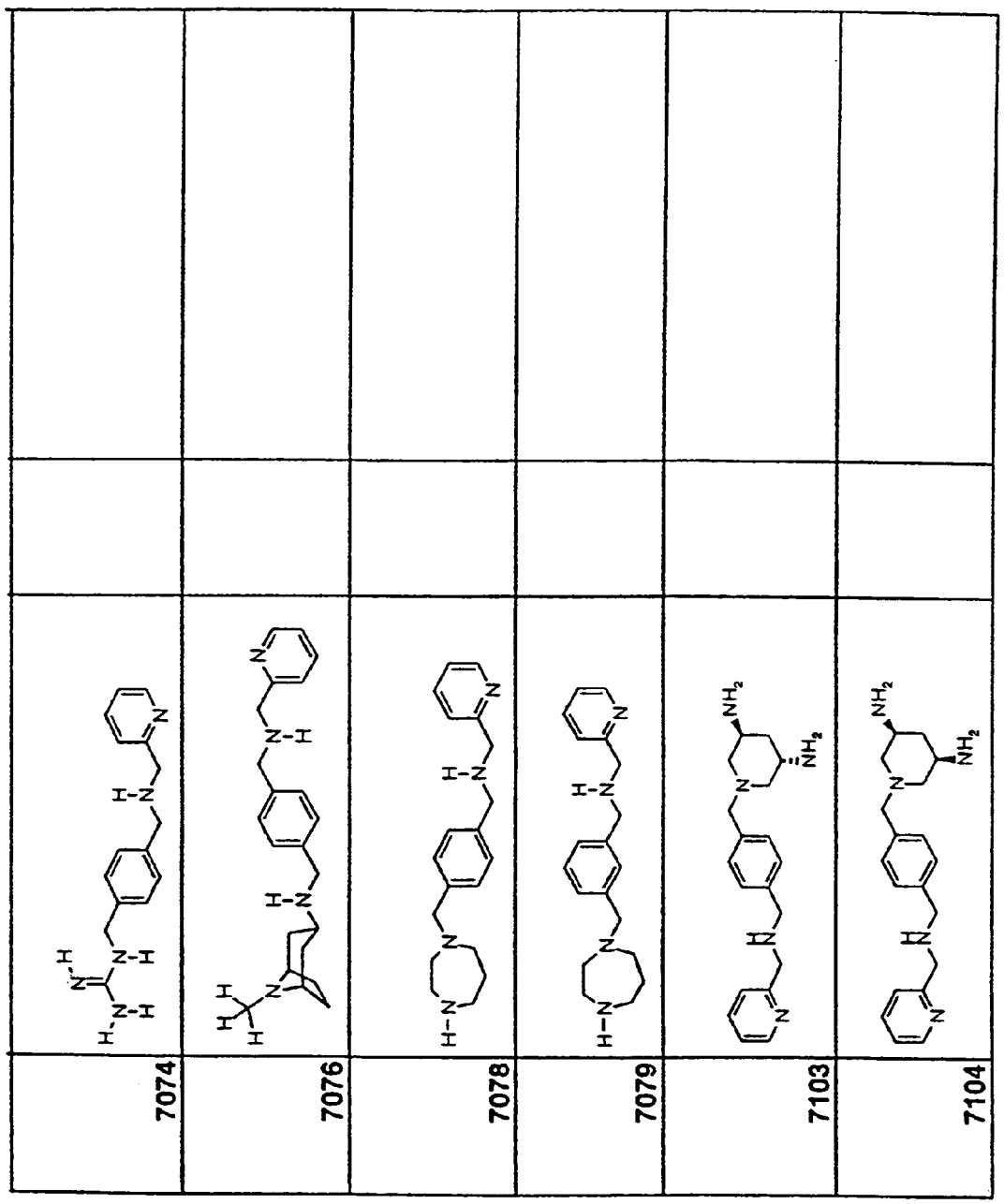
Figure 1 BBB

CHEMOKINE RECEPTOR BINDING HETEROCYCLIC COMPOUNDS

CROSS-REFERENCE TO RELATED APPLICATIONS

This application is a divisional of U.S. patent application Ser. No. 09/535,314 filed Mar. 24, 2000, now U.S. Pat. No. 6,750,348, which claims priority from U.S. provisional application Ser. No. 60/125,823, filed Mar. 24, 1999. The contents of these documents are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrates protective effects against infection of target cells by a human immunodeficiency virus (HIV).

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1–18, 1998). These chemotactic cytokines, or chemokines, constitute a family of proteins, approximately 8–10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the α-chemokines are designated "CXCR".

Chemokines are considered to be principal mediators in the initiation and maintenance of inflammation. More specifically, chemokines have been found to play an important role in the regulation of endothelial cell function, including proliferation, migration and differentiation during angiogenesis and re-endothelialization after injury (Gupta et al., *J. Biolog. Chem.*, 7:4282–4287, 1998). Two specific chemokines have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR-5 (Wyatt et al., *Science*, 280:1884–1888 (1998)). HIV-1 isolates arising subsequently in the infection bind to the CXCR-4 chemokine receptor. In view of the fact that the feline immunodeficiency virus, another related retrovirus, binds to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273–276 1997). During the course of infection within a patient, it appears that a majority of HIV particles shift from the M-tropic to the more aggressive T-tropic viral phenotype (Miedema et al., *Immune. Rev.*, 140:35 (1994)) Curiously, the M-tropic viral phenotype correlates with the virus's ability to enter the cell following binding of the CCR-5 receptor, while the T-tropic viral phenotype correlates with viral entry into the cell following binding and membrane fusion with the CXCR-4 receptor. Clinically observations suggest that patients who possess genetic mutations in the CCR-5 or CXCR-4 appear resistant or less susceptible to HIV infection.

However, the binding of chemokine receptors to their natural ligands appears to serve a more evolutionary and central role than only as mediators of HIV infection. The chemokine receptor, CXCR-4 has been found to be essential for the vascularization of the gastrointestinal tract (Tachibana et al., *Nature*, 393:591–594 (1998)) as well as haematopoiesis and cerebellar development (Zou et al., *Nature*, 393:591–594 (1998)). Interference with any of these important functions served by the binding of pre-B-cell growth-stimulating factor/stromal derived factor (PBSF/SDF-1) to the CXCR-4 chemokine receptor results in lethal deficiencies in vascular development, haematopoiesis and cardiogenesis. Similarly, fetal cerebellar development appears to rely upon the effective functioning of CXCR-4 in neuronal cell migration and patterning in the central nervous system. This G-protein-coupled chemokine receptor appears to play a critical role in ensuring the necessary patterns of migration of granule cells in the cerebellar anlage.

In attempting to better understand the relationship between chemokines and their receptors, recent experiments to block the binding of HIV to the CXCR-4 chemokine receptor were carried out through the use of monoclonal antibodies or small molecules that appear to suggest a useful therapeutic strategy (Schols et al., *J. Exp. Med.* 186:1383–1388(1997); Schols et al., *Antiviral Research* 35:147–156 (1997)). Small molecules, such as bicyclams, appear to specifically interfere with the CXCR-4 binding and not CCR-5 binding (Donzella et al., *Nature Medicine*, 4:72–77 (1998)). These experiments demonstrated interference with HIV entry and membrane fusion into the target cell in vitro. Additional experiments monitoring the calcium flux or $Ca^{2+}$ mobilization assay demonstrated that a bicyclam also functioned as an antagonist to signal transduction resulting from the binding of stromal derived factor or SDF-1α, the natural chemokine to CXCR-4. SDF-1 has been shown to be essential for CXCR-4 dependent migration of human stem cell function in non-obese diabetic (NOD) severe combined immunodeficient (SCID) mice (Peled et al., *Science* 283: 845–848 (1998)). The role of CXCR-4 appears critical for migration to SDF-1 and localization of stem cells in bone marrow.

U.S. Pat. Nos. 5,583,131, 5,698,546 and 5,817,807, which are herein incorporated in their entirety by reference, disclose cyclic compounds that are active against HIV-1 and HIV-2 in in vitro tests. It was subsequently discovered and further disclosed in copending application U.S. Ser. No. 09/111,895 that these compounds exhibit anti-HIV activity by binding to the chemokine receptor CXCR4 expressed on the surface of certain cells of the immune system. This competitive binding thereby protects these target cells from infection by HIV which utilize the CXCR-4 receptor for entry. In addition, these compounds antagonize the binding, signaling and chemotactic effects of the natural CXC-chemokine for CXCR-4, stromal cell-derived factor 1α (SDF-1).

Additionally we have shown that these cyclic polyamine antiviral agents described in the above-mentioned patents have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

We further disclosed that these novel compounds demonstrate protective effects against HIV infection of target cells by binding in vitro to the CC-5 receptor (CCR-5).

Herein, we disclose novel compounds that exhibit protective effects against HIV infection of target cells by binding to chemokine receptors, including CXCR4 and CCR5, in a similar manner to the previously disclosed macrocyclic compounds. (see Table 1 for comparative examples).

SUMMARY OF THE INVENTION

The present invention provides novel compounds that bind chemokine receptors and interfere with the binding of the natural ligand thereto. The compounds of the present invention are useful as agents demonstrating protective effects on target cells from HIV infection. Other embodiments of the present invention are compounds that act as antagonists or agonists of chemokine receptors, which are useful as agents capable of reconstituting the immune system by increasing the level of $CD4^+$ cells; as antagonist agents of apoptosis in immune cells, such as $CD8^+$ cells, and neuronal cells; as antagonist agents of migration of human bone marrow B lineage cells to stromal-derived factor 1, as well as other biological activities related to the ability of these compounds to inhibit the binding of chemokines to their receptors. Accordingly, the present invention provides a compound of Formula I

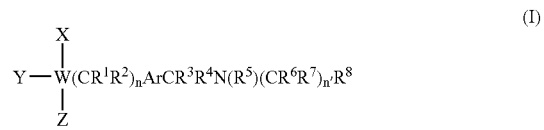

wherein, W is a nitrogen atom and Y is absent or, W is a carbon atom and Y=H;

$R^1$ to $R^7$ may be the same or different and are independently selected from hydrogen or straight, branched or cyclic $C_{1-6}$ alkyl;

$R^8$ is a substituted heterocyclic group or a substituted aromatic group

Ar is an aromatic or heteroaromatic ring each optionally substituted at single or multiple, non-linking positions with electron-donating or withdrawing groups;

n and n' are independently, 0–2;

X is a group of the formula:

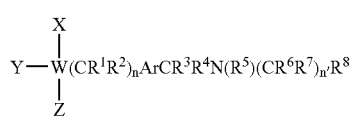

Wherein, Ring A is an optionally substituted, saturated or unsaturated 5 or 6-membered ring, and P is an optionally substituted carbon atom, an optionally substituted nitrogen atom, sulfur or oxygen atom. Ring B is an optionally substituted 5 to 7-membered ring. Ring A and Ring B in the above formula can be connected to the group W from any position via the group V, wherein V is a chemical bond, a $(CH_2)_{n''}$ group (where n''=0–2) or a C=O group. Z is, (1) a hydrogen atom, (2) an optionally substituted $C_{1-6}$ alkyl group, (3) a $C_{0-6}$ alkyl group substituted with an optionally substituted aromatic or heterocyclic group, (4) an optionally substituted $C_{0-6}$ alkylamino or $C_{3-7}$ cycloalkylamino group, (5) an optionally substituted carbonyl group or sulfonyl.

In the above Formula I, examples of the optionally substituted 5 or 6-membered ring A are benzene, pyridine, pyrimidine, pyrazine, pyridazine, triazine, piperidine, piperazine, imidazole, pyrazole, triazole, oxazole, thiazole. Six-membered rings are preferred for ring A, particularly benzene, pyridine and piperidine.

The invention also provides a compound of Formula I

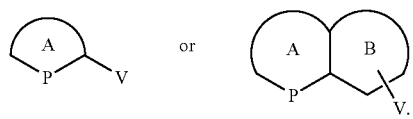

In which, W, Y, n, n', Ar, $R^1$–$R^8$ are defined as above,

X and Z are independently selected from H, optionally substituted $C_{1-6}$ alkyl or $C_{0-6}$ alkaryl or $C_{0-6}$ alkylheterocyclyl groups. The X and Z groups may also bind each other to form an optionally substituted 5- to 7-membered cyclic amine group such as tetrahydropyrrole, pyrrolidine, piperazine, homopiperazine, piperidine, morpholine, thiomorpholine, pyrrole, imidazole etc., or an optionally substituted pyran, thiopyran or cycloalkyl ring or the groups X and Z optionally fused to the group Ar.

The optional substituents are defined herein infra.

One preferred embodiment of the present invention is a pharmaceutical composition comprising a therapeutically effective amount of the compound according to Formula I. Another preferred embodiment of this invention is a method of treating a disease of the human body or the bodies of other mammals comprising the administration of a pharmaceutical composition comprising a therapeutically effective amount of the compound according to Formula I. A still further embodiment of the present invention provides a method for blocking or interfering with the binding by a chemokine receptor with its natural ligand, comprising the contacting of said chemokine receptor with an effective amount of the compound according to Formula I.

This invention may also provide for the use of a compound of Formula I in the manufacture of a medicament for the treatment of a disease in which blocking or interfering with binding of a chemokine receptor with its natural ligand is advantageous, comprising formulating a composition comprising a therapeutically effective amount of the compound of Formula I. It is further contemplated that this invention is also useful for providing a method of protecting target cells possessing chemokine receptors, the binding to which by a pathogenic agent results in disease or pathology, comprising administering to a mammalian subject a pharmaceutical composition comprising a therapeutically effective amount of the compound according to Formula I.

The invention also includes what may be termed as "pro-drug", that is, protected forms of the compounds, which release the compound after administration to a patient. For example, the compound may carry a protective groups which is split off by hydrolysis in body fluids e.g. in the bloodstream, thus releasing active compound or is oxidized or reduced in body fluids to release the compound. A discussion of pro-drugs may be found in "Smith and Williams' Introduction to the Principles of Drug Design", H. J. Smith, Wright, Second Edition, London 1988.

Acid addition salts, which are pharmaceutically acceptable such as salt with inorganic base, a salt with organic base, a salt with inorganic acid, a salt with organic acid, a salt with basic or acidic amino acid, etc. Examples of the salt with the inorganic base include a salt with alkali metal (e.g. sodium, potassium, etc.), alkaline earth metal (e.g. calcium, magnesium, etc.), aluminum, ammonium, etc. Examples of the salt with the organic base include a salt with trimethylamine, triethylamine, pyridine, picoline, ethanolamine, diethanolamine, triethanolamine, dicyclohexylamine, N,N'-dibenzylethylenediamine etc. Examples of the salt with the inorganic acid include a salt with hydrochloric acid, hydrobromic acid, nitric acid, sulfuric acid, phosphoric acid, etc. Examples of the salt with the organic acid include a salt with formic acid, oxalic acid, acetic acid, tartaric acid, methanesulfonic acid, benzenesulfonic acid, malic acid, methanesulfonic acid, benzenesulfonic acid, p-toluenesulfonic acid, etc. Examples of the salt with the basic amino acid include a salt with arginine, lysine, ornithine, etc. Examples of the salt with the acidic amino acid include a salt with aspartic acid, glutamic acid, etc. Non-toxic in the present tense has to be considered with reference to the prognosis for the infected patient without treatment.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DETAILED DESCRIPTION OF THE INVENTION

Figure 1:
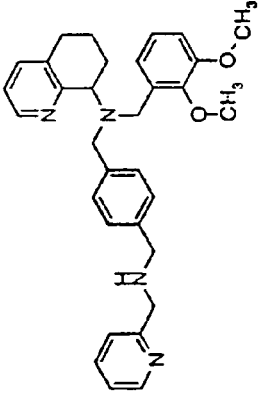
FIG. 1, shows structural formulas of compounds of the present invention.
Figure 1:
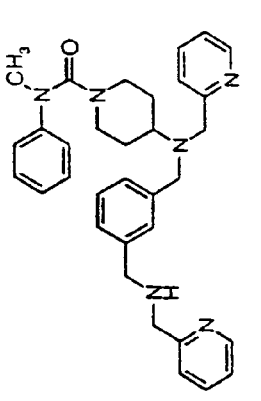
Figure 1:
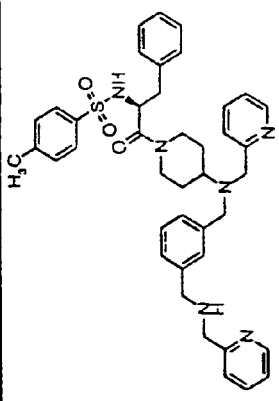
Figure 1:
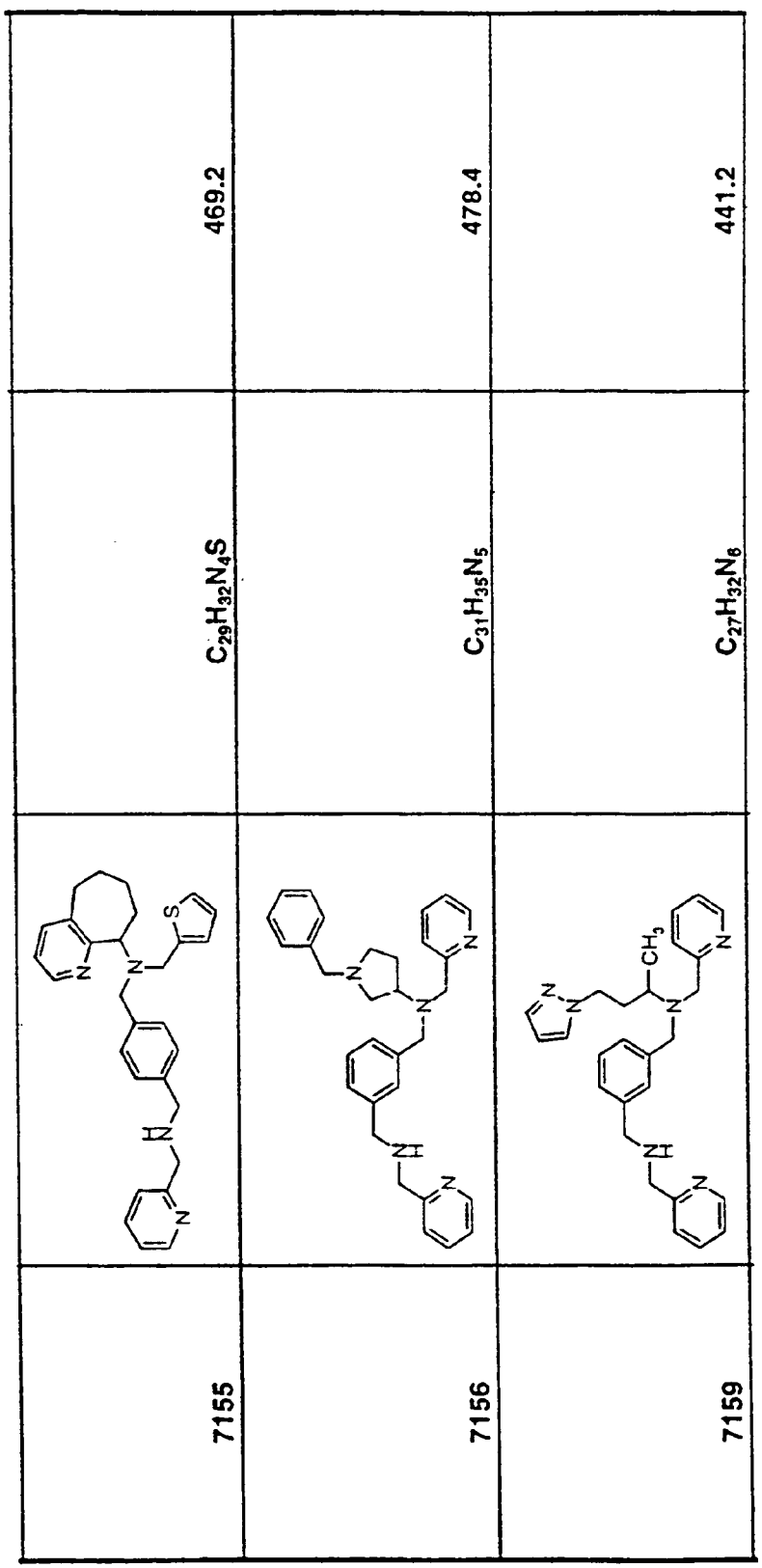
Figure 1:
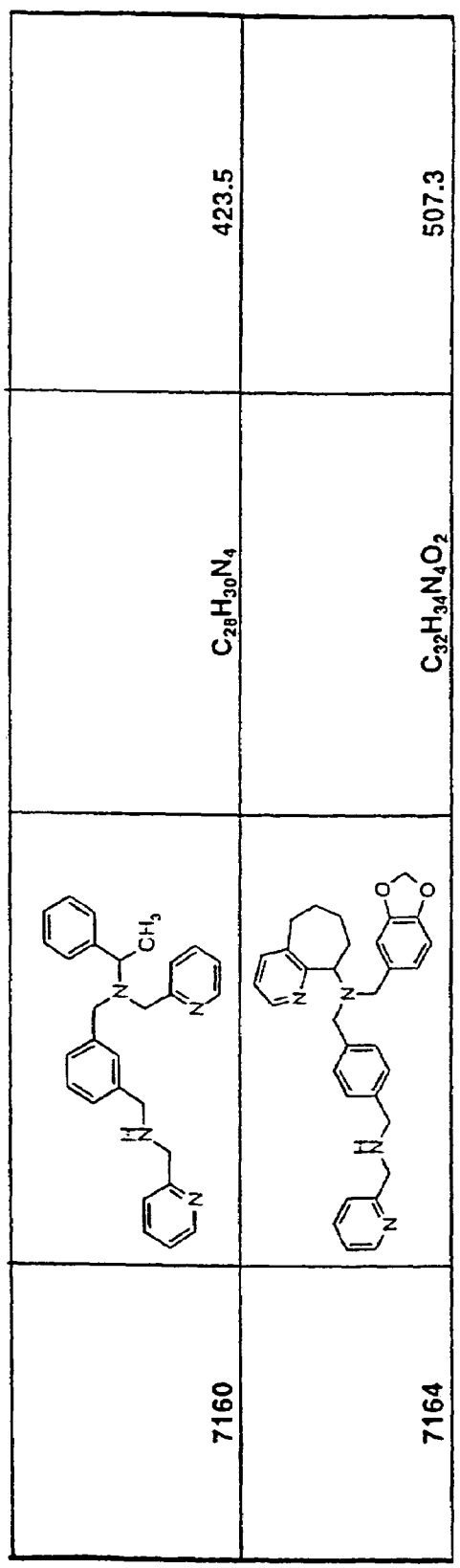
Figure 1:
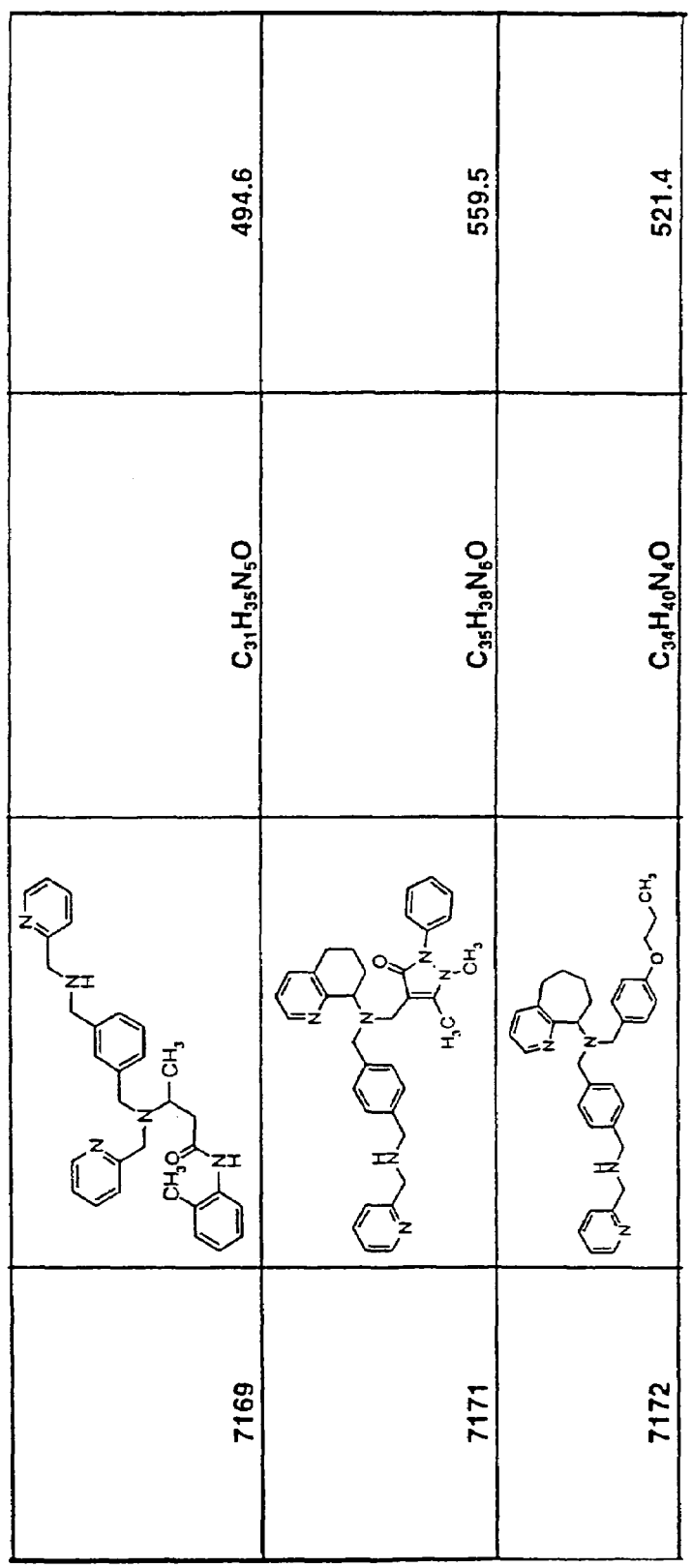
Figure 1:
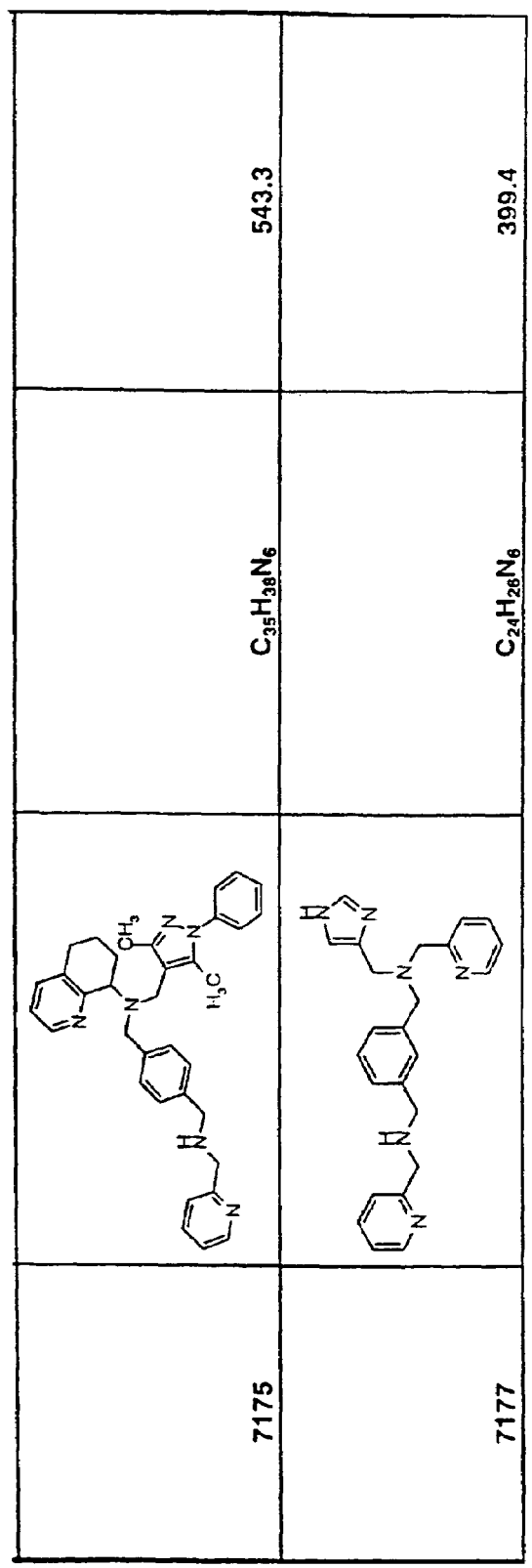
Figure 1:
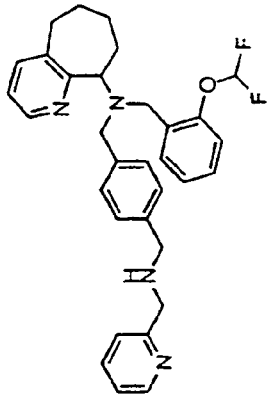
Figure 1:
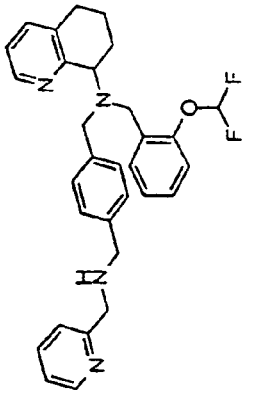
Figure 1:
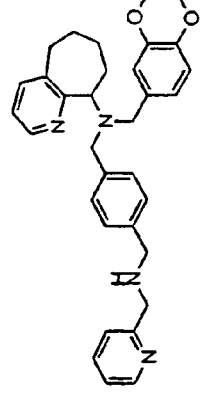
Figure 1:
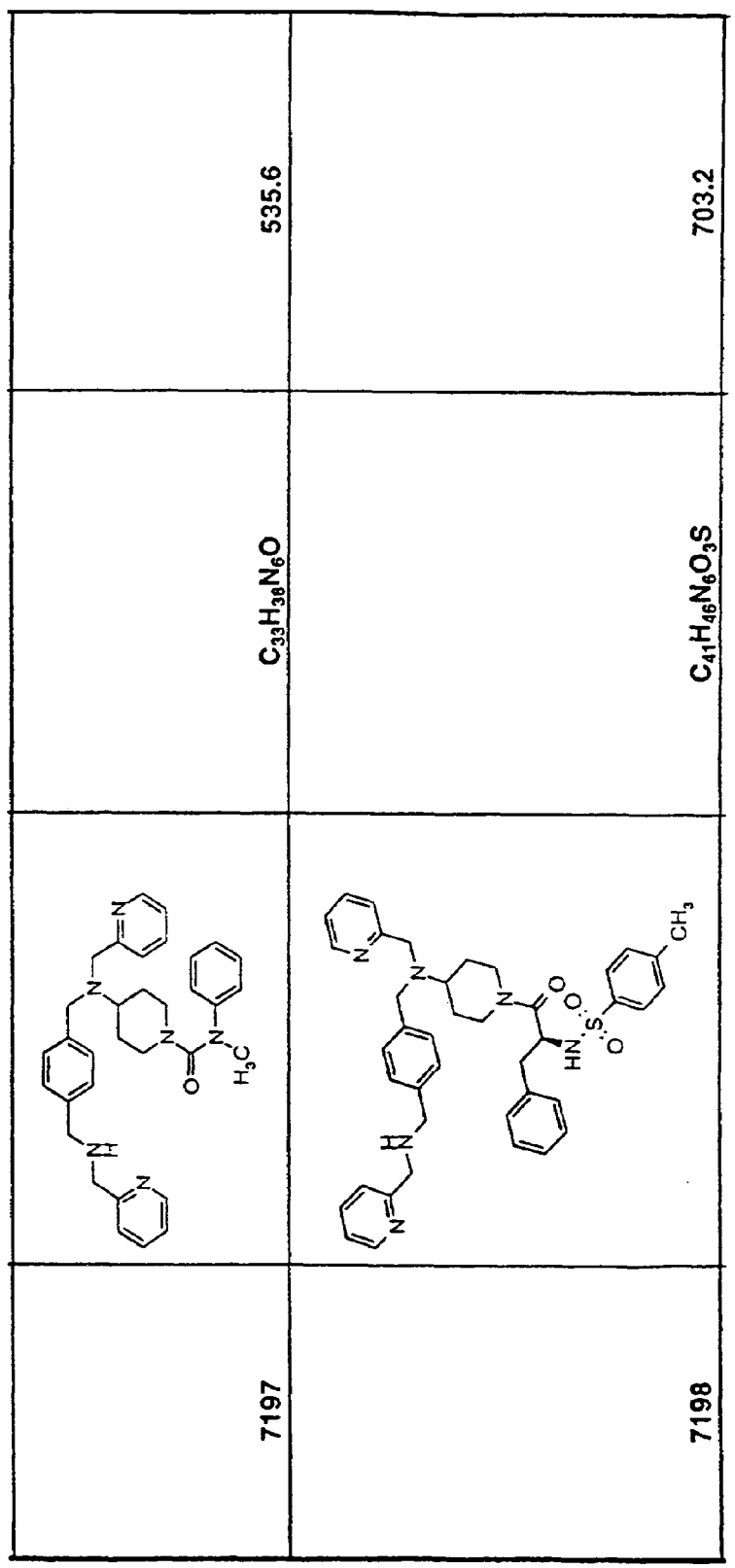
Figure 1:
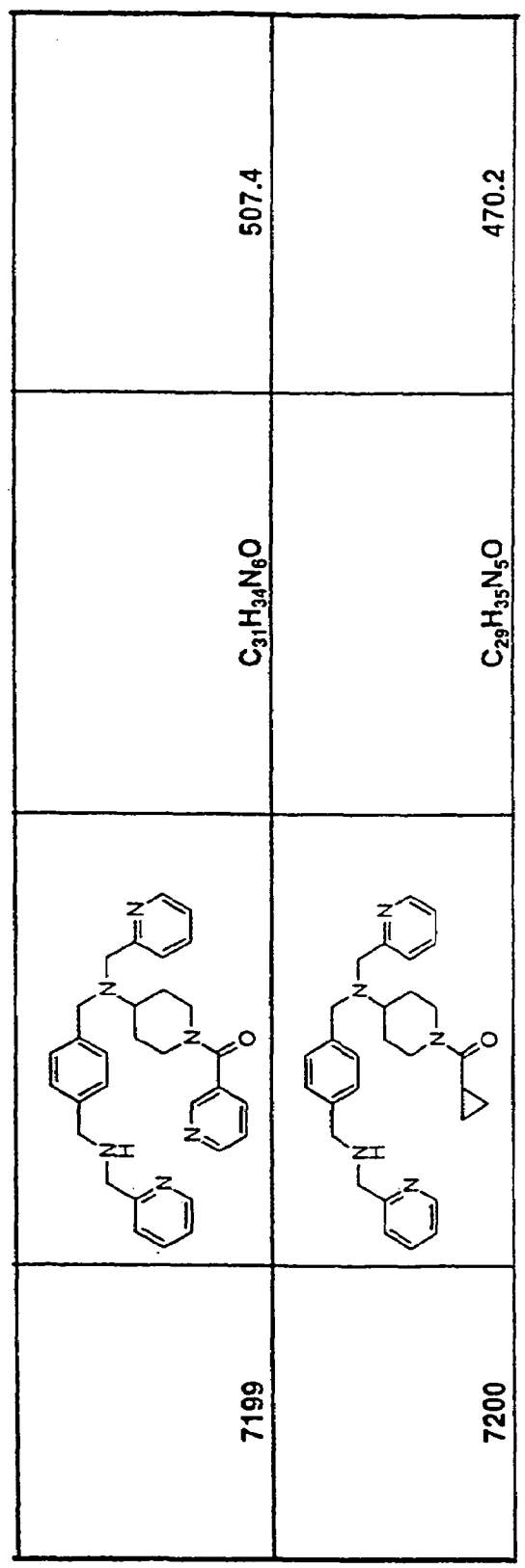
Figure 1:
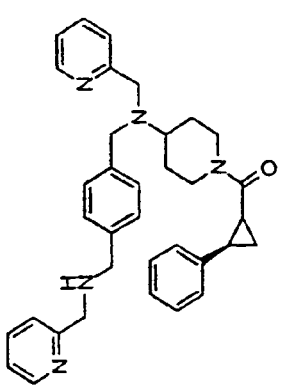
Figure 1:
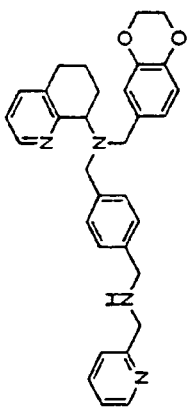
Figure 1:
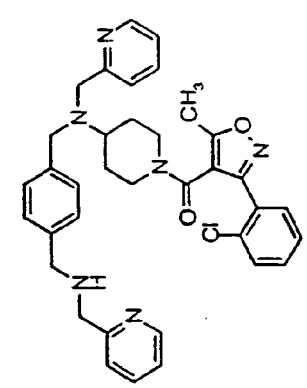
Figure 1:
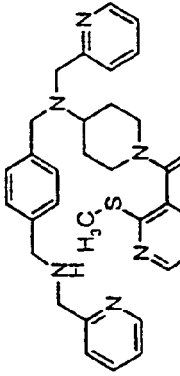
Figure 1:
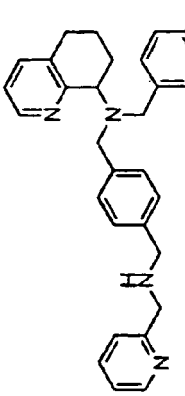
Figure 1:
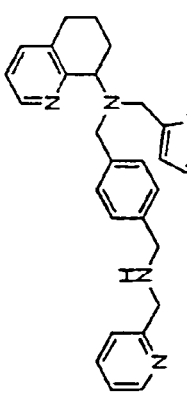
Figure 1:
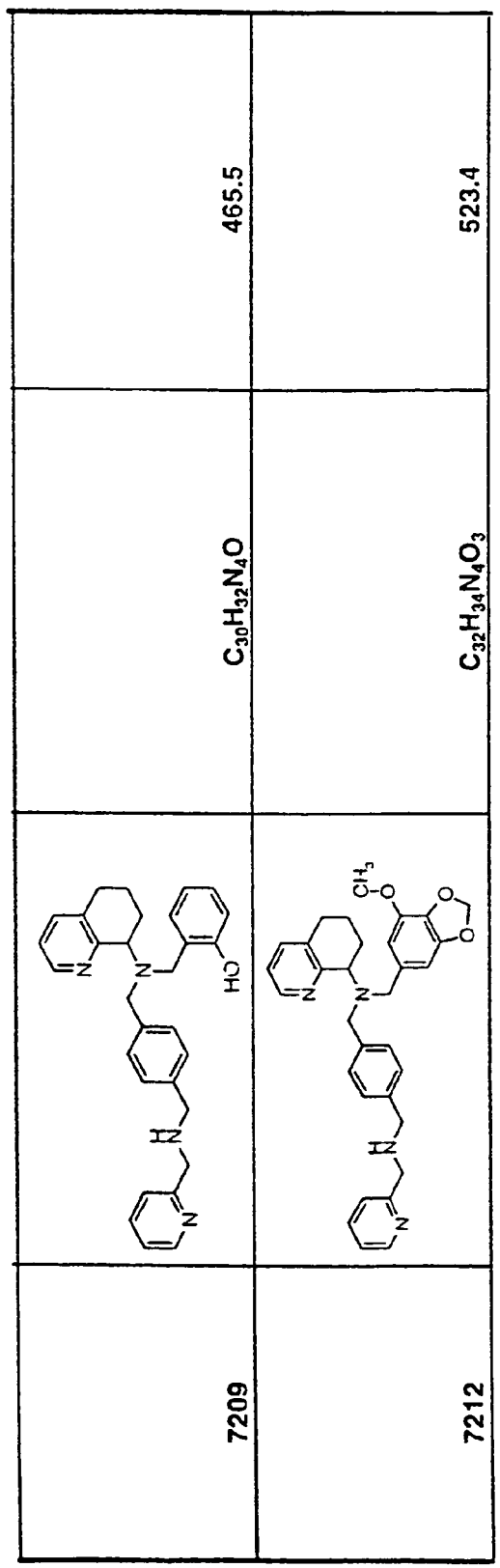
Figure 1:
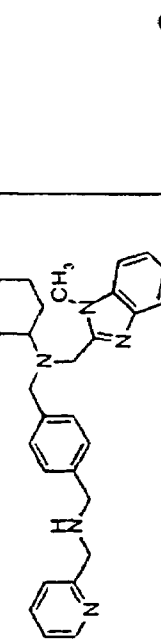
Figure 1:
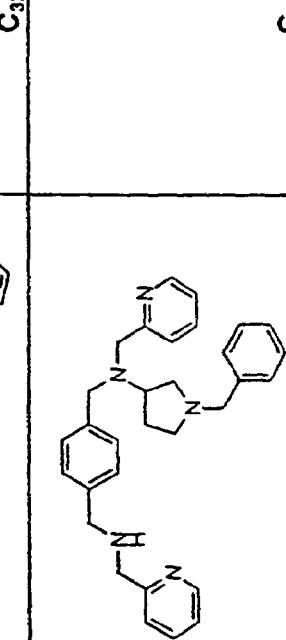
Figure 1:
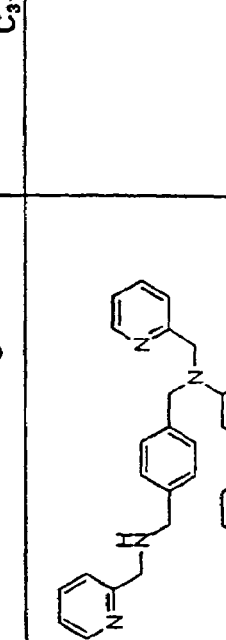
Figure 1:
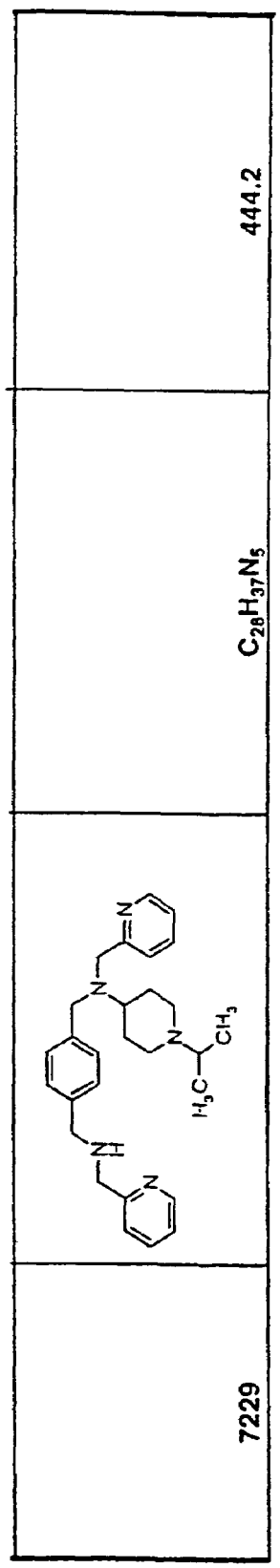
Figure 1:
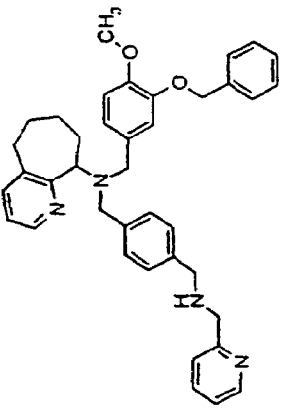
Figure 1:
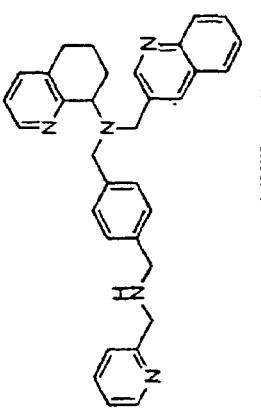
Figure 1:
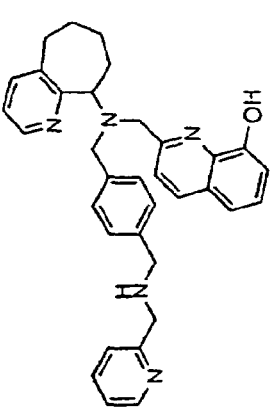
Figure 1:
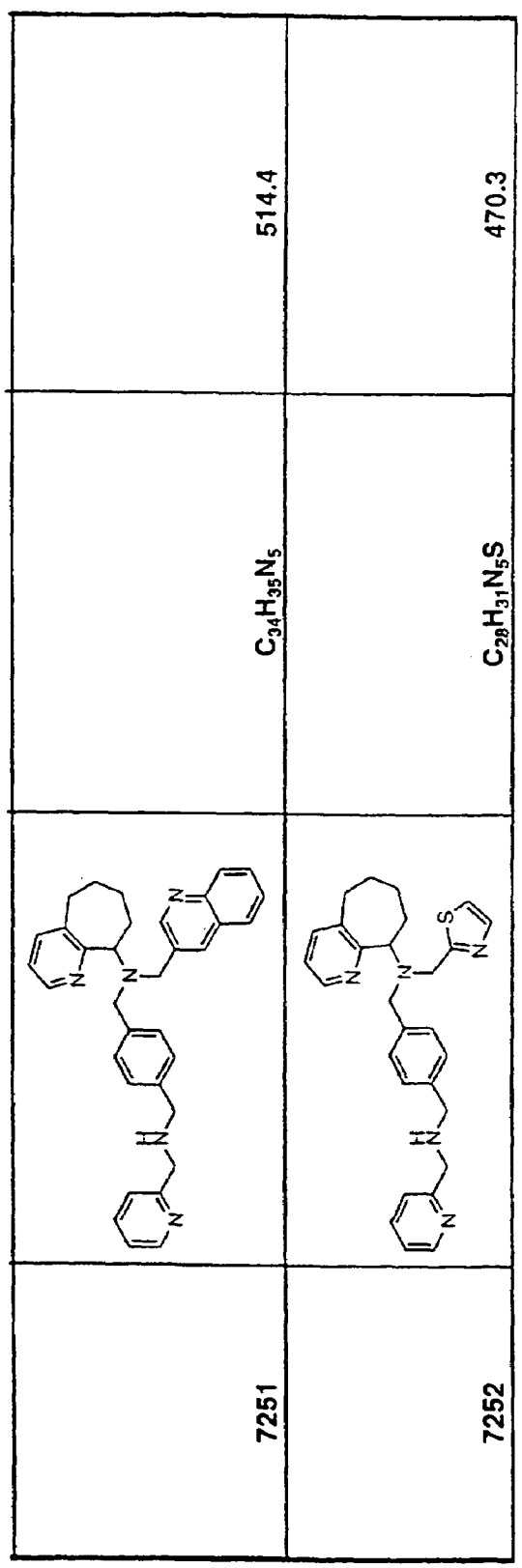
Figure 1:
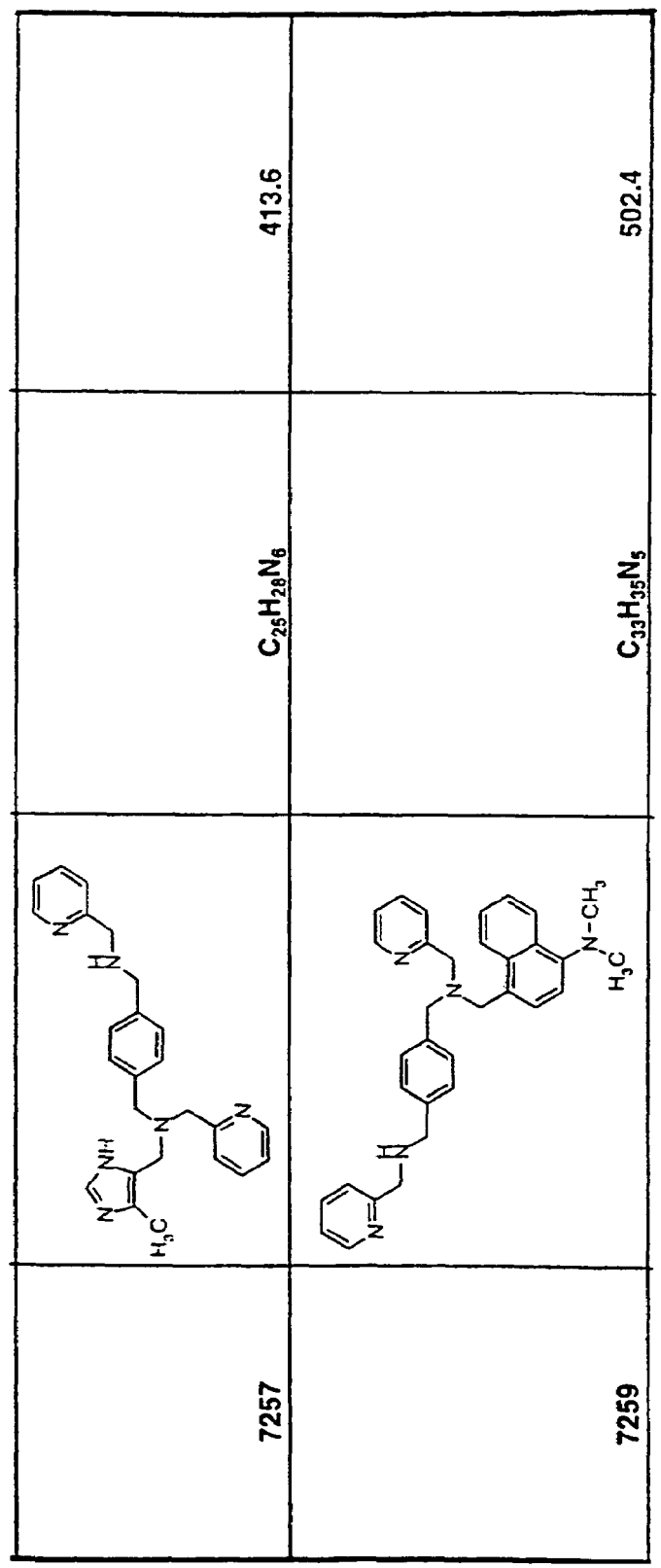
Figure 1:
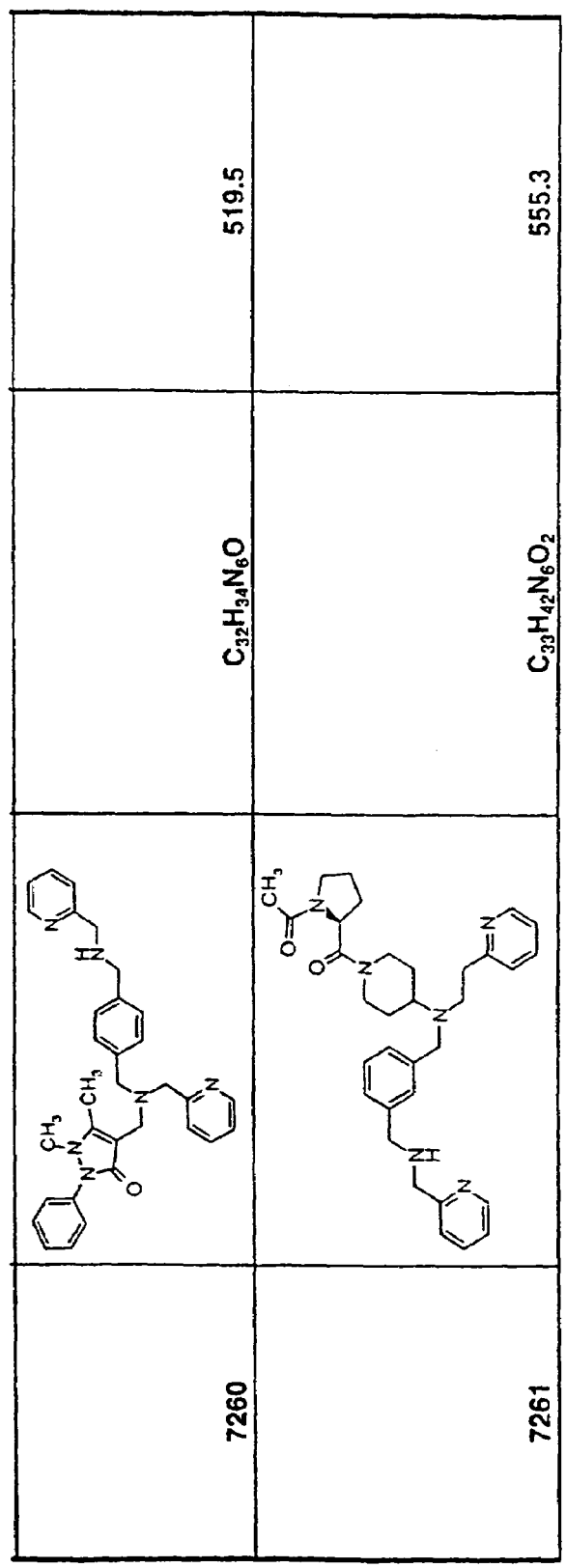
Figure 1:
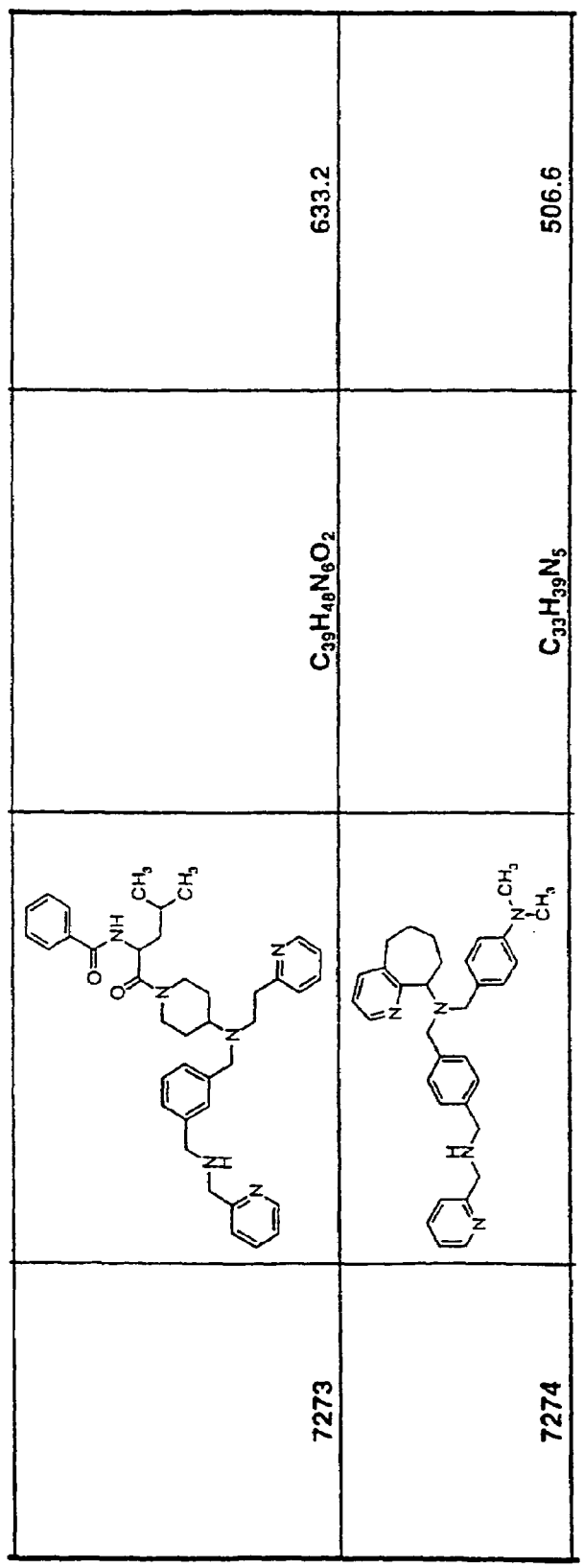
Figure 1:
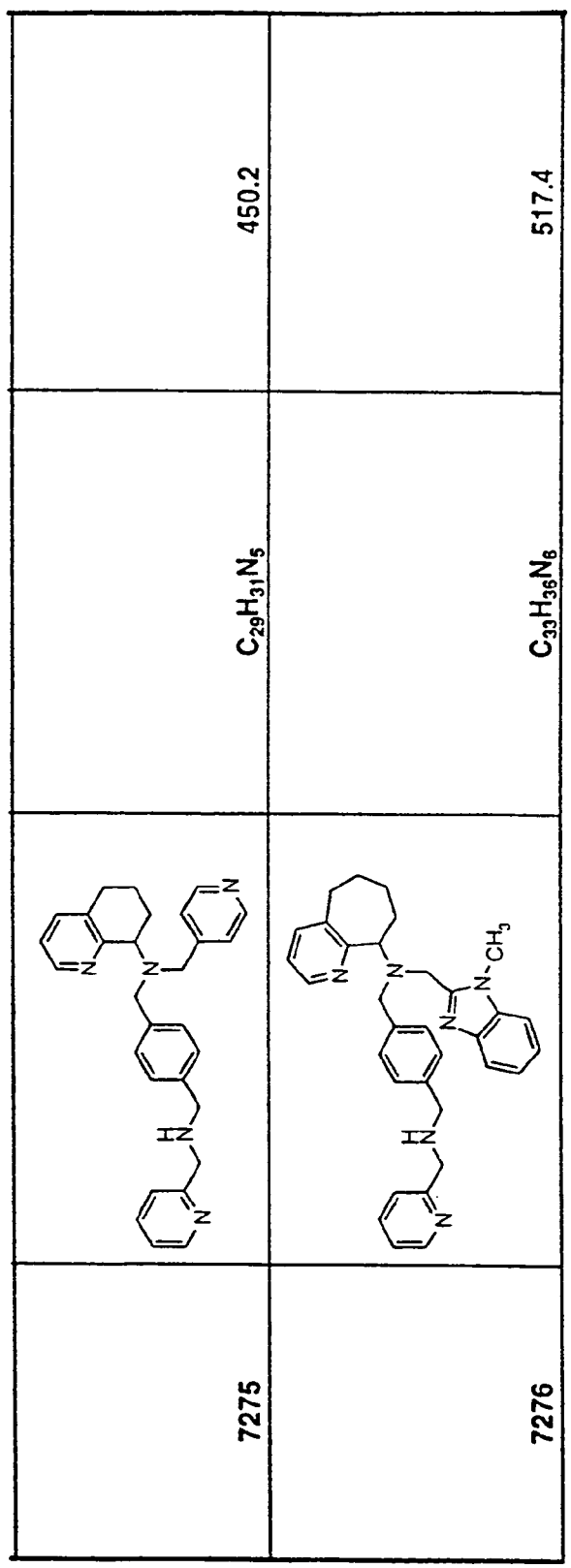
Figure 1:
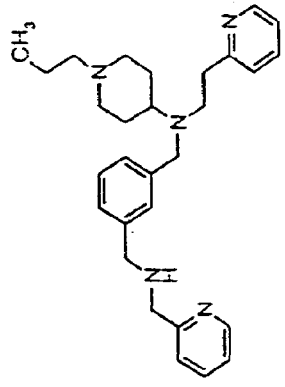
Figure 1:
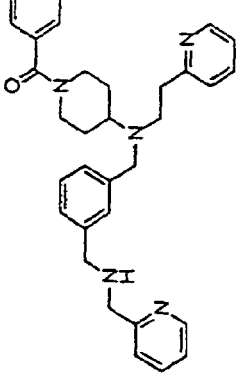
Figure 1:
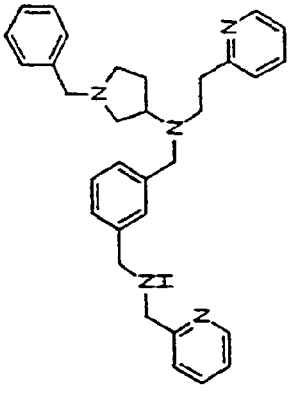
Figure 1:
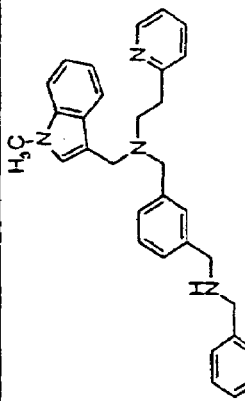
Figure 1:
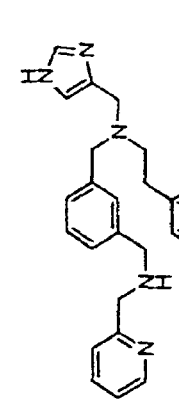
Figure 1:
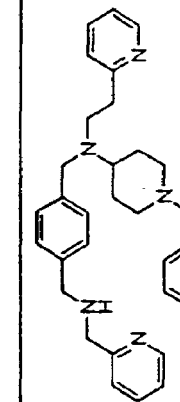
Figure 1:
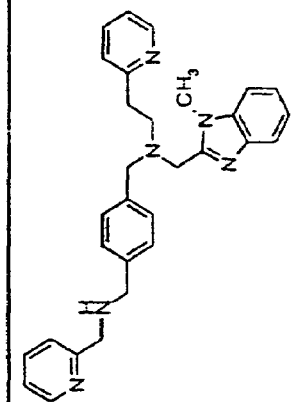
Figure 1:
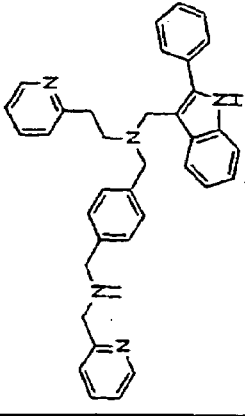
Figure 1:
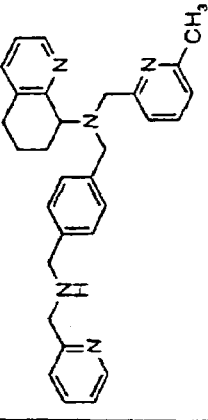
Figure 1:
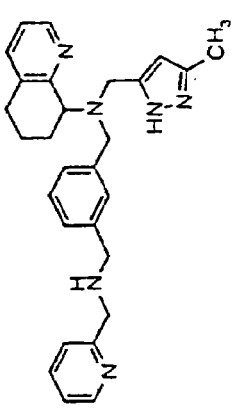
Figure 1:
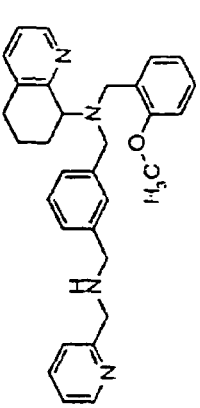
Figure 1:
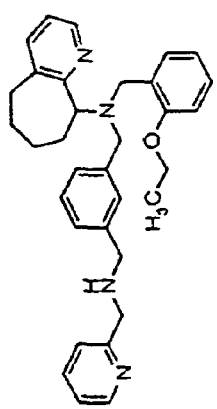
Figure 1:
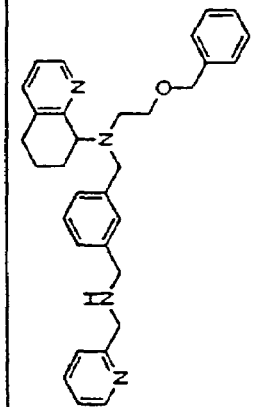
Figure 1:
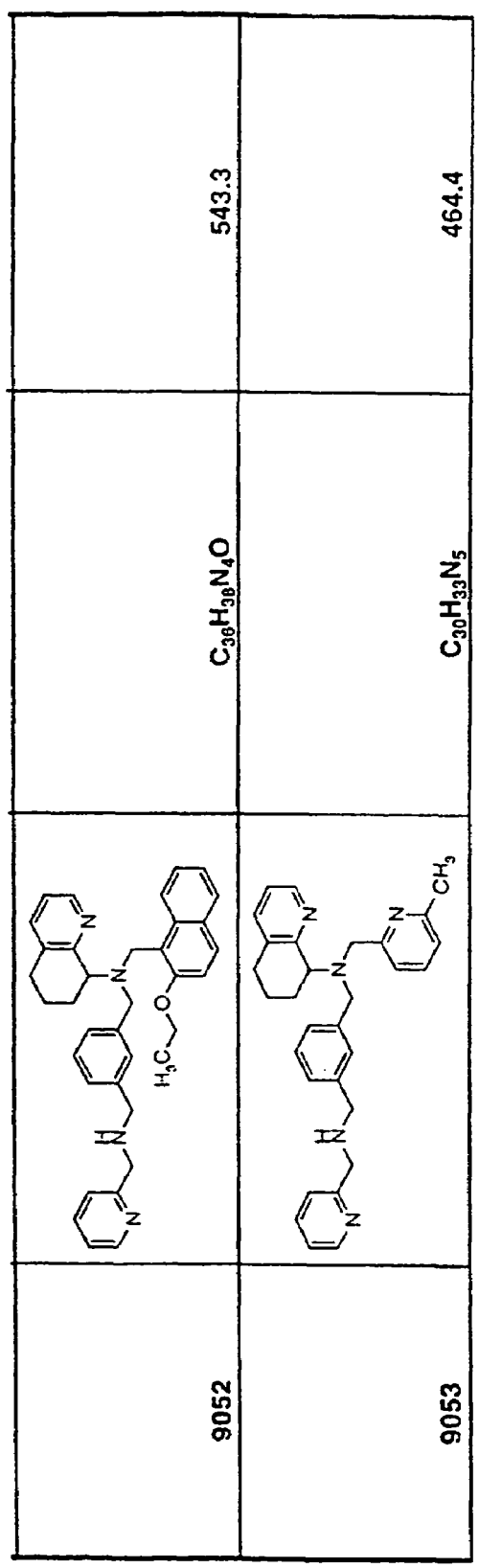
Figure 1:
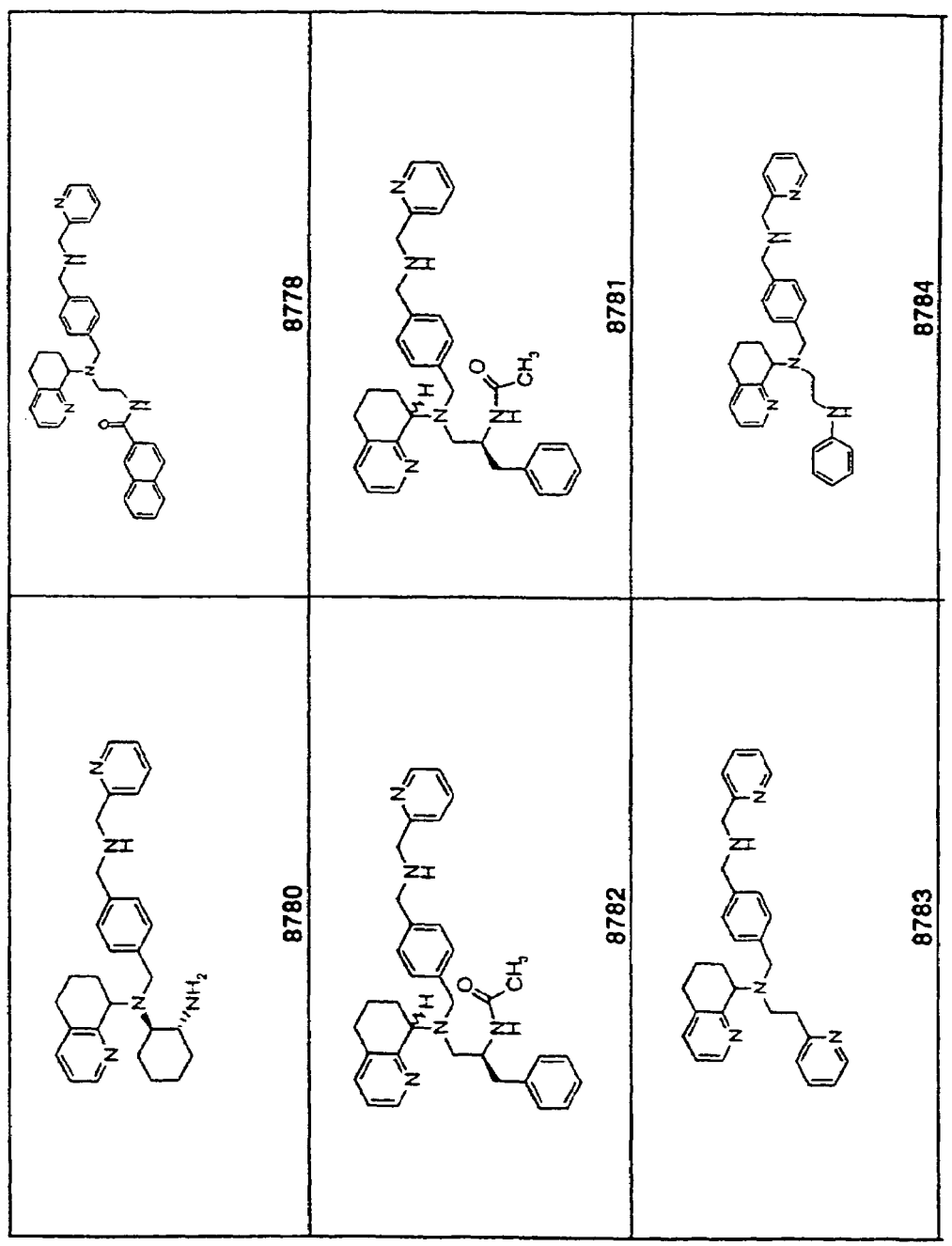
Figure 1:
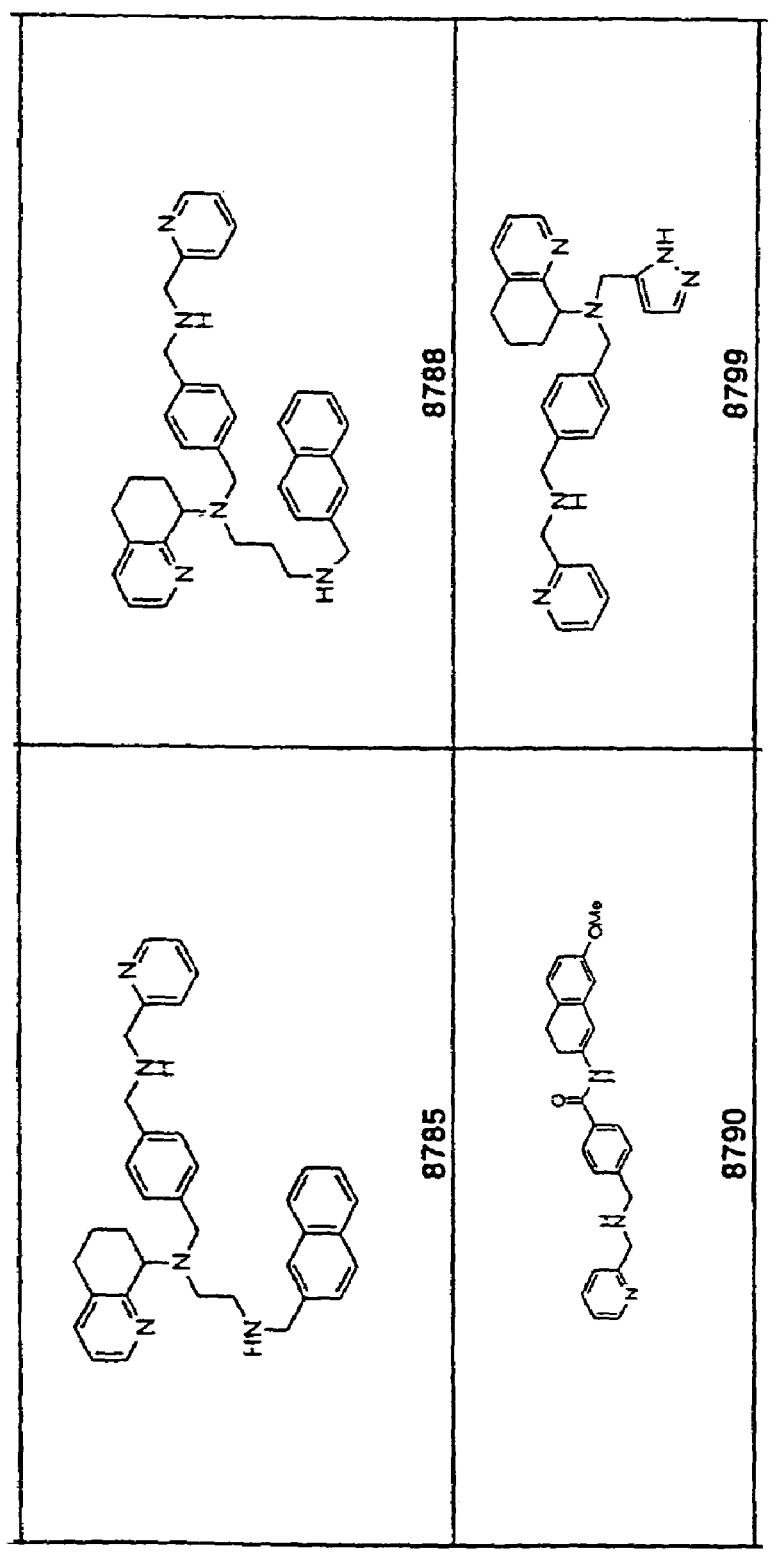
Figure 1:
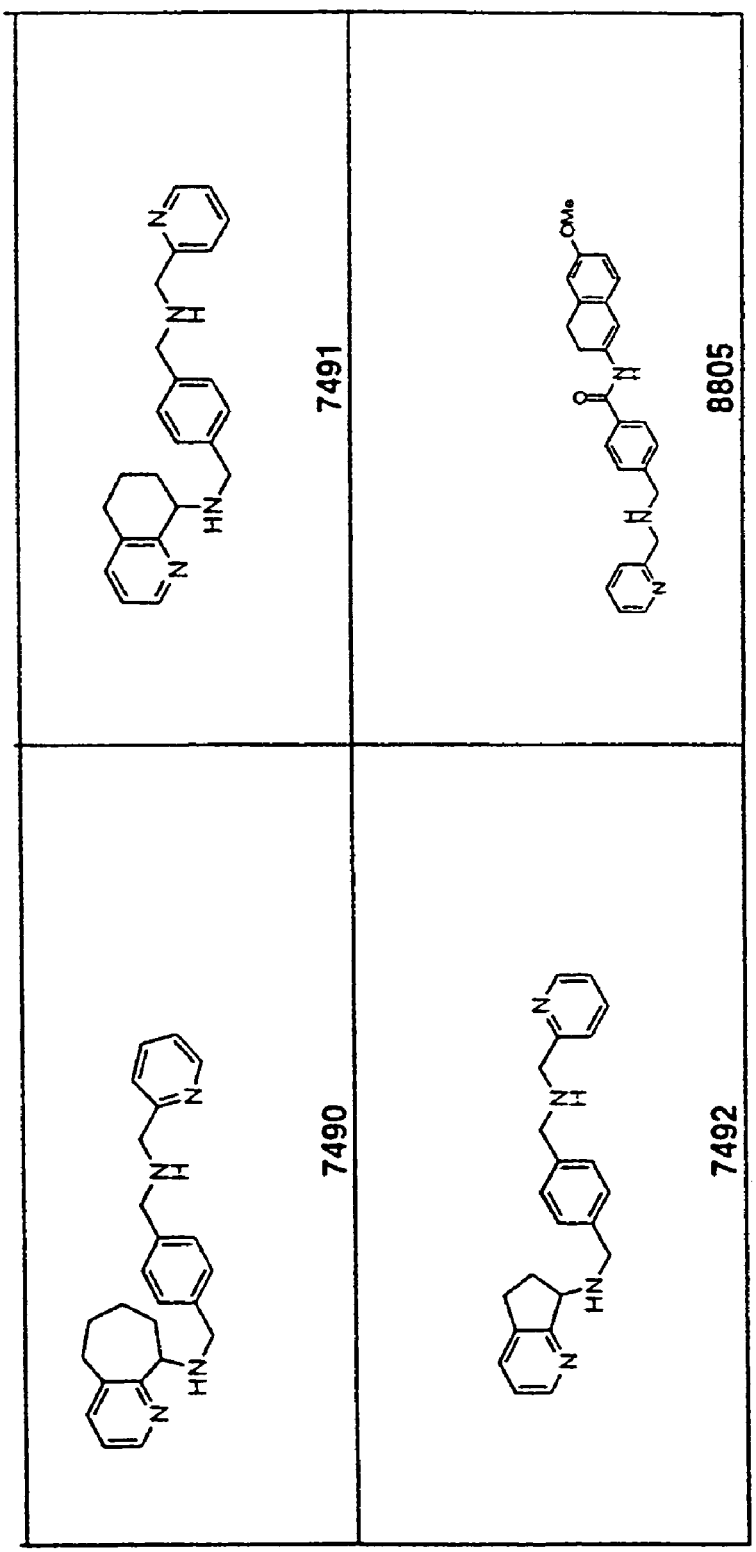
Figure 1:
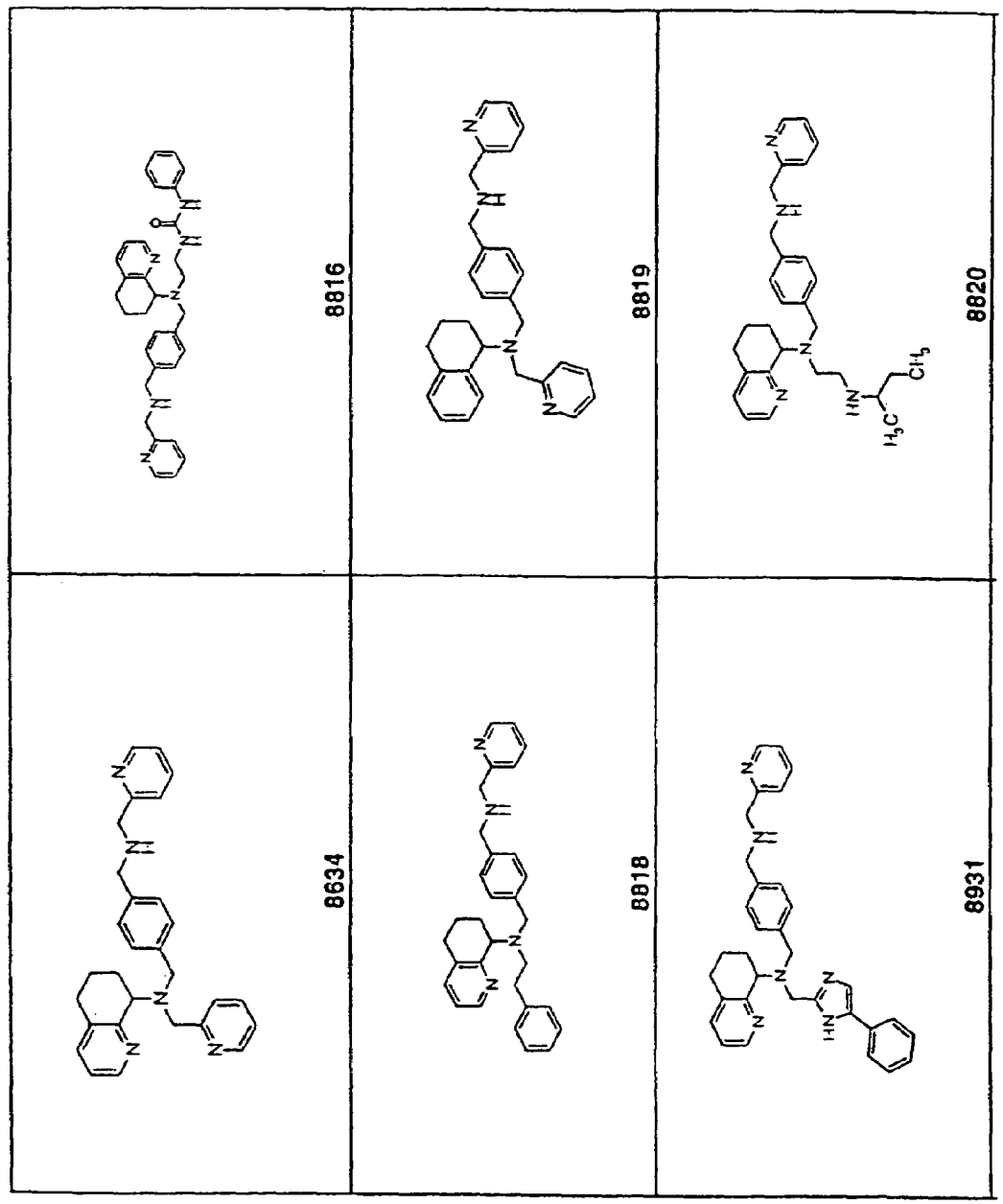
Figure 1:
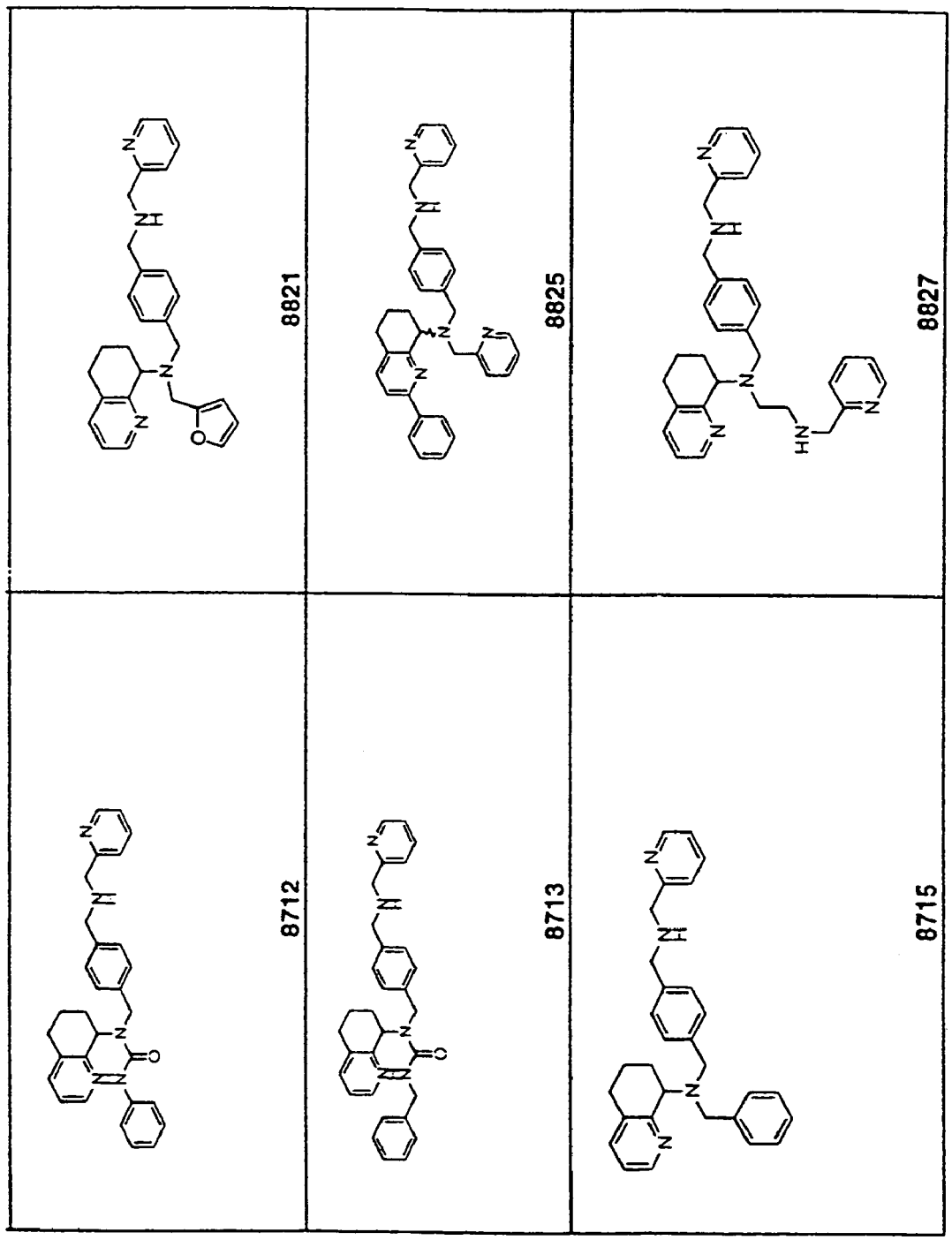
Figure 1:
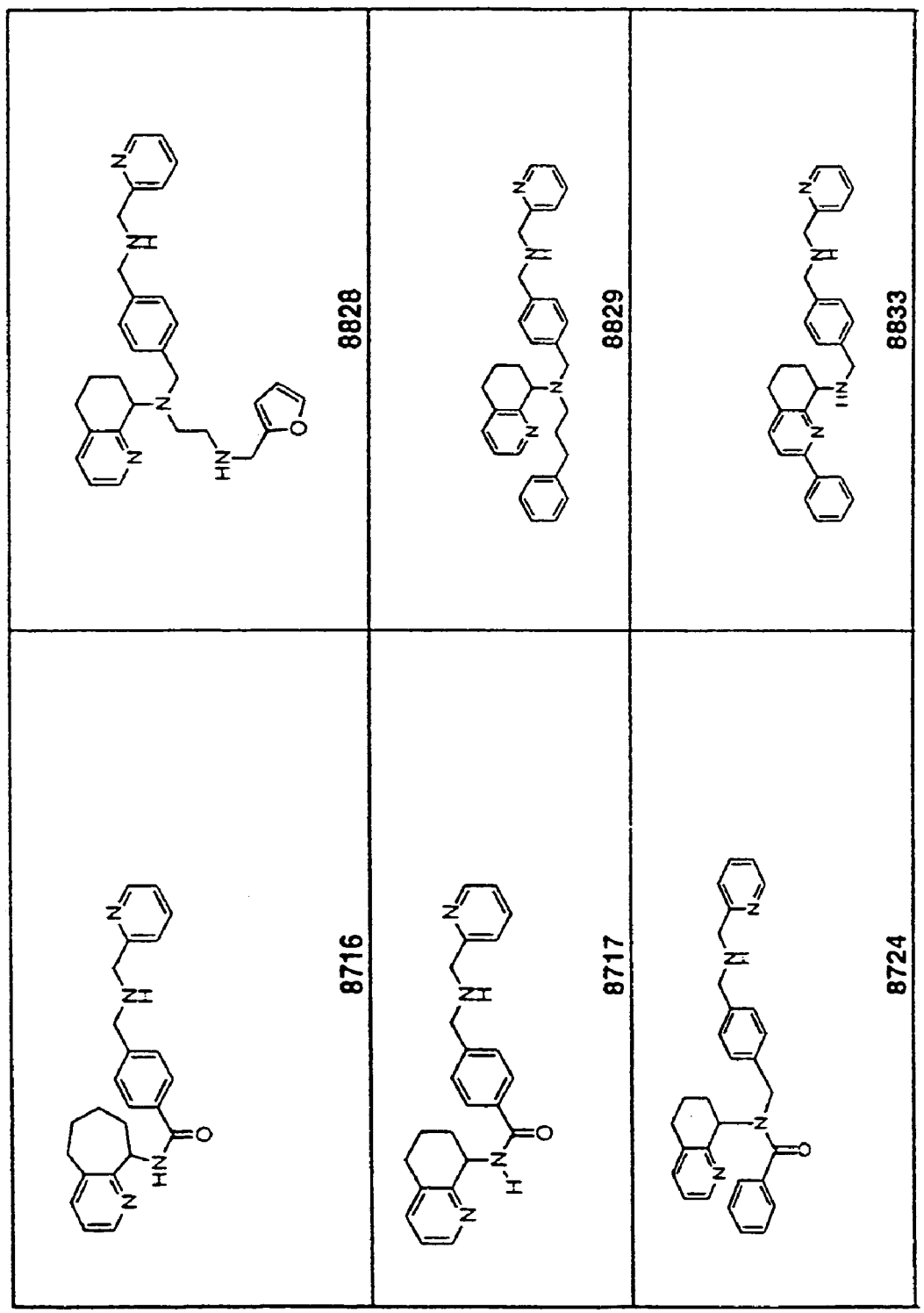
Figure 1:
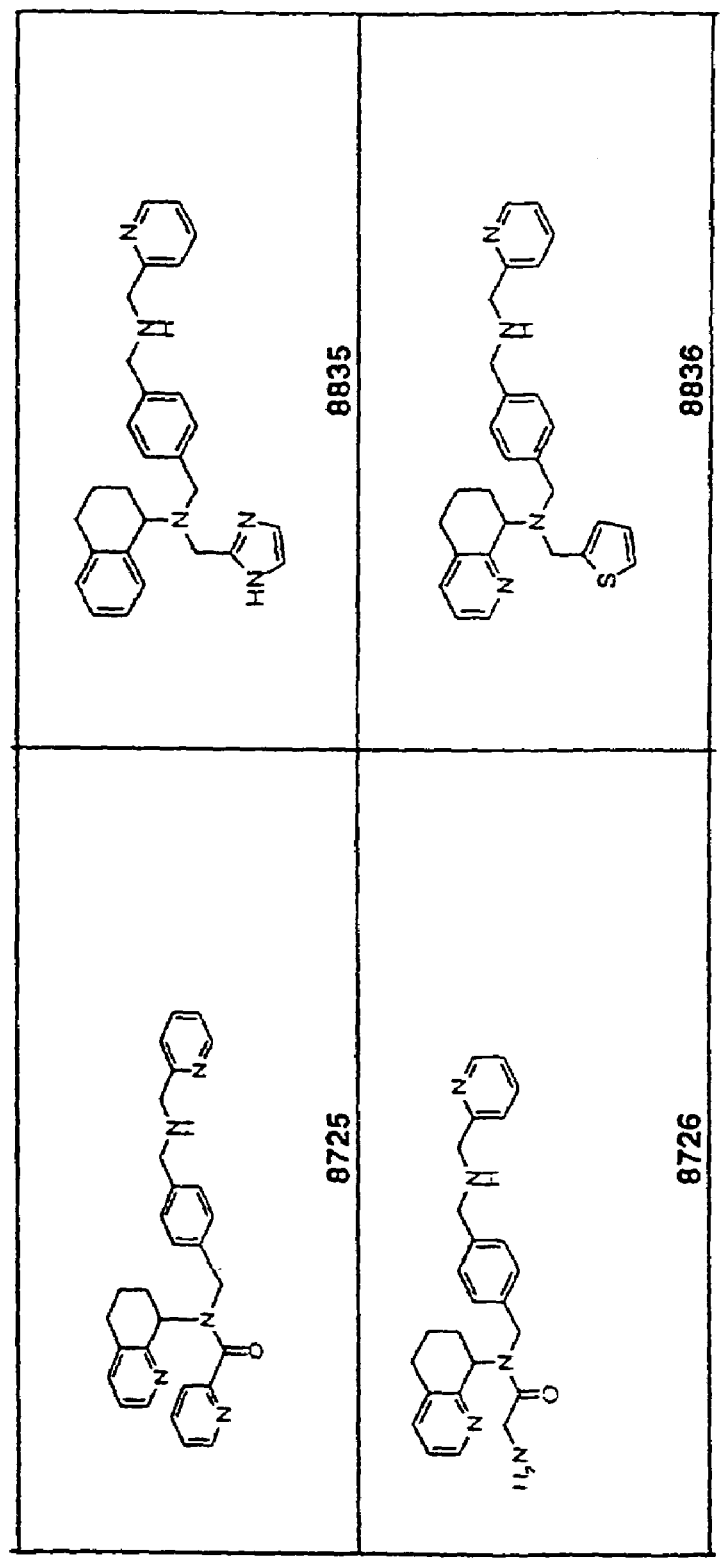
Figure 1:
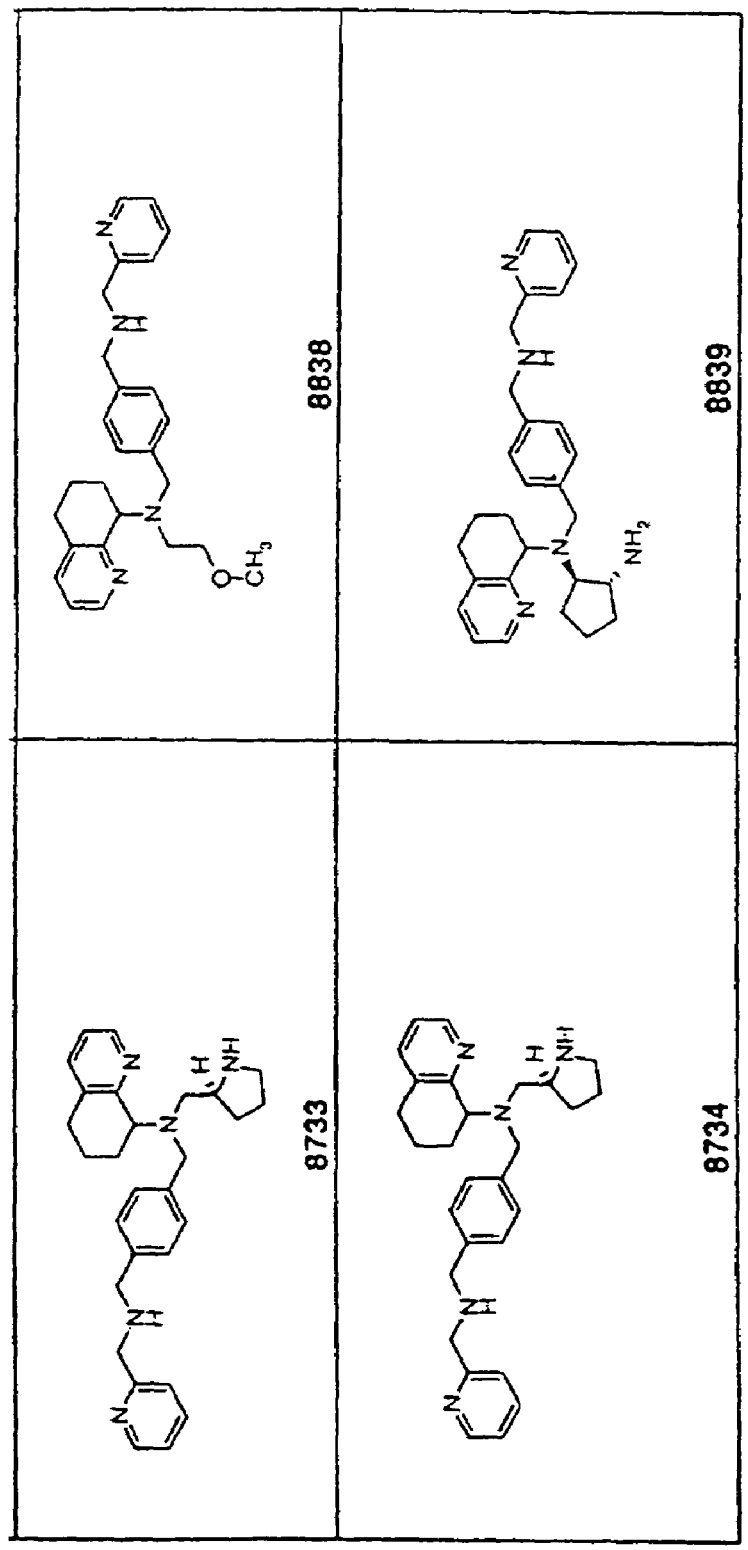
Figure 1:
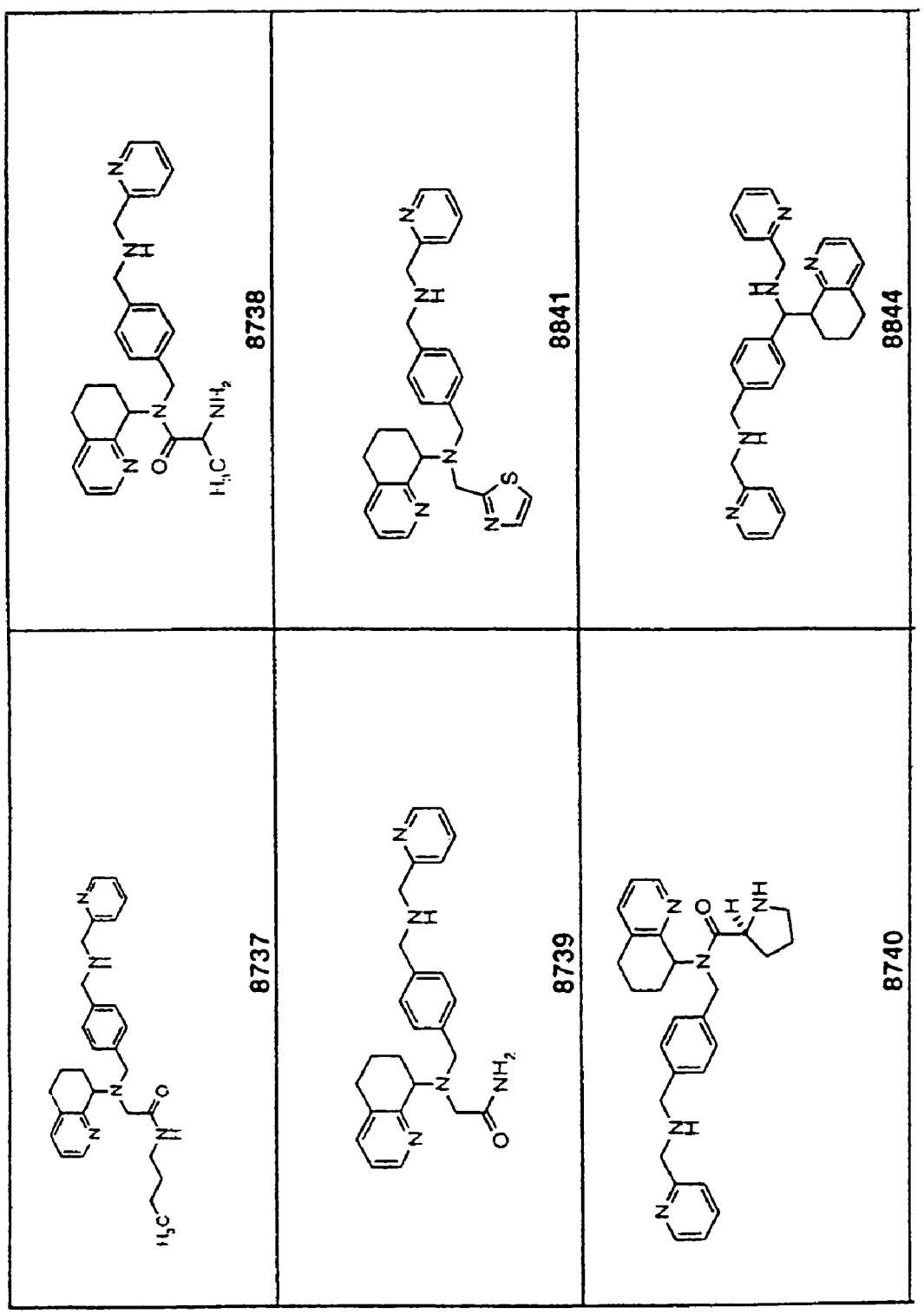
Figure 1:
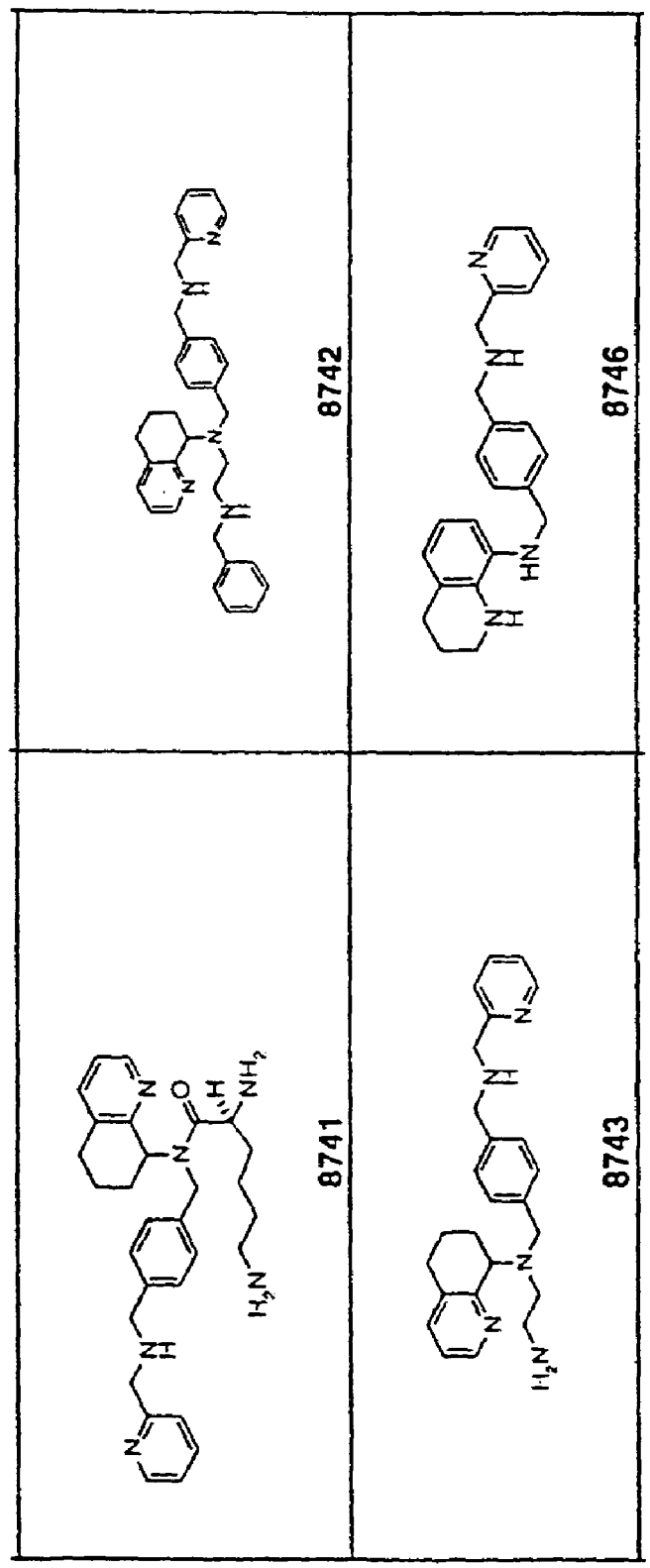
Figure 1:
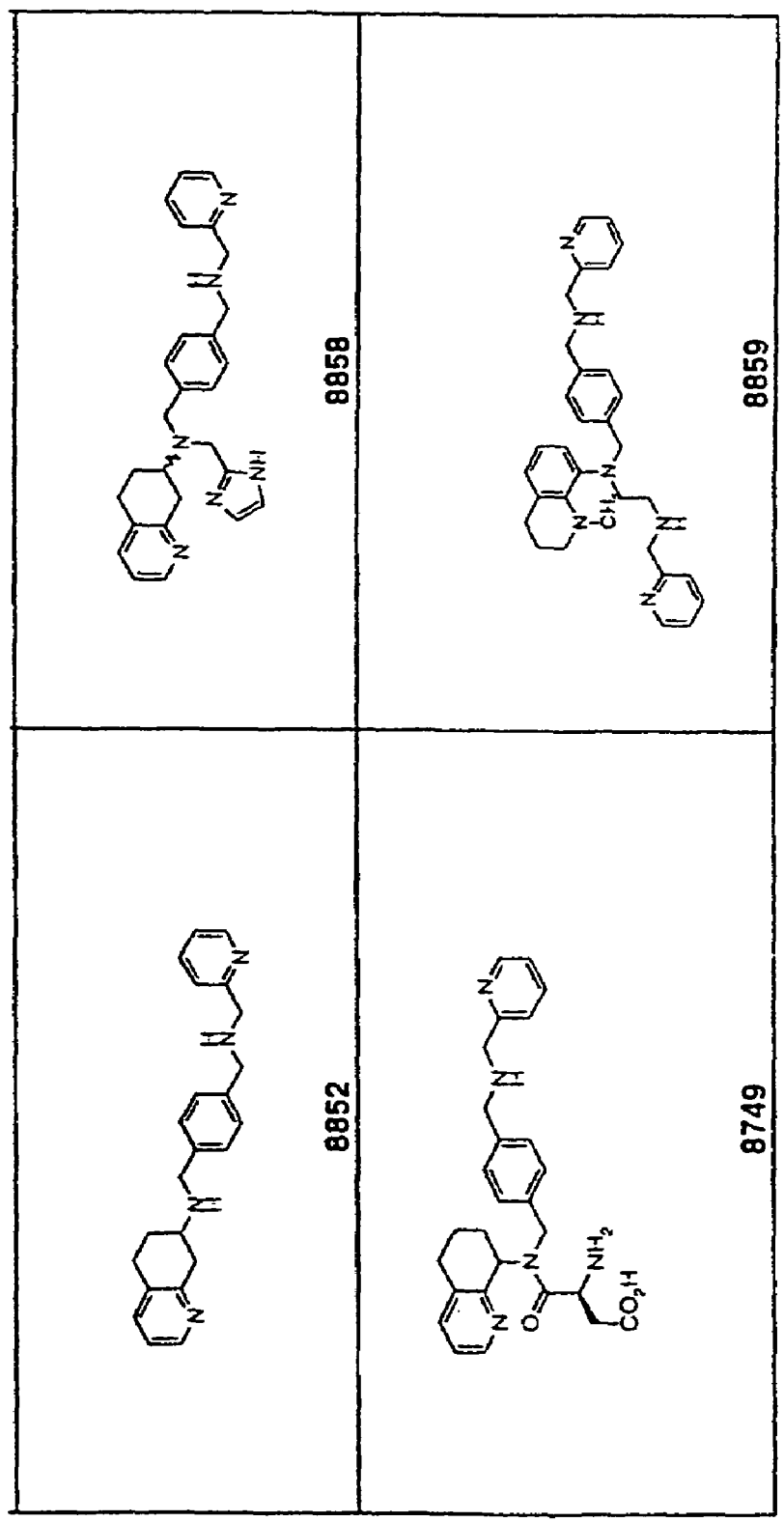
Figure 1:
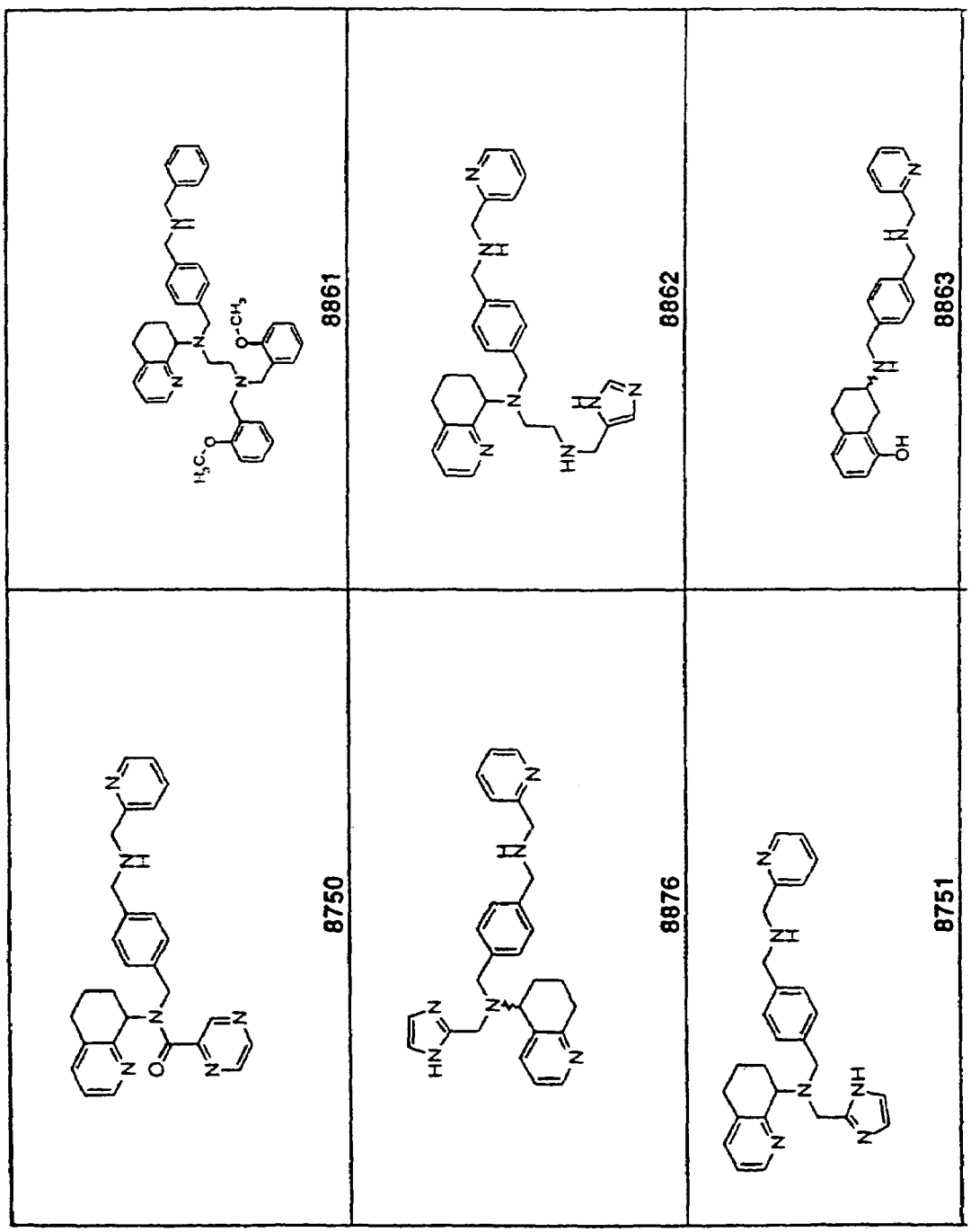
Figure 1:
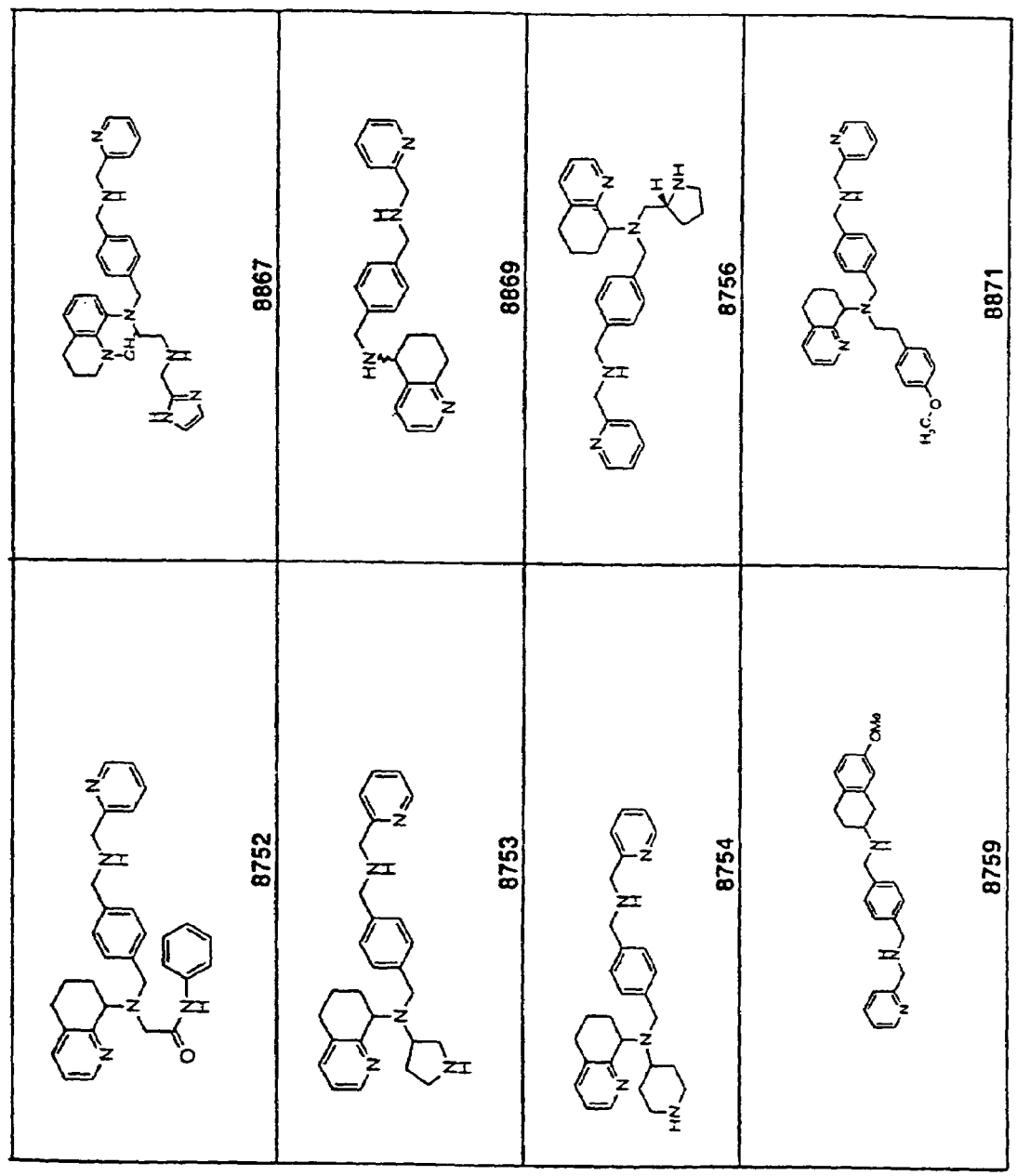
Figure 1:
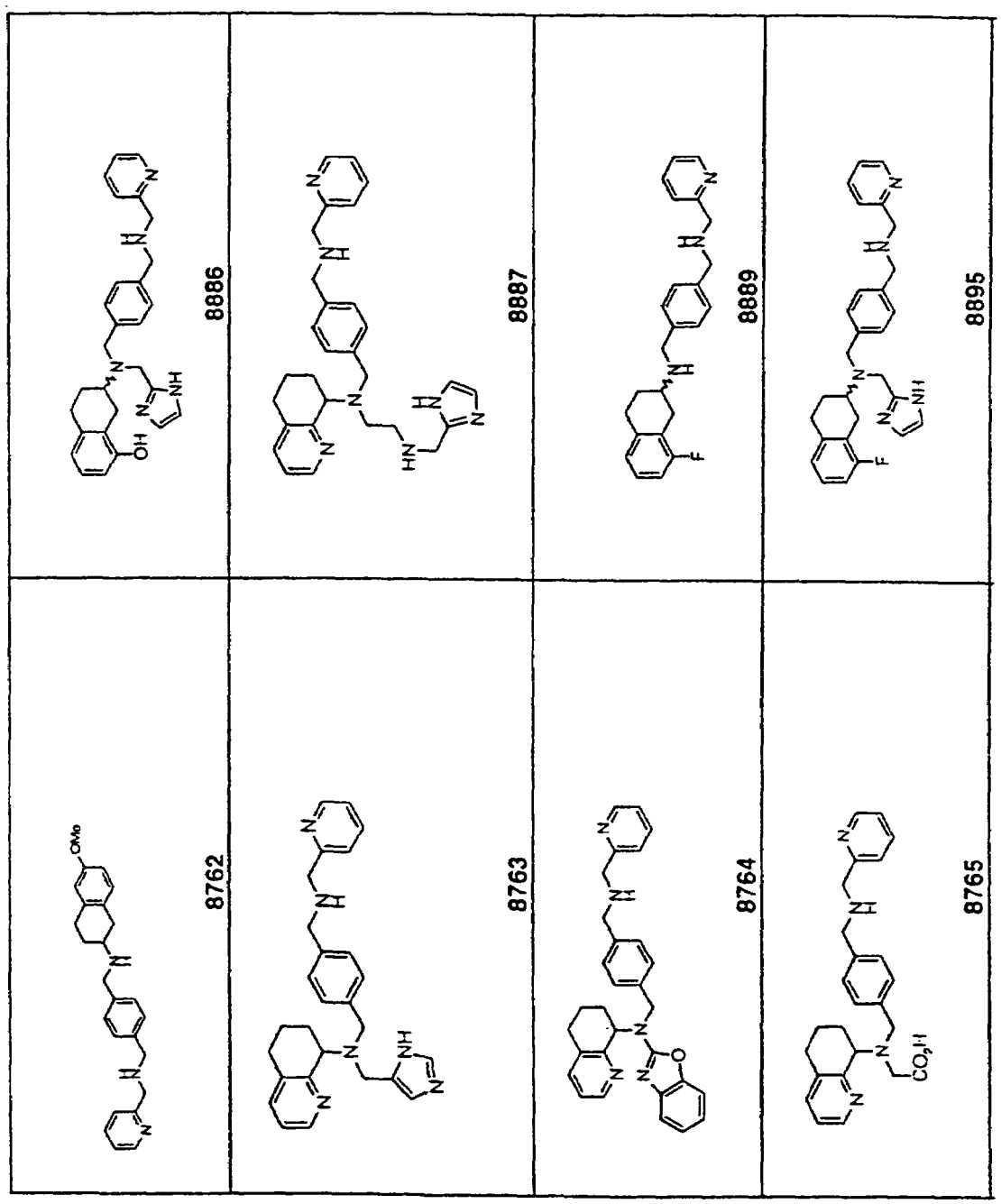
Figure 1:
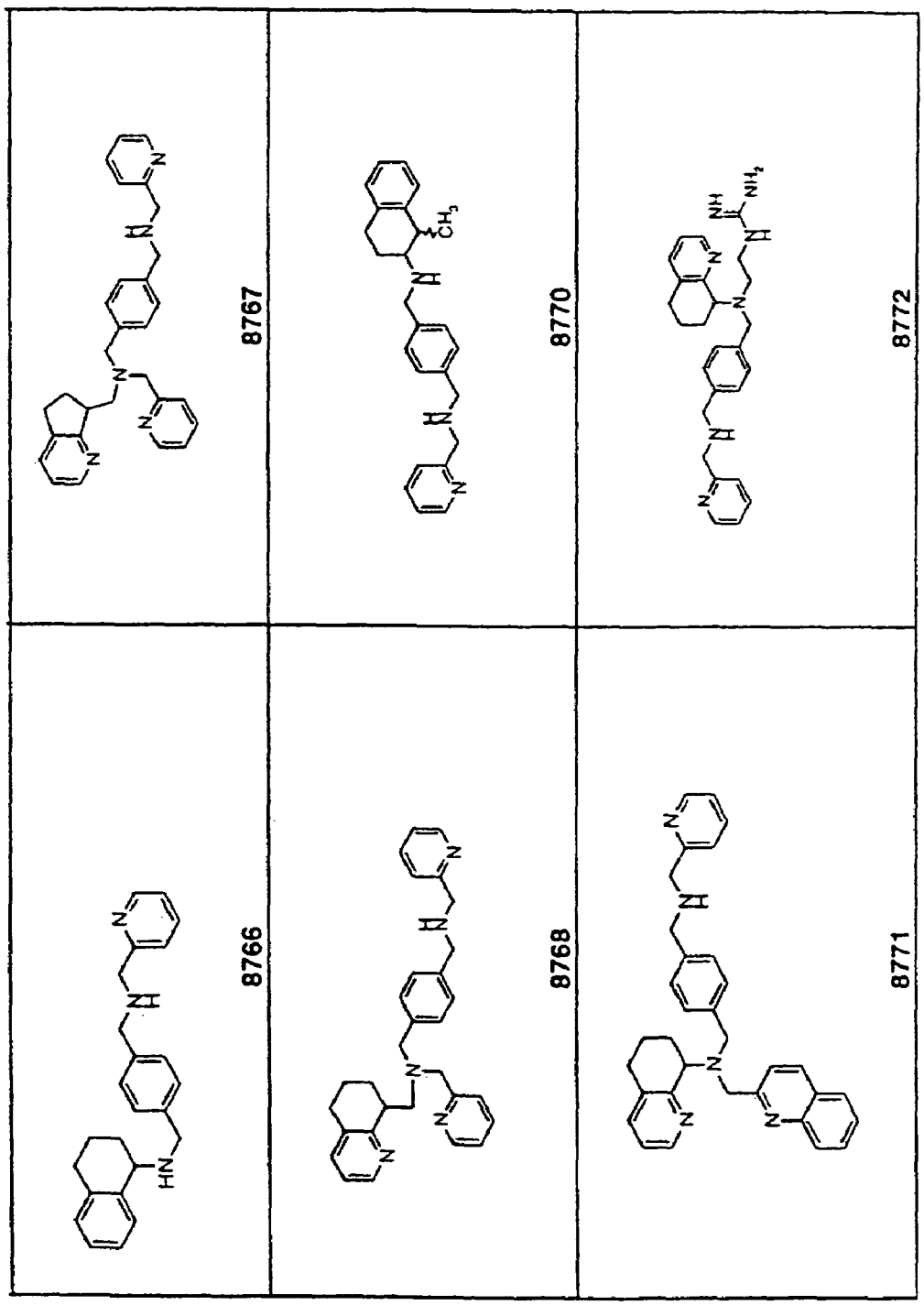
Figure 1:
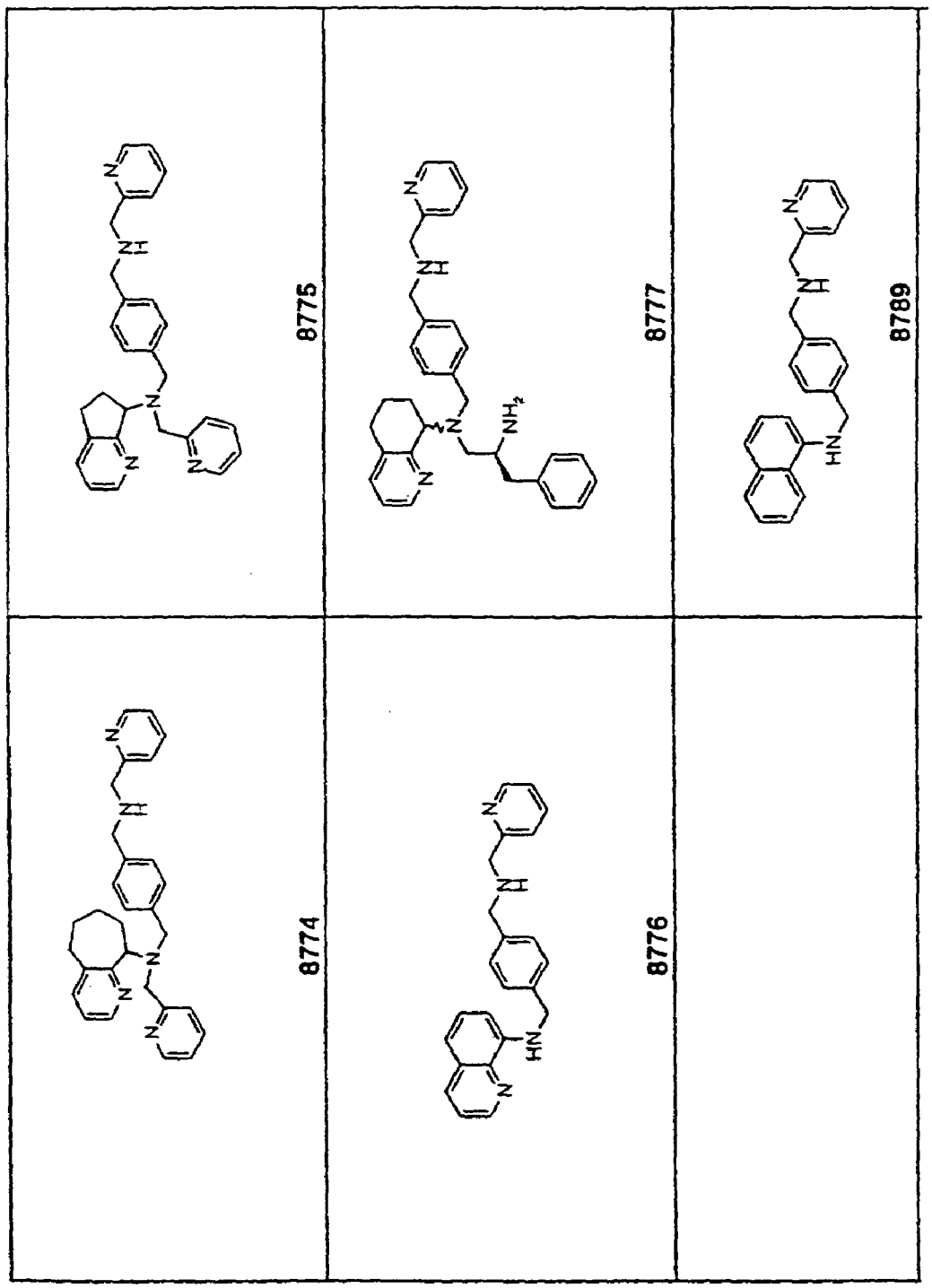
Figure 1:
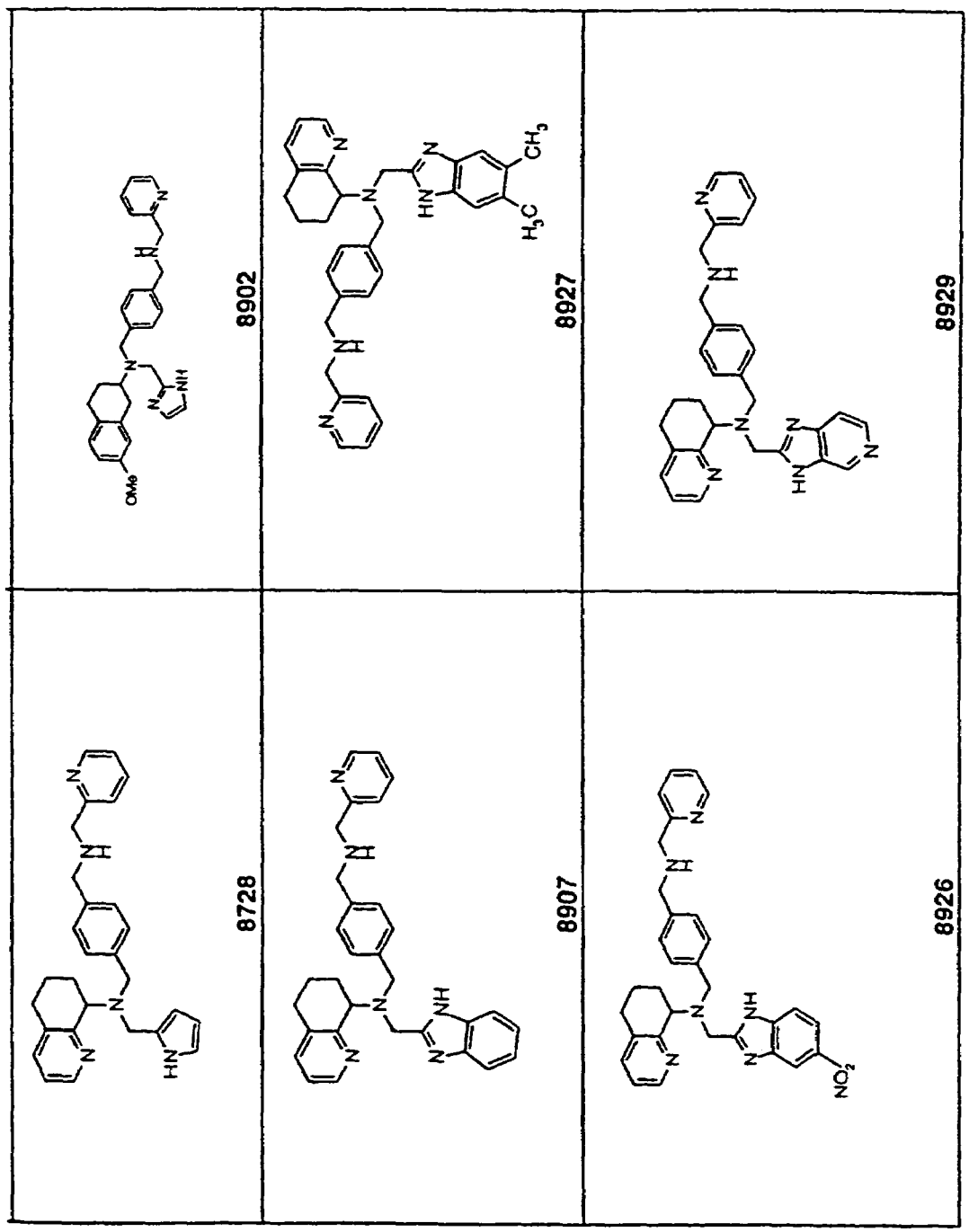

The present invention is directed to compounds of Formula 1 which can act as agents that modulate chemokine receptor activity. Such chemokine receptors includes but are not limited to CCR-1, CCR-2, CCR-3, CCR-4, CCR-5, CXCR-3, and CXCR-4.

In one embodiment, the present invention provides novel compounds of Formula I that demonstrates protective effects on target cells from HIV infection in a manner as to bind specifically to the chemokine receptor, which effect the binding of a natural ligand or chemokine to the receptor such as CCR-5 and/or CXCR-4 of a target cell.

In another embodiment, compounds of Formula 1 may be useful as agents which affect chemokine receptors, such as CCR-1, CCR-2, CCR-3, CCR-4, CCR-5, CXCR-3, CXCR-4 where such chemokine receptors have been correlated as being important mediators of many human inflammatory as well as immunoregulatory diseases.

Other diseases that are also implicated with chemokine as mediators include angiogenesis, and tumorigenesis such as brain, and breast tumors. Thus, a compound that modulates the activity of such chemokine receptors would be useful for the treatment or prevention of such diseases.

The term "modulators" as used herein is intended to encompass antagonist, agonist, partial antagonist, and or partial agonist, inhibitors, and activators. In the preferred embodiment of the present invention, compounds of Formula I demonstrates protective effect against HIV infection by inhibiting the binding of HIV to a chemokine receptor such as CCR-5 and/or CXCR-4, of a target cell, which comprises contacting the target cell with an amount of the compound which is effective at inhibiting the binding of the virus to the chemokine receptor.

Compounds that inhibits chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

Whereas compounds that activate or promote chemokine receptor function may be used for the treatment of diseases that are associated with immunosuppression such as individuals undergoing chemotherapy, radiation therapy, enhanced wound healing and bum treatment, therapy for autoimmune disease or other drug therapy (e.g., corticosteroid therapy) or combination of conventional drugs used in the treatment of autoimmune diseases and graft/transplantation rejection, which causes immunosuppression; immunosuppresion due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., *Toxocara*), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, Herpesvirus *saimiri*, and Kaposi's sarcoma herpesvirus, also known as human herpesvirus 8, and poxvirus *Moluscum contagiosum*.

It will be understood that that compounds of Formula 1 may be used in combination with any other pharmaceutical composition where such combined therapy may be useful to modulate chemokine receptor activity and thereby prevent and treat inflammatory and immunoregulatory diseases.

It is also contemplated that the present invention may be used in combinations with one or more agents useful in the prevention or treatment of HIV. Examples of such agents include:

(1) nucleotide reverse transcriptase inhibitor such as zidovudine, didanosine, lamivudine, zalcitabine, abacavir, stavudine, adefovir, adefovir dipivoxil, fozivudine todoxil, etc.;
(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, etc.; and
(3) protease inhibitors such as saquinavir, ritonavir, indinavir, nelfinavir, amprenavir, palinavir, lasinavir, etc.

It will be understood that the scope of combinations of compounds of Formula 1 of this invention with HIV agents is not limited to (1), (2), and or (3), but includes in principle any combination with any pharmaceutical composition useful for the treatment of HIV. Further, in such combinations the compounds of the present invention and other HIV agents may be administered separately or in conjunction. In addition, the administration of one element may be prior to, concurrent to, or subsequent to the administration of other agent(s).

The compounds of Formula 1 in the present invention may be administered by oral, parenteral (e.g., intramuscular, intraperitoneal, intravenous, intracisternal injection or infusion, subcatenous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The compounds of Formula 1 are all active and used to treat animals, including mice, rats, horses, cattle, sheep, dogs, casts, and monkey. The compounds of the invention are also effective for use in humans.

The compounds of Formula 1 of the present invention may form hydrates or solvates. Compounds of Formula 1 of the present invention can exist as any stereoisomeric forms and mixtures of stereoisomeric forms thereof where it is possible to isolate individual isomers with known separation and purification method, if desired. When the compound of the Formula 1 of the present invention is racemate, it can be separated into (S)-compound and (R)-compound with usual optical resolution and individual optical isomers and a mixture thereof are included in the scope of the of the present invention.

This invention also relates to a pharmaceutical composition comprising a pharmaceutically acceptable carrier or diluent and an effective amount of compound of Formula 1. A compound of Formula 1 may be administered alone or as an admixture with a pharmaceutically acceptable carrier (e.g. solid formulations such as tablets, capsules, granules, powders, etc.; liquid formulations such as syrups, injections, etc.) may be orally or non-orally administered. Examples of non-oral formulations include injection, drops, suppositories, pessaryies.

In the treatment or prevention of conditions which require chemokine receptor modulation an appropriate dosage level will generally be about 0.01 to 500 mg per kg patient body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

The present invention further provides novel compounds that bind chemokine receptors and interfer with the binding of the natural ligand thereto. The compounds of the present invention are useful as agents demonstrating protective effects on target cells from HIV infection. The compounds of the present invention are also useful as antagonists or agonists of chemokine receptors, which serve as agents capable of reconstituting the immune system by increasing the level of CD4$^+$ cells; as antagonist agents of apoptosis in immune cells, such as CD8$^+$ cells, and neuronal cells; as antagonist agents of migration of human bone marrow B lineage cells to stromal-derived factor 1, as well as other biological activities related to the ability of these compounds to inhibit the binding of chemokines to their receptors.

Accordingly, the present invention provides a compound of Formula I

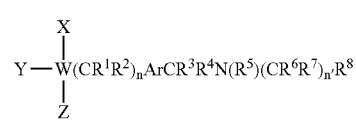

(I)

wherein, W is a nitrogen atom and Y is absent or, W is a carbon atom and Y=H;

$R^1$ to $R^7$ may be the same or different and are independently selected from hydrogen or straight, branched or cyclic $C_{1-6}$ alkyl;

$R^8$ is a substituted heterocyclic group or a substituted aromatic group

Ar is an aromatic or heteroaromatic ring each optionally substituted at single or multiple, non-linking positions with electron-donating or withdrawing groups;

n and n' are independently, 0–2;

X is a group of the formula:

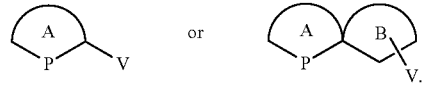

Wherein, Ring A is an optionally substituted, saturated or unsaturated 5 or 6-membered ring, and P is an optionally substituted carbon atom, an optionally substituted nitrogen atom, sulfur or oxygen atom. Ring B is an optionally substituted 5 to 7-membered ring. Ring A and Ring B in the above formula can be connected to the group W from any position via the group V, wherein V is a chemical bond, a $(CH_2)_{n''}$ group (where n''=0–2) or a C=O group. Z is, (1) a hydrogen atom, (2) an optionally substituted $C_{1-6}$ alkyl group, (3) a $C_{0-6}$ alkyl group substituted with an optionally substituted aromatic or heterocyclic group, (4) an optionally substituted $C_{0-6}$ alkylamino or $C_{3-7}$ cycloalkylamino group, (5) an optionally substituted carbonyl group or sulfonyl.

In the above Formula I, examples of the optionally substituted 5 or 6-membered ring A are benzene, pyridine, pyrimidine, pyrazine, pyridazine, triazine, piperidine, piperazine, imidazole, pyrazole, triazole, oxazole, thiazole. Six-membered rings are preferred for ring A, particularly benzene, pyridine and piperidine.

Examples of the optionally substituted ring B are benzene, 5 to 7-membered cycloalkyl rings (e.g. cyclopentyl, cyclohexyl, cycloheptyl, cyclopentenyl, cyclohexenyl, cycloheptenyl), furan, dihydrofuran, tetrahydrofuran, thiophene, dihydrothiophene, tetrahydrothiophene (thiolane), pyran, dihydropyran, tetrahydropyran, thiapyran, dihydrothiapyran, tetrahydrothiapyran (pentamethylene sulfide), oxepine, thiepin (and their corresponding saturated heterocycloalkanes) in addition to those listed above for ring A. Six-membered rings are also preferred for ring B, with the preferred combination of the rings A and B being, dihydronaphthalene, tetrahydronaphthalene, dihydroquinoline and tetrahydroquinoline.

In the above examples, the "optional substituents" in Rings A and B may be halogen, nitro, cyano, carboxylic acid, an optionally substituted alkyl, alkenyl or cycloalkyl groups, an optionally substituted hydroxyl group, an optionally substituted thiol group, an optionally substituted amino or acyl group, an optionally substituted carboxylate, carboxamide or sulfonamide group, an optionally substituted aromatic or heterocyclic group.

Examples of halogen include fluorine, chlorine, bromine, iodine, etc., with fluorine and chlorine preferred.

Examples of the optionally substituted alkyl include $C_{1-10}$ alkyl, including methyl, ethyl propyl etc., examples of the optionally substituted alkenyl groups include, $C_{2-10}$ alkenyl such as allyl, crotyl, 2-pentenyl, 3-hexenyl, etc., and examples of the optionally substituted cycloalkyl groups include $C_{3-10}$ cycloalkyl such as cyclopropyl, cyclobutyl, cyclopentyl, cyclohexyl, cycloheptyl, etc. In these cases, $C_{1-6}$ alkyl, alkenyl and cycloalkyl are preferred. The optional substituent may also be an optionally substituted aralkyl (e.g. phenyl$C_{1-4}$ alkyl) or heteroalkyl for example, phenylmethyl (benzyl), phenethyl, pyridinylmethy, pyridinylethyl etc. The heterocyclic group may be a 5 or 6 membered ring containing 1–4 heteroatoms.

Examples of the optionally substituted hydroxyl and thiol groups include an optionally substituted alkyl (e.g. $C_{1-10}$ alkyl) such as methyl, ethyl, propyl, isopropyl, butyl, isobutyl, sec-butyl, tert-butyl, pentyl etc., preferably ($C_{1-6}$)alkyl; an optionally substituted cycloalkyl (e.g. $C_{3-7}$ cycloalkyl, etc. such as cyclopropyl, cyclobutyl, cyclopentyl, cyclohexyl, cycloheptyl, etc.); an optionally substituted aralkyl (e.g. phenyl-$C_{1-4}$ alkyl, e.g. benzyl, phenethyl, etc.). Where there are two adjacent hydroxyl or thiol substituents, the heteroatoms may be connected via an alkyl group such as $O(CH_2)_nO$ and $S(CH_2)_nS$ (where n=1–5). Examples include methylenedioxy, ethylenedioxy etc. Oxides of thio-ether groups such as sulfoxides and sulfones are also encompassed.

Further examples of the optionally substituted hydroxyl group include an optionally substituted $C_{2-4}$ alkanoyl (e.g. acetyl, propionyl, butyryl, isobutyryl, etc.), $C_{1-4}$ alkylsufonyl (e.g. methanesulfonyl, ethanesulfonyl, etc.) and an optionally substituted aromatic and heterocyclic carboxyl group including benzoyl, pyridinecarboxyl, etc.

The substituents on the optionally substituted amino group may bind to each other to form a cyclic amino group (e.g. 5- to 6-membered cyclic amino, etc. such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.) the number of preferred substituents are 1 to 3.

The amino group may also be substituted once or twice (to form a secondary or tertiary amine) with a group such as an optionally substituted alkyl group including $C_{1-10}$ alkyl (e.g. methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g. phenyl$C_{1-4}$ alkyl) or heteroalkyl for example, phenyl, pyridine, phenylmethyl (benzyl), phenethyl, pyridinylmethyl, pyridinylethyl etc. The heterocyclic group may be a 5 or 6 membered ring containing 1–4 heteroatoms. The optional substituents of the "optionally substituted amino groups are the same as defined above for the "optionally substituted cyclic amino group."

The amino group may be substituted with an optionally substituted $C_{2-4}$ alkanoyl e.g. acetyl, propionyl, butyryl, isobutyryl etc., or a $C_{1-4}$ alkylsulfonyl (e.g. methanesulfonyl, ethanesulfonyl, etc.) or a carbonyl or sulfonyl substituted aromatic or heterocyclic ring, e.g. benzenesulfonyl, benzoyl, pyridinesulfonyl, pyridinecarbonyl etc. The heterocycles are as defined above.

Examples of the optionally substituted acyl group as the substituents on the rings A and B include a carbonyl group or a sulfonyl group binding to hydrogen; an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted alkenyl (e.g. $C_{2-10}$ alkenyl such as allyl, crotyl, 2-pentenyl, etc., preferably lower ($C_{2-6}$)alkenyl, etc.); an optionally substituted cycloalkenyl (e.g. $C_{3-7}$ cycloalkenyl, etc., such as 2-cyclopentenyl, 2-cyclohexenyl, 2-cyclopentenylmethyl, 2-cyclohexenylmethyl, etc.) an optionally substituted 5- to 6-membered monocyclic aromatic group (e.g. phenyl, pyridyl, etc.).

Examples of the optionally substituted carboxylate group (ester groups) include an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$)alkyl, etc.); an optionally substituted cycloalkyl (e.g. $C_{3-7}$ cycloalkyl, etc. such as cyclopropyl, cyclobutyl, cyclopentyl, cyclohexyl, cycloheptyl, etc.); an optionally substituted alkenyl (e.g. $C_{2-10}$ alkenyl such as allyl, crotyl, 2-pentenyl, 3-hexenyl, etc., preferably lower ($C_{2-6}$)alkenyl, etc.); an optionally substituted cycloalkenyl (e.g. $C_{3-7}$ cycloalkenyl, etc., such as 2-cyclohexenylmethyl, etc.); an optionally substituted aryl (e.g. phenyl, naphthyl, etc.) and $C_{1-4}$ aryl for example, benzyl, phenethyl etc. Groups such as methoxymethyl, methoxyethyl etc., are also encompassed.

Examples of the optionally substituted carboxamide and sulfonamide groups are identical in terms of the amine definition as the "optionally substituted amino group" defined above.

Examples of the optionally substituted aromatic or heterocyclic groups as substituents for Rings A and B are phenyl, naphthyl, or a 5- or 6-membered heterocyclic ring containing 1–4 heteroatoms. The optional substituents are essentially identical to those listed above for Rings A and B.

In the above examples the number of substituents on Rings A and B may be 1–4, preferably 1–2. The substituents on the optionally substituted groups are the same as the optionally substituted groups described above. Preferred substituents are halogen (fluorine, chlorine etc.), nitro, cyano, hydroxy group, thiol group, amino group, carboxyl group, carboxylate group, sulfonate group, sulfonamide group, carboxamide group, an optionally halogenated $C_{1-4}$ alkoxy (e.g. trifluoromethoxy, etc.), $C_{2-4}$ alkanoyl (e.g. acetyl, propionyl, etc.) or aroyl, a $C_{1-4}$ alkylsulfonyl (e.g. methanesulfonyl, ethanesulfonyl, etc.), an optionally substituted aryl or heterocyclic group. The number of substituents on the said groups are preferably 1 to 3.

In the above Formula I, Z may be (2) an optionally substituted $C_{1-6}$ alkyl group where the optional substituents are identical to those described for Rings A and B above.

In the above Formula I, Z may be (3) a $C_{0-6}$ alkyl group optionally substituted with an optionally substituted fused or unfused, aromatic or heterocyclic group. Examples of the optionally substituted aromatic groups include benzene and naphthalene, or dihydronaphthalene and tetrahydronaphthalene. Examples of optionally substituted heterocyclic groups include 5 to 6-membered saturated, partially saturated, or aromatic heterocyclic rings containing 1 to 4 heteroatoms selected from nitrogen, oxygen and sulfur. The heterocycles may be pyridine, quinoline, isoquinoline, imidazole, benzimidazole, azabenzimidazole, benzotriazole, furan, benzofuran, thiazole, benzothiazole, oxazole, benzoxazole, pyrrole, indole, indoline, indazole, pyrrolidine, pyrrolidone, pyrroline, piperidine, piperazine, tetrahydroquinoline, tetrahydroisoquinoline, pyrazole, thiophene, isoxazole, isothiazole, triazole, tetrazole, oxadiazole, thiadiazole, morpholine, thiamorpholine, pyrazolidine, imidazolidine, imidazoline, tetrahydropyran, dihydropyran, benzopyran, dioxane, dithiane, tetrahydrofuran, tetrahydrothiophene, dihydrofuran, dihydrothiophene etc. Oxides of the nitrogen and sulfur containing heterocycles are also included in the present invention. The optionally substituted aromatic and heterocyclic groups can be connected to the $C_{0-6}$ alkyl group via any position on the fused ring, or the aromatic or heterocyclic groups. For example, the aromatic group or heterocyclic group may be directly connected to the group W through a chemical bond to a carbon or nitrogen position, or connected via an alkyl group to a carbon or nitrogen position, or connected via an alkyl group to the nitrogen, oxygen or sulfur of an amino, hydroxyl or thiol substituent. The optional substituents for the fused or unfused aromatic or heterocyclic ring are identical to those described for Rings A and B above.

In the above Formula I, Z may be (4) an optionally substituted $C_{0-6}$ alkyl or $C_{3-7}$ cycloalkyl amino group. Examples of the optionally substituted $C_{0-6}$ alkyl amino groups include straight or branched chains including methylamino, ethylamino, propylamino, isopropylamino, butylamino, isobutylamino etc. Encompassed in the present invention are also optionally substituted $C_{3-7}$ cycloalkyl amino groups such as cyclopropylamino, cyclobutylamino, cyclopentylamino, cyclohexylamino etc. The amino group may be substituted with an optionally substituted $C_{1-6}$ alkyl group, a $C_{0-6}$ alkyl group substituted with an optionally substituted, fused or unfused aromatic group or heterocyclic group. The aromatic groups and heterocyclic groups are defined in (3) above. The amino group may be substituted once or twice (to form a secondary or tertiary amine) with the groups described above and may be identical or non-identical. The amino group may also be the nitrogen atom of a guanidine, carbamate or urea group. The optional substituents are identical to those described above for Rings A and B.

In the above Formula I, Z may be (5) an optionally substituted carbonyl or sulfonyl group. For example, the carbonyl or sulfonyl group may be substituted with an optionally substituted straight, cyclic or branched alkyl groups, e.g. a $C_{1-7}$ alkyl group such as acetyl, propionyl, cyclopropanoyl, cyclobutanoyl, isopropanoyl, isobutanoyl etc. or methanesulfonyl, ethanesulfonyl etc. or an optionally substituted aromatic or heterocyclic carbonyl or sulfonyl group such as benzoyl, pyridinecarbonyl, benzenesulfonyl etc. The aromatic and heterocyclic groups are the same as defined for (3) above. The optionally substituted carbonyl or sulfonyl group may also be an optionally substituted $C_{1-6}$ alkyl aromatic or heterocyclic group such as defined in (3) above, exemplified by phenylacetyl, phenylpropanoyl, pyridineacetyl, pyridinepropanoyl, phenylmethanesulfonyl etc., or the carbonyl of an optionally substituted amino acid derivative. The carbonyl may also be the carbonyl group of a urea or carbamate in which an optionally substituted $C_{1-6}$ alkyl or $C_{1-6}$ alkyl group optionally substituted with an aromatic or heterocyclic group (as defined in (3) above) is connected to nitrogen or oxygen, respectively. The optional substituents are identical to those described above for Rings A and B.

The invention also provides a compound of Formula I

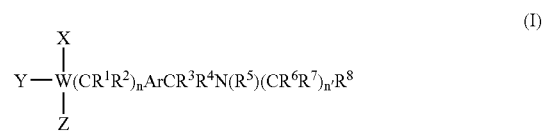

(I)

In which, W, Y, n, n', Ar, $R^1$–$R^8$ are defined as above,

X and Z are independently selected from H, optionally substituted $C_{1-6}$ alkyl or $C_{0-6}$ alkaryl or $C_{0-6}$ alkylheterocyclyl groups. The X and Z groups may also bind each other to form an optionally substituted 5- to 7-membered cyclic amine group such as tetrahydropyrrole, pyrrolidine, piperazine, homopiperazine, piperidine, morpholine, thiomorpholine, pyrrole, imidazole etc., or an optionally substituted pyran, thiopyran or cycloalkyl ring etc.

The optional substituents are defined as above.

The novel compounds of the present invention may be formulated as pharmaceutical compositions that may be administered topically; percutaneously, including intravenously; orally; and by other standard routes of pharmaceutical administration to mammalian subjects as determined according to routine clinical practice. The compounds of the present invention are useful as agents demonstrating protective effects on target cells from HIV infection (Blanco et al., *Antimicrob. Agts. and Chemother*. 44: 51–56, 2000). The compounds of the present invention are may serve to interfere with the binding of natural ligands to chemokine receptors on a wide range of cell populations, including chemokine receptors CXCR4 and CCR5 as well as other chemokine receptors of the C-X-C and C-C motifs. The compounds of the present invention are considered further useful as antagonists or agonists of such chemokine receptors. Such chemokine antagonist agents capable of interfering in the chemokine binding to its respective chemokine receptor would be useful to reconstitute the immune system by increasing the level of CD4+ cells (Biard-Piechaczyk, et al., *Immunol. Lett.*, 70: 1–3 1999); as antagonist agents of apoptosis in immune cells, such as CD8+ cells (Herbin, et al., *Nature* 395: 189–193, 1998), and as antagonist agents of apoptosis in neuronal cells (Ohagen et al., *J. of Virol.*, 73: 897–906, 1999; and Hesselgesser, et al., *Curr. Biol.* 8: 595–598, 1998). Chemokine receptor antagonist agents would be useful to inhibit the migration of human bone marrow B lineage cells to stromal-derived factor 1 (See, for example: E. Fedyk, et al., *J. of Leukocyte Biol.*, 66:667–673, 1999), as well as other biological activities related to the ability of these compounds to inhibit the binding of chemokines to their respective receptors.

Anti-HIV Assays.

Compounds were tested for their ability to inhibit HIV-1 replication in MT-4 cells or PBMC's (peripheral blood mononucleocytes) using published procedures (for example, see: Labrosse et al. *J. Virol.* 1998, 6381–6388; Simmons et al. *J. Virol.* 1998, 8453–8457; Donzella et al. *Nature Medicine* 1998, 72–77; Schols et al. *J. Exp. Med.* 1997, 1383–1388; De Clercq et al. *Antiviral Res.* 1997, 147–156; and Bridger et al. U.S. patent application Ser. No. 09/111,895). In addition to the above references, experimental methods for performing anti-viral assays can also be found in: Bridger et al. *J. Med. Chem.* 1995, 38, 366–378; Bridger et al. *J. Med. Chem.* 1996, 39, 109–119; Bridger et al. U.S. Pat. No. 5,698,546; Bridger et al. U.S. Pat. No. 5,583,131; Bridger et al. U.S. Pat. No. 5,817,807; De Clercq et al. *Antimicrob. Agents and Chemother.* 1994, 38, 668–674.

These assays were considered representative of inhibition via binding to the chemokine receptors CXCR4 and CCR5 respectively due to prior inhibition studies and the following inherent properties of the cells and viruses:

1. The HIV-1 strains NL4.3 and III$_B$ are T-tropic strains that exclusively use CXCR4 as the co-receptor for entry into cells. MT-4 Cells express CXCR4 but not CCR5.

The HIV-1 strain BaL is M-tropic (macrophage tropic) strain that exclusively uses CCR5 as a co-receptor for entry into cells. PBMC's (from healthy donors) express all chemokine receptors including CXCR4 and CCR5.

Prior mechanistic studies that characterize the direct interaction of 1,1'-[1,4-phenylenebis(methylene)]bis-1,4,8,11-tetraazacyclotetradecane octahydrochloride dihydrate (described in U.S. Pat. No. 5,583,131) and related compounds with the chemokine receptors CXCR4 and CCR5 can be found in references as cited supra.

Preparation of Starting Materials and General Procedures.

AMD7088: Preparation of N-(2-nitrobenzenesulfonyl)-N,N'-bis(2-pyridinylmethyl)-1,4-benzene-dimethanamine 2-Aminomethylpyridine (34.76g, 315 mmol) and terephthaldicarboxaldehyde (20.32 g, 150 mmol) were refluxed in benzene (500 mL) in a Dean Stark apparatus, overnight. The benzene was removed in vacuo and the bis-imine residue was taken up in dry methanol (250 mL) and transferred to a Parr bottle. To the solution was added 10% palladium on carbon (7.63 g) and the mixture was hydrogenated at 30 psi hydrogen, for 20 hours. The product mixture was filtered through celite and concentrated in vacuo to give an orange oil (47.62 g, 100%). Without further purification, the orange oil (46.8 g, 147 mmol) was dissolved in dry dichloromethane (1300 mL) and triethylamine (20.3 g, 199 mmol). 2-Nitrobenzenesulfonyl chloride (30.3g, 132 mmol) was added in one portion to the stirred solution, and after one hour, the mixture was washed with water and brine, dried over MgSO$_4$ and concentrated to an olive-brown oil (79.09 g). The product was purified by column chromatography on silica gel (4% MeOH in CH$_2$Cl$_2$) to give AMD7088 (16.02 g): $^1$H NMR (300 MHz, CDCl$_3$) δ 8.55 (d, 1H, J=5 Hz), 8.38 (d, 1H, J=5 Hz), 7.95 (d, 1H, J=9 Hz), 7.45–7.70 (m, 5H), 7.05–7.30 (m, 8H), 4.58 (s, 4H), 3.88 (s, 2H), 3.77 (s, 2H); $^{13}$C NMR (75.5 MHz, CDCl$_3$) δ 159.9, 156.4, 149.7, 149.6, 148.6, 140.2, 137.0, 136.9, 134.3, 134.2, 133.7, 132.0, 131.4 (2C), 129.1 (2C), 128.9, 124.6, 122.8 (2C), 122.7, 122.4, 54.8, 53.4, 52.6, 51.9. ES-MS m/z 504.2 (M+H). Anal Calcd for (C$_{26}$H$_{24}$N$_5$O$_4$S) 0.7(H$_2$O): C, 60.62; H, 4.97; N, 13.59. Found: C, 60.73; H, 4.99; N, 13.49.

AMD7090: Preparation of N-(2-nitrobenzenesulfonyl)-N,N'-bis(2-pyridinylmethyl)-1,3-benzene-dimethanamine In a similar manner, 2-pyridinecarboxaldehyde (32.46 g, 0.30 mol) and m-xylenediamine (20.64g, 0.15 mol) were stirred in dry methanol (500 mL) at 30° C. $^1$H NMR indicated consumption of the starting aldehyde after 1 hour. The mixture was then concentrated to approximately half volume, treated with 10% Pd on carbon (5.0 g), and the mixture was hydrogenated at 30 psi hydrogen, overnight. The reaction mixture was filtered through celite, concentrated in vacuo, and the residue dissolved in dry dichloromethane. To this solution was added triethylamine (15.33 g, 150 mmol) followed by a solution of 2-nitrobenzenesulfonyl chloride (30.84 g, 135 mmol) in dry dichloromethane (200 mL) dropwise with vigorous stirring. The reaction was allowed to stir overnight at room temperature and the solution was then washed with water (2×500 mL) and brine (1000 mL), dried (MgSO$_4$), and concentrated to give a red-brown oil (73.64g). The product was purified by column chromatography on silica gel (4% MeOH in CH$_2$Cl$_2$) to give AMD7090 (31.34 g, 46% overall yield). $^1$H NMR (300 MHz, CDCl$_3$) δ 8.55 (d, 1H, J=5 Hz), 8.38 (d, 1H, J=5 Hz), 7.94 (d, 1H, J=9 Hz), 7.45–7.70 (m, 5H), 7.05–7.30 (m, 8H), 4.60 (s, 4H), 3.85 (s, 2H), 3.71 (s, 2H); $^{13}$C NMR (75.5 MHz, CDCl$_3$) δ 159.8, 156.3, 149.7, 149.6, 148.3, 140.8, 137.0, 136.9, 135.6, 134.5, 133.7, 132.0, 131.4, 129.1, 128.8, 128.3, 127.7, 124.5, 122.9, 122.8, 122.7, 122.4, 54.8, 53.5, 52.7, 52.1. ES-MS m/z 504.2 (M+H). Anal Calcd for (C$_{26}$H$_{24}$N$_5$O$_4$S) 0.7(H$_2$O): C, 60.62; H, 4.97; N, 13.59. Found: C, 60.58; H, 5.00; N, 13.44.

AMD7089: Preparation of N-(2-nitrobenzenesulfonyl)-N-(2-pyridinylmethyl)-N'-[2-(2-pyridinyl)ethyl]-1,4-benzenedimethanamine To a stirred solution of N-[1-Methylene-4-(hydroxymethylene)phenylene]-N-(2-nitrobenzenesulfonyl)-2-(aminomethyl)pyridine (see Bridger et al. U.S. patent application Ser. No. 09/111,895) (30.0g, 72.5 mmol) in dichloromethane (300 mL) was added manganese oxide (63.0 g, 725 mmol, 10 Equiv.) and the reaction mixture was allowed to stir overnight at room temperature. The mixture was filtered through celite, and concentrated to give 30.1 g (100%) of the desired aldehyde as a light yellow solid. Without further purification, the aldehyde (72.5 mmol) was dissolved in methanol (500 mL) and to this solution was added 2-(2-aminoethyl)-pyridine (10.63 g, 87 mmol) and the mixture was heated to 40° C. with stirring until the starting aldehyde was consumed by $^1$H NMR analysis. The solution was cooled to room temperature and sodium cyanoborohydride (9.62 g, 145 mmol) was added in one portion. The reaction mixture was stirred for one hour, quenched with 0.1N sodium hydroxide (500 mL) and the methanol was then evaporated in vacuo. The aqueous solution was extracted with ethyl acetate (3×500 mL) and the combined organic extracts were washed with water and brine, dried (MgSO$_4$) and concentrated to give 36.12 grams of crude product. The product was purified by column chromatography on silica gel (4% MeOH in CH$_2$Cl$_2$) to give AMD7089 (16.32 g, 43% overall yield) as a yellow oil. $^1$H NMR (300 MHz, CDCl$_3$) δ 8.55 (d, 1H, J=5 Hz), 8.38 (d, 1H, J=5 Hz), 7.94 (d, 1H, J=9 Hz), 7.45–7.70 (m, 5H), 7.00–7.20 (m, 8H), 4.57 (s, 4H), 3.79 (s, 2H), 3.02 (s, 4H); $^{13}$C NMR (75.5 MHz, CDCl$_3$) δ 160.2, 156.2, 149.6, 149.5, 148.3, 138.2, 137.1, 137.0, 134.9, 134.5, 133.7, 132.0, 131.4, 139.3 (2C), 129.1 (2C), 124.6, 123.8, 122.9, 122.8, 122.0, 53.1, 52.7, 51.9, 48.5, 36.9. ES-MS m/z 518.3 (M+H). Anal Calcd for (C$_{27}$H$_{26}$N$_5$O$_4$S) 0.6(H$_2$O): C, 61.49; H, 5.20; N, 13.28. Found: C, 61.44; H, 5.25; N, 13.32.

AMD7091: Preparation of N-(2-nitrobenzenesulfonyl)-N-(2-pyridinylmethyl)-N-[2-(2-pyridinyl)ethyl]-1,3-benzenedimethanamine AMD7091 (the meta-analog of AMD7089) was prepared in a similar manner. Thus, the corresponding meta-alcohol gave AMD7091 (21.6 g, 26% overall yield): $^1$H NMR (300 MHz, CDCl$_3$) δ 8.55 (d, 1H, J=5 Hz), 8.38 (d, 1H, J=5 Hz), 7.94 (d, 1H, J=9 Hz), 7.45–7.70 (m, 5H), 7.00–7.20 (m, 8H), 4.57 (s, 4H), 3.69 (s, 2H), 3.42 (s, 2H), 2.97(s, 2H); $^{13}$C NMR (75.5 MHz, CDCl$_3$) δ 160.5, 156.3, 149.6, 149.5, 148.3, 140.8, 137.0, 136.9, 135.6, 134.4, 133.7, 132.0, 131.3, 129.0, 128.7, 128.1, 127.6, 124.5, 123.7, 122.8, 122.7, 121.7, 53.8, 52.8, 52.2, 49.1, 38.5. ES-MS m/z 519.1 (M+H). Anal Calcd for (C$_{27}$H$_{26}$N$_5$O$_4$S) 0.4(H$_2$O): C, 61.79; H, 5.34; N, 13.34. Found: C, 61.79; H, 5.39; N, 13.10.

AMD7474: Preparation of 8-hydroxy-5,6,7,8-tetrahydroquinoline

To a stirred solution of 5,6,7,8-tetrahydroquinoline (74.3 g, 0.558 mol) in glacial acetic acid (275 mL) at room temperature was added 30% H$_2$O$_2$ (55 mL) and the solution was heated to 70° C. After 6 hours, the reaction mixture was cooled to room temperature, additional H$_2$O$_2$ (55 mL) was added, and the solution was heated at 70° C. overnight. The reaction mixture was cooled to room temperature and concentrated under reduced pressure. The residue was dissolved in CHCl$_3$ (300 mL) and treated with solid Na$_2$CO$_3$ (175 g). After 1 hour, the supernatant was decanted and the residue was washed with warm CHCl$_3$ (3×300 mL). The combined supernatants were filtered and concentrated to provide 121 g of a yellow oil. The oil was dissolved in acetic anhydride (400 mL) and heated at 90° C. overnight. The mixture was cooled to room temperature and concentrated. Distillation (Kugelrohr, bp 110–140° C. @ 1 Torr) of the resultant oil provided 99.2 g of 8-acetoxy-5,6,7,8-tetrahydroquinoline.

To a solution of 8-acetoxy-5,6,7,8-tetrahydroquinoline (99.2 g) in methanol (450 mL) was added K$_2$CO$_3$ (144 g, 1.04 mol) and the mixture was stirred at room temperature overnight. The mixture was poured into water (500 mL) and extracted with CHCl$_3$ (3×500 mL) and the combined organic extracts were dried (Na$_2$SO$_4$), and concentrated to provide 71.6 g of 8-hydroxy-5,6,7,8-tetrahydroquinoline as a brown oil. A purified sample (silica gel, 25:1 CH$_2$Cl$_2$-CH$_3$OH) exhibited the following spectral properties: $^1$H NMR (CDCl$_3$) δ 1.75–1.89 (m, 2H), 1.96–2.06 (m, 1H), 2.25–2.33 (m, 1H), 2.74–2.90 (m, 2H), 4.23 (br s, 1H, OH), 4.72 (dd, 1H J=7.8, 6.3 Hz), 7.12 (dd, 1H, J=7.5, 4.8 Hz), 7.41 (d, 1H, J=7.5 Hz), 8.41 (d, 1H, J=4.8 Hz); $^{13}$C NMR (CDCl$_3$) δ 19.60, 28.84, 31.27, 68.87, 122.74, 132.19, 137.40, 147.06, 158.50. ES-MS m/z 150 (M+H).

In a similar manner:

Cyclopentenopyridine gave 7-hydroxy-6,7-dihydro-5H-cyclopenta[b]pyridine (AMD 7473). $^1$H NMR (CDCl$_3$) δ 2.01–2.13 (m, 1H), 2.50–2.61(m, 1H), 2.78–2.89 (m, 1H), 3.06 (ddd, 1H, J=15.9, 9.0, 4.2 Hz), 4.85 (br s, 1H, OH), 5.25 (t, 1H J=6.9 Hz), 7.15 (dd, 1H, J=7.5, 4.8 Hz), 7.57 (d, 1H, J=7.5 Hz), 8.43 (d, 1H, J=4.8 Hz); $^{13}$C NMR (CDCl$_3$) δ 27.90, 33.17, 74.46, 123.07, 133.86, 136.97, 148.05, 165.50. ES-MS m/z 136 (M+H).

Cycloheptenopyridine gave 9-hydroxy-6,7,8,9-tetrahydro-5H-cyclohepta[b]pyridine (AMD7475). $^1$H NMR (CDCl$_3$) δ 1.17–1.30 (m, 1H), 1.34–1.48 (m, 1H), 1.81–2.11 (m, 3H), 2.23 (br d, 1H, J=13.5 Hz), 2.72–2.76 (m, 2H), 4.76 (d, 1H, J=11.1 Hz), 5.94 (s, 1H, OH), 7.12 (dd, 1H, J=7.2, 4.8 Hz), 7.44 (d, 1H, J=7.2 Hz), 8.36 (d, 1H, J=4.8 Hz); $^{13}$C NMR (CDCl$_3$) δ 27.44, 29.41, 34.71, 36.72, 72.57, 122.45, 136.05, 137.56, 144.75, 161.38. ES-MS m/z 164 (M+H).

AMD7488: Preparation of 8-amino-5,6,7,8-tetrahydroquinoline

To a stirred solution of 8-hydroxy-5,6,7,8-tetrahydroquinoline (71.6 g, 0.480 mol) in CH$_2$Cl$_2$ (500 mL, 1.0 M) at room temperature was added triethylamine (126 mL, 0.904 mol) followed by methanesulfonyl chloride (55 mL, 0.711 mol). The resulting mixture was heated to 40° C. overnight then cooled to room temperature. The mixture was poured into water (350 mL), diluted with CH$_2$Cl$_2$ (350 mL), and the phases were separated. The organic phase was washed with brine (2×250 mL), dried (Na$_2$SO$_4$), and concentrated. The resultant oil was dissolved in DMF (570 mL), treated with sodium azide (63.1 g, 0.971 mol), and heated at 70° C. overnight. The mixture was cooled to room temperature, then evaporated and the residual slurry was poured into brine (500 mL) and extracted with ether (4×500 mL). The combined organic extracts were washed with brine (2×100 mL), dried (Na$_2$SO$_4$), and concentrated. The crude material was filtered through a short plug of silica gel (CH$_2$Cl$_2$) to provide 41.0 g (46% from 5,6,7,8-tetrahydroquinoline) of 8-azido-5,6,7,8-tetrahydroquinoline as a red oil.

To a solution of the azide (41.0 g, 0.256 mol) in methanol (250 mL) was added Pd/C (10%, 4.1 g) and the mixture was hydrogenated at 30 psi on a Parr shaker. The mixture was filtered through celite and the cake was washed with methanol. The combined filtrates were evaporated and the residual oil was distilled (Kugelrohr, bp 115–140° C. @ 0.2 Torr) to provide 26.8 g (71%) of 8-amino-5,6,7,8-tetrahydroquinoline (AMD7488) as a pale yellow oil. $^1$H NMR (MeOH-d$_4$) δ 1.81–1.98 (m, 2H), 2.03–2.15 (m, 1H), 2.38–2.46 (m, 1H), 2.88–2.92 (m, 2H), 4.41 (dd, 1H, J=9.3, 6.3 Hz), 7.30 (dd, 1H, J=7.5, 4.5 Hz), 7.62 (d, 1H, J=7.5 Hz), 8.47 (d, 1H, J=4.5 Hz); $^{13}$C NMR (MeOH-d$_4$) δ 21.12, 28.72, 28.89, 52.28, 124.86, 134.35, 138.96, 148.49, 152.57. ES-MS m/z 149 (M+H).

In a similar manner:

7-hydroxy-6,7-dihydro-5H-cyclopenta[b]pyridine gave 7-amino-6,7-dihydro-5H-cyclopenta[b]pyridine. $^1$H NMR (CDCl$_3$) δ 1.72–1.82 (m, 3H), 2.54–2.59 (m, 1H), 2.79–2.94 (m, 2H), 4.33 (dd, 1H, J=9.0, 9.0 Hz), 7.09 (dd, 1H, J=7.5, 4.8 Hz), 7.52 (d, 1H, J=7.5 Hz), 8.41 (d, 1H, J=4.8 Hz).

9-hydroxy-6,7,8,9-tetrahydro-5H-cyclohepta[b]pyridine gave 9-amino-6,7,8,9-tetrahydro-5H-cyclohepta[b]pyridine. $^1$H NMR (MeOH-d$_4$) δ 1.24–1.36 (m, 1H), 1.56–1.68 (m, 1H), 1.89–2.17 (m, 4H), 2.85–2.89 (m, 2H), 4.63 (d, 1H, J=11.4 Hz), 7.26 (dd, 1H, J=7.5, 4.5 Hz), 7.64 (d, 1H, J=7.5 Hz), 8.41 (br d, 1H, J=4.5 Hz). $^{13}$C NMR (MeOH-d$_4$) δ 27.81, 30.45, 33.18, 34.57, 55.97, 124.43, 137.80, 138.90, 147.03, 157.34. ES-MS m/z 163 (M+H).

AMD8760: Preparation of N-(2-nitrobenzenesulfonyl)-N-(2-pyridinylmethyl)-N'-(5,6,7,8-tetrahydro-8-quinolinyl)-1,4-benzenedimethanamine General Procedure A: Direct Reductive Amination with NaBH$_3$CN To a stirred solution of the amine (1 equivalent) in anhydrous methanol (concentration ~0.1 M), at room temperature, was added the carbonyl compound (~1-2 equivalents) in one portion. Once the carbonyl had dissolved (~5 minutes), NaBH$_3$CN (~2–4 equiv.) was added in one portion and the resultant solution was stirred at room temperature. The solvent was removed under reduced pressure and CH$_2$Cl$_2$ (20 mL/mmol of amine) and brine or 1.0 M aqueous NaOH (10 mL/mmol amine) were added to the residue. The phases were separated and the aqueous phase was extracted with CH$_2$Cl$_2$ (3×10 mL/mmol amine). The combined organic phases were dried (Na$_2$SO$_4$) and concentrated. The crude material was purified chromatography.

Using General Procedure A:

Reaction of N-[1-methylene-4-(carboxaldehyde)phenylene]-N-(2-nitrobenzenesulfonyl)-2-(aminomethyl)pyridine (21.2 g, 51 mmol) with 8-amino-5,6,7,8-tetrahydroquinoline (7.61 g, 51 mmol) followed by column chromatography on silica gel (5% MeOH/CH$_2$Cl$_2$) gave the title compound (11.0 g, 40%) as an orange oil. $^1$H NMR (CDCl$_3$) δ 1.74–1.84 (m, 2H), 1.99–2.05 (m, 1H), 2.02–2.05 (m, 1H), 2.72–2.86 (m, 2H), 3.13 (br s, 1H), 3.79–3.94 (m, 3H), 4.57 (s, 2H), 4.60 (s, 2H), 7.07–7.11 (m, 4H), 7.20–7.24 (m, 3H), 7.37 (d, 1,H, J=7.4 Hz), 7.53, (t, 2H, J=8.4 Hz) 7.64 (br s, 2H), 7.94 (d, 1H, J=7.8 Hz), 8.40 (t, 2H, J=5.9 Hz); $^{13}$C NMR (CDCl$_3$) δ 19.70, 28.61, 28.85, 51.43, 51.54, 52.37, 57.56, 122.26, 122.78, 122.82, 124.55, 128.91 (2), 129.12 (2), 131.39, 131.98, 132.87, 133.65, 133.98, 134.60, 136.98, 137.28, 140.87, 147.20, 148.30, 149.60, 156.34, 157.77. ES-MS m/z 544 (M+H). Anal. Calcd. for C$_{29}$H$_{29}$N$_5$O$_4$S.0.1CH$_2$Cl$_2$: C, 63.30; H, 5.33; N, 12.68. Found: C, 63.53; H, 5.35, N, 12.58.

Resolution of N-(2-nitrobenzenesulfonyl)-N-(2-pyridinylmethyl)-N'-(5 6,7,8-tetrahydro-8quinolinyl)-1,4-benzenedimethanamine.

To a stirred solution of N-(2-nitrobenzenesulfonyl)-N-(2-pyridinylmethyl)-N'-(5,6,7,8-tetrahydro-8-quinolinyl)-1,4-benzenedimethanamine (1.641 g, 3.02 mmol) in CH$_2$Cl$_2$ (10 mL) was added (S)-(−)-1-phenylethyl isocyanate (0.50 mL, 3.57 mmol) and the mixture stirred at room temperature for 2 hours. The reaction mixture was poured into brine (40 mL) and diluted with CH$_2$Cl$_2$ (15 mL). The phases were separated and the aqueous phase was extracted with CH$_2$Cl$_2$ (4×15 mL). The combined organic extracts were dried (Na$_2$SO$_4$), filtered and concentrated under reduced pressure. Purification and separation of the resulting mixture of diastereomeric ureas by column chromatography on silica gel (CH$_2$Cl$_2$/i-PrOH, 97.5/2.5) afforded a low polarity diastereomer (0.790 g, 38%) and a high polarity diastereomer (0.740 g, 35%), both as orange foams.

$^1$H NMR (CDCl$_3$): low polarity diastereomer: δ 1.31 (d, 3H, J=6 Hz), 1.82–1.90 (m, 2H), 1.94–1.99 (m, 1H), 2.18–2.22 (m, 1H), 2.73 (br s, 2H), 4.15 (d, 1H, J=18 Hz), 4.31 (d, 1H, J=18 Hz), 4.55 (s, 2H), 4.58 (s, 2H), 4.98–5.03 (m, 2H), 5.49–5.52 (br m, 1H), 7.03–7.31 (m, 12H), 7.34 (d, 1H, J=6.9 Hz), 7.50–7.60 (m, 2H), 7.62–7.68 (m, 2H), 7.99 (d, 1H, J=7.5 Hz), 8.41 (br s, 2H).

$^1$H NMR (CDCl$_3$): high polarity diastereomer: δ 1.32 (d, 3H, J=6 Hz), 1.76–1.83 (m, 2H), 1.93–1.98 (m, 1H), 2.14–2.19 (m, 1H), 2.72 (br s, 2H), 4.08 (d, 1H, J=18 Hz), 4.33 (d, 1H, J=18 Hz), 4.54 (s, 2H), 4.59 (s, 2H), 4.97–5.01 (m, 2H), 5.54–5.59 (br m, 1H), 7.05–7.28 (m, 12H), 7.35 (d, 1H, J=7.8 Hz), 7.49–7.57 (m, 2H), 7.62–7.68 (m, 2H), 7.98 (d, 1H, J=7.5 Hz), 8.41 (d, 1H, J=4.2 Hz), 8.45 (d, 1H, J=4.8 Hz).

The diastereomeric purity of the urea's was determined by reversed phase HPLC using the following conditions: Instrument: Hewlett Packard 1100 HPLC (VWD2); Column: Zorbax SB, C8, 3.5 μm (100 A), 150 mm×3.0 mm; Mobile Phases: A: H$_2$O, B: MeCN; Gradient: 50% B (0 min), 80% B (20 min), 50% B (21 min); Total Run Time: 40 min; Flow Rate: 0.350 mL/min; Temperature: 40° C.; Detector: UV @ 254 nm; Injection volume: 5 μL.

Retention time of the low polarity diastereomer=13.8 min (100% de).

Retention time of the high polarity diastereomer=13.2 min (100% de).

Acid Hydrolysis of the Diastereomerically Pure Urea Derivatives.

A stirred solution of the low polarity diastereomer (0.600 g, 0.867 mmol) in EtOH/concentrated HCl (6:1, 28 mL) was heated to reflux until the starting material had been consumed by TLC (24.5 hours). The mixture was cooled to room temperature, concentrated under reduced pressure and partitioned between CH$_2$Cl$_2$ (25 mL) and 1 N NaOH (40 mL). The aqueous phase was washed with CH$_2$Cl$_2$ (2×25 mL) and the combined organic layers were dried (Na$_2$SO$_4$), filtered and concentrated in vacuo.

To a solution of the resultant crude product from above (3 mg) in CH$_2$Cl$_2$ (1 mL) was added (S)-(−)-1-phenylethyl isocyanate (5 μL, 0.036 mmol) and the mixture was stirred overnight (16 hours). The reaction was concentrated and the crude urea was analyzed by HPLC using the conditions described above to give a diastereomeric ratio of 17.6:1 (5.4% racemization had occurred during hydrolysis of the urea).

The remainder of the crude product from above was purified by column chromatography on silica gel (CH$_2$Cl$_2$/MeOH, 96:4 to 9:1) to afford an enantiomerically enriched sample of N-(2-nitrobenzenesulfonyl)-N-(2-pyridinylmethyl)-N'-(5,6,7,8-tetrahydro-8-quinolinyl)-1,4-benzenedimethanamine (0.286 g, 61% yield, 89% ee) as a pale yellow foam. $^1$H NMR (CDCl$_3$) δ 1.59 (br s, 1H), 1.72–1.81 (m, 2H), 2.00–2.05 (m, 1H), 2.16–2.20 (m, 1H), 2.76–2.86 (m, 2H), 3.79–3.83 (m, 1H), 3.81 (d, 1H, J=12 Hz), 3.93 (d, 1H, J=15 Hz), 4.57 (s, 2H), 4.60 (s, 2H), 7.07–7.11 (m, 4H), 7.20–7.24 (m, 3H), 7.37 (d, 1H, J=7.4 Hz), 7.51–7.57 (m, 2H), 7.61–7.67 (m, 2H), 7.94 (d, 1H, J=7.8 Hz), 8.40 (br t, 2H, J=5.9 Hz).

Similarly, a stirred solution of the higher polarity diastereomer (0.400 g, 0.578 mmol) in EtOH/concentrated HCl (6:1, 28 mL) was heated to reflux until the starting material had been consumed by TLC (24.5 hours). The reaction was worked-up and a small sample was reacted with (S)-(−)-1- phenylethyl isocyanate as described above. Analysis of the crude urea by HPLC gave a diastereomeric ratio of 12.6:1 (7.4% racemization had occurred during hydrolysis of the urea). The remainder of the crude product was purified by column chromatography on silica gel ($CH_2Cl_2$/MeOH, 96:4 to 9:1) to afford an enantiomerically enriched sample of N-(2-nitrobenzenesulfonyl)-N-(2-pyridinylmethyl)-N'-(5,6,7,8-tetrahydro-8-quinolinyl)-1,4-benzenedimethanamine (0.241 g, 77% yield, 85% ee) as a pale yellow foam.

AMD8812: Preparation of N-(2-nitrobenzenesulfonyl)-N-(2-pyridinylmethyl)-N'-(6,7,8,9-tetrahydro-5H-cyclohepta[b]pyridin-9-yl)-1,4-benzenedimethanamine Using General Procedure A:

Reaction of the aldehyde from above (26.9 g, 66 mmol) with 9-amino-6,7,8,9-tetrahydro-5H-cyclohepta[b]pyridine (10.6 g, 66 mmol) followed by column chromatography on silica gel (5% MeOH/EtOAc) gave the title compound (16.9 g, 46%) as a white foam. $^1$H NMR ($CDCl_3$) δ 1.39–1.60 (m, 2H), 1.69–1.77 (m, 2H), 2.01–2.08 (m, 2H), 2.70 (t, 1H, J=12.0 Hz), 2.85–2.91 (m, 1H), 3.25 (br s, 1H), 3.76 (q, 2H, J=12.0 Hz), 3.95 (d, 1H, J=9.0 Hz), 4.57 (br s, 4H), 7.02–7.23 (m, 7H), 7.35 (d, 1H, J=7.4 Hz), 7.52–7.64 (m, 4H) 7.94 (d, 1H, J=7.7 Hz), 8.37 (dd, 2H, J=11.4, 4.4 Hz); $^{13}$C NMR ($CDCl_3$) δ 27.68, 29.20, 33.84, 34.62, 51.87, 52.13, 52.54, 63.08, 122.12, 122.74, 122.87, 124.57, 128.98 (2), 129.07 (2), 131.36, 132.08, 133.77, 134.01, 134.49, 137.02, 137.43 (2), 140.68, 146.13, 148.27, 149.64, 156.23, 162.10. ES-MS m/z 558 (M+H). Anal. Calcd. for $C_{30}H_{31}N_5O_4S \cdot 0.3CH_2Cl_2$: C, 62.41; H, 5.46; N, 12.01. Found: C, 62.63; H, 5.54; N, 12.17.

AMD8840: N-(2-nitrobenzenesulfonyl)-N-(2-pyridinylmethyl)-N'-(5,6,7,8-tetrahydro-8-quinolinyl)-1,3-benzenedimethanamine Using General Procedure A:

Reaction of N-[1-methylene-3-(carboxaldehyde)phenylene]-N-(2-nitrobenzenesulfonyl)-2-(aminomethyl)pyridine (36.0 g, 87 mmol) with 8-amino-5,6,7,8-tetrahydroquinoline (12.9 g, 87 mmol) followed by column chromatography on silica (EtOAc) gave the title compound (17.5 g, 47%) as a yellow oil. $^1$H NMR ($CDCl_3$) δ 1.73–1.79 (m, 2H), 1.99–2.05 (m, 1H), 2.11–2.19 (m, 1H), 2.71–2.83 (m, 2H), 3.72–3.88 (m, 3H), 4.59 (s, 2H), 4.63 (s, 2H), 7.03–7.11 (m, 4H), 7.17 (t, 1H, J=6.9 Hz), 7.25 (d, 2H, 7.0 Hz), 7.32 (d, 1H, J=7.4 Hz), 7.51–7.61 (m, 4H), 7.95 (d, 1H J =7.8 Hz), 8.40 (t, 2H, J=5.9 Hz); $^{13}$C NMR ($CDCl_3$) δ 19.61, 28.59, 28.86, 51.59, 51.70, 52.58, 57.60, 60.40, 121.87, 122.35, 122.42, 124.14, 127.03, 127.84, 128.38, 128.63, 130.99, 131.57, 132.49, 133.23, 134.14, 135.08, 136.59, 136.88, 141.13, 146.79, 147.86, 149.18, 156.00, 157.40. ES-MS m/z 544 (M+H). Anal. Calcd. for $C_{29}H_{29}N_5O_4S \cdot 0.1CH_3COOCH_2CH_3$: C, 63.92; H, 5.44; N, 12.68. Found: C, 63.65; H, 5.47; N, 12.42.

AMD8843: Preparation of N-(2-nitrobenzenesulfonyl)-N-(2-pyridinylmethyl)-N'-(6,7,8,9-tetrahydro-5H-cyclohepta[b]pyridin-9-yl)-1,3-benzenedimethanamine General Procedure B: Direct Reductive Amination with $NaBH(OAc)_3$ To a stirred solution of the amine (1 equivalent) in $CH_2Cl_2$ (concentration ~0.2 M), at room temperature, was added the carbonyl compound (~1–2 equivalents), glacial acetic acid (0–2 equivalents) and, $NaBH(OAc)_3$ (~1.5–3 equiv.) and the resultant solution was stirred at room temperature. The reaction mixture was poured into either saturated aqueous $NaHCO_3$ or 1.0 M aqueous NaOH (10 mL/mmol amine). The phases were separated and the aqueous phase was extracted with $CH_2Cl_2$ (3×10 mL/mmol amine). The combined organic phases were dried ($Na_2SO_4$) and concentrated. The crude material was purified chromatography.

Using General Procedure B:

Reaction of the aldehyde from above (22.3 g, 54 mmol) with 9-amino-6,7,8,9-tetrahydro-5H-cyclohepta[b]pyridine (8.8 g, 54 mmol) followed by column chromatography on silica gel (5% MeOH/EtOAc) gave the title compound (AMD8843) (22.1 g, 73%) as a yellow oil. $^1$H NMR ($CDCl_3$) δ 1.42–1.61 (m, 2H), 1.75–1.80 (m, 2H), 2.03 (d, 2H, J=13.8 Hz), 2.54 (br s, 1H), 2.71 (t, 1H, J=12.0 Hz), 2.86–2.93 (m, 1H), 3.72 (q, 2H, J=12.0 Hz), 3.92 (d, 1H, J=10.5 Hz), 4.58 (s, 2H), 4.61 (s, 2H), 7.03–7.24 (m, 7H), 7.35 (d, 1H, J=7.4 Hz), 7.51–7.62 (m, 4H) 7.93 (d, 1H, J=7.7 Hz), 8.38 (dd, 2H, J=8.0, 4.4 Hz); $^{13}$C NMR ($CDCl_3$) δ 27.34, 28.69, 33.55, 34.23, 51.75, 51.93, 52.47, 62.77, 121.59, 122.33, 122.42, 124.11, 126.95, 127.84, 128.41, 128.57, 130.99, 131.56, 133.23, 134.15, 135.01, 136.57, 136.93, 137.05, 141.35, 145.75, 147.86, 149.18, 155.96, 162.13. ES-MS m/z 558 (M+H). Anal. Calcd. for $C_{30}H_{31}N_5O_4S$: C, 64.61; H, 5.60; N, 12.56. Found: C, 64.80; H, 5.69; N, 12.30.

Preparation of N-(t-butoxycarbonyl)-N-(2-pyridinylmethyl)-N'-(5,6,7,8-tetrahydro-8-quinolinyl)-1,4-benzenedimethanamine.

4-[[(2-pyridinylmethyl)amino]methyl]benzyl alcohol

Terephthaldicarboxaldehyde (40.75 g, 0.304 mol), methanol (250 mL), palladium on activated carbon, (10%, 4.24 g) and 2-(aminomethyl)pyridine (3.1 mL, 0.003 mol, 0.01 mol equiv) were combined in a hydrogenation vessel and the reaction mixture was shaken on a Parr hydrogenator for 3.5 hours at 38 psi of hydrogen. The mixture was filtered through celite and the cake was washed with methanol. The solution was dried over $Na_2SO_4$, filtered, then reduced in volume to ~200 mL under reduced pressure. To this stirred solution is then added a solution of 2-(aminomethyl)pyridine (28 mL, 0.272 mol, 0.9 mol. Equiv.) in methanol (50 mL) over 15 minutes. This was allowed to stir overnight at room temperature. The solution was transferred to a hydrogenation flask and palladium on activated carbon (10%, 2.60 g, 0.06) was added and the flask was shaken on a Parr hydrogenator for 4 hours at 39 psi of hydrogen. The mixture was filtered through celite and the cake was washed with methanol. The filtrates were then evaporated and the crude material was filtered through silica gel (180 g, 9:1 $CH_2Cl_2$:$CH_3OH$) to provide the title compound (67.45 g, 93%) as a yellow oil. $^1$H NMR ($CDCl_3$) δ 2.28 (br, 2H), 3.82 (s, 2H), 3.90 (s, 2H), 4.65 (s, 2H), 7.16 (br t, 1 H, J=6.0 Hz), 7.26–7.35 (m, 5H), 7.64 (td, 1H, J=7.7, 1.7 Hz), 8.54 (br d, 1H, J=4.5 Hz).

4-[[N-(-t-butoxycarbonyl)-N-(2-pyridinylmethyl)amino]methyl]benzyl alcohol

To a stirred solution of the alcohol from above (17.39 g, 76.3 mmol) in THF (260 mL) was added triethylamine (10 drops) and distilled water (10 drops). Di-tert-butyl dicarbonate (19.93 g, 91.3 mmol, 1.2 mol equiv) was added dropwise and the reaction mixture was stirred for 4 hours at room temperature. Distilled water (250 mL) and ethyl acetate (250 mL) were added and the phases separated. The aqueous phase was washed with ethylacetate (2×250 mL) and the combined organic phases were dried (Na$_2$SO$_4$) and filtered. The solvent was removed from the filtrate under reduced pressure to give the crude product (30.62 g) as a yellow oil. This crude product was purified by chromatography on silica gel (19:1 CH$_2$Cl$_2$:CH$_3$OH). The impure fractions were re-purified on silica gel (49:1 CH$_2$Cl$_2$:CH$_3$OH) to give the desired alcohol (21.57 g, 86%) as a yellow oil. $^1$H NMR (CDCl$_3$) δ 1.42 (br s) and 1.49 (br s) (total 9H), 4.45 (br s) and 4.53 (br s) (total 4H), 4.67 (s, 2H), 7.15–7.33 (m, 6H), 7.64 (td, 1H, J=7.7, 1.5 Hz), 8.50 (br d, 1H, J=4.8 Hz).

4-[[N-(-t-butoxycarbonyl)-N-(2-pyridinylmethyl) amino]methyl]benzylaldehyde

To a stirred solution of the alcohol from above (4.59 g, 14.0 mmol) in dichloromethane (250 mL) was added manganese(IV) oxide (<5 μm particle size, 85%, 12.39 g, 121 mmol, 8.7 mol equiv) and the mixture was stirred overnight at room temperature. The mixture was filtered through celite and the cake was washed with dichloromethane. The solvent was removed from the filtrate under reduced pressure to give the crude material (4.40 g) as a yellow oil. Purification by column chromatography on silica gel (97:3 CH$_2$Cl$_2$:CH$_3$OH) gave the title compound (3.27 g, 72%). $^1$H NMR (CDCl$_3$) δ 1.45 (s, 9H), 4.48–4.63 (m, 4H), 7.16–7.26 (m, 4H), 7.65 (td, 1H, J=7.7, 1.5 Hz), 7.83 (d, 2H, 9.0 Hz), 8.53 (d, 1H, J=4.5 Hz), 9.99 (s, 1H).

N-(t-butoxycarbonyl)-N-(2-pyridinylmethyl)-N'-(5,6,7,8-tetrahydro-8-quinolinyl)-1,4-benzenedimethanamine Using general procedure B: A stirred solution of 8-amino-5,6,7,8-tetrahydroquinoline (4.16 g, 28.1 mmol) and 4-[[N-(-t-butoxycarbonyl)-N-(2-pyridinylmethyl)amino]methyl] benzylaldehyde (9.15 g, 28.1 mmol) in CH$_2$Cl$_2$ (300 mL) was reacted with sodium triacetoxyborohydride (8.50 g, 40.1 mmol) overnight. Purification of the crude product by column chromatography on silica gel (EtOAc) gave the title compound (9.65 g, 75%) as a yellow oil. $^1$H NMR (CDCl$_3$) mixture of rotational isomers δ 1.41 (br s) and 1.48 (br s) (total 9H), 1.76–1.83 (m, 2H), 2.02–2.06 (m, 1H), 2.15–2.18 (m, 1H), 2.75–2.83 (m, 2H), 3.81–3.85 (m, 1H), 3.86 (d, 1H, J=12 Hz), 3.97 (d, 1H, J=12 Hz), 4.44 (br s, 2H), 4.53 (br s, 2H), 7.04 (dd, 1H, J=7.8, 4.8 Hz), 7.12–7.25 (m, 4H), 7.33–7.37 (m, 3H), 7.62 (td, 1H, J=7.5, 1.8 Hz), 8.38 (dd, 1H, J=4.8, 1.2 Hz), 8.52 (dd, 1H, J=5.7, 1.8 Hz).

Preparation of N-(diethylphosphoryl)-N-(2-pyridinylmethyl)-N'-(5,6,7,8-tetrahydro-8-quinolinyl)-1,4-benzenedimethanamine Using identical procedures to those described above following reaction of 4-[[(2-pyridinylmethyl)amino]methyl] benzyl alcohol with diethyl chlorophosphate gave the title compound. $^1$H NMR (CDCl$_3$) δ 1.29 (t, 6H, J=6.3 Hz), 1.72–1.84 (m, 2H), 1.99–2.06 (m, 1H), 2.16–2.22 (m, 1H), 2.70–2.89 (m, 2H), 3.84–3.87 (m, 1H), 3.86 (d, 1H, J=12.6 Hz), 3.97 (d, 1H, J=12.6 Hz), 4.03–4.15 (m, 4H), 4.17 (d, 2H, J=12 Hz), 4.22 (d, 2H, J=12 Hz), 7.06 (dd, 1H, J=7.8, 4.8 Hz), 7.14 (ddd, 1H, J=7.5, 4.8, 0.9 Hz), 7.25 (d, 2H, J=7.8 Hz), 7.34 (d, 2H, J=7.8 Hz), 7.36–7.39 (m, 2H), 7.63 (td, 1H, J=7.8, 0.9 Hz), 8.38 (dd, 1H, J=4.5, 1.5 Hz), 8.53 (br d, 1H, J=4.1 Hz); $^{13}$C NMR (CDCl$_3$) δ 15.82 (d, J=7.1 Hz), 19.33, 28.23, 28.47, 48.86, 50.05, 51.16, 57.21, 62.11 (d, J=5.3 Hz), 121.47, 121.71, 121.97, 127.97 (2 carbons), 128.57 (2 carbons), 132.05, 135.59, 136.03, 136.49, 139.39, 146.42, 148.82, 156.97, 157.91. ES-MS m/z 495 (M+H).

TABLE 1

| | |
|---|---|
| EXAMPLE 1 AMD7490: | N-(2-pyridinylmethyl)-N'-(6,7,8,9-tetrahydro-5H-cyclohepta[b]pyridin-9-yl)-1,4-benzenedimethanamine |
| EXAMPLE 2 AMD7491 | N-(2-pyridinylmethyl)-N'-(5,6,7,8-tetrahydro-8-quinolinyl)-1,4-benzenedimethanamine |
| EXAMPLE 3 AMD7492: | N-(2-pyridinylmethyl)-N'-(6,7-dihydro-5H-cyclopenta[b]pyridin-7-yl)-1,4-benzenedimethanamine |
| EXAMPLE 4 AMD8766: | N-(2-pyridinylmethyl)-N'-(1,2,3,4-tetrahydro-1-naphthalenyl)-1,4-benzenedimethanamine |
| EXAMPLE 5 AMD8789: | N-(2-pyridinylmethyl)-N'-(1-naphthalenyl)-1,4-benzenedimethanamine |
| EXAMPLE 6 AMD8776: | N-(2-pyridinylmethyl)-N'-(8-quinolinyl)-1,4-benzenedimethanamine |
| EXAMPLE 7 AMD8859: | N-(2-pyridinylmethyl)-N'-[2-[(2-pyridinylmethyl)amino]ethyl]-N'-(1-methyl-1,2,3,4-tetrahydro-8-quinolinyl)-1,4-benzene dimethanamine |
| EXAMPLE 8 AMD8867: | N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzene dimethanamine. |
| EXAMPLE 9 AMD8746: | N-(2-pyridinylmethyl)-N'-(1,2,3,4-tetrahydro-8-quinolinyl)-1,4-benzenedimethanamine |
| EXAMPLE 10 AMD8835: | N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine |
| EXAMPLE 11 AMD8833: | N-(2-pyridinylmethyl)-N'-(2-phenyl-5,6,7,8-tetrahydro-8-quinolinyl)-1,4-benzenedimethanamine |
| EXAMPLE 12 AMD8825: | N,N-bis(2-pyridinylmethyl)-N'-(2-phenyl-5,6,7,8-tetrahydro-8-quinolinyl)-1,4-benzenedimethanamine |
| EXAMPLE 13 AMD8869: | N-(2-pyridinylmethyl)-N'-(5,6,7,8-tetrahydro-5-quinolinyl)-1,4-benzenedimethanamine |
| EXAMPLE 14 AMD8876: | N-(2-pyridinylmethyl)-N'-(1H-imidazol-2-ylmethyl)-N'-(5,6,7,8-tetrahydro-5-quinolinyl)-1,4-benzenedimethanamine |
| EXAMPLE 15 AMD8751: | N-(2-pyridinylmethyl)-N'-(1H-imidazol-2-ylmethyl)-N'-(5,6,7,8-tetrahydro-8-quinolinyl)-1,4-benzenedimethanamine |
| EXAMPLE 16 AMD8777: | N-(2-pyridinylmethyl)-N'-[(2-amino-3-phenyl)propyl]-N'-(5,6,7,8-tetrahydro-8-quinolinyl)-1,4-benzenedimethanamine |
| EXAMPLE 17 AMD8763: | N-(2-pyridinylmethyl)-N'-(1H-imidazol-4-ylmethyl)-N'-(5,6,7,8-tetrahydro-8-quinolinyl)-1,4-benzenedimethanamine |
| EXAMPLE 18 AMD8771: | N-(2-pyridinylmethyl)-N'-(2-quinolinylmethyl)-N'-(5,6,7,8-tetrahydro-8-quinolinyl)-1,4-benzenedimethanamine |
| EXAMPLE 19 AMD8778: | N-(2-pyridinylmethyl)-N'-(2-(2-naphthoyl)aminoethyl)-N'-(5,6,7,8-tetrahydro-8-quinolinyl)-1,4-benzenedimethanamine |
| EXAMPLE 20 AMD8781: | N-(2-pyridinylmethyl)-N'-[(S)-(2-acetylamino-3-phenyl)propyl]-N'-(5,6,7,8-tetrahydro-8-quinolinyl)-1,4-benzenedimethanamine |
| EXAMPLE 21 AMD8782: | N-(2-pyridinylmethyl)-N'-[(S)-(2-acetylamino-3-phenyl)propyl]-N'-(5,6,7,8-tetrahydro-8-quinolinyl)-1,4-benzenedimethanamine |
| EXAMPLE 22 AMD8788: | N-(2-pyridinylmethyl)-N'-[3-((2-naphthalenylmethyl)amino)propyl]-N'-(5,6,7,8-tetrahydro-8-quinolinyl)-1,4-benzenedimethanamine |
| EXAMPLE 23 AMD8733 and AMD8734: | N-(2-pyridinylmethyl)-N'-[2-(S)-pyrollidinylmethyl]-N'-(5,6,7,8-tetrahydro-8-quinolinyl)-1,4-benzenedimethanamine |
| EXAMPLE 24 AMD8756: | N-(2-pyridinylmethyl)-N'-[2-(R)-pyrollidinylmethyl]-N'-(5,6,7,8-tetrahydro-8-quinolinyl)-1,4-benzenedimethanamine |
| EXAMPLE 25 AMD8799: | N-(2-pyridinylmethyl)-N'-[3-pyrazolylmethyl]-N'-(5,6,7,8-tetrahydro-8-quinolinyl)-1,4-benzenedimethanamine |
| EXAMPLE 26 AMD8728: | N-(2-pyridinylmethyl)-N'-[2-pyrrolylmethyl]-N'-(5,6,7,8-tetrahydro-8-quinolinyl)-1,4-benzenedimethanamine. |

TABLE 1-continued

| Example | Name |
|---|---|
| EXAMPLE 27 AMD8836: | N-(2-pyridinylmethyl)-N'-[2-thiopheneylmethyl]-N'-(5,6,7,8-tetrahydro-8-quinolinyl)-1,4-benzenedimethanamine |
| EXAMPLE 28 AMD8841: | N-(2-pyridinylmethyl)-N'-[2-thiazolylmethyl]-N'-(5,6,7,8-tetrahydro-8-quinolinyl)-1,4-benzenedimethanamine |
| EXAMPLE 29 AMD8821: | N-(2-pyridinylmethyl)-N'-[2-furanylmethyl]-N'-(5,6,7,8-tetrahydro-8-quinolinyl)-1,4-benzenedimethanamine |
| EXAMPLE 30 AMD8742: | N-(2-pyridinylmethyl)-N'-[2-[(phenylmethyl)amino]ethyl]-N'-(5,6,7,8-tetrahydro-8-quinolinyl)-1,4-benzenedimethanamine |
| EXAMPLE 31 AMD8743: | N-(2-pyridinylmethyl)-N'-(2-aminoethyl)-N'-(5,6,7,8-tetrahydro-8-quinolinyl)-1,4-benzenedimethanamine |
| EXAMPLE 32 AMD8753: | N-(2-pyridinylmethyl)-N'-3-pyrrolidinyl-N'-(5,6,7,8-tetrahydro-8-quinolinyl)-1,4-benzenedimethanamine |
| EXAMPLE 33 AMD8754: | N-(2-pyridinylmethyl)-N'-4-piperidinyl-N'-(5,6,7,8-tetrahydro-8-quinolinyl)-1,4-benzenedimethanamine |
| EXAMPLE 34 AMD8784: | N-(2-pyridinylmethyl)-N'-[2-[(phenyl)amino]ethyl]-N'-(5,6,7,8-tetrahydro-8-quinolinyl)-1,4-benzenedimethanamine |
| EXAMPLE 35 AMD8759: | N-(2-pyridinylmethyl)-N'-(7-methoxy-1,2,3,4-tetrahydro-2-naphthalenyl)-1,4-benzenedimethanamine |
| EXAMPLE 36 AMD8762: | N-(2-pyridinylmethyl)-N'-(6-methoxy-1,2,3,4-tetrahydro-2-naphthalenyl)-1,4-benzenedimethanamine. |
| EXAMPLE 37 AMD8770: | N-(2-pyridinylmethyl)-N'-(1-methyl-1,2,3,4-tetrahydro-2-naphthalenyl)-1,4-benzenedimethanamine. |
| EXAMPLE 38 AMD8790: | N-(2-pyridinylmethyl)-N'-(7-methoxy-3,4-dihydronaphthalenyl)-1-(aminomethyl)-4-benzamide |
| EXAMPLE 39 AMD8805: | N-(2-pyridinylmethyl)-N'-(6-methoxy-3,4-dihydronaphthalenyl)-1-(aminomethyl)-4-benzamide. |
| EXAMPLE 40 AMD8902: | N-(2-pyridinylmethyl)-N'-(1H-imidazol-2-ylmethyl)-N'-(7-methoxy-1,2,3,4-tetrahydro-2-naphthalenyl)-1,4-benzenedimethanamine. |
| EXAMPLE 41 AMD8863: | N-(2-pyridinylmethyl)-N'-(8-hydroxy-1,2,3,4-tetrahydro-2-naphthalenyl)-1,4-benzenedimethanamine. |
| EXAMPLE 42 AMD 8886: | N-(2-pyridinylmethyl)-N'-(1H-imidazol-2-ylmethyl)-N'-(8-hydroxy-1,2,3,4-tetrahydro-2-naphthalenyl)-1,4-benzenedimethanamine. |
| EXAMPLE 43 AMD8889: | N-(2-pyridinylmethyl)-N'-(8-Fluoro-1,2,3,4-tetrahydro-2-naphthalenyl)-1,4-benzenedimethanamine. |
| EXAMPLE 44 AMD8895: | N-(2-pyridinylmethyl)-N'-(1H-imidazol-2-ylmethyl)-N'-(8-Fluoro-1,2,3,4-tetrahydro-2-naphthalenyl)-1,4-benzenedimethanamine. |
| EXAMPLE 45 AMD8852: | N-(2-pyridinylmethyl)-N'-(5,6,7,8-tetrahydro-7-quinolinyl)-1,4-benzenedimethanamine |
| EXAMPLE 46 AMD8858: | N-(2-pyridinylmethyl)-N'-(1H-imidazol-2-ylmethyl)-N'-(5,6,7,8-tetrahydro-7-quinolinyl)-1,4-benzenedimethanamine |
| EXAMPLE 47 AMD8785 | N-(2-pyridinylmethyl)-N'-[2-[(2-naphthalenylmethyl)amino]ethyl]-N'-(5,6,7,8-tetrahydro-8-quinolinyl)-1,4-benzenedimethanamine |
| EXAMPLE 48 AMD8820: | N-(2-pyridinylmethyl)-N'-[2-(isobutylamino)ethyl]-N'-(5,6,7,8-tetrahydro-8-quinolinyl)-1,4-benzenedimethanamine |
| EXAMPLE 49 AMD8827: | N-(2-pyridinylmethyl)-N'-[2-[(2-pyridinylmethyl)amino]ethyl]-N'-(5,6,7,8-tetrahydro-8-quinolinyl)-1,4-benzenedimethanamine |
| EXAMPLE 50 AMD8828: | N-(2-pyridinylmethyl)-N'-[2-[(2-furanylmethyl)amino]ethyl]-N'-(5,6,7,8-tetrahydro-8-quinolinyl)-1,4-benzenedimethanamine |
| EXAMPLE 51 AMD8772: | N-(2-pyridinylmethyl)-N'-(2-guanidinoethyl)-N'-(5,6,7,8-tetrahydro-8-quinolinyl)-1,4-benzenedimethanamine |
| EXAMPLE 52 AMD8861: | N-(2-pyridinylmethyl)-N'-[2-[bis-[(2-methoxy)phenylmethyl]amino]ethyl]-N'-(5,6,7,8-tetrahydro-8-quinolinyl)-1,4-benzene dimethanamine |
| EXAMPLE 53 AMD8862 | N-(2-pyridinylmethyl)-N'-[2-[(1H-imidazol-4-ylmethyl)amino]ethyl]-N'-(5,6,7,8-tetrahydro-8-quinolinyl)-1,4-benzene dimethanamine |
| EXAMPLE 54 AMD8887: | N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine |
| EXAMPLE 55 AMD8816: | N-(2-pyridinylmethyl)-N'-[2-(phenylureido)ethyl]-N'-(5,6,7,8-tetrahydro-8-quinolinyl)-1,4-benzenedimethanamine |
| EXAMPLE 56 AMD8737: | N-(2-pyridinylmethyl)-N'-[[N''-(n-butyl)carboxamido]methyl]-N'-(5,6,7,8-tetrahydro-8-quinolinyl)-1,4-benzenedimethanamine |
| EXAMPLE 57 AMD8739: | N-(2-pyridinylmethyl)-N'-(carboxamidomethyl)-N'-(5,6,7,8-tetrahydro-8-quinolinyl)-1,4-benzenedimethanamine |
| EXAMPLE 58 AMD8752: | N-(2-pyridinylmethyl)-N'-[(N''-phenyl)carboxamidomethyl]-N'-(5,6,7,8-tetrahydro-8-quinolinyl)-1,4-benzenedimethanamine |
| EXAMPLE 59 AMD8765: | N-(2-pyridinylmethyl)-N'-(carboxymethyl)-N'-(5,6,7,8-tetrahydro-8-quinolinyl)-1,4-benzenedimethanamine |
| EXAMPLE 60 AMD8715: | N-(2-pyridinylmethyl)-N'-(phenylmethyl)-N'-(5,6,7,8-tetrahydro-8-quinolinyl)-1,4-benzenedimethanamine |
| EXAMPLE 61 AMD8907: | N-(2-pyridinylmethyl)-N'-(1H-benzimidazol-2-ylmethyl)-N'-(5,6,7,8-tetrahydro-8-quinolinyl)-1,4-benzenedimethanamine |
| EXAMPLE 62 AMD8927: | N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine (hydrobromide salt). |
| EXAMPLE 63 AMD8926: | N-(2-pyridinylmethyl)-N'-(5-nitro-1H-benzimidazol-2-ylmethyl)-N'-(5,6,7,8-tetrahydro-8-quinolinyl)-1,4-benzenedimethanamine. |
| EXAMPLE 64 AMD 8929: | N-(2-pyridinylmethyl)-N'-[(1H)-5-azabenzimidazol-2-ylmethyl]-N'-(5,6,7,8-tetrahydro-8-quinolinyl)-1,4-benzenedimethanamine |
| EXAMPLE 65 AMD8931: | N-(2-pyridinylmethyl)-N-(4-phenyl-1H-imidazol-2-ylmethyl)-N'-(5,6,7,8-tetrahydro-8-quinolinyl)-1,4-benzenedimethanamine. |
| EXAMPLE 66 AMD8783: | N-(2-pyridinylmethyl)-N'-[2-(2-pyridinyl)ethyl]-N'-(5,6,7,8-tetrahydro-8-quinolinyl)-1,4-benzenedimethanamine |
| EXAMPLE 67 AMD8764: | N-(2-pyridinylmethyl)-N'-(2-benzoxazolyl)-N'-(5,6,7,8-tetrahydro-8-quinolinyl)-1,4-benzenedimethanamine |
| EXAMPLE 68 AMD8780: | N-(2-pyridinylmethyl)-N'-(trans-2-aminocyclohexyl)-N'-(5,6,7,8-tetrahydro-8-quinolinyl)-1,4-benzenedimethanamine |
| EXAMPLE 69 AMD8818: | N-(2-pyridinylmethyl)-N'-(2-phenylethyl)-N'-(5,6,7,8-tetrahydro-8-quinolinyl)-1,4-benzenedimethanamine |
| EXAMPLE 70 AMD8829: | N-(2-pyridinylmethyl)-N'-(3-phenylpropyl)-N'-(5,6,7,8-tetrahydro-8-quinolinyl)-1,4-benzenedimethanamine |
| EXAMPLE 71 AMD8839: | N-(2-pyridinylmethyl)-N'-(trans-2-aminocyclopentyl)-N'-(5,6,7,8-tetrahydro-8-quinolinyl)-1,4-benzenedimethanamine |
| EXAMPLE 72 AMD8726: | N-[[4-[[(2-pyridinylmethyl)amino]methyl]phenyl]methyl]-N-(5,6,7,8-tetrahydro-8-quinolinyl)-glycinamide |
| EXAMPLE 73 AMD8738: | N-[[4-[[(2-pyridinylmethyl)amino]methyl]phenyl]methyl]-N-(5,6,7,8-tetrahydro-8-quinolinyl)-(L)-alaninamide |
| EXAMPLE 74 AMD8749: | N-[[4-[[(2-pyridinylmethyl)amino]methyl]phenyl]methyl]-N-(5,6,7,8-tetrahydro-8-quinolinyl)-(L)-aspartamide |
| EXAMPLE 75 AMD8750: | N-[[4-[[(2-pyridinylmethyl)amino]methyl]phenyl]methyl]-N-(5,6,7,8-tetrahydro-8-quinolinyl)-pyrazinamide |
| EXAMPLE 76 AMD8740: | N-[[4-[[(2-pyridinylmethyl)amino]methyl]phenyl]methyl]-N-(5,6,7,8-tetrahydro-8-quinolinyl)-(L)-prolinamide |
| EXAMPLE 77 AMD8741: | N-[[4-[[(2-pyridinylmethyl)amino]methyl]phenyl]methyl]-N-(5,6,7,8-tetrahydro-8-quinolinyl)-(L)-lysinamide |
| EXAMPLE 78 AMD8724: | N-[[4-[[(2-pyridinylmethyl)amino]methyl]phenyl]methyl]-N-(5,6,7,8-tetrahydro-8-quinolinyl)-benzamide |
| EXAMPLE 79 AMD8725: | N-[[4-[[(2-pyridinylmethyl)amino]methyl]phenyl]methyl]-N-(5,6,7,8-tetrahydro-8-quinolinyl)-picolinamide |
| EXAMPLE 80 | N'-Benzyl-N-[[4- |

TABLE 1-continued

| | |
|---|---|
| AMD8713: | [[(2-pyridinylmethyl)amino]methyl]phenyl]methyl]-N-(5,6,7,8-tetrahydro-8-quinolinyl)-urea. |
| EXAMPLE 81 AMD8712: | N'-phenyl-N-[[4-[[(2-pyridinylmethyl)amino]methyl]phenyl]methyl]-N-(5,6,7,8-tetrahydro-8-quinolinyl)-urea. |
| EXAMPLE 82 AMD8716: | N-(6,7,8,9-tetrahydro-5H-cyclohepta[b]pyridin-9-yl)-4-[[(2-pyridinylmethyl)amino]methyl]benzamide |
| EXAMPLE 83 AMD8717: | N-(5,6,7,8-tetrahydro-8-quinolinyl)-4-[[(2-pyridinylmethyl)amino]methyl]benzamide |
| EXAMPLE 84 AMD8634: | N,N'-bis(2-pyridinylmethyl)-N'-(5,6,7,8-tetrahydro-8-quinolinyl)-1,4-benzenedimethanamine |
| EXAMPLE 85 AMD8774: | N,N'-bis(2-pyridinylmethyl)-N'-(6,7,8,9-tetrahydro-5H-cyclohepta[b]pyridin-9-yl)-1,4-benzenedimethanamine |
| EXAMPLE 86 AMD8775: | N,N'-bis(2-pyridinylmethyl)-N'-(6,7-dihydro-5H-cyclopenta[b]pyridin-7-yl)-1,4-benzenedimethanamine |
| EXAMPLE 87 AMD8819: | N,N'-bis(2-pyridinylmethyl)-N'-(1,2,3,4-tetrahydro-1-naphthalenyl)-1,4-benzenedimethanamine |
| EXAMPLE 88 AMD8768: | N,N'-bis(2-pyridinylmethyl)-N'-[(5,6,7,8-tetrahydro-8-quinolinyl)methyl]-1,4-benzenedimethanamine |
| EXAMPLE 89 AMD8767: | N,N'-bis(2-pyridinylmethyl)-N'[(6,7-dihydro-5H-cyclopenta[b]pyridin-7-yl)methyl]-1,4-benzenedimethanamine |
| EXAMPLE 90 AMD8838: | N-(2-pyridinylmethyl)-N-(2-methoxyethyl)-N'-(5,6,7,8-tetrahydro-8-quinolinyl)-1,4-benzenedimethanamine |
| EXAMPLE 91 AMD8871: | N-(2-pyridinylmethyl)-N-[2-(4-methoxyphenyl)ethyl]-N'-(5,6,7,8-tetrahydro-8-quinolinyl)-1,4-benzenedimethanamine |
| EXAMPLE 92 AMD8844: | N,N'-bis(2-pyridinylmethyl)-1,4-(5,6,7,8-tetrahydro-8-quinolinyl)benzenedimethanamine |
| EXAMPLE 95 AMD7129: | N-[(2,3-dimethoxyphenyl)methyl]-N'-(2-pyridinylmethyl)-N-(5,6,7,8-tetrahydro-8-quinolinyl)-1,4-benzenedimethanamine |
| EXAMPLE 96 AMD7130: | N,N'-bis(2-pyridinylmethyl)-N-[1-(N"-phenyl-N"-methylureido)-4-piperidinyl]-1,3-benzenedimethanamine |
| EXAMPLE 97 AMD7131: | N,N'-bis(2-pyridinylmethyl)-N-[N"-p-toluenesulfonylphenylalanyl)-4-piperidinyl]-1,3-benzenedimethanamine |
| EXAMPLE 98 AMD7136: | N,N'-bis(2-pyridinylmethyl)-N-[1-[3-(2-chlorophenyl)-5-methyl-isoxazol-4-oyl]-4-piperidinyl]1,3-benzenedimethanamine |
| EXAMPLE 99 AMD7138: | N-[(2-hydroxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 100 AMD7140: | N-[(4-cyanophenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 101 AMD7141: | N-[(4-cyanophenyl)methyl]-N'-(2-pyridinylmethyl)-N-(5,6,7,8-tetrahydro-8-quinolinyl)-1,4-benzenedimethanamine |
| EXAMPLE 102 AMD7142: | N-[(4-acetamidophenyl)methyl]-N'-(2-pyridinylmethyl)-N-(5,6,7,8-tetrahydro-8-quinolinyl)-1,4-benzenedimethanamine |
| EXAMPLE 103 AMD7145: | N-[(4-phenoxyphenyl)methyl]-N'-(2-pyridinylmethyl)-N-(6,7,8,9-tetrahydro-5H-cyclohepta[b] pyridin-9-yl)-1,4-benzenedimethanamine |
| EXAMPLE 104 AMD7147: | N-[(1-methyl-2-carboxamido)ethyl]-N,N'-bis(2-pyridinylmethyl)-1,3-benzenedimethanamine |
| EXAMPLE 105 AMD7151: | N-[(4-benzyloxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 106 AMD7155: | N-[(thiophene-2-yl)methyl]-N'-(2-pyridinylmethyl)-N-(6,7,8,9-tetrahydro-5H-cyclohepta[b]pyridin-9-yl)-1,4-benzenedimethanamine |
| EXAMPLE 107 AMD7156: | N-[1-(benzyl)-3-pyrrolidinyl]-N,N'-bis(2-pyridinylmethyl)-1,3-benzenedimethanamine. |
| EXAMPLE 108 AMD7159: | N-[[1-methyl-3-(pyrazol-3-yl)]propyl]-N,N'-bis(2-pyridinylmethyl)-1,3-benzenedimethanamine. |
| EXAMPLE 109 AMD7160: | N-[1-(phenyl)ethyl]-N,N'-bis(2-pyridinylmethyl)-1,3-benzenedimethanamine. |
| EXAMPLE 110 AMD7164: | N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 111 AMD7166: | N-[1-benzyl-3-carboxymethyl-4-piperidinyl]-N,N'-bis(2-pyridinylmethyl)-1,3-benzenedimethanamine. |
| EXAMPLE 112 AMD7167: | N-[(3,4-methylenedioxyphenyl)methyl]-N'-(2-pyridinylmethyl)-N-(5,6,7,8-tetrahydro-8-quinolinyl)-1,4-benzenedimethanamine |
| EXAMPLE 113 AMD7168: | N-(3-pyridinylmethyl)-N'-(2-pyridinylmethyl)-N-(6,7,8,9-tetrahydro-5H-cyclohepta[b]pyridin-9-yl)-1,4-benzenedimethanamine |
| EXAMPLE 114 AMD7169: | N-[[1-methyl-2-(2-tolyl)carboxamido]ethyl]-N,N'-bis(2-pyridinylmethyl)-1,3-benzenedimethanamine. |
| EXAMPLE 115 AMD7171: | N-[(1,5-dimethyl-2-phenyl-3-pyrazolinone-4-yl)methyl]-N'-(2-pyridinylmethyl)-N-(5,6,7,8-tetrahydro-8-quinolinyl)-1,4-benzenedimethanamine |
| EXAMPLE 116 AMD7172: | N-[(4-propoxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 117 AMD7175: | N-(1-phenyl-3,5-dimethylpyrazol-4-ylmethyl)-N'-(2-pyridinylmethyl)-N-(5,6,7,8-tetrahydro-8-quinolinyl)-1,4-benzenedimethanamine |
| EXAMPLE 118 AMD7177: | N-[1H-imidazol-4-ylmethyl]-N,N'-bis(2-pyridinylmethyl)-1,3-benzenedimethanamine. |
| EXAMPLE 119 AMD7180: | N-[(3-methoxy-4,5-methylenedioxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 120 AMD7182: | N-[(3-cyanophenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 121 AMD7184: | N-[(3-cyanophenyl)methyl]-N'-(2-pyridinylmethyl)-N-(5,6,7,8-tetrahydro-8-quinolinyl)-1,4-benzenedimethanamine |
| EXAMPLE 122 AMD7185: | N-(5-ethylthiophene-2-ylmethyl)-N'-(2-pyridinylmethyl)-N-(6,7,8,9-tetrahydro-5H-cyclohepta[b]pyridin-9-yl)-1,4-benzenedimethanamine |
| EXAMPLE 123 AMD7186: | N-(5-ethylthiophene-2-ylmethyl)-N'-(2-pyridinylmethyl)-N-(5,6,7,8-tetrahydro-8-quinolinyl)-1,4-benzenedimethanam ine |
| EXAMPLE 124 AMD7187: | N-[(2,6-difluorophenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 125 AMD7188: | N-[(2,6-difluorophenyl)methyl]-N'-(2-pyridinylmethyl)-N-(5,6,7,8-tetrahydro-8-quinolinyl)-1,4-benzenedimethanamine |
| EXAMPLE 126 AMD7189: | N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 127 AMD7195: | N-(2-difluoromethoxyphenylmethyl)-N'-(2-pyridinylmethyl)-N-(5,6,7,8-tetrahydro-8-quinolinyl)-1,4-benzenedimethanamine |
| EXAMPLE 128 AMD7196: | N-(1,4-benzodioxan-6-ylmethyl)-N'-(2-pyridinylmethyl)-N-(6,7,8,9-tetrahydro-5H-cyclohepta[b]pyridin-9-yl)-1,4-benzenedimethanamine |
| EXAMPLE 129 AMD7197: | N, N'-bis(2-pyridinylmethyl)-N-[1-(N"-phenyl-N"-methylureido)-4-piperidinyl]-1,4-benzenedimethanamine |
| EXAMPLE 130 AMD7198: | N, N'-bis(2-pyridinylmethyl)-N-[N"-p-toluenesulfonylphenylalanyl)-4-piperidinyl]-1,4-benzenedimethanamine. |
| EXAMPLE 131 AMD7199: | N-[1-(3-pyridinecarboxamido)-4-piperidinyl]-N,N'-bis(2-pyridinylmethyl)-1,4-benzenedimethanamine. |

TABLE 1-continued

| Example | AMD | Name |
|---|---|---|
| EXAMPLE 132 | AMD7200: | N-[1-(cyclopropylcarboxamido)-4-piperidinyl]-N,N'-bis(2-pyridinylmethyl)-1,4-benzenedimethanamine |
| EXAMPLE 133 | AMD7201: | N-[1-(1-phenylcyclopropylcarboxamido)-4-piperidinyl]-N,N'-bis(2-pyridinylmethyl)-1,4-benzenedimethanamine. |
| EXAMPLE 134 | AMD7202: | N-(1,4-benzodioxan-6-ylmethyl)-N'-(2-pyridinylmethyl)-N-(5,6,7,8-tetrahydro-8-quinolinyl)-1,4-benzenedimethanamine |
| EXAMPLE 135 | AMD7203: | N-[1-[3-(2-chlorophenyl)-5-methyl-isoxazol-4-carboxamido]-4-piperidinyl]-N,N'-bis(2-pyridinylmethyl)-1,4-benzenedimethanamine |
| EXAMPLE 136 | AMD7204: | N-[1-(2-thiomethylpyridine-3-carboxamido)-4-piperidinyl]-N,N'-bis(2-pyridinylmethyl)-1,4-benzenedimethanamine |
| EXAMPLE 137 | AMD7207: | N-[(2,4-difluorophenyl)methyl]-N'-(2-pyridinylmethyl)-N-(5,6,7,8-tetrahydro-8-quinolinyl)-1,4-benzenedimethanamine |
| EXAMPLE 138 | AMD7208: | N-(1-methylpyrrol-2-ylmethyl)-N'-(2-pyridinylmethyl)-N-(5,6,7,8-tetrahydro-8-quinolinyl)-1,4-benzenedimethanamine |
| EXAMPLE 139 | AMD7209: | N-[(2-hydroxyphenyl)methyl]-N'-(2-pyridinylmethyl)-N-(5,6,7,8-tetrahydro-8-quinolinyl)-1,4-benzenedimethanamine |
| EXAMPLE 140 | AMD7212: | N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine |
| EXAMPLE 141 | AMD7216: | N-(3-pyridinylmethyl)-N'-(2-pyridinylmethyl)-N-(5,6,7,8-tetrahydro-8-quinolinyl)-1,4-benzenedimethanamine |
| EXAMPLE 142 | AMD7217: | N-[2-(N''-morpholinomethyl)-1-cyclopentyl]-N,N'-bis(2-pyridinylmethyl)-1,4-benzenedimethanamine |
| EXAMPLE 143 | AMD7220: | N-[(1-methyl-3-piperidinyl)propyl]-N,N'-bis(2-pyridinylmethyl)-1,4-benzenedimethanamine |
| EXAMPLE 144 | AMD7222: | N-(1-methylbenzimidazol-2-ylmethyl)-N'-(2-pyridinylmethyl)-N-(5,6,7,8-tetrahydro-8-quinolinyl)-1,4-benzenedimethanamine |
| EXAMPLE 145 | AMD7223: | N-[1-(benzyl)-3-pyrrolidinyl]-N,N'-bis(2-pyridinylmethyl)-1,4-benzenedimethanamine |
| EXAMPLE 146 | AMD7228: | N-[[(1-phenyl-3-(N''-morpholino)]propyl]-N,N'-bis(2-pyridinylmethyl)-1,4-benzenedimethanamine |
| EXAMPLE 147 | AMD7229: | N-[1-(iso-propyl)-4-piperidinyl]-N,N'-bis(2-pyridinylmethyl)-1,4-benzenedimethanamine |
| EXAMPLE 148 | AMD7230: | N-[1-(ethoxycarbonyl)-4-piperidinyl]-N'-(2-pyridinylmethyl)-N-(5,6,7,8-tetrahydro-8-quinolinyl)-1,4-benzenedimethanamine |
| EXAMPLE 149 | AMD7231: | N-[(1-methyl-3-pyrazolyl)propyl]-N'-(2-pyridinylmethyl)-N-(5,6,7,8-tetrahydro-8-quinolinyl)-1,4-benzenedimethanamine |
| EXAMPLE 150 | AMD7235: | N-[1-methyl-2-(N'',N''-diethylcarboxamido)ethyl]-N,N'-bis(2-pyridinylmethyl)-1,4-benzenedimethanamine |
| EXAMPLE 151 | AMD7236: | N-[1-methyl-2-phenylsulfonyl)ethyl]-N'-(2-pyridinylmethyl)-N-(5,6,7,8-tetrahydro-8-quinolinyl)-1,4-benzenedimethanamine |
| EXAMPLE 152 | AMD7238: | N-[(2-chloro-4,5-methylenedioxyphenyl)methyl]-N'-(2-pyridinylmethyl)-N-(5,6,7,8-tetrahydro-8-quinolinyl)-1,4-benzenedimethanamine |
| EXAMPLE 153 | AMD7239: | N-[1-methyl-2-[N''-(4-chlorophenyl)carboxamido]ethyl]-N'-(2-pyridinylmethyl)-N-(5,6,7,8-tetrahydro-8-quinolinyl)-1,4-benzenedimethanamine |
| EXAMPLE 154 | AMD7241: | N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine |
| EXAMPLE 155 | AMD7242: | N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 156 | AMD7244: | N-(3-quinolylmethyl)-N'-(2-pyridinylmethyl)-N-(5,6,7,8-tetrahydro-8-quinolinyl)-1,4-benzenedimethanamine |
| EXAMPLE 157 | AMD7245: | N-[(8-hydroxy)-2-quinolylmethyl]-N'-(2-pyridinylmethyl)-N-(6,7,8,9-tetrahydro-5H-cyclohepta[b]pyridin-9-yl)-1,4-benzenedimethanamine |
| EXAMPLE 158 | AMD7247: | N-(2-quinolylmethyl)-N'-(2-pyridinylmethyl)-N-(6,7,8,9-tetrahydro-5H-cyclohepta[b]pyridin-9-yl)-1,4-benzenedimethanamine |
| EXAMPLE 159 | AMD7249: | N-[(4-acetamidophenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 160 | AMD7250: | N-[1H-imidazol-2-ylmethyl)-N,N'-bis(2-pyridinylmethyl)-1,4-benzenedimethanamine |
| EXAMPLE 161 | AMD7251: | N-(3-quinolylmethyl)-N'-(2-pyridinylmethyl)-N-(6,7,8,9-tetrahydro-5H-cyclohepta[b]pyridin-9-yl)-1,4-benzenedimethanamine |
| EXAMPLE 162 | AMD7252: | N-(2-thiazolylmethyl)-N'-(2-pyridinylmethyl)-N-(6,7,8,9-tetrahydro-5H-cyclohepta[b]pyridin-9-yl)-1,4-benzenedimethanamine |
| EXAMPLE 163 | AMD7253: | N-(4-pyridinylmethyl)-N'-(2-pyridinylmethyl)-N-(6,7,8,9-tetrahydro-5H-cyclohepta[b]pyridin-9-yl)-1,4-benzenedimethanamine |
| EXAMPLE 164 | AMD7254: | N-[(5-benzyloxy)benzo[b]pyrrol-3-ylmethyl]-N,N'-bis(2-pyridinylmethyl)-1,4-benzenedimethanamine |
| EXAMPLE 165 | AMD7256: | N-(1-methylpyrazol-2-ylmethyl)-N'-(2-pyridinylmethyl)-N-(6,7,8,9-tetrahydro-5H-cyclohepta[b]pyridin-9-yl)-1,4-benzenedimethanamine |
| EXAMPLE 166 | AMD7257: | N-[(4-methyl)-1H-imidazol-5-ylmethyl]-N,N'-bis(2-pyridinylmethyl)-1,4-benzenedimethanamine |
| EXAMPLE 167 | AMD7259: | N-[[(4-dimethylamino)-1-napthalenyl]methyl]-N,N'-bis(2-pyridinylmethyl)-1,4-benzenedimethanamine |
| EXAMPLE 168 | AMD7260: | N-[1,5-dimethyl-2-phenyl-3-pyrazolinone-4-ylmethyl]-N,N'-bis(2-pyridinylmethyl)-1,4-benzenedimethanamine |
| EXAMPLE 169 | AMD7261: | N-[1-[(1-acetyl-2-(R)-prolinyl]-4-piperidinyl]-N-[2-(2-pyridinyl)ethyl]-N'-(2-pyridinylmethyl)-1,3-benzenedimethanamine |
| EXAMPLE 170 | AMD7262: | N-[1-[2-acetamidobenzoyl-4-piperidinyl]-4-piperidinyl]-N-[2-(2-pyridinyl)ethyl]-N'-(2-pyridinylmethyl)-1,3-benzenedimethanamine |
| EXAMPLE 171 | AMD7270: | N-[(2-cyano-2-phenyl)ethyl]-N'-(2-pyridinylmethyl)-N-(6,7,8,9-tetrahydro-5H-cyclohepta[b]pyridin-9-yl)-1,4-benzenedimethanamine |
| EXAMPLE 172 | AMD7272: | N-[(N''-acetyltryptophanyl)-4-piperidinyl]-N-[2-(2-pyridinyl)ethyl]-N'-(2-pyridinylmethyl)-1,3-benzenedimethanamine |
| EXAMPLE 173 | AMD7273: | N-[(N''-benzoylvalinyl)-4-piperidinyl]-N-[2-(2-pyridinyl)ethyl]-N'-(2-pyridinylmethyl)-1,3-benzenedimethanamine |
| EXAMPLE 174 | AMD7274: | N-[(4-dimethylaminophenyl)methyl]-N'-(2-pyridinylmethyl)-N-(6,7,8,9-tetrahydro-5H-cyclohepta[b]pyridin-9-yl)-1,4-benzenedimethanamine |
| EXAMPLE 175 | AMD7275: | N-(4-pyridinylmethyl)-N'-(2-pyridinylmethyl)-N-(5,6,7,8-tetrahydro-8-quinolinyl)-1,4-benzenedimethanamine |
| EXAMPLE 176 | AMD7276: | N-(1-methylbenzimadazol-2-ylmethyl)-N'-(2-pyridinylmethyl)-N-(6,7,8,9-tetrahydro-5H-cyclohepta[b]pyridin-9-yl)-1,4-benzenedimethanamine |
| EXAMPLE 177 | AMD7277: | N-[1-butyl-4-piperidinyl]-N-[2-(2-pyridinyl)ethyl]-N'-(2-pyridinylmethyl)-1,3-benzenedimethanamine |
| EXAMPLE 178 | AMD7278: | N-[1-benzoyl-4-piperidinyl]-N-[2-(2-pyridinyl)ethyl]-N'-(2-pyridinylmethyl)-1,3-benzenedimethanamine |
| EXAMPLE 179 | AMD7290: | N-[1-(benzyl)-3-pyrrolidinyl]-N-[2-(2-pyridinyl)ethyl]-N'-(2-pyridinylmethyl)-1,3-benzenedimethanamine |
| EXAMPLE 180 | AMD7309: | N-[(1-methyl)benzo[b]pyrrol-3-ylmethyl]-N-[2-(2-pyridinyl)ethyl]-N'-(2-pyridinylmethyl)-1,3-benzenedimethanamine |
| EXAMPLE 181 | AMD7311: | N-[1H-imidazol-4-ylmethyl]-N-[2-(2-pyridinyl)ethyl]-N'-(2-pyridinylmethyl)-1,3-benzenedimethanamine |
| EXAMPLE 182 | AMD7359: | N-[1-(benzyl)-4-piperidinyl]-N-[2-(2-pyridinyl)ethyl]-N'-(2-pyridinylmethyl)-1,4-benzenedimethanamine |

TABLE 1-continued

| EXAMPLE 183 AMD7374: | N-[1-methylbenzimidazol-2-ylmethyl]-N-[2-(2-pyridinyl)ethyl]-N'-(2-pyridinylmethyl)-1,4-benzenedimethanamine |
|---|---|
| EXAMPLE 184 AMD7379: | N-[(2-phenyl)benzo[b]pyrrol-3-ylmethyl]-N-[2-(2-pyridinyl)ethyl]-N'-(2-pyridinylmethyl)-1,4-benzenedimethanamine |
| EXAMPLE 185 AMD9025: | N-[(6-methylpyridin-2-yl)methyl]-N'-(2-pyridinylmethyl)-N-(5,6,7,8-tetrahydro-8-quinolinyl)-1,4-benzenedimethanamine |
| EXAMPLE 186 AMD9031: | N-(3-methyl-1H-pyrazol-5-ylmethyl)-N'-(2-pyridinylmethyl)-N-(5,6,7,8-tetrahydro-8-quinolinyl)-1,3-benzenedimethanamine |
| EXAMPLE 187 AMD9032: | N-[(2-methoxyphenyl)methyl]-N'-(2-pyridinylmethyl)-N-(5,6,7,8-tetrahydro-8-quinolinyl)-1,3-benzenedimethanamine |
| EXAMPLE 188 AMD9039: | N-[(2-ethoxyphenyl)methyl]-N'-(2-pyridinylmethyl)-N-(6,7,8,9-tetrahydro-5H-cyclohepta[b]pyridin-9-yl)-1,3-benzenedimethanamine |
| EXAMPLE 189 AMD9045: | N-(benzyloxyethyl)-N'-(2-pyridinylmethyl)-N-(5,6,7,8-tetrahydro-8-quinolinyl)-1,3-benzenedimethanamine |
| EXAMPLE 190 AMD9052: | N-[(2-ethoxy-1-naphthalenyl)methyl]-N'-(2-pyridinylmethyl)-N-(5,6,7,8-tetrahydro-8-quinolinyl)-1,3-benzenedimethanamine |
| EXAMPLE 191 AMD9053: | N-[(6-methylpyridin-2-yl)methyl]-N'-(2-pyridinylmethyl)-N-(5,6,7,8-tetrahydro-8-quinolinyl)-1,3-benzenedimethanamine |

Having now generally described the invention, the same will be more readily understood through reference to the following examples which are provided by way of illustration, and are not intended to be limiting of the present invention, unless specified.

EXAMPLES

Example 1

AMD7490: Preparation of N-(2-pyridinylmethyl)-N'-(6,7,8,9-tetrahydro-5H-cyclohepta[b]pyridin-9-yl)-1,4-benzenedimethanamine (hydrobromide salt)

General Procedure C: Deprotection of the 2-nitobenzenesulfonyl Group (nosyl).

To a stirred solution of the nosyl-protected amine (1 equivalent) in anhydrous $CH_3CN$ (or DMF) (concentration ~0.05 M), at room temperature, was added thiophenol (4–8 equiv.) followed by powdered $K_2CO_3$ (8–12 equivalents). The resulting bright yellow solution was stirred at room temperature (or 50° C.) for 1–24 hours. The solvent was removed under reduced pressure and $CH_2Cl_2$ (10 mL/mmol amine) and water (2 mL/mmol amine) were added to the residue. The phases were separated and the aqueous phase was extracted with $CH_2Cl_2$ (3×5 mL). The combined organic phases were dried ($Na_2SO_4$) and concentrated. Purification of the crude material by chromatography provided the free base.

Alternative work-up: the reaction mixture was filtered and concentrated to provide a yellow oil which was purified by chromatography on basic alumina (eluant $CH_2Cl_2$ then 20:1 $CH_2Cl_2$-$CH_3OH$) and provided the free base as a colorless oil.

To a stirred solution of AMD8812 (0.250 g, 0.448 mmol) in anhydrous $CH_3CN$ (9 mL) was added thiophenol (0.16 mL, 1.56 mmol) followed by powdered $K_2CO_3$ (0.263 g, 1.90 mmol). The reaction mixture was heated at 50° C. overnight then cooled to room temperature. The mixture was filtered and concentrated to provide a yellow oil which was purified by column chromatography on basic alumina ($CH_2Cl_2$ then 20:1 $CH_2Cl_2$-$CH_3OH$) to give the free base as a colorless oil (0.071 g).

General Procedure D: Salt Formation using Saturated HBr (g) in Acetic Acid.

To a solution of the free base in glacial acetic acid (or dioxane) (2 mL) was added, a saturated solution of HBr(g) in acetic acid (or dioxane) (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification (where necessary), the solid can be dissolved in methanol and re-precipitated with a large volume of ether. Washing the solid with ether by decantation, followed by drying of the solid in vacuo (0.1 Torr) gave the desired compound.

Using general procedure D: the free base from above (0.071 g, 0.19 mmol) gave AMD7490 (0.135 g). $^1H$ NMR ($D_2O$) δ 1.27–1.39 (m, 1H), 1.66–2.14 (m, 4H); 2.22–2.31 (m, 1H), 2.82–2.88 (m, 2H), 4.43 (d, 2H, J=4.5 Hz), 4.47 (s, 2H), 4.62 (s, 2H), 4.73 (dd, 1H, J=10.8, 1.5 Hz), 7.37 (dd, 1H, J=5.0, 7.8 Hz), 7.59 (d, 2H, J=8.3 Hz), 7.65 (d, 2H, J=8.3 Hz), 7.73 (dd, 1H, J=1.5, 7.5 Hz), 7.85 (d, 1H, J=7.5 Hz), 7.90 (d, 1H, J=8.4 Hz), 8.35 (td, 1H, J=7.8, 1.0 Hz), 8.45 (dd, 1H, J=1.5, 5.1 Hz), 8.37 (dd, 1H, J=1.0, 5.4 Hz); $^{13}C$ NMR ($D_2O$) δ 26.18, 28.59, 30.21, 33.02, 48.82, 50.07, 51.41, 61.52, 124.41, 127.04 (2 carbons), 131.18 (2 carbons), 131.25 (2 carbons), 131.88, 133.35, 137.98, 139.70, 144.38, 145.59, 146.35, 147.38, 153.76. ES-MS m/z 373 (M+H). Anal. Calcd. for $C_{24}H_{28}N_4.4.0HBr.1.2CH_3CO_2H.1.8H_2O$: C, 39.60; H, 5.09; N, 7.00; Br, 39.92. Found: C, 39.52; H, 5.04; N, 7.02; Br, 40.18.

Example 2

AMD7491: Preparation of N-(2-pyridinylmethyl)-N'-(5,6,7,8-tetrahydro-8-quinolinyl)-1,4-benzenedimethanamine (hydrobromide salt)

To a stirred solution of 8-amino-5,6,7,8-tetrahydroquinoline (0.233, 1.58 mmol) in $CH_2Cl_2$ (16 mL) was added triethylamine (0.33 mL, 2.37 mmol) followed by 2-nitrobenzenesulfonyl chloride (0.374 g, 1.69 mmol). The resultant solution was stirred at room temperature for 24 hours then poured into saturated aqueous $NaHCO_3$ (20 mL). The phases were separated and the aqueous phase was extracted with $CH_2Cl_2$ (3×20 mL). The combined organic extracts were washed with water (2×10 mL), dried ($Na_2SO_4$), and concentrated. Purification of the crude material by flash chromatography (silica gel (24 g), 30:1 $CH_2Cl_2$-$CH_3OH$) provided 0.270 g of a yellow foam.

The foam from above was dissolved in $CH_3CN$ (16 mL), treated with N-[1-methylene-4-(chloromethylene)phenylene]-N-(2-nitrobenzenesulfonyl)-2-(aminomethyl)pyridine (Bridger et al. WO 00/02870) (0.412 g, 0.89 mmol) and $K_2CO_3$ (0.279 g, 2.02 mmol) and heated to reflux for 22 hours. The mixture was cooled to room temperature, concentrated, and partitioned between $CH_2Cl_2$ (30 mL) and water (10 mL). The phases were separated and the aqueous phase was extracted with $CH_2Cl_2$ (2×10 mL). The combined organic extracts were dried ($Na_2SO_4$) and concentrated.

Purification of the crude material by column chromatography (silica gel, 30:1 $CH_2Cl_2$-$CH_3OH$) provided 0.448 g of a yellow solid.

The yellow solid was reacted with thiophenol (0.40 mL, 3.90 mmol) and $K_2CO_3$ (0.628 g, 4.54 mmol) in $CH_3CN$ (11 mL) using general procedure C. The crude product was purified on basic alumina ($CH_2Cl_2$ followed by 20:1 $CH_2Cl_2$-$CH_3OH$) followed by radial chromatography on silica gel (1 mm plate, 20:1:1 $CHCl_3$-$CH_3OH$-$NH_4OH$) to provide the free base (0.035 g) as a colorless oil. Conversion to the hydrobromide salt using General Procedure D gave AMD7491 (0.079 g) as a white solid. $^1H$ NMR ($D_2O$) δ 1.92–2.11 (m, 2H), 2.25–2.47 (m, 2H), 2.93–3.11 (m, 2H), 4.46 (s, 2H), 4.47 (d, 1H, J=13.2 Hz), 4.55 (d, 1H, J=13.2 Hz), 4.62 (s, 2H), 4.74–4.79 (m, 1H, overlaps with HOD), 7.59–7.69 (m, 5H), 7.81–7.90 (m, 2H), 8.05 (d, 1H, J=7.8 Hz), 8.33 (tt, 1H, J=7.8, 1.5 Hz), 8.58 (br d, 1H, J=4.5 Hz), 8.77 (br d, 1H, J=5.4 Hz); $^{13}C$ NMR ($D_2O$) δ 18.01, 24.58, 27.18, 48.99, 49.11, 51.35, 55.79, 126.20, 126.91 (2 carbons), 131.26 (2 carbons), 131.32 (2 carbons), 132.11, 132.64, 137.53, 143.56, 144.02, 145.02, 146.45, 146.56, 147.56. ES-MS m/z 359 (M+H). Anal. Calcd. for $C_{23}H_{26}N_4$.4.1HBr.1.8$H_2O$: C, 38.23; H, 4.70; N, 7.75; Br, 45.33. Found: C, 38.21; H, 4.63; N, 7.55; Br, 45.50.

Example 3

AMD7492: Preparation of N-(2-pyridinylmethyl)-N'-(6,7-dihydro-5H-cyclopenta[b]pyridin-7-yl)-1,4-benzenedimethanamine (hydrobromide salt)

To a stirred solution of 7-amino-6,7-dihydro-5H-cyclopenta[b]pyridine (0.150 g, 1.12 mmol) in anhydrous methanol (7 mL), at room temperature, was added N-[1-methylene-4-(carboxaldehyde)phenylene]-N-(2-nitrobenzenesulfonyl)-2-(aminomethyl)pyridine (0.30 g, 0.733 mmol) and the solution was stirred at room temperature overnight. $NaBH_3CN$ (0.137 g, 2.18 mmol) was added to the solution and the reaction mixture was stirred at room temperature for 24 hours. The solvent was removed under reduced pressure and the residue was dissolved in 1.0 M aqueous NaOH (10 mL). The aqueous solution was extracted with $CH_2Cl_2$ (3×10 mL) and the combined organic extracts were dried ($Na_2SO_4$) and concentrated. Purification of the crude material by radial chromatography on silica gel (2 mm plate, 25:1 $CH_2Cl_2$-$CH_3OH$) provided 0.254 g of the secondary amine as a red oil.

Using General Procedures C and D: The oil from above was reacted with thiophenol (0.17 mL, 1.66 mmol) and $K_2CO_3$ (0.280 g, 2.03 mmol) in $CH_3CN$ (10 mL). The crude material was purified by chromatography on basic alumina (25 g, eluant $CH_2Cl_2$ followed by 20:1 $CH_2Cl_2$-$CH_3OH$) to give 0.053 g of the free amine as a brown oil. Salt formation gave AMD7492 (0.124 g) as a white solid. $^1H$ NMR ($D_2O$) δ 2.43–2.52 (m, 1H), 2.77–2.86 (m, 1H); 3.17 (ddd, 1H, J=17.1, 9.0, 4.8 Hz), 3.31 (dd, 1H, J=17.1, 8.1 Hz), 4.47 (s, 2H), 4.53 (s, 2H), 4.63 (s, 2H), 5.10 (dd, 1H, J=4.5, 8.4 Hz), 7.61 (s, 4H), 7.73 (dd, 1H, J=5.4, 7.8 Hz), 7.84–7.92 (m, 2H), 8.21 (d, 1H, J=72 Hz), 8.35 (td, 1H, J=7.8, 1.5 Hz), 8.61 (d, 1H, J=5.1 Hz), 8.77 (d, 1H, J=5.4 Hz); $^{13}C$ NMR ($D_2O$) δ 27.45, 28.34, 48.88, 49.64, 51.37, 61.32, 126.91, 127.01, 127.04, 131.20 (2 carbons), 131.35 (2 carbons), 132.11, 132.60, 139.92, 142.65, 144.29, 145.69, 146.39, 147.39, 153.21. ES-MS m/z 345 (M+H). Anal. Calcd. for $C_{22}H_{24}N_4$.3.9HBr.0.2 $CH_3CO_2H$.1.7$H_2O$: C, 38.29; H, 4.60; N, 7.97; Br, 44.35. Found: C, 38.21; H, 4.62; N, 7.94; Br, 44.44.

Example 4

AMD8766: Preparation of N-(2-pyridinylmethyl)-N'-(1,2,3,4-tetrahydro-1-naphthalenyl)-1,4-benzenedimethanamine (hydrobromide salt)

General Procedure E: Reductive Amination via Hydrogenation.

1-amino-1,2,3,4-tetrahydronapthalene (0.104 g, 0.70 mmol) was condensed with N-[1-methylene-4-(carboxaldehyde)phenylene]-N-(t-butyloxycarbonyl)-2-(amino methyl) pyridine (0.182 g, 0.56 mmol) in methanol (5.5 mL) overnight. Palladium on activated carbon (10%, 48 mg) was added and the mixture was hydrogenated (1 atmosphere) at room temperature overnight. The reaction mixture was filtered through celite and the cake was washed with methanol. The combined filtrates were evaporated under reduced pressure and the residue was purified by radial chromatography on silica gel (2 mm plate, 25:1 $CH_2Cl_2$-$CH_3OH$) to give a colourless oil (0.100 g). Conversion to the hydrobromide salt using General Procedure D gave AMD8766 as a white solid (0.099 g). $^1H$ NMR ($D_2O$) δ 1.85–1.91 (m, 2H), 2.03–2.16 (m, 1H), 2.22–2.31 (m, 1H), 2.78 (ddd, 1H, J=17.4, 7.5, 7.5 Hz), 2.90 (ddd, 1H, J=17.4, 5.1, 5.1 Hz), 4.33 (d, 2H, J=4.2 Hz), 4.43 (s, 2H), 4.55 (dd, 1H, J=4.5, 4.5 Hz), 4.62 (s, 2H), 7.24–7.37 (m, 4H), 7.52–7.58 (m, 4H), 7.84–7.94 (m, 2H), 8.36 (td, 1H, J=7.8, 1.5 Hz), 8.74 (br d, 1H, J=5.4 Hz); $^{13}C$ NMR ($D_2O$) δ 17.92, 25.25, 28.15, 48.45, 48.57, 51.41, 56.36, 126.81, 127.20, 127.31, 129.77, 129.92, 129.99, 130.51, 131.18 (2 carbons), 131.29 (2 carbons), 131.79, 132.92, 139.33, 144.87, 145.87, 146.99. ES-MS m/z 358 (M+H). Anal. Calcd. for $C_{24}H_{27}N_3$.3.0HBr.0.5$H_2O$: C, 47.32; H, 5.13; N, 6.90; Br, 39.35. Found: C, 47.40; H, 5.04; N, 6.96; Br, 39.25.

Example 5

AMD8789: Preparation of N-(2-pyridinylmethyl)-N'-(1-naphthalenyl)-1,4-benzenedimethanamine (hydrobromide salt)

1-Aminonapthalene (0.100 g, 0.70 mmol) was condensed with N-[1-methylene-4-(carboxaldehyde)phenylene]-N-(t-butyloxycarbonyl)-2-(aminomethyl)pyridine (0.182 g, 0.56 mmol) in methanol (6 mL) overnight and the corresponding imine was reduced with $NaBH_4$ (0.051 g, 1.35 mmol) (see General Procedures A and B). Purification of the crude material by radial chromatography on silica gel (2 mm plate, 100:1 $CH_2Cl_2$-$CH_3OH$) provided 0.168 g of a colorless oil.

The oil was converted to the hydrobromide salt using HBr/acetic acid (General Procedure D) to give a white solid (0.156 g). The solid was partitioned between $CH_2Cl_2$ (10 mL) and 10 M aqueous solution of NaOH (5 mL). The phases were separated and the aqueous phase was extracted with $CH_2Cl_2$ (3×10 mL). The combined organic extracts were dried ($Na_2SO_4$) and concentrated. Purification of the residue by radial chromatography on silica gel (1 mm plate, 100:5:1 $CH_2Cl_2$-$CH_3OH$-$NH_4OH$) gave a colorless oil (0.04 g). Formation of the hydrobromide salt for a second time using General Procedure D provided a pure sample of AMD8789 (0.040 g) as a white solid. $^1H$ NMR ($D_2O$) δ 4.32 (s, 2H), 4.41 (s, 2H), 4.79 (s, 2H, overlaps with HOD), 7.25 (d, 2H, J=7.8 Hz), 7.31–7.37 (m, 3H), 7.46 (dd, 1H, J=7.8, 7.8 Hz), 7.54–7.66 (m, 2H), 7.74–7.79 (m, 2H), 7.86 (d, 1H, J=8.4 Hz), 7.99 (d, 2H, J=8.1 Hz), 8.26 (t, 1H, J=7.8 Hz), 8.70 (d, 1H, J=5.1 Hz); $^{13}C$ NMR ($D_2O$) δ 48.95, 50.99, 54.62, 120.39, 125.43, 125.98, 126.38, 126.48, 127.66, 129.55, 129.81, 130.90, 131.84, 132.02, 132.19, 134.45, 143.07, 147.09, 147.95. ES-MS m/z 354 (M+H). Anal. Calcd. for $C_{24}H_{23}N_3 \cdot 2.9HBr \cdot 1.3H_2O$: C, 47.14; H, 4.70; N, 6.87; Br, 37.89. Found: C, 47.22; H, 4.76; N, 6.63; Br, 37.88.

Example 6

AMD8776: Preparation of N-(2-pyridinylmethyl)-N'-(8-quinolinyl)-1,4-benzenedimethanamine (hydrobromide salt)

To a stirred solution of 8-aminoquinoline (0.130 g, 0.902 mmol) in $CH_3CN$ (17 mL) was added N-[1-methylene-4-(chloromethylene)phenylene]-N-(2-nitrobenzenesulfonyl)-2-(aminomethyl)pyridine (0.364 g, 0.843 mmol) followed by $K_2CO_3$ (0.237 g, 1.72 mmol) and NaI (0.013 g, 0.084 mmol). The reaction mixture was heated to reflux for 5 days then cooled to room temperature. The mixture was concentrated and the residue was partitioned between $CH_2Cl_2$ (20 mL) and water (10 mL). The phases were separated and the aqueous phase was extracted with $CH_2Cl_2$ (3×20 mL). The combined organic extracts were dried ($Na_2SO_4$) and concentrated. Purification of the crude material by radial chromatography on silica gel (2 mm plate, 100:1 $CH_2Cl_2$-$CH_3OH$) provided 0.205 g of a yellow solid.

Using General Procedure C: The yellow solid (0.205 g, 0.38 mmol) was reacted with thiophenol (0.20 mL, 1.95 mmol) and $K_2CO_3$ (0.503 g, 3.64 mmol) in $CH_3CN$ (7 mL). Purification of the crude product by radial chromatography on silica gel (2 mm plate, 200:10:2 $CH_2Cl_2$-$CH_3OH$-$NH_4OH$) gave the free base as a yellow oil (0.107 g). Conversion to the hydrobromide salt using General Procedure D gave the crude product, which was re-precipitated from methanol/ether and dried in vacuo to give AMD8776 as a red-orange solid (0.153 g). $^1H$ NMR ($D_2O$) δ 4.37 (s, 2H), 4.55 (s, 2H), 4.64 (s, 2H), 7.20 (d, 1H, J=7.2 Hz), 7.42–7.64 (m, 6H), 7.77–7.93 (m, 3H), 8.26–8.33 (m, 1H), 8.69 (d, 1H, J=4.8 Hz), 8.88 (d, 1H, J=8.4 Hz), 8.92 (d, 1H, J=5.4 Hz); $^{13}C$ NMR ($D_2O$) δ 48.11, 48.53, 51.49, 116.37, 119.53, 121.98, 126.95, 127.06, 129.09 (2 carbons), 129.76, 130.41, 130.52, 130.53, 130.83 (2 carbons), 137.79, 139.52, 143.60, 144.40, 146.09, 146.90, 147.30. ES-MS m/z 355 (M+H). Anal. Calcd. for $C_{23}H_{22}N_4 \cdot 3.0HBr \cdot 0.9H_2O$: C, 45.04; H, 4.40; N, 9.13; Br, 39.08. Found: C, 45.14; H, 4.22; N, 9.06; Br, 38.86.

Example 7

AMD8859: Preparation of N-(2-pyridinylmethyl)-N'-[2-[(2-pyridinylmethyl)amino]ethyl]-N'-(1-methyl-1,2,3,4-tetrahydro-8-quinolinyl)-1,4-benzenedimethanamine Preparation of 8-amino-1,2,3,4-tetrahydroquinoline.

A mixture of 8-nitroquinoline (1.035 g, 5,94 mmol) and platinum oxide (35 mg, 0.15 mmol, 2.5 mol %) in glacial acetic acid was hydrogenated (20 psi) on a Parr Shaker at room temperature for 20 hours. The mixture was filtered through celite and the cake was washed with methanol. The solvent was removed from the filtrate to afford a red oil. The oil was dissolved in a mixture of $CH_2Cl_2$ (25 mL) and saturated aqueous $NaHCO_3$ (10 mL) and a 10 M aqueous solution of sodium hydroxide was added dropwise until the aqueous phase was basic (pH ~14) to litmus paper. The phases were separated and the aqueous phase was extracted with $CH_2Cl_2$ (3×10 mL). The combined organic extracts were washed once with water (10 mL), dried ($Na_2SO_4$), and concentrated. The residue was filtered (100:1 $CH_2Cl_2$-$CH_3OH$) through a short pad of silica gel (30 g) and afforded 0.699 g (79%) of 8-amino-1,2,3,4-tetrahydroquinoline as an oil. $^1H$ NMR ($CDCl_3$) δ 1.89–1.97 (m, 2H), 2.79 (t, 2H, J=6.3 Hz), 3.34 (t, 2H, J=5.4 Hz), 3.20–3.60 (br signal, 3H, N$\underline{H}$ & N$\underline{H}_2$), 6.55–6.64 (m, 3H); $^{13}C$ NMR ($CDCl_3$) δ 22.79, 27.44, 42.98, 114.50, 118.47, 121.56, 123.70, 134.24 (2 carbons).

8-(tert-butoxycarbonylamino)-1,2,3,4-tetrahydroquinoline.

To a stirred solution of 8-amino-1,2,3,4-tetrahydroquinoline (0.530 g, 3.58 mmol) in THF (30 mL) and water (3 mL), at room temperature, was added di-tert-butyl dicarbonate (0.782 g, 3.58 mmol). After 5 hours, the mixture was poured into water (10 mL) and diluted with ethyl acetate (50 mL). The phases were separated and the aqueous phase was extracted with ethyl acetate (3×10 mL). The combined organic extracts were dried ($MgSO_4$) and concentrated. Purification of the crude material by radial chromatography (4 mm plate, 5:1 hexanes-ethyl acetate) provided 0.650 g (73%) of 8-(-tert-butoxycarbonylamino)-1,2,3,4-tetrahydroquinoline as a white solid. $^1H$ NMR ($CDCl_3$) δ 1.51 (s, 9H), 1.86–1.94 (m, 2H), 2.78 (t, 2H, J=6.3 Hz), 3.32 (t, 2H, J=5.4 Hz), 3.88 (br s, 1H, N$\underline{H}$), 6.01 (br s, 1H, N$\underline{H}$), 6.64 (dd, 1H, J=7.8, 7.2 Hz), 6.82 (d, 1H, J=7.2 Hz), 7.13 (d, 1H, J=7.8 Hz); $^{13}C$ NMR ($CDCl_3$) δ 21.97, 27.20, 28.34 (3 carbons), 42.20, 80.36, 117.25, 122.37, 123.65, 126.55 (2 carbons), 138.38, 154.08. ES-MS m/z 271 (M+Na).

1-Methyl-8-(N-tert-butoxycarbonylamino)-1,2,3,4-tetrahydroquinoline

To a stirred solution of 8-(N-tert-butoxycarbonylamino)-1,2,3,4-tetrahydroquinoline (0.876 g, 3.52 mmol) in $CH_2Cl_2$ (35 mL), at room temperature was added excess methyl iodide (2 mL, 32.12 mmol). The mixture was stirred at room temperature for 48 hours. The mixture was poured into saturated aqueous $NaHCO_3$ (25 mL) and diluted with $CH_2Cl_2$ (25 mL). The phases were separated and the aqueous phase was extracted with $CH_2Cl_2$ (3×25 mL). The combined organic extracts were dried ($Na_2SO_4$) and concentrated. Purification of the crude material by flash chromatography (36 g silica gel, 10:1 hexanes-ethyl acetate) provided 0.83 g (90%) of 1-methyl-8-(N-tert-butoxycarbonylamino)-1,2,3,4-tetrahydroquinoline as a colorless oil. $^1H$ NMR ($CDCl_3$) δ 1.53 (s, 9H), 1.84–1.92 (m, 2H), 2.62 (s, 3H), 2.79 (t, 2H, J=6.6 Hz), 3.03–3.07 (m, 2H), 6.73 (d, 1H, J=7.8 Hz), 6.95 (dd, 1H, J=7.8, 7.8 Hz), 7.18 (br s, 1H, N$\underline{H}$), 7.82 (br d, 1H, J=7.8 Hz).

1-Methyl-8-amino-1,2,3,4-tetrahydroquinoline

Anhydrous HCl (gas) was bubbled through a stirred solution of 1-methyl-8-(N-tert-butoxycarbonylamino)-1,2,3,4-tetrahydroquinoline (0.83 g, 3.16 mmol) in methanol (30 mL), at room temperature, for 10 minutes. The resultant solution was stirred at room temperature for 1 hour then concentrated under reduced pressure. The residue was partitioned between $CH_2Cl_2$ (50 mL) and aqueous NaOH (10 N, 10 mL). The phases were separated and the aqueous phase was extracted with $CH_2Cl_2$ (3×10 mL). The combined organic extracts were dried ($Na_2SO_4$) and concentrated to afford 0.468 g (88%) of 1-methyl-8-amino-1,2,3,4-tetrahydroquinoline as a white solid. $^1$H NMR (CDCl$_3$) δ 1.83–1.91 (m, 2H), 2.69 (s, 3H), 2.78 (t, 2H, J=6.6 Hz), 3.07–3.11 (m, 2H), 3.84 (br s, 2H, NH$_2$), 6.52 (d, 1H, J=7.5 Hz), 6.56 (d, 1H, J=7.5 Hz), 6.81 (dd, 1H, J=7.5, 7.5 Hz).

Preparation of N-(2-nitrobenzenesulfonyl)-N-(2-pyridinylmethyl)-N-(1-methyl-1,2,3,4-tetrahydro-8-quinolinyl)-1,4-benzenedimethanamine Using general procedure B: Reaction of 1-methyl-8-amino-1,2,3,4-tetrahydroquinoline (0.451 g, 2.78 mmol) and N-[1-methylene-4-(carboxaldehyde)phenylene]-N-(2-nitrobenzenesulfonyl)-2-(aminomethyl)pyridine (1.268 g, 3.08 mmol) with NaBH(OAc)$_3$ (0.896 g, 4.23 mmol) in CH$_2$Cl$_2$ (28 mL) for 3.5 hours followed by purification of the crude material by flash chromatography (36 g silica gel, 1:2 hexanes-ethyl acetate) provided 1.44 g (93%) of the title compound as an orange solid. $^1$H NMR (CDCl$_3$) δ 1.84–1.93 (m, 2H), 2.68 (s, 3H), 2.79 (t, 2H, J=6.6 Hz), 3.06–3.09 (m, 2H), 4.27 (s, 2H), 4.59 (s, 2H), 4.62 (s, 2H), 4.73 (t, 1H, J=4.8 Hz), 6.35 (d, 1H, J=7.8 Hz), 6.48 (d, 1H, J=7.5 Hz), 6.85 (dd, 1H, J=7.8, 7.5 Hz), 7.09–7.14 (m, 3H), 7.23–7.26 (m, 3H), 7.52–7.57 (m, 2H), 7.61–7.68 (m, 2H), 7.95 (d, 1H, J=7.8 Hz), 8.42 (d, 1H, J=4.5 Hz).

N-(2-nitrobenzenesulfonyl)-N-(2-pyridinylmethyl)-N'-[2-(aminoethyl)]-N'-(1-methyl-1,2,3,4-tetrahydro-8-quinolinyl)-1,4-benzenedimethanamine.

Using General Procedure B: The solid from above (0.724 g, 1.30 mmol) was reacted with N-tert-butoxycarbonyl-2-amino-acetaldehyde (0.484 g, 3.04 mmol), NaBH(OAc)$_3$ (0.633 g, 2.99 mmol), glacial acetic acid (0.17 mL, 2.97 mmol) in CH$_2$Cl$_2$ (13 mL) for 21 hours. Purification of the crude material by radial chromatography on silica gel (4 mm plate, 1:1 hexanes-ethyl acetate) provided 0.91 g of a yellow oil. The oil was dissolved in CH$_2$Cl$_2$ (1 mL) and treated with trifluoroacetic acid (1 mL). The resultant solution was stirred at room temperature for 3 hours then concentrated under reduced pressure. The residue was dissolved in CH$_2$Cl$_2$ (20 mL) and saturated aqueous NaHCO$_3$ (20 mL) and the aqueous phase was made basic (pH 14) using 10 M aqueous NaOH (~2 mL). The phases were separated and the aqueous phase was extracted with CH$_2$Cl$_2$ (3×20 mL). The combined organic extracts were dried (Na$_2$SO$_4$) and concentrated. Purification of the crude material by radial chromatography on silica gel (2 mm plate, 20:1 CH$_2$Cl$_2$-MeOH containing 1% NH$_4$OH) provided the title compound (0.469 g, 60% for two steps) as a yellow solid. $^1$H NMR (CDCl$_3$) δ 1.44 (br s, 2H, NH$_2$), 1.79–1.87 (m, 2H), 2.73 (t, 2H, J=6.3 Hz), 2.79 (t, 2H, J=6.3 Hz), 2.96 (s, 3H), 3.01 (t, 2H, J=6.3 Hz), 3.10–3.14 (m, 2H), 4.27 (s, 2H), 4.56 (s, 2H), 4.59 (s, 2H), 6.70–6.78 (m, 3H), 7.06–7.12 (m, 5H), 7.20 (d, 1H, J=7.8 Hz), 7.50–7.56 (m, 2H), 7.61–7.68 (m, 2H), 7.95 (d, 1H, J=7.8 Hz), 8.41 (d, 1H, J=4.8 Hz).

N-(2-pyridinylmethyl)-N'-[2-[(2-pyridinylmethyl)amino]ethyl]-N'-(1-methyl-1,2,3,4-tetrahydro-8-quinolinyl)-1,4-benzenedimethanamine (AMD8859).

Using General Procedure B: The solid from above (0.216 g, 0.36 mmol), pyridine-2-carboxaldehyde (30 μL, 0.32 mmol), and NaBH(OAc)$_3$ (0.119 g, 0.56 mmol), were reacted in CH$_2$Cl$_2$ (7 mL) for 3 hours. Purification of the crude material by radial chromatography on silica gel (2 mm plate, 20:1 CH$_2$Cl$_2$-CH$_3$OH containing 2% NH$_4$OH) provided 0.215 g of a yellow oil. Using General Procedure C, the title compound was obtained by reaction of the oil from above (0.215 g, 0.31 mmol) with thiophenol (0.20 mL, 1.95 mmol) and K$_2$CO$_3$ (0.555 g, 4.02 mmol) in CH$_3$CN (6 mL). Purification of the crude material by radial chromatography on silica gel (2 mm plate, 40:2:1 CH$_2$Cl$_2$-CH$_3$OH-NH$_4$OH) gave AMD8859 (0.120 g, 68%) as a colorless oil. $^1$H NMR (CDCl$_3$) δ 1.76–1.84 (m, 2H), 2.74 (t, 2H, J=6.6 Hz), 2.78 (t, 2H, J=6.6 Hz), 2.96 (s, 3H), 3.07–3.11 (m, 2H), 3.19 (t, 2H, J=6.5 Hz), 3.81 (s, 4H), 3.92 (s, 2H), 4.30 (s, 2H), 6.70–6.79 (m, 4H), 7.10–7.33 (m, 7H), 7.57–7.67 (m, 2H), 8.52 (br d, 1H, J=4.2 Hz), 8.56 (br d, 1H, J=4.2 Hz); $^{13}$C NMR (CDCl$_3$) δ 18.33, 28.96, 41.63, 46.94, 49.79, 52.67, 53.69, 54.98, 55.46, 56.43, 119.54, 121.08, 122.21, 122.23, 122.41, 122.76, 124.50, 128.43 (2 carbons), 129.50 (2 carbons), 129.96, 136.77, 136.83, 138.03, 138.98, 142.91, 143.19, 149.59, 149.70, 160.22, 160.29. ES-MS m/z 507 (M+H).

Example 8

AMD8867: Preparation of N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzene dimethanamine Reaction of N-(2-nitrobenzenesulfonyl)-N-(2-pyridinylmethyl)-N'-[2-(aminoethyl)]-N'-(1-methyl-1,2,3,4-tetrahydro-8-quinolinyl)-1,4-benzenedimethanamine (0.140 g, 0.23 mmol) with imidazole-2-carboxaldehyde (0.023 g, 0.24 mmol) in CH$_2$Cl$_2$ (7 mL) overnight, followed by reduction of the corresponding imine with NaBH$_4$ (0.039 g, 1.02 mmol) in CH$_2$Cl$_2$ and purification of the crude material by radial chromatography silica gel (2 mm plate, 40:2:1 CH$_2$Cl$_2$-CH$_3$OH-NH$_4$OH) provided 0.108 g of a yellow solid. Using General Procedure C: the free base of the title compound was obtained by reaction of the solid from above (0.108 g, 0.16 mmol) with thiophenol (0.10 mL, 0.97 mmol) and K$_2$CO$_3$ (0.223 g, 1.61 mmol) in CH$_3$CN (4 mL). Purification of the crude product by radial chromatography on silica gel (2 mm plate, 10:1:1 CH$_2$Cl$_2$-CH$_3$OH-NH$_4$OH) gave AMD8867 (0.072 g, 64%) as a colorless oil. $^1$H NMR (CDCl$_3$) δ 1.76–1.83 (m, 2H), 1.90–2.50 (br s 2H, NH), 2.61 (t, 2H, J=6.3 Hz), 2.77 (t, 2H, J=6.3 Hz), 2.93 (s, 3H), 3.03–3.07 9 m, 2H), 3.14 (t, 2H, J=5.7 Hz), 3.72 (s, 2H), 3.81 (s, 2H), 3.93 (s, 2H), 4.26 (s, 2H), 6.74–6.87 (m, 5H), 7.14–7.34 (m, 6H), 7.64 (td, 1H, J=7.8, 1.5 Hz), 8.55 (br d, 1H, J=4.5 Hz), 9.54–10.06 (br s, 1H, NH). $^{13}$C NMR (CDCl$_3$) δ 18.13, 28.86, 41.83, 47.04, 47.28, 49.65, 52.58, 53.65, 54.95, 57.19, 119.79, 121.38, 122.40 (2 carbons), 122.79 (2 carbons), 124.87, 128.59 (2 carbons), 129.50 (2 carbons), 130.22, 136.90, 137.99, 139.16, 143.23, 143.55, 147.70, 149.68, 160.11. ES-MS m/z 496 (M+H). Anal. Calcd. for C$_{30}$H$_{37}$N$_7$.0.7H$_2$O: C, 70.89; H, 7.61; N, 19.29. Found: C, 71.09; H, 7.64; N, 19.39.

Example 9

AMD8746: Preparation of N-(2-pyridinylmethyl)-N'-(1,2,3,4-tetrahydro-8-quinolinyl)-1,4-benzene-dimethanamine (hydrobromide salt)

A stirred solution of 8-amino-1,2,3,4-tetrahydroquinoline (0.136 g, 0.92 mmol) and N-[1-methylene-4-(carboxaldehyde)phenylene]-N-(2-nitrobenzenesulfonyl)-2-(aminomethyl)pyridine (0.370 g, 0.90 mmol) in benzene (20 mL) was heated to reflux under Dean-Stark conditions for 24 hours.

The mixture was concentrated, dissolved in MeOH (10 mL) and THF (2 mL) and treated with NaBH$_3$CN (0.094 g, 1.49 mmol) for 72 hours. The mixture was concentrated and partitioned between CH$_2$Cl$_2$ (20 mL) and a 1.0 M aqueous solution of NaOH (5 mL). The phases were separated and the aqueous phase was extracted with CH$_2$Cl$_2$ (3×10 mL). The combined organic extracts were dried (Na$_2$SO$_4$) and concentrated. Purification of the crude material by flash chromatography (24 g silica gel, 20:1 CH$_2$Cl$_2$-CH$_3$OH) gave the desired product (0.137 g).

Using General Procedures C and D: The intermediate from above (0.137 g, 0.252 mmol) was reacted with thiophenol (0.18 mL, 1.75 mmol) and K$_2$CO$_3$ (0.361 g, 2.61 mmol) in CH$_3$CN (5 mL). Purification of the crude product by radial chromatography on silica gel (2 mm plate, 15:1 CH$_2$Cl$_2$-CH$_3$OH) gave the free base of the title compound as a yellow oil (0.065 g). Conversion to the hydrobromide salt gave AMD8746 as a white solid (0.129 g). $^1$H NMR (D$_2$O) δ 2.07–2.11 (m, 2H), 2.89 (t, 2H, J=6.0 Hz), 3.58 (dd, 2H, J=5.4, 5.4 Hz), 4.43 (s, 2H), 4.52 (s, 2H), 4.65 (s, 2H), 6.62 (d, 1H, J=8.1 Hz), 6.74 (d, 1H, J=8.1 Hz), 7.13 (t, 1H, J=8.1 Hz), 7.48 (s, 4H), 7.89–7.98 (m, 2H), 8.43 (br t, 1H, J=7.8 Hz), 8.77 (d, 1H, J=5.4 Hz); $^{13}$C NMR (D$_2$O) δ 19.43, 25.51, 43.70, 47.32, 48.13, 51.70, 112.57, 118.77, 120.65, 127.42, 127.63, 128.70 (2 carbons), 128.94, 129.36, 130.82 (2 carbons), 132.98, 139.89, 140.77, 145.37, 145.58, 146.71. ES-MS m/z 359 (M+H). Anal. Calcd. for C$_{23}$H$_{26}$N$_4$.3.6HBr.0.8CH$_3$CO$_2$H.2.1H$_2$O: C, 40.17; H, 5.07; N, 7.62; Br, 39.10. Found: C, 40.26; H, 4.71; N, 7.76; Br, 38.91.

Example 10

AMD8835: Preparation of N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine (hydrobromide salt)

1-Amino-1,2,3,4-tetrahydronapthalene (0.154 g, 1.05 mmol) was condensed with imidazole-2-carboxaldehyde (0.103 g, 1.07 mmol) in methanol (10 mL) overnight. The resulting imine was then hydrogenated (30 psi, room temperature) over Pd/C (10%, 34 mg) overnight. The mixture was filtered through celite and the cake was washed with methanol. The combined filtrates were evaporated under reduced pressure and the residue was purified by radial chromatography on silica gel (2 mm plate, 20:1 CH$_2$Cl$_2$-CH$_3$OH containing 1% NH$_4$OH) to give a colorless oil (0.202 g).

The oil was reacted with N-[1-methylene-4-(carboxaldehyde)phenylene]-N-(2-nitrobenzenesulfonyl)-2-(aminomethyl)pyridine (0.368 g, 0.89 mmol) and NaBH$_3$CN (0.137 g, 2.18 mmol) in methanol (9 mL) with stirring at room temperature for 24 hours. The mixture was concentrated and partitioned between CH$_2$Cl$_2$ (30 mL) and water (10 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (2 mm plate, 25:1 CH$_2$Cl$_2$-CH$_3$OH) provided 0.365 g of a white solid.

Using General procedures C and D: The solid from above (0.345 g, 0.55 mmol) was treated with thiophenol (0.35 mL, 3.41 mmol) and K$_2$CO$_3$ (0.773 g, 5.59 mmol) in CH$_3$CN (11 mL). The crude product was purified by radial chromatography on silica gel (2 mm plate, 100:4:1 CH$_2$Cl$_2$-CH$_3$OH-NH$_4$OH) to give the free base of the title compound as a yellow solid (0.096 g). Conversion to the hydrobromide salt gave AMD8835 as a white solid (0.128 g). $^1$H NMR (D$_2$O) δ 1.51–1.62 (m, 1H), 1.90–2.04 (m, 2H), 2.20–2.25 (m, 1H), 2.66–2.80 (m, 2H), 3.98 (s, 2H), 4.21 (d, 1H, J=12.6 Hz), 4.31–4.44 (m, 4H), 4.56 (s, 2H), 7.14–7.30 (m, 5H), 7.40 (s, 4H), 7.75 (br d, 1H, J=7.5 Hz), 7.81 (br d, 1H, J=6.6 Hz), 7.87 (br d, 1H, J=7.8 Hz), 8.32 (br t, 1H, J=7.8 Hz), 8.70 (br d, 1H, J=5.4 Hz); $^{13}$C NMR (D$_2$O) δ 21.48, 22.23, 29.43, 46.15, 48.45, 51.43, 55.95, 62.17, 119.74, 126.94, 127.10, 127.25, 128.37, 128.73, 130.00, 130.20, 130.55, 130.83, 140.64, 144.79, 145.81, 147.03. ES-MS m/z 438 (M+H). Anal. Calcd. for C$_{28}$H$_{31}$N$_5$.4.1HBr.2.4H$_2$O: C, 41.39; H, 4.95; N, 8.62; Br, 40.32. Found: C, 41.14; H, 4.62; N, 9.01; Br, 40.32.

Preparation of
8-hydroxy-2-phenyl-5,6,7,8-tetrahydroquinoline
(AMD8786)

To a vigorously stirred solution of 2-phenylquinoline (6.0 g, 29 mmol) in TFA (30 mL) in a 250 mL round-bottomed flask under nitrogen was added PtO$_2$ (332 mg, 1.5 mmol) in one portion. The resulting mixture was then placed under a hydrogen atmosphere (H$_2$ flush for 5 min, then H$_2$ balloon with a wide-bore needle) and heated to 60° C. Stirring was continued for 5 h, at which time GLC analysis indicated all of the starting material was consumed. The reaction was cooled to room temperature and the TFA was evaporated in vacuo. The residue was rendered basic with a minimum amount of 4 N NaOH and extracted with CHCl$_3$ (3×50 mL), dried (MgSO$_4$) and concentrated in vacuo. Purification of the residue by flash chromatography (silica gel, hexane/EtOAc 10:1) afforded 4.85 g of 2-phenyl-5,6,7,8-tetrahydroquinoline (80% yield).

To a stirred solution of 2-phenyl-5,6,7,8-tetrahydroquinoline (3.80 g, 18 mmol) in glacial acetic acid (10 mL) was added a 30 wt. % aqueous solution of H$_2$O$_2$ (2 mL) and the resulting mixture was stirred at 70° for 18 h; at this point, another portion of H$_2$O$_2$ solution (2 mL) was added and stirring was continued for 2 days. The solution was cooled to room temperature and Na$_2$CO$_3$ (10 g) and CHCl$_3$ (20 mL) were added. The resulting mixture was allowed to sit 15 min then filtered and the aqueous phase was extracted with CHCl$_3$ (3×20 mL); the organic fractions were then combined, dried (MgSO$_4$) and concentrated. The residue was then taken up in acetic anhydride (20 mL) and heated at 90° C. for 4 h with stirring. Removal of the Ac$_2$O under reduced pressure afforded a pale yellow oil which was taken up in methanol (30 mL) and treated with K$_2$CO$_3$ (100 mg, 0.72 mmol). The resulting mixture was stirred overnight. A solution of 4 N NaOH (10 mL) was added and the mixture was extracted with CHCl$_3$ (3×20 mL), dried (MgSO$_4$) and concentrated in vacuo. Purification of the crude product by column chromatography (silica gel, hexane/EtOAc 4:1) afforded 3.0 g of 8-hydroxy-2-phenyl-5,6,7,8-tetrahydroquinoline AMD 8786 (74% yield) as a white solid. $^1$H NMR (CDCl$_3$) δ 1.78–1.81 (m, 2H), 1.97–2.02 (m, 1H), 2.31–2.33 (m, 1H), 2.76–2.79 (m, 2H), 4.43 (s, 1H), 4.71 (t, 1H, J=7 Hz), 7.37–7.46 (m, 4H), 7.52 (d, 1H, J=8 Hz), 7.96 (dd, 2H, J=9, 2 Hz); $^{13}$C NMR (CDCl$_3$) δ 19.4, 27.8, 30.5, 69.0, 119.0, 126.5, 128.5, 128.7, 129.8, 137.6, 138.7, 154.0, 157.5. ES-MS m/z 226 (M+H).

Preparation of
8-amino-2-phenyl-5,6,7,8-tetrahydroquinoline
(AMD8787).

To a stirred solution of 8-hydroxy-2-phenyl-5,6,7,8-tetrahydroquinoline (3.0 g, 13 mmol) in CH$_2$Cl$_2$ (25 mL) at 0° C. and triethylamine (4.0 mL, 29 mmol) was added dropwise, methanesulfonyl chloride (1.6 mL, 21 mmol). The reaction mixture was stirred overnight, then saturated aqueous NaHCO$_3$ (20 mL) was added and the resulting mixture was extracted with CHCl$_3$ (3×20 mL), dried (MgSO$_4$) and concentrated in vacuo. The residue was taken up in DMF (20 mL), then sodium azide (1.7 g, 26 mmol) was added and the mixture was stirred at 60° C. for 5 h. At this time, the mixture was cooled to room temperature, diluted with aqueous brine solution (20 mL) and the resulting mixture was extracted with diethyl ether (3×20 mL). The organic fractions were combined then washed with water (20 mL) and brine (20 mL) then dried (MgSO$_4$) and concentrated in vacuo. The residue was dissolved in MeOH/EtOAc 1:1 (20 mL) and placed in a hydrogenation flask which was flushed with nitrogen. Palladium on carbon (10%, 220 mg) was added and the mixture was shaken in a Parr hydrogenator under 45 psi of hydrogen for 8 h. The reaction was filtered through celite and the cake was washed with CHCl$_3$ (50 mL). Evaporation of the combined filtrates afforded 8-amino-2-phenyl-5,6,7,8-tetrahydroquinoline (AMD8787) (2.2 g, 74%) as a pale yellow oil. $^1$H NMR (CD$_3$OD) δ 1.77–1.87 (m, 2H), 2.00–2.05 (m, 1H), 2.36–2.40 (m, 1H), 2.74–2.85 (m, 2H), 4.30 (dd, 1H, J=9, 5 Hz), 7.31–7.46 (m, 3H), 7.55 (d, 1H, J=8 Hz), 7.69 (d, 1H, J=8 Hz), 8.11 (d, 2H, J=8 Hz); $^{13}$C NMR (CD$_3$OD) δ 18.5, 21.1, 24.0, 52.3, 120.7, 127.7, 129.7, 130.1, 132.3, 139.6, 153.5, 155.7. ES-MS m/z 225 (M+H). This intermediate was used without further purification.

Example 11

AMD8833: Preparation of N-(2-pyridinylmethyl)-N'-(2-phenyl-5,6,7,8-tetrahydro-8-quinolinyl)-1,4-benzenedimethanamine (hydrobromide salt)

N-(2-nitrobenzenesulfonyl)-N-(2-pyridinylmethyl)-N'-(2-phenyl-5,6,7,8-tetrahydro-8-quinolinyl)-1,4-benzenedimethanamine Using General Procedure B:
Reaction of 8-amino-2-phenyl-5,6,7,8-tetrahydroquinoline (100 mg, 0.45 mmol) and N-[1-methylene-4-(carboxaldehyde)phenylene]-N-(2-nitrobenzenesulfonyl)-2-(aminomethyl)pyridine (183 mg, 0.47 mmol) in the presence of NaBH(OAc)$_3$ (189 mg, 0.90 mmol) in MeOH (3 mL) for 3 hours, followed by purification of the crude product by column chromatography (silica gel, CH$_2$Cl$_2$/MeOH/NH$_4$OH 40:2:1) gave the title compound (249 mg, 90%) as a yellow/green foam.

Using General Procedures C and D: The foam from above (249 mg, 0.40 mmol) was reacted with thiophenol (103 µL, 1.0 mmol) and K$_2$CO$_3$ (167 mg, 1.2 mmol) in DMF (3 mL). The crude product was purified by radial chromatography on silica gel (1 mm plate, CH$_2$Cl$_2$/MeOH/NH$_4$OH 20:1:1) to give the free base of AMD8833 (103 mg, 59%). Conversion to the hydrobromide salt gave AMD8833 (121 mg, 57%) as a white solid. $^1$H NMR (CDCl$_3$) δ 1.77–1.84 (m, 2H), 2.00–2.07 (m, 1H), 2.25–2.29 (m, 1H), 2.77–2.81 (m, 2H), 2.96 (br s, 2H), 3.80–3.96 (m, 5H), 4.05 (d, 1H, J=14 Hz), 7.12–7.14 (m, 1H), 7.33–7.50 (m, 10H), 7.63 (t, 1H, J=8 Hz), 7.98 (d, 2H, J=7 Hz), 8.54 (br d, 1H, J=5 Hz); $^{13}$C NMR (CDCl$_3$) δ 20.0, 28.5, 28.8, 51.1, 53.1, 54.3, 57.2, 118.3, 121.8, 122.2, 126.5, 128.1, 128.2, 128.5, 130.8, 136.2, 137.5, 138.4, 139.2, 149.1, 154.0, 156.8, 159.5. ES-MS m/z 435 (M+H). Anal. Calcd. for C$_{29}$H$_{30}$N$_4$.3.5HBr.0.2H$_2$O.0.7C$_2$H$_4$O$_2$: C, 47.94; H, 4.86; N, 7.34; Br, 36.35. Found: C, 47.95; H, 4.91; N, 7.32; Br, 36.35.

Example 12

AMD8825: Preparation of N,N'-bis(2-pyridinylmethyl)-N'-(2-phenyl-5,6,7,8-tetrahydro-8-quinolinyl)-1,4-benzenedimethanamine (hydrobromide salt)

Using General Procedure A:
8-Amino-2-phenyl-5,6,7,8-tetrahydroquinoline (150 mg, 0.67 mmol), pyridine-2-carboxaldehyde (64 µL, 0.67 mmol) and NaBH$_3$CN (84 mg, 1.3 mmol) were reacted in MeOH (3 mL) for 18 h. The crude material isolated from this reaction (180 mg, 85%) was used without further purification.

The intermediate from above (246 mg, 0.54 mmol) was dissolved in CH$_3$CN (11 mL). N-[1-methylene-4-(chloromethylene)phenylene]-N-(2-nitrobenzenesulfonyl)-2-(aminomethyl)pyridine (246 mg, 0.54 mmol) was added, followed by K$_2$CO$_3$ (158 mg, 1.1 mmol) and the reaction mixture was heated at 82° C. for two days. Standard work-up and extraction of the crude gum with diethyl ether (3×30 mL), gave the desired N-alkylated intermediate (305 mg, 74% yield).

Using General Procedures C and D: The intermediate from above (300 mg, 0.42 mmol) was reacted with thiophenol (108 µL, 1.1 mmol) and K$_2$CO$_3$ (174 mg, 1.3 mmol) in DMF (3 mL). Purification of the crude product by column chromatography on silica gel (CHCl$_3$/MeOH/NH$_4$OH 40:2:1) afforded the free base of AMD8825 as a colourless oil (62 mg, 30%). Conversion to the hydrobromide salt gave AMD8825 (90 mg, 79% yield) as a white solid. $^1$H NMR (CDCl$_3$) δ 1.62–1.67 (m, 1H), 1.90–2.00 (m, 2H), 2.21–2.25 (m, 1H), 2.64–2.78 (m, 3H), 3.80 (s, 2H), 3.85–3.94 (m, 4H), 4.09–4.17 (m, 2H), 4.28 (d, 1H, J=14 Hz), 7.03–7.06 (m, 1H), 7.13–7.15 (m, 1H), 7.26–7.30 (m, 3H), 7.37 (d, 1H, J=8 Hz), 7.43 (d, 1H, J=8 Hz), 7.49–7.65 (m, 7H), 7.98 (d, 1H, J=8 Hz), 8.18 (d, 2H, J=7 Hz), 8.43 (d, 1H, J=4 Hz), 8.54 (d, 1H, J=4 Hz); $^{13}$C NMR (CDCl$_3$) δ 21.9, 27.6, 29.0, 53.1, 54.3, 55.9, 57.2, 59.1, 117.7, 121.4, 121.8, 122.2, 122.5, 126.6, 128.0, 128.4, 128.5, 128.7, 132.6, 136.2, 136.3, 137.1, 138.2, 139.6, 148.4, 149.1, 154.1, 158.1, 159.5, 161.9. ES-MS m/z 526 (M+H). Anal. Calcd. for C$_{35}$H$_{25}$N$_5$.4.4HBr.1.6H$_2$O.1.0C$_2$H$_4$O$_2$: C, 45.79; H, 4.84; N, 7.22; Br, 36.56. Found: C, 45.67; H, 4.86; N, 7.20; Br, 36.22.

Preparation of 7-amino-5,6,7,8-tetrahydroquinoline (AMD8850) and 5-amino-5,6,7,8-tetrahydroquinoline (AMD8851).

Following the procedure described by Filippi, J. (Bull. Soc. Chim. Fr. 1968, 1, 259–67).

The Skraup reaction of m-nitroaniline and glycerol in the presence of As$_2$O$_3$ and H$_2$SO$_4$ afforded a 65:35 mixture of 5-nitroquinoline and 7-nitroquinoline, respectively, in a combined yield of 21%. This mixture (6.6 g, 38 mmol) was taken up in EtOAc (50 mL), placed in a 250 mL round-bottom flask, and flushed with nitrogen. Next, 10% Pd/C (0.6 g) was added and the mixture was placed under a hydrogen atmosphere (H$_2$ balloon) and stirred vigorously for 18 h. The residue was filtered through a pad of celite, eluting with CHCl$_3$ (100 mL), and the solvent was removed in vacuo to afford 5.0 g of a 65:35 mixture of 5-aminoquinoline and 7-aminoquinoline, respectively (91% yield). This material was taken up in CH$_2$Cl$_2$ (100 mL) and pyridine (3 mL, 37 mmol) and DMAP (100 mg, 0.82 mmol) followed by Ac$_2$O (5 mL, 53 mmol) were added. Stirring was continued for 1 h, at which point 4 N NaOH (50 mL) was added and the mixture was extracted with $CH_2Cl_2$ (3×50 mL). The combined organic fractions were dried ($MgSO_4$) and concentrated in vacuo to give 6.5 g of a mixture of N-acetylated products (quant. yield).

To a vigorously stirred solution of 5-(N-acetylamino)-quinoline and 7-(N-acetylamino)-quinoline (2.7 g, 14 mmol) in TFA (30 mL) in a 250 mL round-bottom flask under nitrogen was added $PtO_2$ (165 mg, 0.72 mmol). The flask was then flushed with $H_2$ for 5 min, then placed under a $H_2$ atmosphere ($H_2$ balloon) and heated to 60° C. for 18 hours. The reaction mixture was cooled to room temperature and the solvent was evaporated. The residue was rendered basic with a minimum volume of 4 N NaOH and extracted with $CHCl_3$ (3×50 mL), and the combined extracts were dried ($MgSO_4$) and concentrated in vacuo. Purification of the residue by column chromatography on silica gel ($CHCl_3$/MeOH/$NH_4OH$ 20:2:1) afforded 1.35 g of a mixture of 5-(N-acetylamino)-5,6,7,8-tetrahydroquinoline and 7-(N-acetylamino)-5,6,7,8-tetrahydroquinoline, respectively (49% yield). The mixture (1.35 g, 7.1 mmol) was dissolved in MeOH (20 mL) and concentrated HCl (5 mL) was added; the solution was then heated at reflux for 2 days. The reaction was then cooled to room temperature and the volume was reduced by evaporation. The residue was (cautiously) made basic with a minimum amount of saturated aqueous NaOH, then the aqueous phase was extracted with $CHCl_3$ (3×25 mL), and the combined organic extracts were dried ($MgSO_4$) and concentrated in vacuo. Purification of the residue by radial chromatography on silica gel (4 mm plate, $CHCl_3$/MeOH/$NH_4OH$ 20:2:1) afforded two products: 7-amino-5,6,7,8-tetrahydroquinoline (AMD8850) (456 mg, 43%) as a pale yellow oil. $^1H$ NMR ($CDCl_3$) δ 1.45 (br 2, 2H), 1.48–1.54 (m, 1H), 1.88–1.90 (m, 1H), 2.59 (dd, 1H, J=15, 9 Hz), 2.71–2.78 (m, 2H), 3.08 (dd, 1H, J=15, 6 Hz), 3.18–3.24 (m, 1H), 6.93 (dd, 1H, J=8, 5 Hz), 7.27 (br d, 1H, J=8 Hz), 8.25 (br d, 1H, J=5 Hz); $^{13}C$ NMR ($CDCl_3$) δ 26.4, 31.8, 42.1, 46.8, 120.8, 130.8, 136.1, 146.8, 155.4; ES-MS m/z 149 (M+H); and 5-amino-5,6,7,8-tetrahydroquinoline (AMD8851) (503 mg 48%) as a pale yellow oil. $^1H$ NMR ($CDCl_3$) δ 1.57–1.65 (m, 3H), 1.78–1.81 (m, 1H), 1.93–2.00 (m, 2H), 2.79–2.89 (m, 2H), 3.90–3.92 (m, 1H), 7.04 (dd, 1H, J=8, 5 Hz), 7.67 (br d, 1H, J=8 Hz), 8.32 (br d, 1H, J=5 Hz); $^{13}C$ NMR ($CDCl_3$) δ 19.2, 29.5, 32.3, 33.4, 49.1, 121.2, 135.7, 136.0, 147.5, 156.7. ES-MS m/z 149 (M+H).

Example 13

AMD8869: Preparation of N-(2-pyridinylmethyl)-N'-(5,6,7,8-tetrahydro-5-quinolinyl)-1,4-benzenedimethanamine (hydrobromide salt)

N-(tert-Butoxycarbonyl)-N-(2-pyridinylmethyl)-N'-(5,6,7,8-tetrahydro-5-quinolinyl)-1,4-benzenedimethanamine.

Using General Procedure B: Reaction of 5-amino-5,6,7,8-tetrahydroquinoline (100 mg, 0.67 mmol), N-[1-methylene-4-(carboxaldehyde)phenylene]-N-(tert-butoxycarbonyl)-2-(aminomethyl)pyridine (220 mg, 0.67 mmol) and NaBH(OAc)$_3$ (286 mg, 1.3 mmol) in $CH_2Cl_2$ (3 mL) for 18 hours gave, after standard work-up and purification of the crude intermediate by radial chromatography on silica gel (2 mm plate, $CHCl_3$/MeOH/$NH_4OH$ 20:2:1), the desired reductive amination product (274 mg, 89%) as a colourless oil.

Using General Procedure D: the oil from above (65 mg, 0.14 mmol) was converted to the corresponding hydrobromide salt with simultaneous deprotection of the BOC group to give AMD8869 (38 mg, 36%) as a white solid. $^1H$ NMR ($D_2O$) δ 2.13–2.15 (m, 2H), 2.22–2.27 (m, 1H), 2.29–2.32 (m, 1H), 3.17–3.35 (m, 2H), 4.38–4.56 (m, 4H), 4.62 (s, 2H), 4.93 (br s, 1H), 7.59 (br s, 5H), 7.85–7.94 (m, 3H), 8.35 (t, 1H, J=7 Hz), 8.60 (d, 1H, J=8 Hz), 8.72–8.74 (m, 1H); $^{13}C$ NMR ($D_2O$) δ 18.6, 26.2, 29.4, 51.3, 51.7, 53.9, 56.8, 127.9, 129.6, 129.7, 133.4, 133.9, 134.6, 134.8, 145.0, 147.1, 148.7, 149.7, 150.5, 157.6. ES-MS m/z 359 (M+H). Anal. Calcd. for $C_{23}H_{26}N_4.4.4HBr.1.4H_2O$: C, 37.35; H, 4.52; N, 7.57; Br, 47.53. Found: C, 37.43; H, 4.53; N, 7.31; Br, 47.40.

Example 14

AMD8876: Preparation of N-(2-pyridinylmethyl)-N'-(1H-imidazol-2-ylmethyl)-N'-(5,6,7,8-tetrahydro-5-quinolinyl)-1,4-benzenedimethanamine (hydrobromide salt)

Using General Procedure B:
Reaction of N-(tert-Butoxycarbonyl)-N-(2-pyridinylmethyl)-N'-(5,6,7,8-tetrahydro-5-quinolinyl)-1,4-benzenedimethanamine (275 mg, 0.60 mmol), imidazole-2-carboxaldehyde (115 mg, 1.2 mmol) and NaBH(OAc)$_3$ (380 mg, 1.8 mmol) in a mixture of $CH_2Cl_2$ (5 mL) and acetic acid (0.5 mL) for 48 hours, followed by standard work-up and purification of the crude intermediate by radial chromatography on silica gel (2 mm plate, $CHCl_3$/MeOH/$NH_4OH$ 20:2:1) afforded the desired reductive amination product (182 mg, 57%) as a pale yellow oil.

Using General procedure D: the oil from above (182 mg, 0.34 mmol) was converted to the corresponding hydrobromide salt with simultaneous deprotection of the BOC group to give AMD8876 (157 mg, 49%) as a white solid. $^1H$ NMR ($D_2O$) δ 1.93–2.10 (m, 2H), 2.23–2.36 (m, 2H), 3.10–3.17 (m, 2H), 3.77–3.87 (m, 2H), 4.10 (d, 1H, J=16 Hz), 4.27 (d, 1H, J=16 Hz), 4.41 (br s, 3H), 4.69 (br s, 2H), 7.15 (s, 2H), 7.42 (br s, 4H), 7.95 (t, 1H, J=6 Hz), 8.03–8.11 (m, 2H), 8.53–8.57 (m, 2H), 8.78–8.81 (d, 1H, J=4 Hz), 9.13 (d, 1H, J=6 Hz); $^{13}C$ NMR ($D_2O$) δ 22.2, 23.1, 30.3, 49.8, 50.6, 54.1, 58.2, 63.0, 121.7, 127.5, 130.0, 130.3, 132.0, 132.7, 133.2, 141.6, 142.2, 142.6, 147.8, 148.1, 148.3, 148.8, 149.0, 157.0. ES-MS m/z 439 (M+H). Anal. Calcd. for $C_{27}H_{30}N_6.5.6HBr.2.3H_2O$: C, 34.75; H, 4.34; N, 9.01; Br, 47.95. Found: C, 35.09; H, 4.40; N, 8.62; Br, 47.72.

Example 15

AMD8751: Preparation of N-(2-pyridinylmethyl)-N'-(1H-imidazol-2-ylmethyl)-N'-(5,6,7,8-tetrahydro-8-quinolinyl)-1,4-benzenedimethanamine (hydrobromide salt)

To a stirred solution of N-(tert-butoxycarbonyl)-N-(2-pyridinylmethyl)-N'-(5,6,7,8-tetrahydro-8-quinolinyl)-1,4-benzenedimethanamine (174 mg, 0.38 mmol) in dry MeOH (5 mL) was added 2-imidazolecarboxaldehyde (75 mg, 0.78 mmol) and sodium cyanoborohydride (55 mg, 0.88 mmol) and the mixture was stirred for 40 h. The reaction mixture was concentrated in vacuo and partitioned between $CH_2Cl_2$ (30 mL) and aqueous 1 N sodium hydroxide (30 mL). The aqueous layer was washed with $CH_2Cl_2$ (2×20 mL) and the combined organic extracts washed with brine (30 mL), dried ($MgSO_4$), filtered and concentrated in vacuo. Purification of the crude product by column chromatography on silica gel (CH$_2$Cl$_2$/MeOH, 95:5) afforded the imidazole derivative (48 mg, 24%) as a clear oil.

To a solution of the intermediate from above (48 mg, 0.089 mmol) in CH$_2$Cl$_2$ (2 mL) was added trifluoroacetic acid (1 mL) and the mixture was stirred at room temperature for 1.5 h. The reaction mixture was concentrated in vacuo and the crude oil was purified by column chromatography on silica gel (CH$_2$Cl$_2$/MeOH, 85:15) to afford the free amine (38 mg, 97%) as a clear oil. Conversion to the hydrobromide salt using general procedure D gave AMD8751 (37 mg, 45%) as an off-white solid. $^1$H NMR (D$_2$O) δ 1.83–1.88 (br m, 1H), 2.22–2.29 (br m, 2H), 2.35–2.39 (br m, 1H), 3.01–3.02 (br s, 2H), 3.84 (s, 2H), 4.29 (d, 1H, J=15.9 Hz), 4.31 (s, 2H), 4.42 (d, 1H, J=15.9 Hz), 4.50 (s, 2H), 4.60–4.63 (m, 1H), 7.21 (s, 2H), 7.31 (d, 2H, J=7.8 Hz), 7.35 (d, 2H, J=7.8 Hz), 7.76–7.78 (m, 2H), 7.86 (t, 1H, J=6.3 Hz), 8.20–8.24 (br m, 1H), 8.34 (d, 1H, J=7.8 Hz), 8.65 (d, 1H, J=5.4 Hz), 8.71 (d, 1H, J=4.4 Hz); $^{13}$C NMR (D$_2$O) δ 20.47 (2 carbons), 27.79, 49.02, 49.30, 51.12, 55.89, 61.55, 119.31 (2 carbons), 125.93, 126.29, 126.41, 130.10, 130.71 (4 carbons), 138.56, 139.51, 140.71, 142.77, 145.22, 147.34, 148.06, 148.23, 151.09. ES-MS m/z 439 (M+H). Anal. Calcd. for C$_{27}$H$_{30}$N$_6$.4.5HBr.4.0H$_2$O.1:3CH$_3$CO$_2$H: C, 37.31; H, 5.05; N, 8.82; Br, 37.74.

Found: C, 37.31; H, 4.75; N, 8.90; Br, 37.80.

Example 16

AMD8777: Preparation of N-(2-pyridinylmethyl)-N'-[(2-amino-3-phenyl)propyl]-N'-(5,6,7,8-tetrahydro-8-quinolinyl)-1,4-benzenedimethanamine (hydrobromide salt)

Prepared according to the procedure of Smith, G. A. et al. Org. Synth. 1984, 63, 136–139.

To a solution of L-Phenylalaninol (358 mg, 2.37 mmol) in wet THF (5 mL) was added di-t-butyl dicarbonate (715 mg, 3.28 mmol). The mixture was stirred for 16 hours then concentrated in vacuo. Purification of the crude product by column chromatography on silica gel (hexanes/EtOAc, 3:1) afforded the N-Boc-protected alcohol (590 mg, 99%) as a white solid: $^1$H NMR (CDCl$_3$) δ 1.41 (br s, 9H), 2.45 (br s, 1H), 2.84 (d, 2H, J=6.0 Hz), 3.52–3.58 (m, 1H), 3.65–3.70 (m, 1H), 3.85–3.88 (br m, 1H), 4.76 (br s, 1H), 7.20–7.34 (m, 5H).

General Procedure F: Oxidation Using Dess-Martin Periodinane:

To a stirred solution of N-Boc-L-phenylalaninol (258 mg, 1.03 mmol) in CH$_2$Cl$_2$ (5 mL) was added 1,1,1-triacetoxy-1,1-dihydro-1,2-benziodoxol-3(1H)-one (Dess-Martin periodinane) (525 mg, 1.24 mmol) in one portion and the mixture was stirred for 20 min. The reaction mixture was diluted with diethyl ether (30 mL), saturated aqueous sodium bicarbonate (10 mL) and saturated aqueous sodium thiosulfate (10 mL) and stirred for 30 min. The mixture was then diluted with water (10 mL) and ethyl acetate (10 mL) and the layers partitioned. The organic phase was washed with brine (25 mL), dried (MgSO$_4$) and concentrated in vacuo N-Boc-L-phenylalaninal. This was used without further purification in the next step.

Using General procedure A: Reaction of N-(2-nitrobenzenesulfonyl)-N-(2-pyridinylmethyl)-N'-(5,6,7,8-tetrahydro-8-quinolinyl)-1,4-benzenedimethanamine (250 mg, 0.46 mmol), crude N-Boc L-phenylalaninal and sodium cyanoborohydride overnight gave the corresponding reductive amination product as a yellow oil (mixture of diastereomers). Using general procedures C and D: The intermediate was reacted with thiophenol to give the free base (60 mg, 22% over 2 steps) as a yellow oil. Conversion to the corresponding hydrobromide salt with simultaneous deprotection of the BOC group gave AMD8777 (73 mg, 91%) as a pale yellow solid (mixture of diastereomers). $^1$H NMR (D$_2$O) two diastereomers δ 1.61–1.73 (br m, 1H), 1.94–2.22 (m, 3H), 2.65–2.81 (m) and 2.88–2.92 (m) and 2.97–3.16 (m) and 3.64 (br s) and 3.74–3.80 (m) (total 9H), 4.31–4.37 (m) and 4.32 (s) and 4.36 (s) (total 3H), 4.49 (s) and 4.54 (s) (total 2H), 7.14 (d, J=8.5 Hz) and 7.26–7.42 (m) (total 9H), 7.67–7.71 (m) and 7.75–7.81 (m) and 8.20 (d, J=9.7 Hz) and 8.25 (d, J=8.5 Hz) and 8.36 (d, J=6.0 Hz) and 8.54 (d, J=6.0 Hz) and 8.69 (br s) (total 7H); $^{13}$C NMR (D$_2$O) two diastereomers δ 19.33, 20.18, 20.48, 20.54, 27.89, 36.86, 37.04, 49.00, 51.08, 51.24, 51.34, 52.17, 53.00, 54.83, 55.02, 57.58, 58.27, 62.69, 125.60, 125.73, 126.67, 126.73, 128.03, 128.10, 129.54, 129.62, 129.75, 130.12, 130.27, 130.94, 135.73, 139.22, 139.32, 139.38, 139.63, 140.40, 140.91, 143.48, 143.66, 146.69, 146.81, 147.75, 151.14, 151.73. ES-MS m/z 492 (M+H). Anal. Calcd. for C$_{32}$H$_{37}$N$_5$.4.0HBr.3.7H$_2$O: C, 43.58; H, 5.53; N, 7.94; Br, 36.24. Found: C, 43.65; H, 5.23; N, 7.86; Br, 36.03.

Example 17

AMD8763: Preparation of N-(2-pyridinylmethyl)-N'-(1H-imidazol-4-ylmethyl)-N'-(5,6,7,8-tetrahydro-8-quinolinyl)-1,4-benzenedimethanamine (hydrobromide salt)

Using general procedure A: Reaction of N-(tert-butoxycarbonyl)-N-(2-pyridinylmethyl)-N'-(5,6,7,8-tetrahydro-8-quinolinyl)-1,4-benzenedimethanamine (215 mg, 0.47 mmol), 4(5)-imidazolecarboxaldehyde (105 mg, 1.09 mmol) and sodium cyanoborohydride overnight gave the corresponding reductive amination product (145 mg, 59%) as a clear foam.

Using General Procedures C and D: The intermediate from above (145 mg, 0.28 mmol) gave AMD8763 (170 mg, 68%) as a white solid. $^1$H NMR (D$_2$O) δ 1.72–1.78 (br m, 1H), 2.07–2.18 (br m, 2H), 2.27–2.32 (br m, 1H), 2.91 (br d, 2H, J=4.8 Hz), 3.78 (d, 1H, J=13.5 Hz), 3.83 (d, 1H, J=13.8 Hz), 4.00 (d, 1H, J=14.7 Hz), 4.08 (d, 1H, J=14.7 Hz), 4.35 (s, 2H), 4.35–4.42 (m, 1H), 4.63 (s, 2H), 7.35 (s, 4H), 7.43 (s, 1H), 7.71 (dd, 1H, J=8.1, 7.8 Hz), 7.96 (dd, 1H, J=6.9, 6.6 Hz), 8.02 (d, 1H, J=7.8 Hz), 8.19 (d, 1H, J=8.1 Hz), 8.46–8.51 (m, 2H), 8.60 (s, 1H), 8.78 (d, 1H, J=5.3 Hz). $^{13}$C NMR (D$_2$O) δ 19.76, 20.49, 27.66, 46.78, 47.80, 51.61, 54.57, 59.34, 118.33, 125.48, 127.78, 128.10, 129.55, 130.64 and 130.69 (total 5 carbons), 134.27, 139.25, 139.54, 140.15, 144.72, 146.01, 146.50, 147.44, 151.97. ES-MS m/z 439 (M+H). Anal. Calcd. for C$_{27}$H$_{30}$N$_6$.4.5HBr.2.4H$_2$O.0.7CH$_3$CO$_2$H: C, 38.42; H, 4.78; N, 9.46; Br, 40.49. Found: C, 38.30; H, 4.78; N, 9.40; Br, 40.51.

Example 18

AMD8771: Preparation of N-(2-pyridinylmethyl)-N'-(2-quinolinylmethyl)-N'-(5,6,7,8-tetrahydro-8-quinolinyl)-1,4-benzenedimethanamine (hydrobromide salt)

Using general Procedure A: Reaction of N-(tert-butoxycarbonyl)-N-(2-pyridinylmethyl)-N'-(5,6,7,8-tetrahydro-8- quinolinyl)-1,4-benzenedimethanamine (130 mg, 0.28 mmol) with 2-quinolinecarboxaldehyde (95 mg, 0.61 mmol) and sodium cyanoborohydride overnight gave the corresponding reductive amination product (60 mg, 36%) as an orange foam.

Using general procedure D: the intermediate from above (60 mg, 0.28 mmol) was converted to the hydrobromide salt with simultaneous deprotection of the BOC group to give the crude product. The solid was then re-dissolved in dry MeOH (1 mL) and precipitated with diethyl ether. The solid was washed by decantation with ether (3×20 mL) and the remaining traces of solvent were removed by evaporation under reduced pressure followed by drying in vacuo to afford AMD8771 (71 mg, 79%) as an orange solid. $^1$H NMR ($D_2O$) δ 1.84–1.92 (br m, 1H), 2.19–2.34 (m, 2H), 2.47–2.51 (br m, 1H), 3.02 (br s, 2H), 3.73 (s, 2H), 3.81 (d, 1H, J=13.2 Hz), 3.88 (d, 1H, J=12.9 Hz), 4.18 (s, 2H), 4.54 (d, 1H, J=16.8 Hz), 4.72 (d, 1H, J=16.8 Hz), 4.75–4.79 (m, overlap with HOD, 1H), 6.97 (d, 2H, J=8.0 Hz), 7.20 (d, 2H, J=8.0 Hz), 7.64 (d, 1H, J=8.0 Hz), 7.69–7.79 (m, 2H), 7.87–7.95 (m, 2H), 8.03–8.11 (m, 3H), 8.18 (t, 1H, J=8.0 Hz), 8.37 (d, 1H, J=8.0 Hz), 8.66 (d, 1H, J=5.0 Hz), 8.75 (d, 1H, J=6.0 Hz), 8.83 (d, 1H, J=8.3 Hz); $^{13}$C NMR ($D_2O$) δ 20.47, 20.79, 27.96, 48.87, 50.32, 56.69, 56.83, 62.87, 119.83, 122.45, 126.06, 126.36, 126.49, 128.07, 129.52, 129.83, 130.17, 130.47 (2 carbons), 130.95 (2 carbons), 135.45, 137.25, 139.02, 139.77, 141.17, 142.98, 147.08, 147.45, 147.89, 148.18, 150.83, 157.51. ES-MS m/z 500 (M+H). Anal. Calcd. for $C_{33}H_{33}N_5.4.0HBr.3.1H_2O$: C, 45.10; H, 4.89; N, 7.93; Br, 36.25. Found: C, 45.08; H, 4.95; N, 7.97; Br, 36.36.

Example 19

AMD8778: Preparation of N-(2-pyridinylmethyl)-N'-(2-(2-naphthoyl)aminoethyl)-N'-(5,6,7,8-tetrahydro-8-quinolinyl)-1,4-benzenedimethanamine (hydrobromide salt)

N-2-(2-naphthoyl)ethanolamine
To a stirred solution of 2-naphthoic acid (665 mg, 3.87 mmol) and ethanolamine (0.24 mL, 3.87 mmol) in dry $CH_2Cl_2$ (10 mL) was added N,N-diisopropylethylamine (2 mL, 11.5 mmol), 1-hydroxybenzotriazole hydrate (680 mg, 5.04 mmol) and 1-(3-dimethylaminopropyl)-3-ethyl carbodiimide HCl (EDC) (1.00 g, 5.22 mmol) and the mixture was stirred at room temperature for 18 h. The reaction mixture was diluted with $CH_2Cl_2$ (25 mL) and brine (30 mL) and the aqueous layer was separated and extracted with $CH_2Cl_2$ (2×25 mL). The combined organic phases were dried ($MgSO_4$), filtered and evaporated in vacuo to give the crude product as a white solid. Purification of the solid by column chromatography on silica gel (EtOAc) gave the title compound (660 mg, 79%) as a white solid. $^1$H NMR ($CDCl_3$) δ 2.71 (br s, 1H), 3.70 (q, 2H, J=6.0 Hz), 3.89 (q, 2H, J=6.0 Hz), 6.82 (br s, 1H), 7.51–7.58 (m, 2H), 7.84–7.90 (m, 4H), 8.31 (s, 1H).

Using General Procedure F: The alcohol from above (200 mg, 0.93 mmol) was then oxidized to the corresponding aldehyde using the Dess-Martin procedure with Dess-Martin periodinane (535 mg, 1.26 mmol) and used without further purification in the next step.

Using general Procedure A: Reaction of the aldehyde from above with N-(2-nitrobenzenesulfonyl)-N-(2-pyridinylmethyl)-N'-(5,6,7,8-tetrahydro-8-quinolinyl)-1,4-benzenedimethanamine (224 mg, 0.41 mmol) and sodium cyanoborohydride gave, following purification, the corresponding reductive amination product as an orange oil.

Using General Procedures C and D: Reaction of the oil with thiophenol gave the free base (63 mg, 28% over 2 steps) as a pale orange oil which was subsequently converted to the hydrobromide salt giving AMD8778 (93 mg, 89%) as a pale yellow solid. $^1$H NMR ($CD_3OD$) δ 1.79–1.84 (br m, 1H), 2.11–2.22 (br m, 2H), 2.53–2.58 (br m, 1H), 2.88–2.97 (br m, 2H), 3.17 (t, 1H, J=10.8 Hz), 3.35–3.58 (m, 3H), 4.22–4.40 (br m, 4H), 4.50–4.66 (m, 1H), 4.65 (s, 2H), 7.32 (br m, 1H), 7.59–7.70 (m, 4H), 7.75–7.82 (m, 5H), 7.91 (d, 1H, J=8.0 Hz), 7.98–8.09 (m, 4H), 8.30 (td, 1H, J=8.0, 1.0 Hz), 8.48 (br s, 1H), 8.78 (d, 1H, J=5.6 Hz); $^{13}$C NMR ($CD_3OD$) δ 14.44, 20.58, 27.42, 36.73, 50.82, 53.65, 54.60, 61.14, 65.92, 124.00, 124.55, 125.60, 125.74, 127.22, 127.94, 128.38, 128.38, 128.53, 128.62, 129.19, 130.51, 131.21 (2 carbons), 131.37 (2 carbons), 132.38, 132.96, 135.56, 136.48, 141.89, 141.95, 145.30, 146.96, 148.98, 149.84, 171.26. ES-MS m/z 556 (M+H). Anal. Calcd. for $C_{36}H_{37}N_5O.3.6HBr.3.8H_2O$: C, 47.23; H, 5.31; N, 7.65; Br, 31.42. Found: C, 47.18; H, 5.10; N, 7.53; Br, 31.47.

Example 20

AMD8781: Preparation of N-(2-pyridinylmethyl)-N'-[(S)-(2-acetylamino-3-phenyl)propyl]-N'-(5,6,7,8-tetrahydro-8-quinolinyl)-1,4-benzenedimethanamine (hydrobromide salt of the low polarity diastereomer)

N-Acetyl-L-Phenylalaninal:
To a stirred solution of L-phenylalaninol (228 mg, 1.51 mmol) in THF (5 mL) was added acetic anhydride (0.15 mL, 1.59 mmol) and the mixture stirred for 16 h. The reaction mixture was diluted with EtOAc (10 mL) and washed with 1 N HCL (15 mL), saturated aqueous sodium bicarbonate (15 mL) and brine (15 mL). The organic phase was dried ($MgSO_4$), filtered and concentrated in vacuo. Purification of the residue by column chromatography on silica gel afforded the N-acetylated alcohol (220 mg, 75%) as a white solid. $^1$H NMR ($CDCl_3$) δ 1.95 (s, 3H), 2.87 (d, 2H, J=6.0 Hz), 3.17 (br s, 1H), 3.56–3.68 (m, 2H), 4.13–4.21 (m, 1H), 5.97 (br d, 1H, J=6.0 Hz), 7.20–7.34 (m, 5H). The alcohol was then oxidized according to the general Dess-Martin procedure and the crude aldehyde used without further purification.

Reaction of N-(tert-butyloxycarbonyl)-N-(2-pyridinylmethyl)-N'-(5,6,7,8-tetrahydro-8-quinolinyl)-1,4-benzenedimethanamine (268 mg, 0.58 mmol) and crude N-acetyl-L-phenylalaninal gave the desired product (196 mg, 53%) as a mixture of diastereomers. The diastereomers were separated and purified by column chromatography with silica gel ($CH_2Cl_2$/MeOH, 96:4) followed by preparative thin layer chromatography ($CH_2Cl_2$/MeOH, 95:5) a low polarity diastereomer (73 mg) and a high polarity diastereomer (50 mg), each as a clear oil.

Using general procedure D: The low polarity diastereomer (73 mg, 0.12 mmol) was converted to the hydrobromide salt with simultaneous deprotection of the BOC group to afford AMD8781 (84 mg, 85%) as a pale yellow solid. $^1$H NMR ($D_2O$): low polarity diastereomer: δ 1.64–1.69 (br m, 1H), 1.83 (br s, 3H), 1.94–2.24 (m, 3H), 2.67–2.74 (m, 1H), 2.79–2.84 (br m, 3H), 2.92–3.00 (m, 1H), 3.40 (d, 1H, J=13.8 Hz), 4.02–4.13 (br m, 1H), 4.38–4.42 (br s, 5H), 4.56 (s, 2H), 7.23–7.37 (m, 5H), 7.45–7.55 (br m, 5H), 7.76–7.82 (m, 1H), 7.84 (d, 2H, J=8.0 Hz), 8.28 (t, 1H, J=8.0), 8.49 (br d, 1H, J=2.0 Hz), 8.70 (d, 1H, J=4.0 Hz); $^{13}$C NMR ($D_2O$) δ 20.32, 20.46, 22.21, 27.44, 37.47, 48.46, 49.26, 51.40, 54.74, 55.60, 61.44, 125.11, 127.23, 127.37, 127.56, 129.33

(2 carbons), 129.55 (2 carbons), 131.22 (2 carbons), 131.44 (2 carbons), 131.57, 134.44, 137.26, 137.40, 141.80, 144.74, 145.01, 145.75, 146.88, 149.53, 175.66. ES-MS m/z 534 (M+H). Anal. Calcd. for $C_{34}H_{39}N_5O$·3.8HBr·2.9H$_2$O: C, 45.71; H, 5.48; N, 7.84; Br, 33.99. Found: C, 45.74; H, 5.52; N, 7.71; Br, 34.06.

Example 21

AMD8782: Preparation of N-(2-pyridinylmethyl)-N'-[(S)-(2-acetylamino-3-phenyl)propyl]-N'-(5,6,7,8-tetrahydro-8-quinolinyl)-1,4-benzenedimethanamine (hydrobromide salt of the high polarity diastereomer)

Using general procedure D: The high polarity diastereomer from above (50 mg, 0.08 mmol) was converted to the hydrobromide salt with simultaneous deprotection of the BOC group to afford AMD8782 (37 mg, 55%) as a white solid. $^1$H NMR (D$_2$O): high polarity diastereomer: δ 1.65–1.69 (br m, 1H), 1.85–1.93 (m, 1H), 1.87 (s, 3H), 2.02–2.08 (br m, 1H), 2.26–2.29 (br m, 1H), 2.56–2.71 (m, 2H), 2.72–2.82 (br m, 2H), 3.17–3.22 (br m, 2H), 3.77–3.83 (m, 1H), 4.10 (s, 2H), 4.36–4.44 (m, 1H), 4.43 (s, 2H), 4.55 (d, 1H, J=16.2 Hz), 4.64 (d, 1H, J=16.2 Hz), 7.01 (d, 2H, J=7.0 Hz), 7.16–7.27 (m, 3H), 7.49 (s, 4H), 7.49–7.52 (m, 1H), 7.86 (d, 1H, J=8.0 Hz), 7.93–8.01 (m, 2H), 8.44–8.49 (m, 2H), 8.76 (d, 1H, J=5.0 Hz); $^{13}$C NMR (D$_2$O) δ 20.41, 20.67, 22.28, 27.38, 38.53, 47.93, 51.20, 51.52, 56.42, 56.51, 56.79, 125.31, 127.37, 127.60, 127.84, 129.17 (2 carbons), 129.47 (2 carbons), 131.10 and 131.22 (total 5 carbons), 137.41, 137.35, 137.49, 143.07, 143.54, 145.11, 145.97, 146.31, 149.93, 175.01. ES-MS m/z 534 (M+H). Anal. Calcd. for $C_{34}H_{39}N_5O$·3.8HBr·2.7H$_2$O: C, 45.89; H, 5.46; N, 7.87; Br, 34.12. Found: C, 45.95; H, 5.56; N, 7.70; Br, 34.01.

Example 22

AMD8788: Preparation of N-(2-pyridinylmethyl)-N'-[3-((2-naphthalenylmethyl)amino)propyl]-N'-(5,6,7,8-tetrahydro-8-quinolinyl)-1,4-benzenedimethanamine (hydrobromide salt)

To a solution of 3-amino-1-propanol (0.43 mL, 5.56 mmol) and 2-naphthaldehyde (787 mg, 5.05 mmol) in MeOH (10 mL) was added sodium cyanoborohydride (460 mg, 7.3 mmol) and the mixture stirred for 17 h. The resultant crude yellow oil was then stirred with di-t-butyl dicarbonate (1.20 g, 5.60 mmol) in wet THF (40 mL) for 1 hour. After work-up, the residue was purified by column chromatography on silica gel (hexanes/EtOAc, 3:1) to give 3-[N-t-butyloxycarbonyl[N-(2-naphthalenylmethyl)]amino]propanol (1.50 g, 60% over 2 steps) as a clear oil: $^1$H NMR (CDCl$_3$) δ 1.49 (br s, 9H), 1.65 (br s, 1H), 3.46–3.49 (br m, 2H), 3.58–3.63 (br m, 2H), 3.75–3.78 (m, 1H), 4.55 (s, 2H), 7.37 (br d, 1H, J=8.4 Hz), 7.47–7.50 (m, 2H), 7.64 (s, 1H), 7.79–7.84 (m, 3H).

Using general procedure F: The alcohol (230 mg, 0.73 mmol) was oxidized in CH$_2$Cl$_2$ (5 mL) with Dess Martin periodinane (370 mg, 0.87 mmol) for 20 min to give the crude aldehyde which was used without further purification in the next step.

To a solution of N-(tert-butyloxycarbonyl)-N-(2-pyridinylmethyl)-N'-(5,6,7,8-tetrahydro-8-quinolinyl)-1,4-benzenedimethanamine (260 mg, 0.57 mmol) and the crude naphthyl aldehyde from above in MeOH (15 mL) was added sodium cyanoborohydride (62 mg, 0.98 mmol) and the mixture stirred for 16 h. After work-up, the crude material was purified by column chromatography on silica gel (CH$_2$Cl$_2$/MeOH, 96:4) give the desired intermediate (230 mg, 53%) as a colorless oil.

Using general procedure D: the oil from above (125 mg, 0.17 mmol) was converted to the hydrobromide salt with simultaneous deprotection of the BOC group and the solid that formed was re-precipitated from methanol/ether to give AMD8788 (126 mg, 83%) as a beige solid. $^1$H NMR (D$_2$O) δ 1.58–1.63 (br m, 1H), 1.81–2.04 (br m, 4H), 2.13–2.22 (br m, 1H), 2.71–2.75 (br m, 2H), 2.84–3.11 (br m, 4H), 3.89 (d, 1H, J=13.2 Hz), 3.99 (d, 1H, J=13.2 Hz), 4.22–4.27 (m, 1H), 4.31 (s, 2H), 4.36 (s, 2H), 4.61 (s, 2H), 7.36–7.51 (m, 8H), 7.75–8.02 (m, 7H), 8.31 (d, 1H, J=5.0 Hz), 8.45 (dd, 1H, J=12.0, 7.0 Hz), 8.75 (d, 1H, J=6.0 Hz); $^{13}$C NMR (D$_2$O) δ 20.32 (2 carbons), 23.31, 27.35, 44.34, 47.69, 48.78, 51.15, 51.58, 55.10, 60.32, 125.04, 126.91, 127.55, 127.86 (2 carbons), 128.21 (2 carbons), 128.40, 129.56, 130.19, 130.87, 131.05 (2 carbons), 131.33 (2 carbons), 133.10, 133.46, 135.48, 137.50, 143.06, 143.32, 144.55, 145.79, 146.72, 146.90, 150.08. ES-MS m/z 556 (M+H). Anal. Calcd. for $C_{37}H_{41}N_5$·4.8HBr·2.2H$_2$O: C, 45.17; H, 5.14; N, 7.12; Br, 38.99. Found: C, 45.16; H, 5.25; N, 6.87; Br, 39.16.

Example 23

AMD8733 and AMD8734: Preparation of N-(2-pyridinylmethyl)-N'-[2-(S)-pyrollidinylmethyl]-N'-(5,6,7,8-tetrahydro-8-quinolinyl)-1,4-benzenedimethanamine (hydrobromide salt)

To a solution of N-Boc-L-prolinol ((S)-N-BOC-pyrrolidinemethanol) (402 mg, 2.0 mmol) in dichloromethane (20 mL) was added TPAP (70 mg, 0.2 mmol), NMO (351 mg, 3.0 mmol) and 4 Å molecular sieves (1 g). The mixture was then stirred at room temperature for one hour. Following filtration of the material through celite, the mixture was concentrated and the residue was purified by column chromatography on silica gel (10% methanol in dichloromethane) to afford the corresponding aldehyde (320 mg, 80%).

The N-BOC-prolinal (320 mg, 1.6 mmol) from above was then dissolved in methanol (12 mL) to which, N-(tert-butyloxycarbonyl)-N-(2-pyridinylmethyl)-N'-(5,6,7,8-tetrahydro-8-quinolinyl)-1,4-benzenedimethanamine (360 mg, 0.80 mmol) was added. The reaction mixture was stirred at room temperature for one hour, then sodium cyanoborohydride (113 mg, 1.80 mmol) was added (see general procedure A). Following work-up, the crude intermediate was purified by column chromatography on silica gel (5% methanol in dichloromethane) to give two diastereomeric products, in yields of 80 mg (16%) and 64 mg (13%) respectively.

Using general procedure D: the two diastereomeric products were converted to their corresponding hydrobromide salts with simultaneous deprotection of the BOC groups to give 62 mg of AMD8733 and 41 mg of AMD8734, respectively.

AMD8733: $^1$H NMR (D$_2$O) δ 1.61–1.67 (m, 2H), 1.94–2.29 (m, 6H), 2,85 (br s, 2H), 3.06 (d, 2H, J=6.6 Hz), 3.32 (t, 2H, J=7.2 Hz), 3.80 (br s, 2H), 3.80 (m, 1H), 4.26 (s, 2H), 4.33 (dd, 1H, J=9.0, 3.6 Hz), 4.43 (s, 2H), 7.33 (m, 4H), 7.67 (m, 3H), 8.13 (m, 2H), 8.34 (d, 1H, J=4.8 Hz), 8.78 (d, 1H, J=4.3 Hz); $^{13}$C NMR (D$_2$O) δ 19.83, 20.79, 23.31, 27.78, 28.52, 45.65, 49.43, 51.05, 53.94, 56.01, 58.99, 61.20, 125.37, 126.00, 126.17, 130.11, 130.70, 130.79, 136.36, 139.07, 138.33, 140.14, 142.27, 147.41, 147.52, 151.62. ES-MS m/z 442 (M+H). Anal. Calcd. for $C_{28}H_{35}N_5$.4.6HBr.4.8 $H_2O$.1.0AcOH: C, 37.52; H, 5.58; N, 7.29; Br, 38.27. Found: C, 37.19; H, 5.26; N, 7.30; Br, 38.39.

AMD8734: $^1H$ NMR ($D_2O$) δ 1.61 (dd, 1H, J=12.9, 8.4 Hz), 1.67 (m, 1H), 1.94 (qi, 2H, J=7.4 Hz), 2.03 (m, 2H), 2.09 (m, 2H), 2.29 (m, 1H), 2.75 (dd, 1H, J=14.7, 10.2 Hz), 2.92 (m, 1H), 3.07 (m, 1H), 3.18 (m, 1H), 3.23 (dd, 1H, 7.5, 3.9 Hz), 3.69 (m, 2H), 3.83 (m, 1H), 4.33 (s, 2H), 4.41 (m, 1H), 4.57 (s, 2H), 7.41 (br s, 4H), 7.79 (m, 3H), 8.25 (m, 2H), 8.50 (d, 1H, 4.1 Hz), 8.77 (d, 1H, J=5.3 Hz); $^{13}C$ NMR ($D_2O$) δ 14.50, 19.36, 20.48, 20.79, 22.32, 27.67, 27.84, 45.12, 48.80, 51.34, 51.85, 54.94, 58.16, 58.90, 125.62, 126.86, 130.22, 130.90, 139.34, 139.54, 140.69, 144.02, 146.41, 147.48, 147.67, 151.87. ES-MS m/z 442 (M+H). Anal. Calcd. for $C_{28}H_{35}N_5$.4.8HBr.3.6 $H_2O$.1.0AcOH: C, 37.73; H, 5.38; N, 7.33. Found: C, 37.89; H, 5.41; N, 7.36.

Example 24

AMD8756: Preparation of N-(2-pyridinylmethyl)-N'-[2-(R)-pyrollidinylmethyl]-N'-(5,6,7,8-tetrahydro-8-quinolinyl)-1,4-benzenedimethanamine (hydrobromide salt)

In a similar manner to the procedure described above, (R)-pyrrolidinemethanol gave two diastereomeric products, 111 mg and 58 mg, respectively. The less-polar diastereomer (111 mg) was then converted to the corresponding hydrobromide salt with simultaneous deprotection of the BOC group to give AMD8756 (81 mg). $^1H$ NMR ($D_2O$) δ 1.61–1.67 (m, 2H), 1.94–2.29 (m, 6H), 2.85 (br s, 2H), 3.06 (d, 2H, J=6.6 Hz), 3.32 (t, 2H, J=7.2 Hz), 3.80 (br s, 2H), 3.80 (m, 1H), 4.26 (s, 2H), 4.33 (dd, 1H, J=9.0, 3.6 Hz), 4.43 (s, 2H), 7.33 (m, 4H), 7.67 (m, 3H), 8.13 (m, 2H), 8.34 (d, 1H, J=4.8 Hz), 8.78 (d, 1H, J=4.3 Hz); $^{13}C$ NMR ($D_2O$) δ 19.94, 20.63, 23.30, 27.86, 28.62, 45.80, 48.62, 51.42, 54.04, 56.05, 59.12, 61.08, 125.47, 127.15, 127.24, 129.96, 130.83, 130.93, 139.19, 139.49, 140.20, 144.72, 146.06, 147.13, 147.51, 151.62. ES-MS m/z 442 (M+H). Anal. Calcd. for $C_{28}H_{35}N_5$.3.9HBr.4.2$H_2O$: C, 40.38; H, 5.72; N, 8.41; Br, 37.42. Found: C, 40.38; H, 5.53; N, 8.17; Br, 37.55.

Example 25

AMD8799: Preparation of N-(2-pyridinylmethyl)-N'-[3-pyrazolylmethyl]-N'-(5,6,7,8-tetrahydro-8-quinolinyl)-1,4-benzenedimethanamine (hydrobromide salt)

Using general procedure A: Reaction of 3-pyrazolecarboxaldehyde (85 mg, 0.88 mmol) and N-(2-nitrobenzenesulfonyl)-N-(2-pyridinylmethyl)-N'-(5,6,7,8-tetrahydro-8-quinolinyl)-1,4-benzenedimethanamine (320 mg, 0.589 mmol) with sodium cyanoborohydride (55 mg, 0.883 mmol) followed by purification of the crude material by column chromatography on silica gel (5% methanol in dichloromethane), gave the desired product (166 mg, 45%).

Using general procedures C and D: the intermediate from above was reacted with thiophenol (0.17 mL, 1.67 mmol) and potassium carbonate (290 mg, 2.09 mmol) in acetonitrile (10 mL). After work-up, the crude material was purified by column chromatography on silica gel (10% methanol in dichloromethane) to give the free base of the desired product (108 mg, 59%). Conversion to the hydrobromide salt gave AMD8799 (88 mg). $^1H$ NMR ($D_2O$) δ 1.72 (m, 1H), 2.11 (m, 2H), 2.31 (m, 1H), 2.62 (s, 1H), 2.86 (s, 2H), 3.30, 3.63 (s, total of 1H), 4.00 (s, 2H), 4.10 (d, 1H, J=15.3 Hz), 4.20 (d, 1H, J=15.3 Hz), 4.29 (s, 2H), 4.34 (m, 1H), 4.55 (s, 2H), 6.56 (br s, 1H), 7.26 (s, 4H), 7.59 (d, 1H, J=8.1 Hz), 7.80 (m, 3H), 7.95 (d, 1H, J=8.1 Hz), 8.11 (dd, 1H, J=8.4, 5.3 Hz), 8.56 (d, 1H, J=5.8 Hz), 8.81 (d, 1H, J=5.3 Hz); $^{13}C$ NMR ($D_2O$) δ 20.10, 27.59, 48.05, 48.65, 51.47, 55.34, 60.11, 107.27, 125.36, 126.97, 130.97, 133.61, 138.99, 141.33, 144.51, 146.20, 147.32, 150.96. ES-MS m/z 439 (M+H). Anal. Calcd. for $C_{27}H_{30}N_6$.5.3HBr.1.3$H_2O$.1.4HOAc: C, 36.46; H, 4.69; N, 8.98; Br, 45.26. Found: C, 36.57; H, 5.00; N, 9.13; Br, 45.11.

Example 26

AMD8728: Preparation of N-(2-pyridinylmethyl)-N'-[2-pyrrolylmethyl]-N'-(5,6,7,8-tetrahydro-8-quinolinyl)-1,4-benzenedimethanamine To a stirred solution of N-(2-nitrobenzenesulfonyl)-N-(2-pyridinylmethyl)-N'-(5,6,7,8-tetrahydro-8-quinolinyl)-1,4-benzenedimethanamine (0.229 g, 0.420 mmol) in anhydrous methanol (4.2 mL, concentration ~0.1 M), at room temperature, was added pyrrole-2-carboxaldehyde (0.0960 g, 1.00 mmol, ~2 equiv.) as a solid in one portion. Once the aldehyde had dissolved (~5 minutes), $NaBH_3CN$ (0.106 g, 1.68 mmol, ~4 equiv.) was added in one portion and the resultant solution was stirred at room temperature for 115 hours. The solvent was removed under reduced pressure and $CH_2Cl_2$ (40 mL) and 1.0M NaOH (10 mL) were added to the residue. The phases were separated and the aqueous phase was extracted with $CH_2Cl_2$ (3×10 mL). The combined organic phases were dried ($Na_2SO_4$) and concentrated. Purification of the crude material by radial chromatography on silica gel (2 mm plate, eluant 25:1 $CH_2Cl_2$-MeOH) provided the desired intermediate (0.178 g, 68%) as a white solid.

To a stirred solution of the solid from above (0.178 g, 0.286 mmol) in anhydrous $CH_3CN$ (5.5 mL, concentration ~0.05 M), at room temperature, was added thiophenol (0.15 mL, 1.461 mmol, ~5 equiv.) followed by powdered $K_2CO_3$ (0.331 g, 2.40 mmol, ~8 equiv.). The resultant bright yellow solution was stirred for 1 hour at room temperature. The solvent was removed under reduced pressure and $CH_2Cl_2$ (10 mL) and water (1 mL) were added to the residue. The phases were separated and the aqueous phase was extracted with $CH_2Cl_2$ (3×5 mL). The combined organic phases were dried ($Na_2SO_4$) and concentrated. Purification of the crude material by column chromatography on silica gel (20:1 $CH_2Cl_2$-MeOH) afforded AMD8728 (0.085 g, 68%) as a yellow oil. $^1H$ NMR ($CDCl_3$) δ 1.57–1.70 (m, 1H), 1.84–2.14 (m, 3H), 2.40 (br s, 1H, NH), 2.64–2.72 (m, 1H), 2.80–2.89 (m, 1H), 3.58 (d, 1H, J=14.1 Hz), 3.66 (s, 2H), 3.77 (d, 1H, J=14.1 Hz), 3.80 (s, 2H), 3.91 (s, 2H), 4.02 (m, 1H), 5.20 (br s, 1H), 6.09 (dd, 1H, J=3.0, 3.0 Hz), 6.79 (dd, 1H, J=3.0, 3.0 Hz), 7.07 (dd, 1H, J=12.3, 4.8 Hz), 7.14 (dd, 1H, J=6.0, 4.8 Hz), 7.25–7.41 (m, 6H), 7.62 (td, 1H, J=7.8, 1.8 Hz), 8.53 (m, 2H), 10.78 (br s, 1H); $^{13}C$ NMR ($CDCl_3$) δ 21.21, 24.06, 29.48, 47.33, 53.69, 54.11, 54.89, 59.21, 105.98, 107.78, 117.16, 122.14, 122.35, 122.79, 128.55 (2 carbons), 129.14 (2 carbons), 131.21, 134.84, 136.86, 137.25, 138.91, 139.44, 147.37, 149.68, 158.62, 160.15. ES-MS m/z 438 (M+H). Anal. Calcd. for $C_{28}H_{31}N_5$.0.8$CH_3OH$: C, 74.68; H, 7.44; N, 15.12. Found: C, 74.93; H, 7.33; N, 15.12.

Example 27

AMD8836: Preparation of N-(2-pyridinylmethyl)-N'-[2-thiopheneylmethyl]-N'-(5,6,7,8-tetrahydro-8-quinolinyl)-1,4-benzenedimethanamine (hydrobromide salt)

To a stirred solution of N-(t-butyloxycarbonyl)-N-(2-pyridinylmethyl)-N'-(5,6,7,8-tetrahydro-8-quinolinyl)-1,4-benzenedimethanamine (0.280 g, 0.610 mmol) in anhydrous methanol (6 mL), at room temperature, was added thiophene-2-carboxaldehyde (0.25 mL, 2.67 mmol) followed by NaBH$_3$CN (0.081 g, 1.30 mmol) and the resultant solution was stirred at room temperature. After 1 day, an additional amount of NaBH$_3$CN (0.083 g, 1.31 mmol) was added and the solution was stirred at room temperature for an additional 3 days. The solvent was removed under reduced pressure and CH$_2$Cl$_2$ (30 mL) and water (10 mL) were added to the residue. The phases were separated and the aqueous phase was extracted with CH$_2$Cl$_2$ (3×10 mL). The combined organic phases were dried (Na$_2$SO$_4$) and concentrated. Purification of the crude material by radial chromatography on silica gel (2 mm plate, 40:1 CH$_2$Cl$_2$-MeOH) provided 0.173 g of the desired amine as a yellow oil.

Using general procedure D: the oil from above was converted to the hydrobromide salt with simultaneous deprotection of the BOC group to afford AMD8836 (0.225 g) as a white solid. $^1$H NMR (D$_2$O) δ 1.60–1.76 (m, 1H), 2.04–2.16 (m, 2H), 2.33–2.38 (m, 1H), 2.82–2.85 (m, 2H), 4.09 (d, 1H J=13.5 Hz), 4.16 (d, 1H J=13.5 Hz), 4.29 (d, 1H J=14.4 Hz), 4.39 (d, 1H J=14.4 Hz), 4.39 (s, 2H), 4.46 (dd, 1H J=7.8, 5.7 Hz), 4.61 (s, 2H), 6.99 (dd, 1H J=3.6, 4.8 Hz), 7.16 (d, 1H J=3.0 Hz), 7.41–7.52 (m, 6H), 7.87–7.92 (m, 2H), 7.97 (d, 1H J=8.1 Hz), 8.39–8.44 (m, 2H), 8.75 (d, 1H, J=5.7 Hz); $^{13}$C NMR (D$_2$O) δ 20.29, 20.43, 27.49, 48.27, 50.14, 51.48, 54.64, 59.65, 124.97, 127.31, 127.47, 127.93, 128.24, 130.27, 130.72, 130.91 (2 carbons), 131.18 (2 carbons), 136.31, 136.65, 138.00, 142.77, 143.56, 145.29, 145.52, 146.75, 150.92; ES-MS m/z 455 (M+H). Anal. Calcd. for C$_{28}$H$_{30}$N$_4$S.4.0HBr.1.9H$_2$O: C, 41.39; H, 4.69; N, 6.90; Br, 39.34; S, 3.95. Found: C, 41.45; H, 4.72; N, 6.90; Br, 39.30; S, 3.87.

Example 28

AMD8841: Preparation of N-(2-pyridinylmethyl)-N'-[2-thiazolylmethyl]-N'-(5,6,7,8-tetrahydro-8-quinolinyl)-1,4-benzenedimethanamine (hydrobromide salt)

To a stirred solution of N-(t-butyloxycarbonyl)-N-(2-pyridinylmethyl)-N'-(5,6,7,8-tetrahydro-8-quinolinyl)-1,4-benzenedimethanamine (0.295 g, 0.643 mmol) in anhydrous methanol (6.5 mL), at room temperature, was added thiazole-2-carboxaldehyde (0.33 mL, 3.76 mmol) followed by NaBH$_3$CN (0.131 g, 2.09 mmol) and the resultant solution was stirred at room temperature. After 2 days, an additional amount of NaBH$_3$CN (0.134 g, 2.10 mmol) was added and the solution was stirred at room temperature for an additional 4 days. The solvent was removed under reduced pressure and CH$_2$Cl$_2$ (20 mL) and water (10 mL) were added to the residue. The phases were separated and the aqueous phase was extracted with CH$_2$Cl$_2$ (3×10 mL). The combined organic phases were dried (Na$_2$SO$_4$) and concentrated. Purification of the crude material by radial chromatography on silica gel (2 mm plate, 40:1 CH$_2$Cl$_2$-MeOH containing 1% NH$_4$OH) afforded 0.164 g of the protected amine as a yellow oil.

Using general procedure D: the oil from above was converted to the hydrobromide salt with simultaneous deprotection of the BOC group to provide AMD8841 (0.178 g) as a white solid. $^1$H NMR (D$_2$O) δ 1.71–1.79 (m, 1H), 2.08–2.19 (m, 2H), 2.29–2.35 (m, 1H), 2.92–2.95 (m, 2H), 3.91 (s, 2H), 4.31 (s, 2H), 4.37 (d, 1H J=16.5 Hz), 4.43–4.58 (m, 4H), 7.37 (d, 2H J=8.1 Hz), 7.43 (d, 2H J=8.1 Hz), 7.74–7.89 (m, 5H), 8.22–8.32 (m, 2H), 8.56 (d, 1H, J=5.7 Hz), 8.71 (d, 1H, J=5.4 Hz); $^{13}$C NMR (D$_2$O) δ 20.38, 20.52, 27.75, 48.69, 51.32, 51.99, 55.52, 59.93, 123.57, 125.78, 126.91, 126.97, 130.16, 130.76 (2 carbons), 130.97 (2 carbons), 136.70, 138.74, 139.68, 140.66, 144.22, 146.28, 147.37, 147.73, 151.26, 173.19. ES-MS m/z 456 (M+H). Anal. Calcd. for C$_{27}$H$_{29}$N$_5$S.3.9HBr.1.9H$_2$O: C, 40.27; H, 4.59; N, 8.70; Br, 38.69; S, 3.98. Found: C, 40.40; H, 4.59; N, 8.43; Br, 38.53; S, 3.92.

Example 29

AMD8821: Preparation of N-(2-pyridinylmethyl)-N'-[2-furanylmethyl]-N'-(5,6,7,8-tetrahydro-8-quinolinyl)-1,4-benzenedimethanamine (hydrobromide salt)

To a stirred solution of N-(t-butyloxycarbonyl)-N-(2-pyridinylmethyl)-N'-(5,6,7,8-tetrahydro-8-quinolinyl)-1,4-benzenedimethanamine (0.206 g, 0.449 mmol) in anhydrous methanol (10 mL), at room temperature, was added furfural (0.19 mL, 2.29 mmol) followed by NaBH$_3$CN (0.070 g, 1.11 mmol) and the resultant solution was stirred at room temperature overnight. The solvent was removed under reduced pressure and CH$_2$Cl$_2$ (20 mL) and 1.0 M aqueous NaOH (10 mL) were added to the residue. The phases were separated and the aqueous phase was extracted with CH$_2$Cl$_2$ (3×10 mL). The combined organic phases were dried (Na$_2$SO$_4$) and concentrated. Purification of the crude material by column chromatography silica gel (25:1 CH$_2$Cl$_2$-MeOH) provided 0.103 g of the protected amine as a yellow oil.

Using general procedure D: the oil from above was converted to the hydrobromide salt with simultaneous deprotection of the BOC group to afford AMD8821 (0.086 g) as a purple solid. $^1$H NMR (D$_2$O) δ 1.67–1.78 (m, 1H), 2.06–2.17 (m, 2H), 2.28–2.37 (m, 1H), 2.83 (br d, 2H, J=5.7 Hz), 4.11–4.24 (m, 4H), 4.38 (s, 2H), 4.44 (dd, 1H, J=10.5, 6.0 Hz), 4.58 (s, 2H), 6.30 (br s, 1H), 6.46 (d, 1H, J=3.3 Hz), 7.40–7.55 (m, 6H), 7.81–7.91 (m, 3H), 8.34 (br t, 1H, J=8.1 Hz), 8.41 (br d, 1H, J=4.8 Hz), 8.72 (br d, 1H, J=5.4 Hz); $^{13}$C NMR (D$_2$O) δ 20.27, 20.51, 27.45, 47.90, 48.73, 51.35, 55.29, 60.21, 111.34, 112.65, 124.70, 126.85, 126.90, 130.87 (3 carbons), 131.16 (2 carbons), 136.11, 137.50, 142.80, 143.15, 144.10, 144.52, 146.31, 147.44, 147.69, 150.91. ES-MS m/z 439 (M+H). Anal. Calcd. for C$_{28}$H$_{30}$N$_4$O.3.9HBr.3.1H$_2$O: C, 41.52; H, 4.99; N, 6.92; Br, 38.47. Found: C, 41.55; H, 4.88; N, 6.73; Br, 38.42.

Example 30

AMD8742: Preparation of N-(2-pyridinylmethyl)-N'-[2-[(phenylmethyl)amino]ethyl]-N'-(5,6,7,8-tetrahydro-8-quinolinyl)-1,4-benzenedimethanamine (hydrobromide salt)

Using general procedure A: N-(t-butyloxycarbonyl)-N-(2-pyridinylmethyl)-N'-(5,6,7,8-tetrahydro-8-quinolinyl)-1, 4-benzenedimethanamine (143 mg, 0.32 mmol), N-(t-butyloxycarbony)-N-benzylaminoacetaldehyde (150 mg, 0.60 mmol) and sodium cyanoborohydride (50 mg, 0.79 mmol) were reacted in MeOH (3 mL). Evaporation of the solvent and purification of the crude material by column chromatography on silica gel (30:70, EtOAc/CH$_2$Cl$_2$) gave the desired intermediate (110 mg, 51%) as yellow oil.

Using general procedure D: the intermediate from above (110 mg, 0.16 mmol) was converted to the hydrobromide salt with simultaneous deprotection of the BOC groups to give AMD8742 (96 mg). $^1$H NMR (CD$_3$OD) δ 1.79–1.89 (m, 1H), 2.05–2.09 (m, 1H), 2.13–2.20 (m, 1H), 2.32–2.36 (m, 1H), 2.96–2.99 (m, 3H), 3.07–3.16 (m, 1H), 3.25–3.47 (m, 2H), 3.79 (d, 1H, J=12.3 Hz), 3.85 (d, 1H, J=12.3 Hz), 4.22 (s, 2H), 4.32–4.35 (b, 2H), 4.37–4.44 (b, 3H), 7.41–7.44 (m, 3H), 7.55–7.59 (b, 5H), 7.67–7.70 (m 3H), 7.86 (dd, 1H, J=7.8, 7.8 Hz), 7.98–8.00 (m, 1H), 8.31–8.33 (d, 1H, J=7.8 Hz), 8.70–8.72 (b, 1H), 8.76 (d, 1H, J=5.7 Hz); $^{13}$C NMR (CD$_3$OD) δ 21.26, 21.97, 29.11,46.88, 50.78 (b), 52.31, 52.73, 56.37, 60.40, 126.36 (b), 126.94, 130.64, 131.15, 131.82, 132.17, 132.59, 140.58, 141.48, 141.60, 141.65 (b), 148.71, 149.23 (b), 151.29 (b), 153.39. ES-MS m/z 492.4 (M+H). Anal. Calcd. for C$_{32}$H$_{37}$N$_5$·4.0HBr·3.0H$_2$O: C, 44.21; H, 5.45; N, 8.06; Br, 36.76. Found: C, 44.33; H, 5.54; N, 7.95; Br, 36.89.

Example 31

AMD8743: Preparation of N-(2-pyridinylmethyl)-N'-(2-aminoethyl)-N'-(5,6,7,8-tetrahydro-8-quinolinyl)-1,4-benzenedimethanamine (hydrobromide salt)

Using general procedure A: N-(t-butyloxycarbonyl)-N-(2-pyridinylmethyl)-N'-(5,6,7,8-tetrahydro-8-quinolinyl)-1,4-benzenedimethanamine (179 mg, 0.39 mmol), N-Boc-aminoacetaldehyde (120 mg, 0.75 mmol) and sodium cyanoborohydride (55 mg, 0.88 mmol) were reacted in MeOH (3 mL). Evaporation of the solvent and purification of the crude material by column chromatography on silica gel (1.5×20 cm, 30:70 EtOAc/CH$_2$Cl$_2$) gave the desired intermediate (200 mg, 85%) as a yellow oil.

Using general procedure D: the intermediate from above (200 mg, 0.33 mmol) was converted to the hydrobromide salt with simultaneous deprotection of the BOC groups to give AMD8743 (150 mg). $^1$H NMR (CD$_3$OD) δ 1.81–1.87 (m, 1H), 2.02–2.21 (m, 2H), 2.33–2.37 (m, 1H), 2.87–3.17 (m, 5H), 3.23–3.28 (m, 1H), 3.78–3.83 (d, 1H, J=13.5 Hz), 3.87–3.92 (d, 1H, J=13.5 Hz), 4.42 (s, 2H), 4.42–4.44 (m, 1H), 4.60–4.63 (m, 2H), 7.57 (d, 2H, J=7.8 Hz), 7.70 (d, 2H, J=7.8), 7.85–7.98 (m, 3H), 8.33 (dd, 2H, J=1.2, 8.1 Hz), 8.79–8.81 (m, 2H); $^{13}$C NMR (CD$_3$OD) δ 19.24, 20.00, 27.18, 37.29, 50.66, 54.34, 58.34, 124.95, 125.82 (b), 129.50, 130.17, 130.37, 138.71, 139.66, 145.00 (b), 146.72, 151.44; ES-MS m/z 402.3 (M+H); Anal. Calcd. for C$_{25}$H$_{31}$N$_5$·4.3HBr·2.6H$_2$O: C, 37.71; H, 5.13; N, 8.79; Br, 43.15. Found: C, 37.80; H, 5.03; N, 8.61; Br, 43.11.

Example 32

AMD8753: Preparation of N-(2-pyridinylmethyl)-N'-3-pyrrolidinyl-N'-(5,6,7,8-tetrahydro-8-quinolinyl)-1,4-benzenedimethanamine (hydrobromide salt)

To the solution of N-(t-butyloxycarbonyl)-N-(2-pyridinylmethyl)-N'-(5,6,7,8-tetrahydro-8-quinolinyl)-1,4-benzenedimethanamine (195 mg, 0.43 mmol) and N-Boc-3-pyrrolidone (91 mg, 0.49 mmol) in methanol (3 ml) was added trimethylorthoformate (2 ml) and three drops of acetic acid, at room temperature. This mixture was allowed to stir for 30 min. at room temperature and sodium cyanoborohydride (130 mg, 2.09 mmol) was added. Stirring was continued for a further 18 hours at room temperature and then the reaction mixture was concentrated. The residue was dissolved in ethylacetate (300 mL), and washed with saturated aqueous NaHCO$_3$ and brine, then dried (Na$_2$SO$_4$) and evaporated. Purification of the residue by column chromatography on silica gel (1.5×20 cm, 50:50 EtOAc/CH$_2$Cl$_2$) gave the desired product (120 mg, 45%) as a mixture of diastereomers.

Using general procedure D: the intermediate from above (120 mg, 0.19 mmol) was converted to the hydrobromide salt with simultaneous deprotection of the BOC groups to give AMD8753 (45 mg) as a mixture of diastereomers. $^1$H NMR (D$_2$O) δ 1.73–1.83 (m, 1H), 2.13–2.21 (m, 2H), 2.28–2.49 (m, 3H), 2.91 (b, 2H), 3.26–3.69 (m, 4H), 3.83–4.02 (m, 3H), 4.33 (s, 2H), 4.33–4.54 (m, 1H), 4.64 (s, 2H), 7.38 (d, 2H, J=7.8 Hz), 7.50 (d, 2H, J=7.8), 7.67–7.70 (b, 1H), 7.79–7.84 (b, 2H), 8.15–8.18 (b, 1H), 8.25–8.28 (b, 1H), 8.37–8.39 (b, 1H), 8.72–8.74 (b, 1H); $^{13}$C NMR (D$_2$O) δ 20.76, 21.96, 27.58, 28.77, 44.80, 45.18, 46.72 (b), 47.79, 49.08, 50.34, 50.60, 51.28, 58.11, 58.61, 61.00 (b), 125.37, 126.60, 129.95, 130.67, 138.97, 139.79, 139.99, 144.20(b), 146.98(b), 147.36, 152.48; ES-MS m/z 428.20 (M+H); Anal. Calcd. for C$_{27}$H$_{33}$N$_5$·3.8HBr·2H$_2$O·0.4C$_2$H$_4$O$_2$: C, 42.00; H, 5.37; N, 8.81; Br, 38.19. Found: C, 42.10; H, 5.47; N, 8.76; Br, 37.97.

Example 33

AMD8754: Preparation of N-(2-pyridinylmethyl)-N'-4-piperidinyl-N'-(5,6,7,8-tetrahydro-8-quinolinyl)-1,4-benzenedimethanamine (hydrobromide salt)

Reaction of N-(t-butyloxycarbonyl)-N-(2-pyridinylmethyl)-N'-(5,6,7,8-tetrahydro-8-quinolinyl)-1,4-benzenedimethanamine (215 mg, 0.47 mmol), N-Boc-4-piperidone (188 mg, 0.94 mmol) and sodium cyanoborohydride (119 mg, 1.89 mmol) in a mixture of methanol (3 ml), trimethylorthoformate (2 ml) and three drops of acetic acid, followed by evaporation of the solvent and purification of the residue by column chromatography on silica gel (1.5×20 cm, 50:50 EtOAc/CH$_2$Cl$_2$) gave the desired intermediate (205 mg, 67%) as a yellow oil.

Using general procedure D: the intermediate from above (205 mg, 0.32 mmol) was converted to the hydrobromide salt with simultaneous deprotection of the BOC groups to give AMD8754 (120 mg). $^1$H NMR (D$_2$O) δ 1.85–1.88 (m, 1H), 1.92–2.05 (m, 2H), 2.08–2.26 (m, 2H), 2.30–2.34 (m, 2H), 2.50 (d, 1H, J=13.8 Hz), 2.91–2.93 (m, 2H), 3.06 (t, 2H, J=12.3 Hz), 3.23 (t, 1H, J=11.4 Hz), 3.58 (t, 2H, J=14.9 Hz), 3.97 (d, 1H, J=13.8 Hz), 4.03 (d, 1H, J=13.8 Hz), 4.32 (s, 2H), 4.44–4.47 (m 3H), 7.38 (d, 2H, J=7.8 Hz), 7.46 (d, 2H, J=7.8 Hz), 7.62–7.72 (m, 3H), 8.10 (d, 1H, J=7.8 Hz), 8.12–8.16 (m, 1H), 8.39 (d, 1H, J=5.4 Hz), 8.68 (m, 1H); $^{13}$C NMR (D$_2$O) δ 20.97, 24.08, 27.01, 27.48, 28.13, 44.42, 49.71, 50.32, 51.08, 57.31, 57.72, 125.22, 125.92, 130.03, 130.63, 130.72, 139.27, 139.49, 139.66, 142.50, 146.61, 147.50, 153.20; ES-MS m/z 442.2 (M+H); Anal. Calcd. for C$_{28}$H$_{35}$N$_5$·3.8HBr·3.8H$_2$O: C, 42.06; H, 5.60; N, 8.76; Br, 37.98. Found: C, 42.20; H, 5.57; N, 8.59; Br, 37.76.

Example 34

AMD8784: Preparation of N-(2-pyridinylmethyl)-N'-[2-[(phenyl)amino]ethyl]-N'-(5,6,7,8-tetrahydro-8-quinolinyl)-1,4-benzenedimethanamine (hydrobromide salt)

Reaction of N-(t-butyloxycarbonyl)-N-(2-pyridinylmethyl)-N'-(5,6,7,8-tetrahydro-8-quinolinyl)-1,4-benzenedimethanamine (174 mg, 0.38 mmol), 2-[N-(t-butyloxycarbonyl)-N-phenyl]acetaldehyde (165 mg, 0.66 mmol) and sodium cyanoborohydride (70 mg, 1.11 mmol) in MeOH (4 mL) followed by evaporation of the solvent and purification of the residue by column chromatography on silica gel (1.5×20 cm, 30:70 EtOAc/$CH_2Cl_2$) gave the desired product (220 mg, 86%) as a yellow oil.

Using general procedure D: the intermediate from above (220 mg, 0.32 mmol) was converted to the hydrobromide salt with simultaneous deprotection of the BOC groups to give AMD8784 (120 mg). $^1$H NMR ($D_2O$) δ 1.73–1.83 (m, 1H), 2.00–2.16 (m, 2H), 2.30–2.34 (m, 1H), 2.91–3.04 (m, 3H), 3.16–3.24 (m, 1H), 3.51–3.59 (m, 2H), 3.78 (d, 1H, J=13.5 Hz), 3.85 (d, 1H, J=13.5 Hz), 4.32 (s, 2H), 4.39 (s, 2H), 4.39–4.44 (m, 1H), 7.16 (d, 2H, J=6.9 Hz), 7.36–7.44 (m, 7H), 7.63–7.71 (m, 3H), 8.09–8.17 (m, 2H), 8.44 (d, 1H, J=4.5 Hz), 8.64 (d, 1H, J=6.0 Hz); $^{13}$C NMR ($D_2O$) δ 20.11, 20.44, 27.65,47.49, 48.20, 49.48, 51.14, 54.71, 59.89, 121.59, 125.54, 126.00, 126.15, 128.88, 130.10, 130.70, 130.91, 135.96, 138.46, 139.89, 140.24, 142.17, 146.60, 147.65, 148.55, 151.37; ES-MS m/z 478.3 (M+H); Anal. Calcd. for $C_{31}H_{35}N_5·3.4HBr·2.8H_2O$: C, 46.36; H, 5.52; N, 8.72; Br, 33.82. Found: C, 46.15; H, 5.30; N, 8.55; Br, 34.11.

General Procedure G: Reductive Amination Using Trimethyl Orthoformate

To a stirred solution of the amine (1 equivalent) in anhydrous methanol (concentration ~0.1 M), at room temperature, was added the carbonyl compound (1.4 equiv.), trimethyl orthoformate (one half the volume of methanol), and a catalytic amount of acetic acid. Once the carbonyl had dissolved (~30 minutes), $NaBH_3CN$ (3.9 equiv.) was added in one portion and the resultant solution was stirred at room temperature for the indicated time. The solvent was removed under reduced pressure and $CH_2Cl_2$ (20 mL/mmol of amine) and aqueous $NaHCO_3$ (10 mL/mmol amine) solution was added to the residue. The phases were separated and the aqueous phase was extracted with $CH_2Cl_2$ (3×10 mL/mmol amine). The combined organic phases were dried ($Na_2SO_4$) and concentrated. The crude material was purified by chromatography.

General Procedure H: Enamide Formation

To a stirred solution of the carbonyl compound (1 equivalent) in anhydrous toluene (concentration ~0.3 M), at room temperature, was added the amide (2–3 equiv.), Amberlyst 15 (50% weight of the carbonyl compound), and 4 Å molecular sieves. The resultant solution was heated up to reflux for the indicated time. The mixture was filtered and the resin was washed with toluene (6 mL/mmol carbonyl compound). The combined solution was heated to 60° C. and 1% aqueous $NaHCO_3$ (12 mL/mmol carbonyl compound) solution was added to the residue. The phases were separated and the organic phase was dried ($Na_2SO_4$) and concentrated. The crude material was purified by chromatography.

General Procedure I: Alkylation Reaction 2-[(2-nitrobenzenesulfonylamino)methyl]pyridine with benzylic bromides.

To a stirred solution of the bromide (1 equiv.) in anhydrous MeCN (concentration ~0.1 M) at room temperature, was added the 2-[(2-nitrobenzenesulfonyl amino)methyl] pyridine (1–1.2 equiv.), $K_2CO_3$ (2 equiv.). The resultant solution was stirred at 60° C. under a nitrogen atmosphere for the indicated time. The solvent was removed under reduced pressure and $CH_2Cl_2$ (100 mL/mmol amide) was added to the residue. The solution was filtered through celite, and concentrated in vacuo. The crude material was purified by chromatography.

Example 35

AMD8759: Preparation of N-(2-pyridinylmethyl)-N'-(7-methoxy-1,2,3,4-tetrahydro-2-naphthalenyl)-1,4-benzenedimethanamine Using General Procedure G: 7-methoxy-2-tetralone (60 mg, 0.34 mmol), N-(2-nitrobenzenesulfonyl)-N-(2-pyridinylmethyl)-1,4-benzenedimethanamine (100 mg, 0.24 mmol) and $NaBH_3CN$ (59 mg, 0.94 mmol) in MeOH (3 mL), trimethyl orthoformate (1.7 mL) and acetic acid (3 drops) were reacted for 3.5 hours. Following work-up, the crude material was purified by chromatography on silica gel ($CH_2Cl_2$/MeOH/$NH_4OH$ 98:1:1) to give the desired product (71 mg, 52%) as a yellow foam.

Using general Procedure D: the foam from above (65 mg, 0.11 mmol) was reacted with thiophenol (35 μL, 0.34 mmol) and $K_2CO_3$ (78 mg, 0.57 mmol) in DMF (1.1 mL). The crude product was purified by radial chromatography on silica gel (1 mm plate, $CH_2Cl_2$/MeOH/$NH_4OH$ 23:1:1) to give AMD8759 (25 mg, 57%) as a yellow oil. $^1$H NMR ($CDCl_3$) δ 1.64–1.68 (m, 1H), 1.95 (s, 2H), 2.05–2.09 (m, 1H), 2.64–2.83 (m, 3H), 2.96–3.05 (m, 2H), 3.77 (s, 3H), 3.83 (s, 2H), 3.89 (s, 2H), 3.92 (s, 2H), 6.62 (s, 1H), 6.67–6.70 (m, 1H), 6.99 (d, 2H, J=8.3 Hz), 7.16–7.18 (m, 1H), 7.26–7.32 (m, 4H), 7.61–7.64 (m, 1H), 8.56 (d, 1H, J=4.5 Hz); $^{13}$C NMR ($CDCl_3$) δ 27.49, 30.11, 37.36, 51.24, 53.07, 53.62, 54.89, 55.65, 112.53, 114.27, 122.31, 122.73, 128.61 (2 carbons), 128.78 (2 carbons), 129.89, 136.79 (2 carbons), 139.27, 139.63, 149.71(2 carbons), 157.97, 160.17. ES-MS m/z 388 (M+H). Anal. Calcd. for $C_{25}H_{29}N_3O·0.4H_2O$: C, 76.07; H, 7.61; N, 10.65. Found: C, 76.09; H, 7.62; N, 10.55.

Example 36

AMD8762: Preparation of N-(2-pyridinylmethyl)-N'-(6-methoxy-1,2,3,4-tetrahydro-2-naphthalenyl)-1,4-benzenedimethanamine Using General Procedure G: 6-methoxy-2-tetralone (112 mg, 0.63 mmol), N-(2-nitrobenzenesulfonyl)-N-(2-pyridinylmethyl)-1,4-benzenedimethanamine (186 mg, 0.45 mmol) and $NaBH_3CN$ (110 mg, 1.76 mmol) in a mixture of MeOH (5 mL), trimethyl orthoformate (2.8 mL) and acetic acid (5 drops) were reacted for 3.5 hours. Purification of the crude material by chromatography on silica gel ($CH_2Cl_2$/MeOH/$NH_4OH$ 98:1:1) gave the desired product (102 mg, 40%) as a yellow foam.

Using General Procedure C: the intermediate from above (102 mg, 0.18 mmol) was reacted with thiophenol (54 μL, 0.53 mmol) and $K_2CO_3$ (122 mg, 0.89 mmol) in DMF (1.7 mL) and the crude material was purified by radial chromatography on silica gel (1 mm plate, $CH_2Cl_2$/MeOH/$NH_4OH$ 98:1:1) to give AMD8762 (51 mg, 74%) as a yellow oil. $^1$H NMR ($CDCl_3$) δ 1.63–1.67 (m, 1H), 1.83 (s, 2H), 2.04–2.08 (m, 1H), 2.57–2.62 (m, 1H), 2.79–3.00 (m, 4H), 3.78 (s, 3H), 3.83 (s, 2H), 3.89 (s, 2H), 3.92 (s, 2H), 6.62 (s, 1H), 6.63–6.67 (m, 2H), 6.99 (d, 2H, J=8.4 Hz), 7.15–7.17 (m, 1H), 7.32 (s, 3H), 7.61–7.63 (m, 1H), 8.56 (d, 1H, J=4.2 Hz); $^{13}$C NMR ($CDCl_3$) δ 28.25, 29.47, 35.90, 50.86, 52.92, 53.22, 54.49, 55.22, 112.03, 113.25, 121.89, 122.32, 127.37, 128.19 (2 carbons), 128.36 (2 carbons), 130.15, 136.38, 137.34, 138.84, 139.33, 149.30, 157.66, 159.79. ES-MS m/z 388 (M+H).

Anal. Calcd. for $C_{25}H_{29}N_3O.0.4H_2O$: C, 76.07; H, 7.61; N, 10.65. Found: C, 76.14; H, 7.55; N, 10.64.

Example 37

AMD8770: Preparation of N-(2-pyridinylmethyl)-N'-(1-methyl-1,2,3,4-tetrahydro-2-naphthalenyl)-1,4-benzenedimethanamine Using General Procedure G: 1-methyl-2-tetralone (109 mg, 0.68 mmol), N-(2-nitrobenzenesulfonyl)-N-(2-pyridinylmethyl)-1,4-benzenedimethanamine (200 mg, 0.48 mmol) and $NaBH_3CN$ (118 mg, 1.87 mmol) were reacted in a mixture of MeOH (5 mL), trimethyl orthoformate (2.8 mL) and acetic acid (5 drops) for 48.5 hours. Purification of the crude material by column chromatography on silica gel ($CH_2Cl_2$/MeOH/$NH_4OH$ 98:1:1) gave the product (41 mg, 15%) as a yellow foam.

Using General Procedure C: the intermediate from above (65 mg, 0.12 mmol) was reacted with thiophenol (36 μL, 0.35 mmol) and $K_2CO_3$ (81 mg, 0.59 mmol) in DMF (1.2 mL). The crude product was purified by radial chromatography on silica gel (1 mm plate, $CH_2Cl_2$/MeOH/$NH_4OH$ 23:1:1) to give AMD8770 (25 mg, 57%) as a yellow oil. $^1$H NMR ($CDCl_3$) δ 1.22 (d, 3H, J=7.2 Hz), 1.30 (d, 1H, J=6.6 Hz), 179–1.86 (m, 3H), 2.84–2.90 (m, 2H), 2.99–3.06 (m, 2H), 3.11–3.15 (m, 1H), 3.84 (s, 4H), 3.91 (s, 2H), 7.09–7.18 (m, 6H), 7.26–7.33 (m, 4H), 7.63–7.64 (m, 1H), 8.56 (d, 1H, J=4.5 Hz); $^{13}$C NMR ($CDCl_3$) δ 17.30, 24.77, 29.05, 36.82, 51.16, 53.66, 54.91, 56.00, 122.35, 122.77, 126.06, 126.20, 128.63 (2 carbons), 128.79 (2 carbons), 129.18, 129.85, 135.96, 136.83, 139.23, 139.82, 142.28, 149.74, 160.19. ES-MS m/z 372 (M+H). Anal. Calcd. for $C_{25}H_{29}N_3.0.4H_2O$: C, 79.28; H, 7.93; N, 11.09. Found: C, 79.42, H, 7.99; N, 10.70.

Example 38

AMD8790: Preparation of N-(2-pyridinylmethyl)-N'-(7-methoxy-3,4-dihydronaphthalenyl)-1-(aminomethyl)-4-benzamide Using General Procedure H: 7-methoxy-2-tetralone (300 mg, 1.71 mmol) and α-bromo-p-toluic amide (732 mg, 3.42 mmol) in toluene (8 mL) containing Amberlyst 15 (150 mg) and 4 Å molecular sieve (600 mg) were reacted for for 24 hours. Purification of the crude material by column chromatography on silica gel ($CH_2Cl_2$) and recrystallisation (EtOAc) gave the desired product (90 mg, 14%) as yellow crystals.

Using General Procedure 1: Reaction of the intermediate from above (90 mg, 0.24 mmol) with 2-[(2-nitrobenzenesulfonylamino)methyl]pyridine (85 mg, 0.29 mmol) and $K_2CO_3$ (66 mg, 0.48 mmol) in MeCN (3 mL) for 24 hours, followed by purification of the crude material by column chromatography on silica gel ($CH_2Cl_2$:/MeOH 99:1) gave the desired product (85 mg, 61%) as a yellow foam.

Using general procedure C: Reaction of the foam (65 mg, 0.12 mmol) with thiophenol (45 μL, 0.44 mmol) and $K_2CO_3$ (100 mg, 0.73 mmol) in DMF (1.5 mL) followed by purification of the crude material by radial chromatography on silica gel (1 mm plate, $CH_2Cl_2$/MeOH 24:1) gave AMD8790 (31 mg, 53%) as a yellow oil. $^1$H NMR ($CD_3OD$) δ 2.57 (t, 2H, J=7.9 Hz), 2.81 (t, 2H, J=6.5 Hz), 3.74 (s, 3H), 3.85 (s, 2H), 3.85 (s, 2H), 6.60 (s, 1H), 6.61–6.62 (m, 1H), 6.98 (d, 1H, J=8.7 Hz), 7.13 (s, 1H), 7.31–7.33 (m, 1H), 7.46–7.49 (m, 3H), 7.78–7.85 (m, 3H), 8.50 (br s, 1H); $^{13}$C NMR ($CDCl_3$) δ 28.47, 28.66, 53.89, 54.96, 56.04, 112.45, 113.03, 114.54, 124.23 (2 carbons), 124.58 (2 carbons), 127.02, 129.21 (2 carbons), 130.04 (2 carbons), 135.51, 137.54, 138.62, 139.15, 145.08, 150.26, 160.40, 169.12. ES-MS m/z 400 (M+H). Anal. Calcd. for $C_{25}H_{25}N_3O_2.0.5H_2O$: C, 73.51; H, 6.42; N, 10.29. Found: C, 73.48, H, 6.42; N, 9.89.

Example 39

AMD8805: Preparation of N-(2-pyridinylmethyl)-N'-(6-methoxy-3,4-dihydronaphthalenyl)-1-(aminomethyl)-4-benzamide Using general procedure H: 6-methoxy-2-tetralone (300 mg, 1.71 mmol) and α-bromo-p-toluic amide (1.1 g, 5.11 mmol) in toluene (15 mL) containing Amberlyst 15 (150 mg) and 4 Å molecular sieve (1 g) were reacted for 24 hours. Purification of the crude material by column chromatography on silica gel ($CH_2Cl_2$) gave the desired product (237 mg, 38%) as yellow crystal.

Using general procedure I: the intermediate from above (237 mg, 0.64 mmol) was reacted with 2-[(2-nitrobenzenesulfonylamino)methyl]pyridine (186 mg, 0.64 mmol) and $K_2CO_3$ (177 mg, 1.28 mmol) in MeCN (6.6 mL) for 24 hours. The crude material was purified by column chromatography on silica gel (EtOAc/Hexane 7:3) to give the desired product (310 mg, 83%) as a yellow foam.

Using general procedure C: The foam (310 mg, 0.53 mmol) was reacted with thiophenol (163 μL, 1.59 mmol) and $K_2CO_3$ (366 mg, 2.65 mmol) in DMF (5.3 mL). Purification of the crude material by radial chromatography on silica gel (1 mm plate, $CH_2Cl_2$/MeOH 24:1) afforded AMD8805 (170 mg, 81%) as a yellow oil. $^1$H NMR ($CD_3OD$) δ 2.58 (t, 2H, J=8.0 Hz), 2.88 (t, 2H, J=8.0 Hz), 3.77 (s, 3H), 3.87 (s, 2H), 3.90 (s, 2H), 6.68–6.70 (m, 1H), 6.70 (s, 1H), 6.94 (d, 1H, J=8.4 Hz), 7.05 (s, 1H), 7.20–7.25 (m, 1H), 7.48–7.50 (m, 3H), 7.83–7.86 (m, 3H), 8.50 (d, 1H, J=4.2 Hz); $^{13}$C NMR ($CDCl_3$) δ 28.47, 28.66, 48.87, 50.91, 54.54, 120.31, 125.88, 126.28, 126.41 (2 carbons), 127.57, 128.29, 129.45 (2 carbons), 130.80 (2 carbons), 131.74 (2 carbons), 131.92, 132.10, 134.36, 142.97, 147.00, 147.86, 169.12. ES-MS m/z 400 (M+H). Anal. Calcd. for $C_{25}H_{25}N_3O_2.0.6H_2O$: C, 73.18; H, 6.44; N, 10.24. Found: C, 73.33, H, 6.41; N, 10.27.

Example 40

AMD8902: Preparation of N-(2-pyridinylmethyl)-N'-(1H-imidazol-2-ylmethyl)-N'-(7-methoxy-1,2,3,4-tetrahydro-2-naphthalenyl)-1,4-benzenedimethanamine Using general procedure G: Reaction of 7-methoxy-2-tetralone (299 mg, 1.70 mmol) and N-(2-nitrobenzenesulfonyl)-N-(2-pyridinylmethyl)-1,4-benzenedimethanamine (500 mg, 1.21 mmol) with $NaBH_3CN$ (296 mg, 4.72 mmol) in a mixture of MeOH (15 mL), trimethyl orthoformate (8.5 mL) and acetic acid (15 drops) for 3.5 hours followed by purification of the crude material by column chromatography on silica gel ($CH_2Cl_2$/MeOH/$NH_4OH$ 98:1:1) gave the desired product (520 mg, 75%) as a yellow foam.

The intermediate from above was reacted in a similar manner with 2-imidazole-carboxaldehyde and the corresponding imidazole intermediate (65 mg, 0.11 mmol) was deprotected (general procedure C) by reaction with thiophenol (35 μL, 0.34 mmol) and K$_2$CO$_3$ (78 mg, 0.57 mmol) in DMF (1.1 mL). Purification of the crude material by radial chromatography on silica gel (1 mm plate, CH$_2$Cl$_2$/MeOH/NH$_4$OH 23:1:1) afforded AMD8902 (25 mg, 57%) as a yellow foam. $^1$H NMR (CDCl$_3$) δ 1.64–1.68 (m, 1H), 1.95 (s, 2H), 2.05–2.09 (m, 1H), 2.64–2.83 (m, 3H), 2.96–3.05 (m, 2H), 3.77 (s, 3H), 3.83 (s, 2H), 3.89 (s, 2H), 3.92 (s, 2H), 6.62 (s, 1H), 6.67–6.70 (m, 1H), 6.99 (d, 2H, J=8.3 Hz), 7.16–7.18 (m, 1H), 7.26–7.32 (m, 4H), 7.61–7.64 (m, 1H), 8.56 (d, 1H, J=4.5 Hz); $^{13}$C NMR (CDCl$_3$) δ 27.49, 30.11, 37.36, 51.24, 53.07, 53.62, 54.89, 55.65, 112.53, 114.27, 122.31, 122.73, 128.61 (2 carbons), 128.78 (2 carbons), 129.89, 136.79 (2 carbons), 139.27, 139.63, 149.71(2 carbons), 157.97, 160.17. ES-MS m/z 388 (M+H). Anal. Calcd. for C$_{25}$H$_{29}$N$_3$O.0.4H$_2$O: C, 76.07; H, 7.61; N, 10.65. Found: C, 76.09; H, 7.62; N, 10.55.

Example 41

AMD8863: Preparation of N-(2-pyridinylmethyl)-N'-(8-hydroxy-1,2,3,4-tetrahydro-2-naphthalenyl)-1,4-benzenedimethanamine Following the procedure of Manitto, P.; Speranza, G.; Monti, D.; Fontana, G. and Panosetti, E. (*Tetrahedron Lett.* 1995, 51, 11531–11546): 8-hydroxy-2-tetralone was prepared from 7-methoxy-1-tetralone.

N-(2-nitrobenzenesulfonyl)-N-(2-pyridinylmethyl)-N'-(8-hydroxy-1,2,3,4-tetrahydro-2-naphthalenyl)-1,4-benzenedimethanamine.

Using General Procedure B: Reaction of 8-hydroxy-2-tetralone (110 mg, 0.68 mmol), N-(2-nitrobenzenesulfonyl)-N-(2-pyridinylmethyl)-1,4-benzenedimethanamine (280 mg, 0.68 mmol) and NaBH(OAc)$_3$ (287 mg, 1.4 mmol) in a mixture of CH$_2$Cl$_2$ (10 mL) and acetic acid (0.2 mL) for 18 hours gave, after work-up, ~400 mg (quant. yield) of the title compound as a yellow foam.

Using general procedure C: the crude product from above (100 mg, 0.18 mmol) was reacted with thiophenol (46 μL, 0.45 mmol) and K$_2$CO$_3$ (75 mg, 0.54 mmol) in DMF (2 mL). Purification of the crude material by radial chromatography on silica gel (1 mm plate, CHCl$_3$/MeOH/NH$_4$OH 20:2:1) afforded AMD8863 (35 mg, 52%) as a white solid. $^1$H NMR (CDCl$_3$) δ 1.59–1.66 (m, 1H), 2.01–2.05 (m, 1H), 2.38 (dd, 1H, J=16, 9 Hz), 2.77–3.08 (m, 4H), 3.82 (s, 2H), 3.91 (s, 2H), 3.93 (s, 2H), 6.47 (d, 1H, J=8 Hz), 6.60 (d, 1H, J=8 Hz), 6.89 (t, 1H, J=8 Hz), 7.17–7.21 (m, 1H), 7.29 (br s, 4H), 7.35 (d, 1H, J=8 Hz), 7.66 (dt, 1H, J=8, 1 Hz), 8.56 (br d, 1H, J=5 Hz); $^{13}$C NMR (CDCl$_3$) δ 28.3, 29.4, 30.4, 50.9, 52.9, 53.1, 53.9, 111.8, 119.8, 122.2, 122.8, 125.9, 128.3, 128.5, 136.8, 137.7, 138.3, 139.2, 148.9, 154.8, 159.3; ES-MS m/z 374 (M+H). Anal. Calcd. for C$_{24}$H$_{27}$N$_3$O.0.3H$_2$O: C, 76.19; H, 7.34; N, 11.11. Found: C, 76.21; H, 7.24; N, 10.96.

Example 42

AMD 8886: Preparation of N-(2-pyridinylmethyl)-N'-(1H-imidazol-2-ylmethyl)-N'-(8-hydroxy-1,2,3,4-tetrahydro-2-naphthalenyl)-1,4-benzenedimethanamine Using General Procedure B: Reaction of N-(2-nitrobenzenesulfonyl)-N-(2-pyridinylmethyl)-N'-(8-hydroxy-1,2,3,4-tetrahydro-2-naphthalenyl)-1,4-benzene dimethanamine (400 mg, 0.72 mmol), imidazole-2-carboxaldehyde (138 mg, 1.4 mmol) and NaBH(OAc)$_3$ (457 mg, 2.2 mmol) in a mixture of CH$_2$Cl$_2$ (20 mL) and acetic acid (0.5 mL) for 48 hours, followed by purification of the crude material by radial chromatography on silica gel (4 mm plate, CHCl$_3$/MeOH/NH$_4$OH 20:1:1) afforded the desired intermediate (175 mg, 41%) as a yellow/green foam.

Using general procedure C: the intermediate from above (175 mg, 0.28 mmol) was reacted with thiophenol (71 μL, 0.68 mmol), and K$_2$CO$_3$ (114 mg, 0.81 mmol) in DMF (3 mL). The crude material was purified by radial chromatography on silica gel (1 mm plate, CHCl$_3$/MeOH/NH$_4$OH 20:2:1) to give AMD8886 (53 mg, 43%) as a white foam. $^1$H NMR (CDCl$_3$) δ 1.62–1.76 (m, 1H), 1.96–2.05 (m, 1H), 2.53–2.66 (m, 1H), 2.70–2.79 (m, 2H), 2.96–3.07 (m, 2H), 3.48 (s, 2H), 3.70 (br s, 2H), 3.79–3.82 (m, 3H), 3.84–3.95 (m, 3H), 6.53–6.62 (m, 2H), 6.88 (t, 1H, J=8 Hz), 6.93 (s, 2H), 7.15–7.19 (m, 1H), 7.24–7.33 (m, 6H), 7.64 (dt, 1H, J=8, 2 Hz), 8.55 (br d, 1H, J=5 Hz); $^{13}$C NMR (CDCl$_3$) δ 25.0, 25.9, 30.0, 47.3, 53.1, 54.1, 54.2, 56.4, 111.9, 119.3, 122.1, 122.6, 123.4, 126.0, 128.4, 128.7, 136.6, 137.5, 138.5, 138.7, 147.9, 149.1, 155.6, 159.3. ES-MS m/z 454 (M+H). Anal. Calcd. for C$_{28}$H$_{31}$N$_5$O.0.9H$_2$O: C, 71.59; H, 7.04; N, 14.91. Found: C, 71.58; H, 6.76; N, 14.70.

Example 43

AMD8 889: Preparation of N-(2-pyridinylmethyl)-N'-(8-Fluoro-1,2,3,4-tetrahydro-2-naphthalenyl)-1,4-benzenedimethanamine Following the procedure of Nixon, J. A.; Pioch, R. P.; Schaus, J. M.; and Titus, R. D. (EP-A-0 343 830, Eli Lilly and Company): 8-fluoro-2-tetralone was prepared from o-fluorophenylacetic acid.

N-(2-nitrobenzenesulfonyl)-N-(2-pyridinylmethyl)-N'-(8-Fluoro-1,2,3,4-tetrahydro-2-naphthalenyl)-1,4-benzenedimethanamine Following General Procedure B: Reaction of 8-fluoro-2-tetralone (159 mg, 0.97 mmol), N-(2-nitrobenzenesulfonyl)-N-(2-pyridinylmethyl)-1,4-benzenedimethanamine (400 mg, 0.97 mmol) and NaBH(OAc)$_3$ (411 mg, 1.9 mmol) in a mixture of CH$_2$Cl$_2$ (10 mL) and acetic acid (0.2 mL) for 18 hours followed by purification of the crude material by column chromatography on silica gel (CHCl$_3$/MeOH/NH$_4$OH 20:2:1) afforded the title compound (500 mg, 92%) as a yellow foam.

Using general procedure C: the intermediate from above (130 mg, 0.23 mmol) was reacted with thiophenol (60 μL, 0.58 mmol) and K$_2$CO$_3$ (96 mg, 0.70 mmol) in DMF (2 mL). Purification of the crude material by radial chromatography on silica gel (1 mm plate, CHCl$_3$/MeOH/NH$_4$OH 20:2:1) afforded AMD8889 (46 mg, 43%) as a white foam. $^1$H NMR (CDCl$_3$) δ 1.58–1.71 (m, 1H), 1.72–1.95 (br s, 2H), 2.00–2.09 (m, 1H), 2.48 (dd, 1H, J=17, 9 Hz), 2.73–3.00 (m, 3H), 3.11 (dd, 1H, J=17, 5 Hz), 3.83 (s, 2H), 3.90 (s, 2H), 3.92 (s, 2H), 6.79–6.88 (m, 2H), 7.02–7.07 (m, 1H), 7.14–7.18 (m, 1H), 7.29–7.39 (m, 5H), 7.63 (dt, 1H, J=15, 2), 8.55–8.57 (m, 1H); $^{13}$C NMR (CDCl$_3$) δ 27.6, 28.9, 29.2, 50.7, 51.8, 53.1, 54.4, 111.8 (d, $^2J_{C-F}$=22 Hz), 121.8, 122.3, 122.7, 123.9, 126.4 (d, $^3J_{C-F}$=9 Hz), 128.1, 128.3, 136.3, 139.0 (d, $^2J_{C-F}$=22 Hz), 149.2, 159.7, 161.0 (d, $J_{C-F}$=244 Hz). ES-MS m/z 376 (M+H). Anal. Calcd. for C$_{24}$H$_{26}$N$_3$F.0.1H$_2$O: C, 76.40; H, 7.00; N, 11.14. Found: C, 76.35; H, 7.02; N, 11.14.

Example 44

AMD8895: Preparation of N-(2-pyridinylmethyl)-N'-(1H-imidazol-2-ylmethyl)-N'-(8-Fluoro-1,2,3,4-tetrahydro-2-naphthalenyl)-1,4-benzenedimethanamine

Using general procedure B: Reaction of N-(2-nitrobenzenesulfonyl)-N-(2-pyridinylmethyl)-N'-(8-Fluoro-1,2,3,4-tetrahydro-2-naphthalenyl)-1,4-benzenedimethanamine (450 mg, 0.81 mmol), imidazole-2-carboxaldehyde (155 mg, 1.6 mmol) and NaBH(OAc)$_3$ (512 mg, 2.4 mmol) in a mixture of CH$_2$Cl$_2$ (10 mL) and acetic acid (1.0 mL) for 72 hours, followed by purification of the crude material by column chromatography on silica gel (CHCl$_3$/MeOH/NH$_4$OH 20:2:1) gave 400 mg (~80% recovery) of a ~1:1 mixture of starting material and product as a yellow foam.

Using general procedure C: the mixture from above (370 mg, ~0.58 mmol) was reacted with thiophenol (150 μL, 1.5 mmol) and K$_2$CO$_3$ (240 mg, 1.7 mmol) in DMF (3 mL). Purification of the crude material by radial chromatography on silica gel (1 mm plate, CHCl$_3$/MeOH/NH$_4$OH 20:1:1) afforded AMD8895 (57 mg, 22%) as a white foam. $^1$H NMR (CDCl$_3$) δ 1.59–1.72 (m, 1H), 2.10–2.16 (m, 1H), 2.64–2.80 (m, 2H), 2.88–3.05 (m, 3H), 3.76 (d, 1H, J=14 Hz), 3.79 (d, 1H, J=14 Hz), 3.81 (s, 2H), 3.86 (s, 2H), 3.92 (s, 2H), 6.77–6.84 (m, 2H), 6.94 (s, 2H), 7.02–7.07 (m, 1H), 7.15 (dd, 1H, J=7, 6 Hz), 7.27–7.31 (m, 6H), 7.63 (dt, 1H, J=8, 2 Hz), 8.55 (br d, 1H, J=4 Hz); $^{13}$C NMR (CDCl$_3$) δ 24.3, 25.2, 29.6, 47.8, 53.1, 54.3, 54.5, 55.4, 111.8 (d, $^2J_{C-F}$=22 Hz), 121.9, 122.3, 123.3, 123.5, 123.9, 126.5 (d, $^3J_{C-F}$=9 Hz), 128.4, 128.5, 136.4, 138.2, 138.7, 138.9 (d, $^2J_{C-F}$=25 Hz), 147.4, 149.3, 159.6, 161.0 (d, $^2J_{C-F}$=244 Hz). ES-MS m/z 456 (M+H). Anal. Calcd. for C$_{28}$H$_{30}$N$_5$F.0.3H$_2$O: C, 72.95; H, 6.69; N, 15.19. Found: C, 72.99; H, 6.86; N, 15.06.

Example 45

AMD8852: Preparation of N-(2-pyridinylmethyl)-N'-(5,6,7,8-tetrahydro-7-quinolinyl)-1,4-benzenedimethanamine (hydrobromide salt)

7-Amino-5,6,7,8-tetrahydroquinoline was prepared by the method of I. A. Cliffe et al. Tetrahedron letters 1991, 32, 6789–6792.

N-(2-nitrobenzenesulfonyl)-N-(2-pyridinylmethyl)-N'-(5,6,7,8-tetrahydro-7-quinolinyl)-1,4-benzenedimethanamine

Using General procedure B: Reaction of 7-amino-5,6,7,8-tetrahydroquinoline (72 mg, 0.47 mmol) and nosyl-protected Trevor aldehyde (200 mg, 0.49 mmol) and NaBH(OAc)$_3$ (206 mg, 0.98 mmol) in CH$_2$Cl$_2$ (5 mL) for 18 hours gave, after workup, the crude product (260 mg, 98% yield) as a green foam. This was used without further purification in the next step.

Using general procedure C: The crude product from above (100 mg, ~0.18 mmol) was reacted with thiophenol (47 μL, 0.45 mmol) and K$_2$CO$_3$ (77 mg, 0.54 mmol) in DMF (2 mL). Purification of the crude material by radial chromatography on silica gel (1 mm plate, CHCl$_3$/MeOH/NH$_4$OH 20:2:1) afforded the corresponding free base (55 mg, 77%) of AMD8852. Using general procedure D: the free base was converted to the hydrobromide salt to give AMD8852 (94 mg, 89%) as a white solid. $^1$H NMR (CDCl$_3$) δ 1.66–1.71 (m, 1H), 1.98 (br s, 2H), 2.02–2.07 (m, 1H), 2.73–2.85 (m, 3H), 3.06–3.09 (m, 1H), 3.21 (dd, 1H, J=18, 6 Hz), 3.81 (s, 2H), 3.88 (s, 2H), 3.90 (s, 2H), 7.01 (dd, 1H, J=8, 5 Hz), 7.13 (dd, 1H, J=7, 5 Hz), 7.26–7.35 (m, 6H), 7.61 (dt, 1H, J=8, 2 Hz), 8.33–8.34 (m, 1H), 8.53 (br d, 1H, J=5 Hz); $^{13}$C NMR (CDCl$_3$) δ 26.4, 28.7, 39.6, 50.7, 52.1, 53.1, 54.4, 121.0, 121.8, 122.3, 128.1, 128.3, 131.4, 136.2, 136.3, 138.8, 139.0, 147.0, 149.2, 155.6, 159.6. ES-MS m/z 359 (M+H). Anal. Calcd. for C$_{23}$H$_{26}$N$_4$.4.1HBr.0.6H$_2$O.0.7C$_2$H$_4$O$_2$: C, 39.44; H, 4.62; N, 7.51; Br, 44.01. Found: C, 39.46; H, 4.80; N, 7.46; Br, 44.03.

Example 46

AMD8858: N-(2-pyridinylmethyl)-N'-(1H-imidazol-2-ylmethyl)-N'-(5,6,7,8-tetrahydro-7-quinolinyl)-1,4-benzenedimethanamine (hydrobromide salt)

Using general procedure B: Reaction of N-(2-nitrobenzenesulfonyl)-N-(2-pyridinylmethyl)-N'-(5,6,7,8-tetrahydro-7-quinolinyl)-1,4-benzenedimethanamine (175 mg, 0.32 mmol), imidazole-2-carboxaldehyde (155 mg, 1.6 mmol) and NaBH(OAc)$_3$ (137 mg, 0.64 mmol) in MeOH (3 mL) for 8 hours at 60° C., followed by purification of the crude material by column chromatography on silica gel (CHCl$_3$/MeOH/NH$_4$OH 20:2:1) gave the desired product (169 mg, 84%) as a yellow/green foam.

Using general procedure C: the intermediate from above (169 mg, 0.27 mmol) was was reacted with thiophenol (70 μL, 0.68 mmol) and K$_2$CO$_3$ (113 mg, 0.81 mmol) in DMF (3 mL). Purification of the crude material by radial chromatography on silica gel (1 mm plate, CHCl$_3$/MeOH/NH$_4$OH 20:2:1) afforded the free base (30 mg, 25%) which was subsequently converted to the hydrobromide salt using general procedure X to give AMD8858 (35 mg, 58%) as a white solid. $^1$H NMR (CDCl$_3$) δ 1.66–1.70 (m, 1H), 2.14–2.19 (M, 1H), 2.26 (br s, 1H), 2.66–2.83 (m, 2H), 3.01–3.12 (m, 3H), 3.64 (d, 1H, J=15 Hz), 3.77–3.82 (m, 3H), 3.86 (s, 2H), 3.90 (s, 2H), 6.92 (s, 2H), 7.01–7.03 (m, 1H), 7.17–7.20 (m, 1H), 7.26–7.34 (m, 6H), 7.62 (dt, 1H, J=8, 2 Hz), 8.31–8.33 (m, 1H), 8.52–8.54 (m, 1H), 9.68 (br s, 1H); $^{13}$C NMR (CDCl$_3$) δ 24.2, 28.1, 35.7, 47.8, 53.1, 54.2, 55.5, 55.7, 121.1, 121.9, 122.3, 128.4, 128.5, 131.4, 136.3, 136.4, 138.2, 139.1, 147.0, 147.3, 149.2, 156.1, 159.6. ES-MS m/z 429 (M+H).

Anal. Calcd. for C$_{27}$H$_{30}$N$_6$.5.2HBr.0.2H$_2$O: C, 37.76; H, 4.23; N, 9.54; Br, 46.80. Found: C, 38.02; H, 4.53; N, 9.20; Br, 46.99.

Example 47

AMD8785: Preparation of N-(2-pyridinylmethyl)-N'-[2-[(2-naphthalenylmethyl)amino]ethyl]-N'-(5,6,7,8-tetrahydro-8-quinolinyl)-1,4-benzenedimethanamine (hydrobromide salt)

To a stirred solution of 3-amino-1,2-propanediol (1.50 g, 16.5 mmol) in dry MeOH (25 mL) was added 2-naphthaldehyde (1.50 g, 9.6 mmol) followed by sodium cyanoborohydride (1.02 g, 16.2 mmol) and the reaction mixture was stirred for 16 hours. The reaction mixture was concentrated in vacuo, diluted with EtOAc (70 mL) and washed with saturated aqueous sodium bicarbonate (70 mL). The aqueous layer was extracted with EtOAc (2×50 mL) and the combined organic layers were then washed with brine (75 mL), dried (MgSO$_4$), filtered and concentrated in vacuo. The residue was used directly in the next step without further purification.

A solution of the crude amine (900 mg) in THF (20 mL) was treated with di-t-butyldicarbonate (1.02 g, 4.68 mmol) for 1 hour. The crude product was purified by column chromatography on silica gel (EtOAc/hexanes, 1:1) to give the BOC-naphthyl-derivatized diol. $^1$H NMR (CDCl$_3$) δ 1.49 (br s, 9H), 3.21–3.49 (m, 4H), 3.53 (br m, 2H), 3.72 (br s, 1H), 4.57–4.68 (br s, 2H), 7.36 (br d, 1H, J=8.1 Hz), 7.47–7.50 (m, 2H), 7.64 (s, 1H), 7.79–7.84 (m, 3H).

To a solution of the diol from above (705 mg, 2.13 mmol) in water/CH$_2$Cl$_2$ (20 mL, 1:1) was added sodium periodate (1.06 g, 4.96 mmol) and the mixture stirred vigourously for 3 hours. The reaction was diluted with CH$_2$Cl$_2$ (25 mL) and washed with water (25 mL). The organic layer was dried (Na$_2$SO$_4$), filtered and concentrated in vacuo. The resultant crude aldehyde was used without further purification in the next step.

To a solution of N-(t-butoxycarbonyl)-N-(2-pyridinylmethyl)-N'-(5,6,7,8-tetrahydro-8-quinolinyl)-1,4-benzenedimethanamine (260 mg, 0.57 mmol) and the crude aldehyde from above in MeOH (15 mL) was added sodium cyanoborohydride (88 mg, 1.4 mmol) and the mixture was stirred for 16 hours. After work-up, the crude material was purified by column chromatography on silica gel (CH$_2$Cl$_2$/MeOH, 96:4 to 95:5) to give the desired intermediate (208 mg, 50%) as a yellow oil.

Using general procedure D: the oil from above (38 mg, 0.05 mmol) was converted to the hydrobromide salt with simultaneous deprotection of the BOC groups to give AMD8785 (37 mg, 83%) as a white solid. $^1$H NMR (D$_2$O) δ 1.67–1.75 (br m, 1H), 1.97–2.12 (br m, 2H), 2.26–2.30 (br m, 1H), 2.87–3.04 (m, 4H), 3.14–3.18 (br d, 2H, J=10.5 Hz), 3.58 (s, 2H), 3.76 (d, 1H, J=13.2 Hz), 3.91 (d, 1H, J=13.2 Hz), 4.13–4.28 (m, 5H), 7.22 (d, 2H, J=8.0 Hz), 7.32 (d, 2H, J=8.0 Hz), 7.40 (d, 1H, J=9.0 Hz), 7.45 (d, 1H, J=8.0 Hz), 7.56–7.62 (m, 3H), 7.74 (dd, 1H, J=7.0, 6.0 Hz), 7.82 (s, 1H), 7.87–7.92 (m, 3H), 8.04 (t, 1H, J=7.5 Hz), 8.20 (d, 1H, J=8.0 Hz), 8.48 (d, 1H, J=5.0 Hz), 8.58 (d, 1H, J=5.0 Hz); $^{13}$C NMR (D$_2$O) δ 19.86, 20.43, 27.72, 45.70, 48.06, 48.80, 50.73, 51.14, 54.94, 59.94, 125.69, 126.27, 126.43, 127.01, 127.65, 127.97, 128.11, 128.25, 128.53, 129.49, 130.05, 130.13, 130.84 (4 carbons), 133.10, 133.51, 139.12, 139.70, 140.49, 142.93, 147.03, 147.65, 147.77, 151.65. ES-MS m/z 542 (M+H). Anal. Calcd. for C$_{36}$H$_{39}$N$_5$.4.0HBr.4.4H$_2$O: C, 45.77; H, 5.53; N, 7.41; Br, 33.83. Found: C, 45.68; H, 5.34; N, 7.16; Br, 34.03.

Example 48

AMD8820: Preparation of N-(2-pyridinylmethyl)-N'-[2-(isobutylamino)ethyl]-N'-(5,6,7,8-tetrahydro-8-quinolinyl)-1,4-benzenedimethanamine (hydrobromide salt)

To a stirred solution of sec-butylamine (1.0 mL, 9.90 mmol) in CH$_2$Cl$_2$ (40 mL) at room temperature was added triethylamine (2.8 mL, 20.1 mmol) and 2-nitrobenzenesulfonyl chloride (2.6 g, 11.7 mmol) as a solid in three portions and the reaction stirred for 16 hours. The mixture was then washed with saturated aqueous sodium bicarbonate (40 mL) and brine (40 mL) and the organic phase dried (Na$_2$SO$_4$), filtered and concentrated in vacuo to give the nosyl-protected amine as a green solid.

To a stirred solution of the nosyl sec-butyl amine (850 mg, 3.30 mmol) in dry DMF (5 mL) was added 2-bromoethanol (0.40 mL, 5.6 mmol) and powdered potassium carbonate (910 mg, 6.6 mmol) and the mixture stirred for 2 days. The reaction was diluted with EtOAc (50 mL) and washed with brine (4×30 mL) and the combined organic layers dried (MgSO$_4$), filtered and concentrated in vacuo. Purification of the crude product by column chromatography on silica gel (EtOAc/hexanes, 1:1) gave the hydroxyethyl product (188 mg, 19%) as a clear oil. $^1$H NMR (CDCl$_3$) δ 0.82 (t, 3H, J=6.0 Hz), 1.12 (d, 3H, J=6.0 Hz), 1.43–1.56 (m, 2H), 2.27 (br s, 1H), 3.40 (t, 2H, J=6.0 Hz), 3.77–3.87 (m, 3H), 7.58–7.61 (m, 1H), 7.67–7.71 (m, 2H), 8.04–8.07 (m, 1H).

Using general procedure F: A solution of this alcohol (308 mg, 1.02 mmol) in CH$_2$Cl$_2$ (10 mL) was oxidized with Dess-Martin periodinane (600 mg, 1.42 mmol) for 45 min to give the crude aldehyde which was used without further purification.

To a solution of N-(t-butoxycarbonyl)-N-(2-pyridinylmethyl)-N'-(5,6,7,8-tetrahydro-8-quinolinyl)-1,4-benzenedimethanamine (224 mg, 0.49 mmol) and the crude aldehyde from above, in MeOH (7 mL) was added sodium cyanoborohydride (65 mg, 1.04 mmol) and the mixture was stirred for 17 hours. After work-up, the crude material was purified by column chromatography on silica gel (CH$_2$Cl$_2$/MeOH, 96:4 to 9:1) to give the desired intermediate as a yellow oil.

Using general procedures C and D: the oil from above was reacted with thiophenol (0.35 mL, 3.4 mmol) and potassium carbonate (555 mg, 4.02 mmol) in CH$_3$CN (5 mL) for 3 hours. Purification of the crude intermediate by column chromatography on silica gel (CH$_2$Cl$_2$/MeOH/NH$_4$OH, 95:5:0 followed by 90:9:1) gave the desired BOC-protected intermediate (49 mg, 18% over 2 steps) as a clear oil. Conversion to the hydrobromide salt with simultaneous deprotection of the BOC group followed by re-precipitation of the crude solid from methanol/ether gave AMD8820 (33 mg, 60%) as a white solid. $^1$H NMR (D$_2$O) mixture of diastereomers δ 0.85 (d, J=7.3 Hz) and 0.89 (d, J=7.3 Hz) (total 3H), 1.19 (t, 3H, J=6.7 Hz), 1.41–1.52 (m, 1H), 1.57–1.82 (m, 2H), 2.02–2.17 (m, 2H), 2.29–2.34 (m, 1H), 2.92–3.22 (m, 7H), 3.80 (s, 2H), 4.36–4.42 (m, 1H), 4.37 (s, 2H), 4.56 (s, 2H), 7.44 (s, 4H), 7.75 (t, 1H, J=7.0 Hz), 7.80–7.89 (m, 2H), 8.24 (d, 1H, J=8.0 Hz), 8.32 (td, 1H, J=8.0, 1.5 Hz), 8.48 (d, 1H, J=5.0 Hz), 8.72 (d, 1H, J=5.5 Hz); $^{13}$C NMR (D$_2$O) mixture of diastereomers δ 9.27, 15.06, 15.28, 19.79, 20.49, 25.77, 26.00, 27.73, 43.17, 43.28, 48.42, 48.67, 51.36, 54.62, 56.20, 56.30, 59.51, 59.64, 125.59, 126.99, 130.10, 130.82, 130.90, 139.17, 139.73, 140.46, 144.30, 146.22, 147.32, 147.55, 151.92. ES-MS m/z 458 (M+H). Anal. Calcd. for C$_{29}$H$_{39}$N$_5$.4.4HBr.3.8H$_2$O: C, 39.49; H, 5.83; N, 7.94. Found: C, 39.44; H, 5.82; N, 7.87.

Example 49

AMD8827: Preparation of N-(2-pyridinylmethyl)-N'-[2-[(2-pyridinylmethyl)amino]ethyl]-N'-(5,6,7,8-tetrahydro-8-quinolinyl)-1,4-benzenedimethanamine (hydrobromide salt)

To a stirred solution of 2-pyridinecarboxaldehyde (1.60 mL, 16.6 mmol) in dry MeOH (10 mL) was added ethanolamine (1.0 mL, 16.6 mmol) and the mixture was stirred for 2 days. The solution was concentrated in vacuo and redissolved in dry MeOH (10 mL). To this solution was added palladium on activated carbon (10%, 250 mg) and the mixture was stirred for 20 hours under an atmosphere of hydrogen. The reaction mixture was filtered through MgSO$_4$, concentrated in vacuo, dissolved in THF (20 mL) and protected with di-t-butyldicarbonate (3.55 g, 16.3 mmol) for 2 hours. Purification of the crude material by column chromatography on silica gel ($CH_2Cl_2$/MeOH, 96:4) gave the desired alcohol as a clear oil: $^1$H NMR ($CDCl_3$) δ 1.22 (br s) and 1.40 (br s) (total 9H), 3.58–3.62 (br m, 2H), 3.81–3.83 (br m, 2H), 4.44 (s, 2H), 6.82–6.84 (br m) and 7.20–7.25 (m) and 7.33 (d, J=9.0 Hz) and 7.68 (t, J=7.5 Hz) and 8.50 (m, 1H) (total 4H).

Using general procedure F: A solution of the alcohol (330 mg, 1.31 mmol) in $CH_2Cl_2$ (5 mL) was oxidized with Dess-Martin periodinane (670 mg, 1.58 mmol) for 45 min to give the crude aldehyde, which was used without further purification in the next step.

Using general procedure A: To a solution of N-(t-butoxycarbonyl)-N-(2-pyridinylmethyl)-N'-(5,6,7,8-tetrahydro-8-quinolinyl)-1,4-benzenedimethanamine (250 mg, 0.46 mmol) and the crude aldehyde in MeOH (10 mL) was added sodium cyanoborohydride (71 mg, 1.13 mmol) and the mixture was stirred for 16 hours. After work-up, the crude intermediate was purified by column chromatography on silica gel ($CH_2Cl_2$/MeOH, 96:4 to 9:1) to give the desired intermediate as a yellow oil.

Using general procedures C and D: The oil from above was reacted with thiophenol (92 μL, 0.90 mmol) and potassium carbonate (130 mg, 0.94 mmol) in $CH_3CN$ (5 mL) for 16 hours. Purification of the crude material by column chromatography on silica gel ($CH_2Cl_2$/MeOH/$NH_4OH$, 95:5:0 followed by 93:6:1) gave the BOC protected intermediate (47 mg, 17% over 2 steps) as a colorless oil. Conversion to the hydrobromide salt with simultaneous deprotection of the BOC group, followed by re-precipitaion of the crude material from methanol/ether gave AMD8827 (62 mg, 84%) as a pale orange solid. $^1$H NMR ($D_2O$) δ 1.71–1.77 (br m, 1H), 2.05–2.17 (br m, 2H), 2.27–2.32 (m, 1H), 2.92 (br d, 2H, J=4.8 Hz), 3.00–3.05 (m, 1H), 3.15–3.19 (m, 1H), 3.30–3.40 (m, 2H), 3.75 (s, 2H), 4.31 (s, 2H), 4.33–4.38 (m, 1H), 4.42 (s, 2H), 4.52 (s, 2H), 7.39 (d, 2H, J=8.0 Hz), 7.43 (d, 2H, J=8.0 Hz), 7.67–7.75 (m, 3H), 7.78–7.88 (m, 2H), 8.18 (td, 1H, J=7.0, 2.0 Hz), 8.22 (d, 1H, J=7.0 Hz), 8.33 (td, 1H, J=7.0, 2.0 Hz), 8.45 (d, 1H, J=6.0 Hz), 8.59 (d, 1H, J=5.0 Hz), 8.70 (d, 1H, J=4.0 Hz); $^{13}$C NMR ($D_2O$) δ 19.70, 20.50, 27.75, 46.21, 48.19, 48.75, 49.76, 51.33, 54.52, 59.25, 125.59, 126.07, 126.30, 126.88 (2 carbons), 130.08, 130.88 (4 carbons), 139.20, 139.52, 140.48, 142.52, 144.01, 146.41, 147.37 (2 carbons), 147.59, 148.12, 151.82. ES-MS n/z 493 (M+H). Anal. Calcd. for $C_{31}H_{36}N_6$·4.9HBr·3.3$H_2O$: C, 39.25; H, 5.05; N, 8.86; Br, 41.28. Found: C, 39.20; H, 4.95; N, 8.67; Br, 41.33.

Example 50

AMD8828: Preparation of N-(2-pyridinylmethyl)-N'-[2-[(2-furanylmethyl)amino]ethyl]-N'-(5,6,7,8-tetrahydro-8-quinolinyl)-1,4-benzenedimethanamine (hydrobromide salt)

To a stirred solution of 2-furanaldehyde (4.0 mL, 48.3 mmol) in dry MeOH (10 mL) was added ethanolamine (1.5 mL, 24.6 mmol) and the mixture stirred for 2 days. The solution was concentrated in vacuo and redissolved in dry MeOH (10 mL). To this solution was added sodium borohydride (0.50 g, 13.2 mmol) in three portions and the mixture stirred for 40 min. The reaction mixture was concentrated in vacuo and partitioned between EtOAc (40 mL) and saturated aqueous sodium bicarbonate (40 mL). The aqueous layer was washed with EtOAc (2×30 mL) and the combined organic phases dried ($MgSO_4$), filtered and concentrated in vacuo. The crude amine was dissolved in THF (30 mL) and protected with di-t-butyldicarbonate (1.95 g, 8.94 mmol) for 3 hours. After work-up, the crude intermediate was purified by column chromatography on silica gel (hexanes/EtOAc, 3:1 followed by 1:1) to give the desired alcohol as a clear oil: $^1$H NMR ($CDCl_3$) δ 1.47 (s, 9H), 2.99 (br s, 1H), 3.45 (br s, 2H), 3.69–3.71 (br m, 2H), 4.41 (br s, 2H), 6.20 (br s) and 6.32 (br s) and 7.35 (s) and 7.40 (s) (total 3H).

Using general procedure F: A solution of the alcohol (280 mg, 1.16 mmol) in $CH_2Cl_2$ (5 mL) was oxidized with Dess-Martin periodinane (650 mg, 1.53 mmol) for 30 min and the crude aldehyde used without further purification.

To a solution of N-(2-nitrobenzenesulfonyl)-N-(2-pyridinylmethyl)-N'-(5,6,7,8-tetrahydro-8-quinolinyl)-1,4-benzenedimethanamine (270 mg, 0.50 mmol) and the crude aldehyde in MeOH (5 mL) was added sodium cyanoborohydride (61 mg, 0.97 mmol) and the mixture was stirred for 17 hours. Following work-up, the crude material was purified by column chromatography on silica gel ($CH_2Cl_2$/MeOH, 96:4) to give the desired intermediate as an orange oil.

The oil from above was dissolved in $CH_2Cl_2$ (2 mL) and treated with trifluoroacetic acid (1 mL) and the mixture was stirred for 30 min. The reaction was concentrated in vacuo then diluted with $CH_2Cl_2$ (25 mL) and saturated aqueous sodium bicarbonate (25 mL). The organic phase was washed with saturated aqueous sodium bicarbonate (2×25 mL), dried ($Na_2SO_4$), filtered and concentrated in vacuo. Purification of the crude product by column chromatography on silica gel ($CH_2Cl_2$/MeOH/$NH_4OH$, 94:5:1) gave the 2-nitrobenzenesulfonyl-protected intermediate (93 mg, 28% over 2 steps) as a yellow oil.

Using general procedures C and D: the oil was reacted with thiophenol (80 μL, 0.78 mmol) and potassium carbonate (140 mg, 1.01 mmol) in $CH_3CN$ (5 mL) for 3 hours. Purification of the crude material by by column chromatography on silica gel ($CH_2Cl_2$/MeOH/$NH_4OH$, 95:5:0 followed by 95:4:1) gave the free base of the title compound (24 mg, 36%). Conversion of the free base (20 mg, 0.04 mmol) to the hydrobromide salt followed by re-precipitation of the crude material from methanol/ether gave AMD8828 (31 mg, 89%) as an off-white solid. $^1$H NMR ($D_2O$) δ 1.71–1.81 (br m, 1H), 2.00–2.16 (br m, 2H), 2.28–2.30 (m, 1H), 2.92–2.94 (m, 3H), 3.11–3.26 (m, 3H), 3.72 (s, 2H), 4.15 (s, 2H), 4.32–4.46 (m, 1H), 4.34 (s, 2H), 4.53 (s, 2H), 6.44 (s, 1H), 6.52 (s, 1H), 7.40 (s, 4H), 7.53 (s, 1H), 7.76 (t, 1H, J=7.0 Hz), 7.78–7.86 (m, 2H), 8.24 (d, 1H, J=7.0 Hz), 8.31 (t, 1H, J=8.0 Hz), 8.47 (d, 1H, J=6.0 Hz), 8.72 (d, 1H, J=6.0 Hz); $^{13}$C NMR ($D_2O$) δ 19.73, 20.50, 27.77, 43.34, 45.18, 48.13, 48.67, 51.37, 54.56, 59.45, 111.53, 113.41, 125.64, 126.95, 126.98, 130.10, 130.82 (2 carbons), 130.93 (2 carbons), 139.17, 139.65, 140.52, 144.25, 144.50, 145.29, 146.28, 147.36, 147.64, 151.82. ES-MS m/z 482 (M+H). Anal. Calcd. for $C_{30}H_{35}N_5O$·4.1HBr·2.0$H_2O$: C, 42.42; H, 5.11; N, 8.24; Br, 38.57. Found: C, 42.32; H, 4.93; N, 7.97; Br, 38.76

Example 51

AMD8772: Preparation of N-(2-pyridinylmethyl)-N'-(2-guanidinoethyl)-N'-(5,6,7,8-tetrahydro-8-quinolinyl)-1,4-benzenedimethanamine (hydrobromide salt)

N-(2-nitrobenzenesulfonyl)-N-(2-pyridinylmethyl)-N'-(2-aminoethyl)-N'-(5,6,7,8-tetrahydro-8-quinolinyl)-1,4-benzenedimethanamine (trifluoroacetic acid salt)

To a solution of N-Boc-3-aminopropane-1,2-diol (191 mg, 1.0 mmol) in water (10 mL) was added sodium periodate (255 mg, 1.2 mmol). The mixture was then stirred rapidly for 2 hours. Work-up via dichloromethane extraction gave the crude aldehyde, which was used directly in the next step without further purification.

The aldehyde from above, N-(2-nitrobenzenesulfonyl)-N-(2-pyridinylmethyl)-N'-(5,6,7,8-tetrahydro-8-quinolinyl)-1,4-benzenedimethanamine (270 mg, 0.5 mmol) and sodium cyanoborohydride (63 mg, 1.0 mmol) were reacted in methanol (10 mL) using general procedure A. Purification of the crude intermediate by column chromatography on silica gel (5% MeOH in $CH_2Cl_2$) gave the desired intermediate (248 mg, 72%). This material was then treated with trifluoroacetic acid (1 mL) in $CH_2Cl_2$ (2 mL) for 1 hour. Evaporation of the solvent afforded the title compound in quantitative yield as the TFA salt.

Preparation of AMD8772.

To a solution of the TFA salt in THF (20 mL) were added triethylamine (0.14 mL, 1.0 mmol) and potassium carbonate (138 mg, 1.0 mmol). After stirring at room temperature for 20 minutes, N,N'-di-Boc-pyrazolecarboxamidine (155 mg, 0.5 mmol) was added and the mixture was stirred at room temperature for 48 hours. The reaction was then treated with saturated aqueous ammonium chloride and extracted with dichloromethane. The combined organic fractions were dried and concentrated and the residue was purified by column chromatography on silica gel (5% MeOH in $CH_2Cl_2$) to afford the desired guanidine (73 mg, 25%).

Using general procedures C and D: the guanidine was reacted with thiophenol (0.045 mL, 0.440 mmol) and potassium carbonate (73 mg, 0.529 mmol) in acetonitrile (5 mL). The crude material was purified by column chromatography on silica gel (10% MeOH in $CH_2Cl_2$) to give the free base of the title compound (28 mg, 50%). Conversion to the hydrobromide salt gave AMD8772 (18 mg). $^1$H NMR ($D_2O$) δ 1.75 (m, 1H), 2.00–2.10 (m, 2H), 2.30 (m, 2H), 2.91 (m, 2H), 3.10 (m, 1H), 3.36 (m, 2H), 3.86 (d, 1H, J=13.5 Hz), 3.92 (d, 1H, J=13.5 Hz), 4.35 (s, 2H), 4.40 (m, 1H), 4.44 (s, 2H), 7.45 (d, 2H, J=7.8 Hz), 7.48 (d, 2H, J=7.8 Hz), 7.59 (m, 1H), 7.61 (dd, 1H, J=7.5, 5.7 Hz), 7.71 (m, 1H), 8.07 (d, 1H, J=7.8 Hz), 8.17 (t, 1H, J=7.8 Hz), 8.49 (d, 1H, J=5.7 Hz), 8.65 (d, 1H, J=4.8 Hz); $^{13}$C NMR ($D_2O$) δ 20.14, 20.44, 27.54, 36.85, 39.06, 49.29, 49.82, 51.20, 54.77, 59.91, 125.33, 126.28, 130.67, 130.92, 137.80, 139.12, 141.20, 142.73, 145.39, 147.25, 148.25, 151.29, 162.11. ES-MS m/z 444 (M+H). Anal. Calcd. for $C_{26}H_{33}N_7$.4.3 HBr.2.7 $H_2O$: C, 37.17; H, 5.12; N, 11.67; Br, 40.90. Found: C, 37.39; H, 3.29; N, 11.53; Br, 40.62.

Example 52

AMD8861: Preparation of N-(2-pyridinylmethyl)-N'-[2-[bis-[(2-methoxy)phenylmethyl]amino]ethyl]-N'-(5,6,7,8-tetrahydro-8-quinolinyl)-1,4-benzene-dimethanamine (hydrobromide salt)

To a stirred solution of N-(2-nitrobenzenesulfonyl)-N-(2-pyridinylmethyl)-N'-(2-aminoethyl)-N'-(5,6,7,8-tetrahydro-8-quinolinyl)-1,4-benzenedimethanamine (see prep. of AMD8772) (253 mg, 0.43 mmol) in $CH_2Cl_2$ (6 mL) was added o-anisaldehyde (72 mg, 0.53 mmol) and sodium triacetoxyborohydride (174 mg, 0.82 mmol) and the mixture was stirred for 6 hours. The reaction was diluted with $CH_2Cl_2$ (25 mL) and saturated sodium bicarbonate (25 mL) and the aqueous layer washed with $CH_2Cl_2$ (2×20 mL). The combined organic extracts were dried ($Na_2SO_4$), filtered and concentrated in vacuo. Purification of the crude material by column chromatography on silica gel ($CH_2Cl_2$/MeOH/NH$_4$OH, 96:4:0 followed by 95:4:1) gave the bis-anisaldehyde reductive amination product (77 mg, 25%) as a clear oil.

Using general procedures C and D: the intermediate from above (77 mg, 0.09 mmol) was reacted with thiophenol (95 mL, 0.91 mmol) and potassium carbonate (95 mg, 0.69 mmol) in $CH_3CN$ (5 mL) for 16 hours. Purification of the crude material by column chromatography on silica gel ($CH_2Cl_2$/MeOH/NH$_4$OH, 96:4:0 followed by 95:4:1) gave the free base of the title compound (45 mg, 75%) as a clear oil. Conversion of the free base (18 mg, 0.028 mmol) to the hydrobromide salt followed by re-precipitaion of the crude material from methanol/ether gave AMD8861 (70 mg, 91%) as a white solid. $^1$H NMR ($D_2O$) δ 1.63–1.73 (br m, 2H), 2.04–2.12 (br m, 2H), 2.45–2.53 (br m, 1H), 2.81–2.87 (br m, 3H), 3.07–3.17 (m, 1H), 3.31–3.37 (m, 1H), 3.57 (d, 1H, J=13.0 Hz), 3.64 (d, 1H, J=13.0 Hz), 3.79 (s, 3H), 3.84 (s, 3H), 3.96–4.01 (m, 1H), 4.19 (d, 1H, J=13.2 Hz), 4.26 (d, 1H, J=13.5 Hz), 4.32 (s, 2H), 4.42 (s, 2H), 4.45 (s, 2H), 6.87–7.00 (m, 3H), 7.07 (d, 1H, J=7.0 Hz), 7.21 (d, 2H, J=7.0 Hz), 7.33–7.37 (m, 1H), 7.36 (br s, 4H), 7.46 (t, 1H, J=8.0 Hz), 7.64–7.67 (m, 1H), 7.67 (d, 1H, J=8.0 Hz), 7.78 (t, 1H, J=7.0 Hz), 8.13 (t, 1H, J=8.0 Hz), 8.25 (d, 1H, J=8.0 Hz), 8.38 (d, 1H, J=5.0 Hz), 8.63 (d, 1H, J=5.0 Hz); $^{13}$C NMR ($D_2O$) δ 20.24, 20.27, 27.56, 46.02, 49.23, 51.19, 51.42, 54.73, 56.23 (3 carbons), 56.29, 58.69, 111.65, 111.87, 117.61, 117.76, 121.82, 121.88, 125.84, 126.13, 126.24, 130.14, 130.40 (2 carbons), 130.79 (2 carbons), 132.21, 132.32, 132.68 (2 carbons), 139.28, 139.38, 140.35, 142.52, 147.35, 147.73, 148.32, 151.64, 157.94, 158.10. ES-MS m/z 642 (M+H). Anal. Calcd. for $C_{41}H_{47}N_5O_2$.4.2HBr.3.1$H_2O$: C, 47.46; H, 5.58; N, 6.75; Br, 32.35. Found: C, 47.51; H, 5.61; N, 6.66; Br, 32.36.

Example 53

AMD8862: Preparation of N-(2-pyridinylmethyl)-N'-[2-[(1H-imidazol-4-ylmethyl)amino]ethyl]-N'-(5,6,7,8-tetrahydro-8-quinolinyl)-1,4-benzene dimethanamine (hydrobromide salt)

To a stirred suspension of 4(5)-imidazolecarboxaldehyde (682 mg, 7.10 mmol) in dry MeOH (5 mL) was added ethanolamine (0.52 mL, 8.52 mmol) and the mixture was stirred for 3.5 hours. To this solution was added sodium borohydride (322 mg, 8.52 mmol) in three portions and the mixture was stirred for 1 hour. The reaction mixture was concentrated in vacuo and diluted with saturated aqueous sodium bicarbonate (40 mL). To this solution was added di-tert-butyldicarbonate (3.2 g, 14.0 mmol) and the mixture stirred for 16 hours, resulting in the formation a white precipitate. The aqueous phase was extracted with EtOAc (2×40 mL) and the combined organic extracts dried (MgSO$_4$), filtered and concentrated in vacuo. Purification of the crude material by column chromatography on silica gel ($CH_2Cl_2$/MeOH, 96:4) gave the desired Boc-protected imidazole alcohol as a clear oil. $^1$H NMR (CDCl$_3$) δ 1.36 (br s, 18H), 3.39 (br s, 2H), 3.65–3.70 (br s, 2H), 4.24 (s, 2H), 5.84 (br s) and 6.30 (br s) (total 1H), 7.15 (s) and 7.23 (s) (total 1H), 7.96 (s, 1H).

Using general procedure F: A solution of the alcohol from above (568 mg, 1.67 mmol) in $CH_2Cl_2$ (10 mL) was oxidized with Dess-Martin periodinane (1.44 g, 3.40 mmol) for 1 hour and the crude aldehyde was used without further purification in the next step.

Using general procedure B: To a solution of N-(2-nitrobenzenesulfonyl)-N-(2-pyridinylmethyl)-N'-(5,6,7,8-tetrahydro-8-quinolinyl)-1,4-benzenedimethanamine (368 mg, 0.68 mmol) and the crude aldehyde from above in CH$_2$Cl$_2$ (10 mL) was added sodium triacetoxyborohydride (204 mg, 0.96 mmol) and the mixture was stirred for 17 hours. Purification of the crude product by column chromatography on silica gel (CH$_2$Cl$_2$/MeOH, 96:4 to 92:8) gave the desired tertiary amine (277 mg, 47%) as a clear oil.

Using general procedures C and D: the oil (277 mg, 0.32 mmol) was reacted with thiophenol (0.17 mL, 1.6 mmol) and potassium carbonate (265 mg, 1.92 mmol) in CH$_3$CN (5 mL) for 1.5 hours. Purification of the crude material by column chromatography on silica gel (CH$_2$Cl$_2$/MeOH/ NH$_4$OH, 96:4:0 followed by 95:4:1) gave the corresponding amine (123 mg, 57%) as a clear oil. Conversion of the free amine (87 mg, 0.13 mmol) to the corresponding hydrobromide salt with simultaneous deprotection of the Boc groups, followed by re-precipitation of the crude material from methanol/ether gave AMD8862 (105 mg, 87%) as a beige solid. $^1$H NMR (D$_2$O) δ 1.71–1.76 (br m, 1H), 2.03–2.14 (br m, 2H), 2.29–2.31 (br m, 1H), 2.91 (br d, 2H, J=4.8 Hz), 2.98–3.05 (m, 1H), 3.14–3.20 (m, 1H), 3.30–3.41 (m, 2H), 3.77 (s, 2H), 4.35 (s, 2H), 4.35–4.40 (m, 1H), 4.41 (s, 2H), 4.56 (s, 2H), 7.40 (d, 2H, J=8.0 Hz), 7.44 (d, 2H, J=8.0 Hz), 7.69 (s, 1H), 7.72 (d, 1H, J=7.0 Hz), 7.86 (t, 1H, J=7.0 Hz), 7.92 (d, 1H, J=8.0 Hz), 8.20 (d, 1H, J=8.0 Hz), 8.37 (t, 1H, J=8.0 Hz), 8.44 (d, 1H, J=6.0 Hz), 8.74 (d, 1H, J=5.0 Hz), 8.79 (s, 1H); $^{13}$C NMR (D$_2$O) δ 19.77, 20.52, 27.71, 40.68, 46.07,48.39, 48.61, 51.48, 54.54, 59.33, 121.64, 123.20, 125.56, 127.27, 127.42, 130.00, 130.88 (4 carbons), 135.80, 139.13, 139.51, 140.37, 145.11, 145.71, 146.86, 147.60, 151.83. ES-MS m/z 482 (M+H). Anal. Calcd. for C$_{29}$H$_{35}$N$_7$.5.1HBr.2.9H$_2$O: C, 36.80; H, 4.89; N, 10.36; Br, 43.05. Found: C, 36.93; H, 4.66; N, 10.28; Br, 42.83.

Example 54

AMD8887: Preparation of N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine (hydrobromide salt)

To a stirred solution of N-(2-nitrobenzenesulfonyl)-N-(2-pyridinylmethyl)-N'-(2-aminoethyl)-N'-(5,6,7,8-tetrahydro-8-quinolinyl)-1,4-benzenedimethanamine (333 mg, 0.57 mmol) in dry MeOH (5 mL) was added 2-imidazolecarboxaldehyde (110 mg, 1.14 mmol) and the mixture was stirred for 17 hours. To this solution was added sodium borohydride (110 mg, 2.91 mmol) in one portion and the mixture was stirred for 40 min. The reaction mixture was concentrated in vacuo and partitioned between CH$_2$Cl$_2$ (25 mL) and saturated aqueous sodium bicarbonate (25 mL). The aqueous layer was washed with CH$_2$Cl$_2$ (2×20 mL) and the combined organic phases were dried (Na$_2$SO$_4$), filtered and concentrated in vacuo. The crude amine was dissolved in THF (10 mL) and protected with di-t-butyldicarbonate (1.0 g, 4.59 mmol). Purification of the crude material by column chromatography on silica gel (CH$_2$Cl$_2$/MeOH, 96:4 followed by 9:1) gave the desired product (110 mg, 22%) as a yellow oil.

Using general procedures C and D: to a solution of the intermediate from above (110 mg, 0.14 mmol) in CH$_3$CN (5 mL) was added thiophenol (72 μL, 0.70 mmol) and potassium carbonate (116 mg, 0.84 mmol). The reaction was stirred for 20 hours. The crude material was purified by column chromatography on silica gel (CH$_2$Cl$_2$/MeOH/NH$_4$OH, 95:5:0 followed by 95:4:1) to give the amine (54 mg, 65%) as an orange oil. Conversion of the free base (25 mg, 0.04 mmol) to a hydrobromide salt gave AMD8887 (30 mg, 67%) as a white solid. $^1$H NMR (D$_2$O) δ 1.73–1.80 (br m, 1H), 2.02–2.14 (br m, 2H), 2.27–2.31 (br m, 1H), 2.90 (br d, 2H, J=5.1 Hz), 2.99–3.03 (m, 1H), 3.06–3.23 (m, 1H), 3.33–3.48 (m, 2H), 3.77 (d, 1H, J=13.2 Hz), 3.84 (d, 1H, J=13.5 Hz), 4.33 (s, 2H), 4.33–4.37 (m, 1H), 4.54 (s, 2H), 4.67 (s, 2H), 7.38 (d, 2H, J=8.1 Hz), 7.43 (d, 2H, J=8.1 Hz), 7.56 (s, 2H), 7.70 (dd, 1H, J=7.5, 6.3 Hz), 7.80 (dd, 1H, J=7.5, 6.6 Hz), 7.84 (d, 1H, J=8.1 Hz), 8.18 (d, 1H, J=8.1 Hz), 8.29 (t, 1H, J=8.1 Hz), 8.43 (d, 1H, J=5.7 Hz), 8.71 (d, 1H, J=5.1 Hz); $^{13}$C NMR (D$_2$O) δ 19.83, 20.50, 27.68, 40.59, 46.71, 48.73 (2 carbons), 51.38, 54.53, 59.41, 121.56 (2 carbons), 125.54, 126.94, 126.99, 130.10, 130.86 (4 carbons), 135.91, 139.21, 139.27, 140.28, 144.24, 146.29, 147.37, 147.50, 151.75. ES-MS m/z 482 (M+H). Anal. Calcd. for C$_{29}$H$_{35}$N$_7$.5.1HBr.3.0H$_2$O: C, 36.73; H, 4.90; N, 10.34; Br, 42.97. Found: C, 36.97; H, 4.57; N, 9.98, Br, 42.78.

Example 55

AMD8816: Preparation of N-(2-pyridinylmethyl)-N'-[2-(phenylureido)ethyl]-N'-(5,6,7,8-tetrahydro-8-quinolinyl)-1,4-benzenedimethanamine (hydrobromide salt)

Reaction of Boc-aminoacetaldehyde (1.0 mmol) with N-(2-nitrobenzenesulfonyl)-N-(2-pyridinylmethyl)-N'-(5,6,7,8-tetrahydro-8-quinolinyl)-1,4-benzenedimethanamine (270 mg, 0.5 mmol) in the presence of sodium cyanoborohydride in methanol afforded N-(2-nitrobenzenesulfonyl)-N-(2-pyridinylmethyl)-N'-[2-[(t-butyloxycarbonyl)amino]ethyl]-N'-(5,6,7,8-tetrahydro-8-quinolinyl)-1,4-benzenedimethanamine (248 mg, 72%). This material was then treated with trifluoroacetic acid (1 mL) in CH$_2$Cl$_2$ (2 mL) for 1 hour. Evaporation of the solvent afforded the primary amine in quantitative yield as the TFA salt.

The amine TFA salt was then treated with aqueous sodium hydroxide (1.0 M) and extracted into dichloromethane. The free base was then dried and concentrated, taken up into dichloromethane and reacted with phenylisocyanate (0.048 mL, 0.42 mmol). Following work-up and purification by column chromatography, the desired urea was obtained (64 mg, 23%).

Using general procedures C and D: reaction of the urea with thiophenol gave the corresponding amine (41 mg, 87%) which was converted to a hydrobromide salt giving AMD8816 (38 mg). $^1$H NMR (D$_2$O) δ: 1.77 (m, 1H), 2.10 (m, 2H), 2.48 (m, 1H), 2.85 (m, 2H), 3.15–1.33 (m, 4H), 4.17 (br s, 2H), 4.39 (s, 2H), 4.56 (s, 2H), 7.11 (d, 1H, J=6.7 Hz), 7.32 (m, 4H), 7.46 (m, 2H), 7.68 (m, 5H), 8.13 (dd, 1H, J=8.1, 5.8 Hz), 8.41 (br s, 1H), 8.62 (d, 1H, J=5.8 Hz), 8.81 (d, 1H, J=5.3 Hz); $^{13}$C NMR (D$_2$O) δ 20.33, 20.70, 27.35, 36.14, 49.10, 50.88, 54.54, 61.69, 66.46, 120.93, 124.38, 124.86, 126.38, 129.76, 131.33, 131.40, 132.01, 133.00, 136.43, 138.40, 142.88, 146.31, 147.11, 147.98, 148.96, 161.32. ES-MS m/z 521 (M+H). Anal. Calcd. for C$_{32}$H$_{36}$N$_6$O.4.1 HBr.1.7H$_2$O: C, 44.55; H, 4.95; N, 8.80; Br, 34.32. Found: C, 44.56; H, 5.04; N, 8.86; Br, 34.28.

Example 56

AMD8737: Preparation of N-(2-pyridinylmethyl)-N'-[[N''-(n-butyl)carboxamido]methyl]-N'-(5,6,7,8-tetrahydro-8-quinolinyl)-1.4-benzenedimethanamine (hydrobromide salt)

2-bromo-N-(n-butyl)-acetamide

To a solution of n-butyl amine (0.62 mL, 6.3 mmol) and Et$_3$N (2 mL, 14 mmol) in CH$_2$Cl$_2$ (10 mL), cooled to 0° C., was added dropwise a solution of bromoacetyl bromide (0.5 mL, 5.7 mmol) in CH$_2$Cl$_2$ (5 mL). The reaction mixture was warmed to room temperature and stirred for 30 min. The mixture was then diluted with CH$_2$Cl$_2$ (15 ml) and washed with aqueous 1 N HCl (15 mL), saturated aqueous sodium bicarbonate (15 mL) and brine (15 mL). The organic phase was dried (MgSO$_4$), filtered and concentrated in vacuo to give the crude product as a dark oil. $^1$H NMR (CDCl$_3$) δ 0.94 (t, 3H, J=6.0 Hz), 1.33–1.56 (m, 4H), 3.32 (q, 2H, J=6.0 Hz), 3.89 (s, 2H), 6.49 (br s, 1H); $^{13}$C NMR (CDCl$_3$) δ 13.58, 19.86, 29.24, 31.15, 39.82, 165.40. This was used without further purification in the next step.

To a stirred solution of N-(2-nitrobenzenesulfonyl)-N-(2-pyridinylmethyl)-N'-(5,6,7,8-tetrahydro-8-quinolinyl)-1,4-benzenedimethanamine (188 mg, 0.35 mmol) in dry CH$_3$CN (5 mL) was added a solution of 2-bromo-N-(n-butyl)-acetamide (170 mg, 0.88 mmol) in CH$_3$CN (2 mL) and powdered potassium carbonate (295 mg, 2.14 mmol). The mixture was stirred for 2 days then concentrated in vacuo and partitioned between CH$_2$Cl$_2$ (30 mL) and water (30 mL). The aqueous layer was washed with CH$_2$Cl$_2$ (2×25 mL) and the combined organic phases were dried (MgSO$_4$), filtered and concentrated in vacuo. Purification of the resultant crude oil by column chromatography with silica gel (CH$_2$Cl$_2$/MeOH, 96:4 followed by 9:1) afforded the desired product (89 mg, 39%) as a colorless oil.

Using General procedures C and D: the intermediate from above (114 mg, 0.17 mmol) was reacted with thiophenol (89 μL, 0.87 mmol) and potassium carbonate (144 mg, 1.04 mmol) in CH$_3$CN (5 mL) for 2 hours. The crude product was purified by column chromatography on silica gel (CH$_2$Cl$_2$/MeOH, 97:3 to 9:1) to give the free base of the title compound (49 mg, 60%) as a pale yellow oil. Conversion of the free base (49 mg, 0.10 mmol) to the hydrobromide salt gave AMD8737 (77 mg, 94%) as a pale yellow solid. $^1$H NMR (D$_2$O) δ 0.78 (t, 3H, J=6.6 Hz), 1.11–1.18 (q, 2H, J=6.9 Hz), 1.23–1.29 (m, 2H), 1.68–1.86 (m, 1H), 2.00–2.13 (m, 2H), 2.28–2.40 (m, 1H), 2.90–2.95 (m, 4H), 3.41 (d, 2H, J=15.9 Hz), 3.56 (d, 2H, J=15.9 Hz), 4.35 (s, 2H), 4.35–4.41 (m, 1H), 4.54 (s, 2H), 7.43 (br s, 4H), 7.68 (t, 1H, J=5.7 Hz), 7.78–7.86 (m, 2H), 8.13 (d, 1H, J=7.8 Hz), 8.30 (t, 1H, J=7.7 Hz), 8.50 (d, 1H, J=5.4 Hz), 8.71 (d, 1H, J=5.1 Hz); $^{13}$C NMR (D$_2$O) δ 13.35, 19.80, 20.46, 20.97, 27.52, 30.72, 39.52, 48.62, 51.40, 55.51, 55.93, 61.56, 125.46, 126.96, 126.98, 130.36, 130.72 (2 carbons), 131.14 (2 carbons), 138.06, 139.60, 140.36, 144.32, 146.08, 146.17, 147.31, 151.25, 172.15. ES-MS m/z 472 (M+H). Anal. Calcd. for C$_{29}$H$_{37}$N$_5$O.4.0HBr.1.3H$_2$O.1.3CH$_3$CO$_2$H: C, 42.32; H, 5.48; N, 7.81; Br, 35.64. Found: C, 42.38; H, 5.47; N, 7.84; Br, 35.66.

Example 57

AMD8739: Preparation of N-(2-pyridinylmethyl)-N'-(carboxamidomethyl)-N'-(5,6,7,8-tetrahydro-8-quinolinyl)-1,4-benzenedimethanamine (hydrobromide salt)

A solution of N-(2-nitrobenzenesulfonyl)-N-(2-pyridinylmethyl)-N'-(5,6,7,8-tetrahydro-8-quinolinyl)-1,4-benzenedimethanamine (151 mg, 0.28 mmol) in CH$_3$CN (5 mL) was treated with 2-bromoacetamide (154 mg, 1.12 mmol) and potassium carbonate (190 mg, 1.38 mmol) for 19 hours. After work-up the crude product was used without further purification.

Using general procedures C and D: the intermediate from above was reacted with thiophenol (0.15 mL, 1.46 mmol) and potassium carbonate (242 mg, 1.75 mmol) in CH$_3$CN (5 mL) for 1.5 hours. The crude material was purified by column chromatography on silica gel (CH$_2$Cl$_2$/MeOH, 95:5 to 9:1) to afford the free base of the title compound (32 mg, 28% for 2 steps) as a colorless oil. Conversion of the free base (32 mg, 0.06 mmol) to the hydrobromide salt gave AMD8739 (35 mg, 68%). $^1$H NMR (D$_2$O) δ 1.73–1.79 (m, 1H), 1.93–2.14 (m, 2H), 2.89 (m, 2H), 3.45 (d, 1H, J=16.2 Hz), 3.62 (d, 1H, J=16.2 Hz), 3.91 (s, 2H), 4.38 (s, 3H), 4.37–4.43 (m, 1H), 4.63 (s, 2H), 7.41 (d, 2H, J=7.5 Hz), 7.47 (d, 2H, J=7.5 Hz), 7.66 (t, 1H, J=6.9 Hz), 7.95 (t, 1H, J=6.9 Hz), 8.02 (d, 1H, J=7.8 Hz), 8.11 (d, 1H, J=7.5 Hz), 8.44–8.49 (m, 2H), 8.77 (d, 1H, J=4.9 Hz); $^{13}$C NMR (D$_2$O) δ 20.46, 20.90, 27.51, 47.80, 51.64, 54.63, 55.45, 60.88, 125.43, 127.74, 128.02, 130.27, 130.79 (2 carbons), 131.15 (2 carbons), 138.07, 139.52, 140.43, 144.77, 146.05 (2 carbons), 146.43, 151.30, 175.37. ES-MS m/z 416 (M+H). Anal. Calcd. for C$_{25}$H$_{29}$N$_5$O.4.8HBr.2.3H$_2$O.0.6CH$_3$CO$_2$H: C, 35.70; H, 4.67; N, 7.95; Br, 43.52. Found: C, 35.74; H, 4.44; N, 8.02; Br, 43.31.

Example 58

AMD8752: Preparation of N-(2-pyridinylmethyl)-N'-[(N''-phenyl)carboxamidomethyl]-N'-(5,6,7,8-tetrahydro-8-quinolinyl)-1,4-benzenedimethanamine (hydrobromide salt)

2-bromoacetanilide (Ronsisvalle, G. et al. J. Med. Chem. 1998, 41, 1574–1580)

To a stirred solution of bromoacetyl chloride (1.36 mL, 16.4 mmol) in dry THF (5 mL) cooled to 0° C., was added dropwise a solution of aniline (1.0 mL, 11.0 mmol) and 4-(dimethylamino)pyridine (0.63 g, 5.2 mmol) in dry THF (10 mL). After 1 h the mixture was quenched with water (25 mL) and extracted with CH$_2$Cl$_2$ (2×30 mL). The organic extracts were washed with a saturated aqueous sodium bicarbonate solution (30 mL), dried (Na$_2$SO$_4$) and concentrated in vacuo to give a white solid. $^1$H NMR (CDCl$_3$) δ 4.03 (s, 2H), 7.20 (td, 1H, J=7.5, 0.9 Hz), 7.36 (td, 2H, J=7.5 Hz, 0.9 Hz), 7.54 (dd, 2H, J=7.5, 0.9 Hz), 8.17 (br m, 1H). The crude solid was used without further purification in the next step.

A solution N-(t-butoxycarbonyl)-N-(2-pyridinylmethyl)-N'-(5,6,7,8-tetrahydro-8-quinolinyl)-1,4-benzenedimethanamine (154 mg, 0.34 mmol) in CH$_3$CN (6 mL) was treated with 2-bromoacetanilide (185 mg, 0.86 mmol) and potassium carbonate (140 mg, 1.0 mmol) and the mixture was stirred for 2 days. Purification of the crude material by column chromatography on silica gel (CH$_2$Cl$_2$/MeOH, 98:2 to 95:5) gave the desired product (47 mg, 24%) as a white foam.

Using general procedure D: the intermediate from above (47 mg, 0.08 mmol) was converted to the hydrobromide salt with simultaneous deprotection of the BOC group to give AMD8752 (57 mg, 87%) as a white solid. $^1$H NMR (D$_2$O) δ 1.85–1.89 (m, 1H), 2.08–2.15 (m, 2H), 2.42–2.46 (m, 1H), 2.97–3.00 (br s, 2H), 3.55 (d, 1H, J=16.2 Hz), 3.73 (d, 1H, J=16.2 Hz), 3.92 (d, 1H, J=12.6 Hz), 4.01 (d, 1H, J=12.6 Hz) 4.30 (br s, 4H), 4.58–4.61 (m, 1H), 6.99 (t, 1H, J=6.6 Hz), 7.17–7.25 (m, 4H), 7.43 (d, 2H, J=7.5 Hz), 7.55 (d, 2H, J=7.5 Hz), 7.79 (t, 1H, J=6.3 Hz), 7.96 (d, 1H, J=8.1 Hz), 8.03 (t, 1H, J=6.6 Hz), 8.25 (d, 1H, J=7.8 Hz), 8.54 (t, 1H, J=8.1 Hz), 8.61 (d, 1H, J=5.1 Hz), 8.81 (d, 1H, J=5.1 Hz); $^{13}$C NMR (D$_2$O) δ 20.54, 21.29, 27.65, 47.20, 51.45, 56.51, 56.92, 62.56, 122.15 (2 carbons), 125.73, 126.06, 127.96, 128.25, 129.43 (2 carbons), 129.99, 130.83 (2 carbons), 131.67 (2 carbons), 136.40, 138.48, 140.12 (2C), 144.80, 145.84, 146.64, 146.76, 151.20, 171.61. ES-MS m/z 492 (M+H). Anal. Calcd. for $C_{31}H_{33}N_5O.4.0HBr.2.3H_2O$: C, 43.46; H, 4.89; N, 8.17; Br, 37.3 1. Found: C, 43.44; H, 4.84; N, 7.99; Br, 37.31.

Example 59

AMD8765: Preparation of N-(2-pyridinylmethyl)-N'-(carboxymethyl)-N'-(5,6,7,8-tetrahydro-8-quinolinyl)-1,4-benzenedimethanamine (hydrobromide salt)

To a solution of N-(t-butoxycarbonyl)-N-(2-pyridinylmethyl)-N'-(5,6,7,8-tetrahydro-8-quinolinyl)-1,4-benzenedimethanamine (230 mg, 0.50 mmol) and t-butyl bromoacetate (0.15 mL, 1.02 mmol) in $CH_3CN$ (8 mL) was added powdered potassium carbonate (220 mg, 1.60 mmol) and the mixture was stirred for 16 hours. The crude material was purified by column chromatography on silica gel ($CH_2Cl_2$/MeOH, 98:2 to 95:5) to give the desired product (160 mg, 56%) as a yellow oil.

Using general procedure D: the oil from above (100 mg, 0.17 mmol) was converted to the hydrobromide salt with simultaneous deprotection of the BOC and t-butyl ester groups to give AMD8765 (147 mg, quantitative) as a pale yellow solid. $^1H$ NMR ($D_2O$) δ 1.71–1.80 (br m, 1H), 1.92–2.12 (br m, 2H), 2.32–2.35 (m, 1H), 2.86–2.88 (m, 2H), 3.51 (d, 1H, J=17.4 Hz), 3.67 (d, 1H, J=17.4 Hz), 3.90 (s, 2H), 4.38–4.41 (m, 1H), 4.38 (s, 2H), 4.66 (s, 2H), 7.40 (d, 2H, J=8.1 Hz), 7.46 (d, 2H, J=8.1 Hz), 7.66 (dd, 1H, J=6.8, 5.7 Hz), 7.67 (d, 1H, J=7.8 Hz), 8.03 (dd, 1H, J=7.2, 6.6 Hz), 8.10 (d, 1H, J=7.8 Hz), 8.11 (d, 1H, J=7.2 Hz), 8.48 (d, 1H, J=5.1 Hz), 8.56 (td, 1H, J=7.8, 1.5 Hz), 8.79 (dd, 1H, J=4.8, 0.9 Hz); $^{13}C$ NMR ($D_2O$) δ 20.51, 20.97, 27.43, 47.33, 51.75, 53.29, 55.21, 60.36, 125.47, 128.15, 128.55, 130.01, 130.81 (2 carbons), 131.08 (2 carbons), 138.47, 139.57, 140.02, 144.04, 145.46, 146.36, 147.49, 151.59, 175.40. ES-MS m/z 417 (M+H). Anal. Calcd. for $C_{25}H_{28}N_4O_2.4.1HBr.1.3H_2O.1.2CH_3CO_2H$: C, 39.00; H, 4.72; N, 6.64; Br, 38.83. Found: C, 39.14; H, 4.62; N, 6.68; Br, 38.54.

Example 60

AMD8715: Preparation of N-(2-pyridinylmethyl)-N'-(phenylmethyl)-N'-(5,6,7,8-tetrahydro-8-quinolinyl)-1,4-benzenedimethanamine (hydrobromide salt)

To a stirred solution of N-(2-nitrobenzenesulfonyl)-N-(2-pyridinylmethyl)-N'-(5,6,7,8-tetrahydro-8-quinolinyl)-1,4-benzenedimethanamine (0.220 g, 0.390 mmol) in $CH_3CN$ (8 mL), at room temperature, was added powdered $K_2CO_3$ (0.153 g, 1.11 mmol) followed by excess benzyl bromide (0.20 mL, 1.68 mmol). After 18 hours, the reaction mixture was concentrated and the residue was partitioned between $CH_2Cl_2$ (10 mL) and water (5 mL). The phases were separated and the aqueous phase was extracted with $CH_2Cl_2$ (2×10 mL). The combined organic extracts were dried ($Na_2SO_4$) and concentrated. Purification of the crude material by radial chromatography (2 mm plate, 20:1 $CH_2Cl_2$—$CH_3OH$) provided the desired product (0.106 g, 44%) as a white solid.

To a stirred solution of the intermediate from above (0.106 g, 0.173 mmol) in anhydrous $CH_3CN$ (3.5 mL, concentration ~0.05 M), at room temperature, was added neat thiophenol (0.10 mL, 0.974 mmol, ~5 equiv.) followed by powdered $K_2CO_3$ (0.140 g, 1.01 mmol, ~5–10 equiv.). The resultant bright yellow solution was stirred for at room temperature overnight. The solvent was removed under reduced pressure and $CH_2Cl_2$ (10 mL) and water (1 mL) were added to the residue. The phases were separated and the aqueous phase was extracted with $CH_2Cl_2$ (3×5 mL). The combined organic phases were dried ($Na_2SO_4$) and concentrated. Purification of the crude material by column chromatography on silica gel (15:1 $CH_2Cl_2$—MeOH) the free base of the title compound (0.052 g, 66%) as a yellow oil.

To a solution of the free base (0.052 g, 0.115 mmol) in a minimum of 1,4-dioxane (~0.5 mL) was added HBr saturated dioxane (~1 mL) dropwise. Ether (15 mL) was added to precipitate a white solid, which was allowed to settle to the bottom of the flask and the supernatant solution was decanted. The solid was washed by decantation with ether (3×15 mL) and the remaining traces of solvent were removed under vacuum. The solid was dried in a vacuum oven (40° C. ® 0.1 Torr) to give AMD8715 (0.071 g) as a white powder. $^1H$ NMR ($D_2O$) δ 1.64–1.82 (m, 1H), 2.15–2.26 (m, 2H), 2.47–2.54 (m, 1H), 2.83 (br s, 2H), 4.29 (s, 2H), 4.33 (s, 2H), 4.40 (s, 2H), 4.52–4.59(m, 3H), 7.41–7.54 (m, 10H), 7.76 (d, 1H, J=7.5 Hz), 7.84 (t, 1H, J=6.5 Hz), 7.91 (d, 1H, J=7.8 Hz), 8.35 (t, 1H, J=7.5 Hz), 8.46 (d, 1H, J=4.5 Hz), 8.74 (d, 1H, J=5.1 Hz); $^{13}C$ NMR ($D_2O$) δ 20.40, 20.56, 27.41, 48.48, 51.37, 54.93, 55.67, 60.99, 124.91, 127.17, 127.27, 129.66 (2 carbons), 129.91, 130.50 (2 carbons), 131.13 (2 carbons), 131.34 (2 carbons), 131.46, 132.28, 134.21, 136.84, 141.53, 144.87, 144.98, 145.84, 146.99, 149.63. ES-MS m/z 449 (M+H). Anal. Calcd. for $C_{30}H_{32}N_4.4.0HBr.2.1H_2O.1.4dioxane$: C, 45.81; H, 5.55; N, 6.00; Br, 34.24. Found: C, 45.68; H, 5.47; N, 6.00; Br, 34.54.

Example 61

AMD8907: Preparation of N-(2-pyridinylmethyl)-N'-(1H-benzimidazol-2-ylmethyl)-N'-(5,6,7,8-tetrahydro-8-quinolinyl)-1,4-benzenedimethanamine (hydrobromide salt)

To a stirred solution of N-(2-nitrobenzenesulfonyl)-N-(2-pyridinylmethyl)-N'-(5,6,7,8-tetrahydro-8-quinolinyl)-1,4-benzenedimethanamine (0.425 g, 0.78 mmol) in anhydrous DMF (7.5 mL) was added di-isopropylethylamine (0.15 mL, 2.80 mmol) followed by chloromethylbenzimidazole (0.129 g, 0.77 mmol). The resultant solution was heated to 80° C. for 24 hours then cooled to room temperature. The mixture was concentrated and the residue was partitioned between $CH_2Cl_2$ (40 mL) and brine (10 mL). The phases were separated and the aqueous phase was extracted with $CH_2Cl_2$ (2×10 mL). The combined organic extracts were dried ($Na_2SO_4$) and concentrated. The crude material was purified by column chromatography on silica gel (20:1 $CH_2Cl_2$—$CH_3OH$ containing 1% $NH_4OH$) followed by radial chromatography on silica gel (2 mm plate, 20:1 $CH_2Cl_2$—$CH_3OH$ containing 1% $NH_4OH$) to provide the desired tertiary amine (0.169 g, 31%) as a yellow solid.

Using general procedures C and D: the yellow solid was treated with thiophenol (0.15 mL, 1.46 mmol) and $K_2CO_3$ (0.354 g, 2.56 mmol) in $CH_3CN$ (5 mL). Purification of the crude material by radial chromatography on silica gel (2 mm plate, 50:1:1 $CH_2Cl_2$—$CH_3OH$—$NH_4OH$) provided the free base of the title compound (0.061 g) as a yellow oil. The oil was converted to the hydrobromide salt to give AMD8907 (0.079 g) as a white solid. $^1H$ NMR ($D_2O$) δ

1.93–1.98 (m, 1H), 2.19–2.31 (m, 2H), 2.41–2.46 (m, 1H), 3.20 (br s, 2H), 3.77–3.88 (m, 4H), 4.16 (s, 2H), 4.44 (d, 1H, J=16.5 Hz), 4.63 (d, 1H, J=16.5 Hz), 4.73–4.79 (m, 1H, overlaps with HOD), 7.04 (d, 2H, J=8.1 Hz), 7.23 (d, 2H, J=7.8 Hz), 7.37 (dd, 2H, J=3.0, 6.3 Hz), 7.54 (dd, 2H, J=3.0, 6.3 Hz), 7.67 (d, 1H, J=7.8 Hz), 7.72 (dd, 1H, J=6.3, 6.9 Hz), 7.91 (dd, 1H, J=6.0, 7.8 Hz), 8.20 (t, 1H, J=7.8 Hz), 8.39 (d, 1H, J=8.1 Hz), 8.67 (d, 1H, J=5.1 Hz), 8.75 (d, 1H, J=5.7 Hz); $^{13}$C NMR (D$_2$O) δ 20.46, 20.97, 27.87, 48.88, 50.22, 50.44, 56.71, 63.26, 113.92, 126.15, 126.43, 126.52, 126.65, 130.04, 130.22, 130.47, 130.92, 138.23, 139.70, 141.05, 142.99, 147.15, 147.95, 148.32, 150.80, 151.79. ES-MS m/z 489 (M+H). Anal. Calcd. for C$_{31}$H$_{32}$N$_6$·4.0HBr·2.0H$_2$O: C, 43.89 H, 4.75; N, 9.91; Br, 37.68. Found: C, 44.08; H, 4.79; N, 9.71; Br, 37.53.

Example 62

AMD8927: Preparation of N-(2-pyridinylmethyl)-N'-(5,6-dimethyl-1H-benzimidazol-2-ylmethyl)-N'-(5,6,7,8-tetrahydro-8-quinolinyl)-1,4-benzene-dimethanamine (hydrobromide salt)

To a stirred solution of 4,5-dimethylphenylene-1,2-diamine (680 mg, 5 mmol) in 4N HCl (12 mL) was added chloroacetic acid (940 mg, 10 mmol). The solution was then heated to reflux for 17 hours, then cooled to room temperature. Solid sodium carbonate was then added slowly, with stirring, until the pH of the solution was approximately 9.0, at which point a beige precipitate formed. The aqueous phase was then diluted with water (10 mL) and extracted repeatedly with ethyl acetate. The combined organic fractions were then dried, concentrated and the residue was purified by column chromatography on silica gel (10% MeOH in CH$_2$Cl$_2$) to afford the desired 2-(chloromethyl)-5,6-dimethylbenzimidazole (530 mg, 54%). $^1$H NMR (CDCl$_3$) δ 1.59 (br s, 1H), 2.31 (s, 6H), 4.83 (s, 2H), 7.42 (s, 2H).

In a similar manner to the procedure described above: Reaction of 2-(chloromethyl)-5,6-dimethylbenzimidazole (195 mg, 1.0 mmol), N-(2-nitrobenzenesulfonyl)-N-(2-pyridinylmethyl)-N'-(5,6,7,8-tetrahydro-8-quinolinyl)-1,4-benzenedimethanamine (543 mg, 1.0 mmol) and diisopropylethylamine (0.26 mL, 1.5 mmol) in DMF (8 mL) afforded, following work-up and purification of the crude material by column chromatography on silica gel (10% MeOH in CH$_2$Cl$_2$), the desired 5,6-dimethylbenzimidazole derivative (280 mg, 38%).

Using general procedures C and D: the intermediate from above was reacted with thiophenol (0.230 mL, 2.25 mmol) and potassium carbonate (414 mg, 3.00 mmol) in acetonitrile (8 mL). The crude material was purified by column chromatography on silica gel (85% CH$_2$Cl$_2$, 10% MeOH and 5% NH$_4$OH) to give the free base of the title compound (181 mg). Conversion of the free base to a hydrobromide salt gave AMD8927 as a pale yellow solid (205 mg). $^1$H NMR (D$_2$O) δ 1.89 (br m, 1H), 2.21 (s, 6H), 2.27–2.41 (m, 4H), 3.03 (br s, 2H), 3.52 (dd, 1H, J=14.9, 7.2 Hz), 3.76 (s, 2H), 3.80 (m, 2H), 4.06 (s, 2H), 4.40 (d, 1H, J=16.5 Hz), 4.56 (d, 1H, J=16.5 Hz), 7.04 (d, 2H, J=7.5 Hz), 7.31 (d, 2H, J=7.5 Hz), 7.30 (s, 2H), 7.61 (d, 1H, J=7.8 Hz), 7.72 (t, 1H, J=6.5 Hz), 7.93 (t, 1H, J=6.8 Hz), 8.19 (t, 1H, J=7.8 Hz), 8.40 (d, 1H, J=7.8 Hz), 8.68 (d, 1H, J=4.8 Hz), 8.76 (d, 1H, J=5.1 Hz). $^{13}$C NMR (D$_2$O) δ 14.52, 19.81, 40.44, 20.94, 27.85, 46.66, 50.14, 56.76, 63.31, 66.46, 113.43, 126.12, 126.49, 129.00, 129.71, 130.11, 130.58, 130.86, 136.74, 138.23, 139.68, 141.03, 142.83, 147.42, 147.93, 148.29, 150.33, 150.81. ES-MS m/z 517 (M+H). Anal. Calcd. for C$_{33}$H$_{36}$N$_6$·4.1HBr·1.6H$_2$O·1.1HOAc: C, 44.82 H, 5.10; N, 8.91; Br, 34.73. Found: C, 44.67; H, 5.08; N, 8.88; Br, 34.89.

Example 63

AMD8926: Preparation of N-(2-pyridinylmethyl)-N'-(5-nitro-1H-benzimidazol-2-ylmethyl)-N'-(5,6,7,8-tetrahydro-8-quinolinyl)-1,4-benzenedimethanamine N-Dimethylsulfamyl-(nitro)-benzimidazole To a pre-cooled (ice bath) solution of 5-nitro-benzimidazole (744 mg, 4.56 mmol) and triethylamine (1 mL, 6.93 mmol) in anhydrous CH$_2$Cl$_2$ (20 mL) was added N,N-dimethyl sulfamoylchloride (0.59 mL, 5.49 mmol) under N$_2$ and ice bath was removed after addition. Stirring was continued for 18 hours under reflux, then reaction mixture was cooled and concentrated. The residue was diluted with ethylacetate (300 mL), and organic phase was washed with 1N NaOH solution, sat. NaHCO$_3$, then brine and dried over Na$_2$SO$_4$. Evaporation of the solvent and purification of the residue by column chromatography on silica gel (2.5×20 cm, 2:8 EtOAc/CH$_2$Cl$_2$) gave the desired products as mixture of two regioisomers (720 mg, 60%) as a yellow solid.

N-Dimethylsulfamyl-2-hydroxymethyl-(nitro)-benzimidazole

To pre-cooled suspended mixture of 1-dimethylsulfamyl-nitro-benzimidazole (mixture of two regioisomers, 421 mg, 1.56 mmol) in THF (2 mL) at −78° C. was added LDA (0.4 M, 6.0 mL, 2.4 mmol). The resulting mixture was allow to stir for 30 min at −78° C., paraformaldehyde (500 mg, excess) in THF (2 mL) was added. Stirring was continued for 18 hours at room temperature. The mixture was diluted with ethylacetate (300 mL), and washed with sat. NaHCO$_3$, and brine then dried over Na$_2$SO$_4$. Evaporation of the solvent and purification of the crude material by column chromatography on silica gel (2.5×20 cm, 3:7 EtOAc/hexanes) gave the desired product as a yellow solid (mixture of two regioisomers) (80 mg, 17%).

To a pre-cooled (ice bath) solution of 1-dimethylsulfamyl-2-hydroxymethyl-(nitro)-benzimidazole (240 mg, 0.80 mmol) and triethylamine (0.9 ml, 6.23 mmol) in anhydrous CH$_2$Cl$_2$ (6 ml) was added methanesulfonyl chloride (1 N in CH$_2$Cl$_2$, 0.8 mL, 0.80 mmol). Stirring was continued for 1 hour at 0° C. The reaction mixture was diluted with ethylacetate (300 mL), and washed with sat. NaHCO$_3$, then brine and dried over Na$_2$SO$_4$. Evaporation of the solvent and purification of the residue by column chromatography on silica gel (1.5×20 cm, 2:8 EtOAc/hexanes) gave the desired product (240 mg, 83%) as a yellow solid.

To a stirred solution of 1-dimethylsulfamyl-2-methanesulfonylmethyl-[4(5)-nitro]benzimidazole (230 mg, 0.63 mmol) and dipropylethylamine (0.35 mL, 2.0 mmol) in anhydrous DMF (4 mL) under N$_2$ was added N-(t-butoxycarbonyl)-N-(2-pyridinylmethyl)-N'-(5,6,7,8-tetrahydro-8-quinolinyl)-1,4-benzenedimethanamine (610 mg, 1.33 mmol). The reaction mixture was allowed to stir at 85° C. for further 18 hours and then concentrated. The residue was diluted with ethylacetate (100 mL) and the orgnic phase was washed with a sat. NaHCO$_3$, then brine and dried over Na$_2$SO$_4$. Evaporation of the solvent and purification of the residue by radial chromatography on silica gel (1 mm plate, 3:97 MeOH/CH$_2$Cl$_2$) gave the desired product (140 mg, 30%) as mixture of two regioisomers.

Preparation of AMD8926

The intermediate from above (120 mg, 0.16 mmol) was dissolved in HCl solution (2 N, 3 mL) and the resulting mixture was allowed to reflux for 4 h. After cooling, the reaction was neutralized by addition of NaHCO$_3$, and the aqueous solution was extracted with CHCl$_3$ (3×50 mL). The combined organic extracts were dried over Na$_2$SO$_4$ and the solvents evaporated. Purification of the residue by radial chromatography on silica gel (1 mm plate, 3:3:97 NH$_4$OH/MeOH/CH$_2$Cl$_2$) gave the desired product (46 mg, 53%). $^1$H NMR (CDCl$_3$) δ 1.64–1.68 (m, 2H), 2.07–2.09 (m, 2H), 2.28–2.30 (m, 1H), 2.71–2.94 (m, 2H), 3.74 (s, 4H), 3.85 (s, 2H), 3.99–4.11 (m, 2H), 4.21–4.28 (m, 1H), 7.13 (dd, 1H, J=5.1, 6.9 Hz), 7.20–7.32 (m, 7H), 7.47 (d, 1H, J=7.5 Hz), 7.53–7.66 (m, 2H), 8.14 (dd, 1H, J=9.8, 9.8 Hz), 8.45–8.53 (m, 2H), 8.71 (m, 1H); $^{13}$C NMR (CDCl$_3$) δ 21.78, 23.98, 29.55, 49.06, 53.51, 53.98, 54.85, 61.09, 122.32, 122.71, 123.00, 128.69, 129.03, 135.39, 136.80, 138.01, 139.67, 147.13, 149.65, 157.55, 160.03. ES-MS m/z 534.3 (M+H). Anal. Calcd. for (C$_{31}$H$_{31}$N$_7$O$_2$).(1H$_2$O): C, 67.50; H, 6.03; N, 17.77; Found: C, 67.29; H, 5.77; N, 17.77.

Example 64

AMD8929: Preparation of N-(2-pyridinylmethyl)-N'-[(1H)-5-azabenzimidazol-2-ylmethyl]-N'-(5,6,7,8-tetrahydro-8-quinolinyl)-1,4-benzenedimethanamine (hydrobromide salt)

General Procedure for Protection of Benzimidazoles with 2-(trimethylsilyl)ethoxymethyl chloride (SEM-Cl)

To a stirred solution of 5-azabenzimidazole (0.300 g, 2.51 mmol) in anhydrous DMF (5 mL) was added N,N-diisopropylethylamine (0.66 mL, 3.80 mmol) followed by 2-(trimethylsilyl)ethoxymethyl chloride (0.54 mL, 3.02 mmol). The resultant solution was heated to 80° C. for 2 h then cooled to room temperature. The reaction mixture was poured into brine (20 mL) and diluted with ethyl acetate (30 mL). The phases were separated and the aqueous phase was extracted with ethyl acetate (3×15 mL). The combined organic extracts were washed with brine (3×5 mL), dried (MgSO$_4$), and concentrated under reduced pressure. Purification of the crude brown oil through a plug of silica gel (CH$_2$Cl$_2$/MeOH, 9:1) provided the 1-(2-trimethylsilylethoxymethyl)-5-azabenzimidazole (0.586 g, 93%) as an orange oil.

General Procedure: Formylation of Benzimidazoles

To a cold (–40° C.), stirred solution of 1-(2-trimethylsilylethoxymethyl)-5-aza-benzimidazole (0.574 g, 2.31 mmol) in dry THF (5 mL) was added a 1.7 M solution of tert-butyllithium in pentane (1.55 mL, 2.63 mmol). The reaction mixture turned deep red. After 20 minutes, DMF (0.50 mL, 6.46 mmol) was added to the reaction mixture and the resultant solution was allowed to warm to room temperature overnight. The mixture was poured into saturated aqueous NH$_4$Cl (25 mL) and diluted with ethylacetate (25 mL). The phases were separated and the aqueous phase was extracted with ethyl acetate (3×25 mL). The combined organic extracts were dried (MgSO$_4$) and concentrated. The residual, yellow oil (0.655 g) was used immediately in the next step.

Using general procedure B: A solution of N-(t-butoxycarbonyl)-N-(2-pyridinylmethyl)-N'-(5,6,7,8-tetrahydro-8-quinolinyl)-1,4-benzenedimethanamine (0.515 g, 1.12 mmol) and the crude 1-[[2-(trimethylsilyl)ethoxy]methyl]-(1H)-5-azabenzimidazole-2-carboxaldehyde (the yellow oil from above) in CH$_2$Cl$_2$ (10 mL) were reacted with sodium triacetoxyborohydride (0.357 g, 1.68 mmol) for 18 hours. Purification of the crude material by column chromatography on silica gel (CH$_2$Cl$_2$/MeOH, 96:4 to 9:1) provided the desired intermediate as a dark oil.

The oil from above (0.202 g, 0.28 mmol) in CH$_2$Cl$_2$/TFA (2:1, 3 mL) was stirred overnight (16 hours) then concentrated in vacuo. The residue was diluted with CH$_2$Cl$_2$ (25 mL) and 1 N NaOH (40 mL). The aqueous layer was washed with CH$_2$Cl$_2$ (2×25 mL) and the combined organic layers dried (Na$_2$SO$_4$), filtered and concentrated in vacuo. Purification of the crude material by column chromatography on silica gel (CH$_2$Cl$_2$/MeOH/NH$_4$OH, 95:4:1) followed by radial chromatography (1 mm plate) on silica gel (CH$_2$Cl$_2$/MeOH/NH$_4$OH, 95:4:1) provided the free base of the title compound (36 mg, 18% 2 steps) as a clear oil.

Using general procedure D: the free base (36 mg, 0.074 mmol) was converted to a hydrobromide salt to give AMD8929 (69 mg, quant.) as a white solid. $^1$H NMR (D$_2$O) δ 1.79–1.85 (br m, 1H), 2.15–2.26 (br m, 2H), 2.36–2.41 (m, 1H), 2.94–2.97 (m, 2H), 3.86 (s, 2H), 4.09 (s, 2H), 4.31 (d, 1H, J=15.9 Hz), 4.41 (s, 2H), 4.44 (d, 1H, J=15.9 Hz), 4.59 (dd, 1H, J=10.5, 6.3 Hz), 7.16 (d, 2H, J=7.8 Hz), 7.30 (d, 2H, J=8.1 Hz), 7.76–7.81 (m, 3H), 7.95 (d, 1H, J=6.6 Hz), 8.23–8.29 (m, 2H), 8.40 (d, 1H, J=6.6 Hz), 8.62 (d, 1H, J=5.7 Hz), 8.68 (dd, 1H, J=5.7, 1.2 Hz), 9.05 (s, 1H); $^{13}$C NMR (D$_2$O) δ 20.51 (2 carbons), 27.75, 48.24, 51.10, 51.51, 55.95, 61.31, 111.24, 125.73, 127.21, 127.28, 129.56, 130.29 (2 carbons), 131.00 (2 carbons), 132.49, 133.79, 137.93, 139.14, 139.34, 140.56, 145.01, 145.73, 146.12, 146.86, 147.72, 151.66, 162.72. ES-MS m/z 490 (M+H). Anal. Calcd. for C$_{30}$H$_{31}$N$_7$O.4.9HBr.2.3H$_2$O: C, 38.85; H, 4.40; N, 10.57; Br, 42.21. Found: C, 38.97; H, 4.31; N, 10.31; Br, 42.12.

Example 65

AMD8931: Preparation of N-(2-pyridinylmethyl)-N-(4-phenyl-1H-imidazol-2-ylmethyl)-N'-(5,6,7,8-tetrahydro-8-quinolinyl)-1,4-benzenedimethanamine To a stirred suspension of sodium hydride (108 mg, 2.70 mmol) in anhydrous DMF (1 mL), at room temperature was added, 4-phenylimidazole (400 mg, 2.78 mmol) in anhydrous DMF (4 mL), and the solution was stirred at room temperature for 1.5 hours. Sem-Cl (520 uL, 2.94 mmol) was added dropwise to the solution, and the mixture was stirred at room temperature for 1 hour. The reaction was quenched with water (10 mL) and the resulting solution was extracted with EtOAc. The organic phases were dried (Na$_2$SO$_4$) and concentrated. The crude material was purified by column chromatography (silica gel, Hexane/EtOAc 50:1) to give the SEM-protected imidazoles [430 mg (58%, major isomer: 1-SEM-4-phenylimidazole) and 70 mg (15%, minor isomer: 1-SEM-5-phenylimidazole)] as yellow oils.

To a stirred solution of the Sem-protected 4-phenylimidazole (380 mg, 1.39 mmol) in anhydrous THF (7.6 mL) cooled to –40° C. was added, a solution of n-BuLi in hexane (2.5 M, 720 μL, 1.80 mmol), and the resultant solution was stirred at –40° C. for 20 minutes. To this solution was added, DMF (323 μL, 4.17 mmol) and the mixture was allowed to stir for 4 hours at –40° C. The reaction was quenched with NH$_4$Cl (5 mL) and the mixture was extracted with EtOAc (3×80 mL). The combined organic phases were dried (Na$_2$SO$_4$) and concentrated to afford the SEM protected 4-phenylimidazole-2-carboxaldehyde (411 mg, 98%) as a yellow solid.

Using general procedure B: To a stirred solution of N-(2-nitrobenzenesulfonyl)-N-(2-pyridinylmethyl)-N'-(5,6,7,8-tetrahydro-8-quinolinyl)-1,4-benzenedimethanamine (244 mg, 0.45 mmol) in THF (5 mL), at room temperature, was added the aldehyde from above (150 mg, 0.50 mmol), glacial acetic acid (250 μL) and NaBH(OAc)₃ (286 mg, 1.35 mmol), and the resultant solution was stirred at room temperature for 1 hour. The solution was diluted with EtOAc (100 mL), filtered through celite, and concentrated in vacuo. The crude material was purified by column chromatography (silica gel, CH₂CH₂/MeOH/NH₄OH 98:1:1) to afford the desired product (266 mg, 71% yield) as a yellow foam.

The foam from above (190 mg, 0.23 mmol) was dissolved in 6 M HCl solution (6 mL), and the resultant solution was stirred at 50° C. for 3 hours. The mixture was neutralized with K₂CO₃, and extracted with EtOAc (3×50 mL). The combined organic phases were dried (Na₂SO₄) and concentrated in vacuo. The crude material was purified by column chromatography (silica gel, CH₂CH₂/MeOH/NH₄OH 98:1:1) to afford the desired product (141 mg, 88%) as a yellow foam.

Using general procedure C: The intermediate from above (135 mg, 0.19 mmol) was reacted with thiophenol (57.3 μL, 0.56 mmol) and K₂CO₃ (128 mg, 0.93 mmol) in DMF (1.9 mL). Purification of the crude material by column chromatography on silica gel (CH₂CH₂/MeOH/NH₄OH 48:1:1) gave AMD8931 (61 mg) as a white foam.

$^1$H NMR (CDCl₃) δ 1.50–1.71 (m, 1H), 1.75–2.03 (m, 3H), 2.22–2.23 (m, 2H), 2.68–2.89 (m, 2H), 3.68 (s, 2H), 3.76 (s, 2H), 3.82 (s, 1H), 3.87 (s, 2H), 4.06 (d, 2H, J=16.2 Hz), 7.10–7.42 (m, 12H), 7.59 (t, 1H, J=7.5 Hz), 7.72 (br s, 2H), 8.52 (d, 1H, J=6.6 Hz), 8.53 (br s, 1H); $^{13}$C NMR (CDCl₃) δ 21.29, 23.18, 29.26, 47.99, 53.19, 53.64, 54.48, 59.75, 121.85, 122.12, 122.32, 124.52, 126.12, 128.15, 128.57, 134.67, 136.36, 137.06, 138.29, 138.97, 147.09, 149.23, 157.71, 159.79.ES-MS m/z 515 (M+H). Anal. Calcd. for C₃₃H₃₄N₆.0.9H₂O: C, 74.66; H, 6.80; N, 15.83. Found: C, 74.53; H, 6.61; N, 15.86.

Example 66

AMD8783: Preparation of N-(2-pyridinylmethyl)-N'-[2-(2-pyridinyl)ethyl]-N'-(5,6,7,8-tetrahydro-8-quinolinyl)-1,4-benzenedimethanamine (hydrobromide salt)

To a stirred solution of N-(2-nitrobenzenesulfonyl)-N-(2-pyridinylmethyl)-N'-(5,6,7,8-tetrahydro-8-quinolinyl)-1,4-benzenedimethanamine (276 mg, 0.51 mmol) and anhydrous K₂CO₃ (750 mg, 5.4 mmol) in anhydrous DMF (3 ml) under N₂ was added 2-(2-methanesulfonylethyl)pyridine (450 mg, 2.2 mmol). The reaction mixture was allowed to stir at 85° C. for further 18 hours and then concentrated. The residue was diluted with ethylacetate (100 mL) and the solution was washed with saturated aqueous NaHCO₃ then brine and dried over Na₂SO₄. Evaporation of the solvent and purification of the crude material by column chromatography on silica gel (1.5×20 cm, 50:50 EtOAc/CH₂Cl₂) gave the desired intermediate (100 mg, 32%) as a yellow oil.

Using general procedures C and D: the intermediate from above was reacted with anhydrous K₂CO₃ (137 mg, 0.99 mmol) and thiophenol (51 μl, 0.49 mmol) in DMF (3 ml). Purification of the crude material by radial chromatography on silica gel (1 mm plate, 3:3:94 MeOH/NH₄OH/CH₂Cl₂) gave the free base of the title compound (90 mg, 76%) as a light yellow oil. Conversion of the free base (90 mg, 0.19 mmol) to the hydrobromide salt gave AMD8783 (130 mg). $^1$H NMR (CD₃OD) δ 1.88–1.89 (m, 1H), 2.11–2.18 (m, 2H), 2.42–2.44 (m, 1H), 2.98–3.03 (m, 2H), 3.20–3.40 (m, 1H), 3.46–3.66 (m, 3H), 4.05 (d, 1H, J=13.8 Hz), 4.17 (d, 1H, J=13.8 Hz), 4.44 (s, 2H), 4.54–4.57 (m, 1H), 4.65 (s, 2H), 7.63 (d, 2H, J=8.1 Hz), 7.71 (d, 2H, J=8.1 Hz), 7.76–7.85 (m, 2H), 7.94–8.06 (m, 3H), 8.19 (d, 1H, J=7.8 Hz), 8.34 (dd, 1H, J=7.2, 7.2 Hz), 8.56 (ddd, 1H, J=1.2, 7.8, 7.8 Hz), 8.74 (dd, 2H, J=5.6, 5.6 Hz), 8.83 (b, 1H); $^{13}$C NMR (CD₃OD) δ 22.06, 28.97, 33.40, 52.18, 52.63, 56.21, 60.83, 67.31, 126.72, 127.04, 127.70, 127.90, 129.59, 132.09, 132.42, 139.65, 140.66, 142.82, 142.96, 144.70, 147.11, 147.51, 148.70, 149.83, 153.35, 155.77. ES-MS m/z 464.2 (M+H). Anal. Calcd. for C₃₀H₃₃N₅.4.0HBr.3.0H₂O: C, 42.83; H, 5.15; N, 8.32; Br, 37.99. Found: C, 43.04; H, 5.18; N, 8.14; Br, 37.75.

Example 67

AMD8764: Preparation of N-(2-pyridinylmethyl)-N'-(2-benzoxazolyl)-N'-(5,6,7,8-tetrahydro-8-quinolinyl)-1,4-benzenedimethanamine (hydrobromide salt)

A solution of N-(2-nitrobenzenesulfonyl)-N-(2-pyridinylmethyl)-N'-(5,6,7,8-tetrahydro-8-quinolinyl)-1,4-benzenedimethanamine (260 mg, 0.48 mmol) and 2-chlorobenzoxazole (115 mg, 0.749 mmol) in CH₃CN (2.5 mL) was heated at reflux under nitrogen atmosphere for 3 hours. Saturated NaHCO₃(aq) (10 mL) was added, and the mixture was extracted with CH₂Cl₂ (1×10 mL, 2×5 mL). The combined organic extracts were dried (MgSO₄) and concentrated in vacuo. The residue was purified by chromatography on silica gel using 70%-90% EtOAc/hexanes then on reverse phase C-18 using 7:3 to 9:1 MeOH/H₂O to give a colourless solid (101 mg, 32%).

Using general procedures C and D: The intermediate from above (92 mg, 0.14 mmol) was reacted with thiophenol (0.045 mL, 0.44 mmol) and K₂CO₃ (80 mg, 0.58 mmol) in CH₃CN (2.2 mL) under nitrogen atmosphere at 40° C. for 1 hour. Brine (15 mL) was added, and the mixture was extracted with CH₂Cl₂ (1×20 mL, 2×10 mL). The combined organic extracts were dried (MgSO₄) and concentrated in vacuo. The residue was purified by column chromatography on neutral alumina using CH₂Cl₂ and 10% MeOH/CH₂Cl₂ to give a light yellow oil (47 mg, 71%). Conversion to the hydrobromide salt gave AMD8764 as a colourless solid (59 mg, 74%). $^1$H NMR (D₂O) δ 1.90–2.26 (m, 4H), 3.03 (br s, 2H), 4.37 (s, 2H), 4.58 (s, 2H), 4.84 (s, 1H), 4.81 (d, 1H, J=18 Hz), 5.02 (d, 1H, J=18 Hz), 5.82 (t, 1H, J=9 Hz), 7.21–7.45 (m, 8H), 7.83 (m, 3H), 8.33 (m, 3H), 8.73 (d, 1H, J=5.4 Hz); $^{13}$C NMR (D₂O) δ 20.40, 26.65, 27.43, 48.62, 51.11, 51.36, 57.16, 110.49, 115.69, 123.29, 125.59, 126.29, 127.01, 127.10, 128.85, 130.24, 130.95, 138.07, 138.95, 140.02, 140.74, 144.48, 146.08, 147.23, 148.02, 148.16, 148.27, 161.78. ES-MS m/z 476 (M+H). Anal. Calcd. for C₃₀H₂₉N₅O.4.2HBr.3.9H₂O: C, 40.68; H, 4.67; N, 7.91; Br, 37.89. Found: C, 40.80; H, 4.55; N, 7.81; Br, 37.71.

Example 68

AMD8780: Preparation of N-(2-pyridinylmethyl)-N'-(trans-2-aminocyclohexyl)-N'-(5,6,7,8-tetrahydro-8-quinolinyl)-1,4-benzenedimethanamine (hydrobromide salt)

N-(2-nitrobenzenesulfonyl)-7-azabicyclo[4.1.0]heptane (N-(2-nitrobenzenesulfonyl)-1,2-cyclohexeneaziridine)

A solution of trans-2-aminocyclohexanol hydrochloride (2.50 g, 16.5 mmol) and 2-nitrobenzenesulfonyl chloride (3.66 g, 16.5 mmol) in CH₂Cl₂ (35 mL) was cooled in an ice bath under nitrogen atmosphere while Et₃N (5.10 mL, 36.6 mmol) was added. The mixture was heated at reflux for 35 minutes, then concentrated in vacuo. Water (25 mL) was added to the residue, and the mixture was extracted with EtOAc (50 mL). The organic extract was washed with brine (3×15 mL), then dried (MgSO$_4$) and concentrated in vacuo to give a grey solid (5.73 g).

A solution of the solid from above and Et$_3$N (2.8 mL, 20 mmol) in CH$_2$Cl$_2$ (30 mL) was stirred at −40° C. under nitrogen atmosphere while methanesulfonyl chloride (1.4 mL, 18 mmol) was added. The mixture was stirred at −40° C. for 10 minutes, then the cold bath was removed and stirring was continued at room temperature for 30 minutes and the solution was then concentrated in vacuo. Water (25 mL) and saturated NaHCO$_3$(aq) (25 mL) were added to the residue, and the mixture was extracted with EtOAc (1×20 mL, 3×10 mL). The combined organic extracts were dried (MgSO$_4$) and concentrated in vacuo to give the crude mesylate as a light yellow solid (6.12 g).

The crude mesylate (258 mg, 0.682 mmol) was stirred as a suspension in benzene (3 mL) at room temperature while a solution of 85% KOH (230 mg, 3.5 mmol) in H$_2$O (1 mL) was added. The mixture was stirred for 30 minutes, and additional benzene (10 mL) was added. The organic phase was separated and washed with brine (10 mL), then dried (MgSO$_4$) and concentrated in vacuo. The residue was purified by column chromatography on silica gel (25% EtOAc/hexanes) to give the desired aziridine as colorless crystals (141 mg, 72% over 3 steps).

A solution of the aziridine from above (92 mg, 0.33 mmol), N-(2-nitrobenzenesulfonyl)-N-(2-pyridinylmethyl)-N'-(5,6,7,8-tetrahydro-8-quinolinyl)-1,4-benzenedimethanamine (213 mg, 0.392 mmol) and Et$_3$N (0.01 mL, 0.07 mmol) in THF (1.1 mL) was heated at 60° C. under nitrogen atmosphere for 48 hours. The solution was diluted with EtOAc (15 mL) and washed with brine (10 mL). The aqueous phase was extracted with EtOAc (2×10 mL). The combined organic extracts were dried (MgSO$_4$) and concentrated in vacuo. The residue was purified by column chromatography on silica gel (70% EtOAc/hexanes) to give a yellow solid (155 mg, 58%).

Using general procedures C and D: The intermediate from above (111 mg, 0.134 mmol) was reacted thiophenol (0.085 mL, 0.83 mmol) and K$_2$CO$_3$ (150 mg, 1.08 mmol) in CH$_3$CN (2.7 mL) under nitrogen atmosphere at 40° C. for 22 hours. Brine (15 mL) was added, and the mixture was extracted with CH$_2$Cl$_2$ (3×10 mL). The combined organic extracts were dried (MgSO$_4$) and concentrated in vacuo. The residue was purified by column chromatography on neutral alumina (CH$_2$Cl$_2$ then 10% MeOH/CH$_2$Cl$_2$) to give the free base of the title compound as a yellow oil (53 mg, 87%). Conversion to the hydrobromide salt followed by re-precipitation of the intermediate solid from methanol/ether gave AMD8780 as a light yellow solid (46 mg, 52%). $^1$H NMR (D$_2$O) mixture of two diastereomers: δ 1.26–2.49 (m, 24H), 2.81–3.18 (m, 6H), 3.40–3.56 (m, 2H), 3.71–3.96 (m, 4H), 4.19 (s, 2H), 4.32 (s, 2H), 4.43 (s, 2H), 4.45 (m, 1H), 4.47 (s, 2H), 7.23 (br s, 6H), 7.36 (m, 5H), 7.54 (m, 1H), 7.70 (m, 4H), 8.11 (m, 4H), 8.50 (d, 1H, J=4.8 Hz), 8.65 (d, 1H, J=4.8 Hz); $^{13}$C NMR (D$_2$O) δ 14.53, 19.53, 20.94, 23.89, 25.09, 25.35, 27.50, 27.95, 29.26, 30.94, 31.40, 47.91, 49.54, 50.96, 51.12, 51.40, 52.78, 56.61, 62.56, 63.63, 66.47, 67.70, 125.25, 125.78, 125.96, 126.06, 126.15, 129.83, 130.17, 130.68, 130.77, 139.13, 139.38, 139.70, 140.32, 140.81, 142.14, 142.27, 147.40, 147.63, 148.54, 151.21, 151.98. ES-MS m/z 456 (M+H). Anal. Calcd. for C$_{29}$H$_{37}$N$_5$.4.0HBr.3.9H$_2$O: C, 41.00; H, 5.79; N, 8.24; Br, 37.62. Found: C, 41.08; H, 5.50; N, 8.05; Br, 37.58.

Example 69

AMD8818: Preparation of N-(2-pyridinylmethyl)-N'-(2-phenylethyl)-N'-(5,6,7,8-tetrahydro-8-quinolinyl)-1,4-benzenedimethanamine (hydrobromide salt)

A solution of 2-phenylethanol (510 mg, 4.17 mmol) and p-toluenesulfonyl chloride (874 mg, 4.58 mmol) in CH$_2$Cl$_2$ (15 mL) was stirred in an ice bath while Et$_3$N (0.70 mL, 5.0 mmol) was added. The cold bath was removed, and the solution was heated at reflux under nitrogen atmosphere for 42 hours. The solution was washed with 10% HCl(aq) (10 mL), saturated NaHCO$_3$(aq) (10 mL), and brine (5 mL), then dried (MgSO$_4$) and concentrated in vacuo to give the tosylate as a yellow oil (783 mg, 68%).

N-(2-nitrobenzenesulfonyl)-N-(2-pyridinylmethyl)-N'-(5,6,7,8-tetrahydro-8-quinolinyl)-1,4-benzenedimethanamine (355 mg, 0.653 mmol), the tosylate from above (356 mg, 1.29 mmol) and K$_2$CO$_3$ (271 mg, 1.96 mmol) were heated at reflux in CH$_3$CN (3 mL) under nitrogen atmosphere for 19 hours. The mixture was diluted with EtOAc (15 mL) and washed with brine (10 mL), then dried (MgSO$_4$) and concentrated in vacuo. The residue was purified by column chromatography on silica gel (60% THF/hexanes) to give a yellow oil (241 mg, 57%).

Using General procedures C and D: The oil from above (225 mg, 0.347 mmol) was reacted with thiophenol (0.11 mL, 1.1 mmol) and K$_2$CO$_3$ (192 mg, 1.39 mmol) in CH$_3$CN (7 mL) with stirring under nitrogen atmosphere at 40° C. for 1.5 hours. Brine (15 mL) was added, and the mixture was extracted with CH$_2$Cl$_2$ (3×10 mL). The combined organic extracts were dried (MgSO$_4$) and concentrated in vacuo. The residue was purified by column chromatography on neutral alumina (CH$_2$Cl$_2$ then 10% MeOH/CH$_2$Cl$_2$) to give the free base of the title compound (79 mg, 49%) as a yellow oil. Conversion of the free base (74 mg, 0.16 mmol) to the hydrobromide salt followed by re-precipitation of the intermediate solid from methanol/ether gave AMD8818 (114 mg, 86%) as a light yellow solid. $^1$H NMR (D$_2$O) δ 1.82 (m, 1H), 2.04–2.19 (m, 2H), 2.50 (m, 1H), 2.85–3.01 (m, 4H), 3.37 (br s, 1H), 3.66 (br s, 1H), 4.32 (m, 2H), 4.42 (s, 2H), 4.58 (s, 2H), 4.76 (m, 1H), 7.09 (m, 2H), 7.29–7.48 (m, 8H), 7.69–7.88 (m, 3H), 8.31 (m, 2H), 8.71 (d, 1H); $^{13}$C NMR (D$_2$O) δ 20.40, 20.91, 27.23, 31.23, 48.72, 51.29, 52.20, 54.75, 62.22, 124.74, 126.99, 128.01, 129.45, 129.62, 131.35, 132.00, 132.36, 135.73, 135.94, 139.85, 144.34, 146.17, 146.50, 147.23, 148.49. ES-MS m/z 463 (M+H). Anal. Calcd. for C$_{31}$H$_{34}$N$_4$.3.9HBr.2.9H$_2$O: C, 44.84; H, 5.30; N, 6.75; Br, 37.53. Found: C, 44.77; H, 5.04; N, 6.59; Br, 37.55.

Example 70

AMD8829: Preparation of N-(2-pyridinylmethyl)-N'-(3-phenylpropyl)-N'-(5,6,7,8-tetrahydro-8-quinolinyl)-1,4-benzenedimethanamine (hydrobromide salt)

A solution of 3-phenylpropanol (510 mg, 3.74 mmol) and p-toluenesulfonyl chloride (770 mg, 4.04 mmol) in CH$_2$Cl$_2$ (15 mL) was stirred in an ice bath while Et$_3$N (0.61 mL, 4.4 mmol) was added. The cold bath was removed, and the solution was heated at reflux under nitrogen atmosphere for 19 hours. The solution was washed with 10% HCl(aq) (5 mL), saturated NaHCO$_3$(aq) (10 mL), and brine (5 mL), then dried (MgSO$_4$) and concentrated in vacuo to give the tosylate as a yellow oil (893 mg, 82%).

N-(2-nitrobenzenesulfonyl)-N-(2-pyridinylmethyl)-N'-(5,6,7,8-tetrahydro-8-quinolinyl)-1,4-benzenedimethanamine (312 mg, 0.574 mmol), the tosylate from above (320 mg, 1.10 mmol) and K$_2$CO$_3$ (250 mg, 1.81 mmol) were heated at reflux in CH$_3$CN (2.5 mL) under nitrogen atmosphere for 24 hours. The mixture was diluted with EtOAc (15 mL) and washed with brine (10 mL), then dried (MgSO$_4$) and concentrated in vacuo. The residue was purified by column chromatography on silica gel (70% THF/hexanes) to give a yellow oil (261 mg, 69%).

Using general procedures C and D: The oil (257 mg, 0.388 mmol) was reacted with thiophenol (0.12 mL, 1.2 mmol), and K$_2$CO$_3$ (215 mg, 1.56 mmol) in CH$_3$CN (7.5 mL) under nitrogen atmosphere with stirring at 40° C. for 1 hour. Brine (10 mL) was added, and the mixture was extracted with CH$_2$Cl$_2$ (3×10 mL). The combined organic extracts were dried (MgSO$_4$) and concentrated in vacuo. The residue was purified by column chromatography on neutral alumina (CH$_2$Cl$_2$ then 10% MeOH/CH$_2$Cl$_2$) to give the free base of the title compound (97 mg, 52%) as a yellow oil. Conversion of the free base (94 mg, 0.20 mmol) to the hydrobromide salt followed by re-precipitation of the crude material from methanol/ether gave AMD8829 (141 mg, 87%) as a yellow solid. $^1$H NMR (D$_2$O) δ 1.75–2.12 (m, 5H), 2.35 (m, 1H), 2.56 (m, 2H), 2.80 (m, 2H), 3.13 (br s, 1H), 3.29 (br s, 1H), 4.24 (m, 2H), 4.41 (s, 2H), 4.56 (s, 2H), 4.76 (m, 1H), 7.09–7.35 (m, 6H), 7.50 (br s, 4H), 7.64 (d, 1H, J=7.5 Hz), 7.85 (m, 2H), 8.34 (m, 1H), 8.45 (br s, 1H), 8.73 (d, 1H, J=5.4); $^{13}$C NMR (D$_2$O) δ 20.32, 20.94, 26.58, 27.36, 32.01, 48.50, 51.31, 62.44, 124.75, 126.90, 127.16, 127.25, 128.82, 129.19, 131.23, 131.82, 132.12, 135.75, 139.65, 140.47, 144.80, 145.89, 146.97, 148.66. ES-MS m/z 477 (M+H). Anal. Calcd. for C$_{32}$H$_{36}$N$_4$.3.9HBr.1.8H$_2$O: C, 46.61; H, 5.32; N, 6.79; Br, 37.79. Found: C, 46.47; H, 5.11; N, 6.64; Br, 37.93.

Example 71

AMD8839: Preparation of N-(2-pyridinylmethyl)-N'-(trans-2-aminocyclopentyl)-N'-(5,6,7,8-tetrahydro-8-quinolinyl)-1,4-benzenedimethanamine (hydrobromide salt)

N-(2-nitrobenzenesulfonyl)-6-azabicyclo[3.1.0]hexane (N-(2-nitrobenzenesulfonyl-1,2-cyclopenteneaziridine).

A solution of (1S,2S)-2-benzyloxycyclopentylamine (417 mg, 2.18 mmol) and 2-nitrobenzenesulfonyl chloride (531 mg, 2.40 mmol) in CH$_2$Cl$_2$ (10 mL) was cooled in an ice bath under nitrogen atmosphere while Et$_3$N (0.36 mL, 2.6 mmol) was added. The mixture was heated at reflux for 1 hour, then washed with H$_2$O (10 mL). The aqueous phase was extracted with CH$_2$Cl$_2$ (5 mL). The combined organic phases were dried (MgSO$_4$) and concentrated in vacuo to give the crude sulfonamide as a dark oil (787 mg).

A solution of the crude sulfonamide (675 mg, 1.79 mmol) and TMSI (0.64 mL, 4.5 mmol) in CH$_3$CN (9 mL) was heated at 40° C. under nitrogen atmosphere for 21 hours. Saturated NaHCO$_3$(aq) (15 mL) was added, and the mixture was extracted with CH$_2$Cl$_2$ (1×15 mL, 2×10 mL). The combined organic extracts were dried (MgSO$_4$) and concentrated in vacuo. The residue was purified by column chromatography on silica gel (50% EtOAc/hexanes) to give the alcohol as a yellow oil (424 mg, 80% over 2 steps).

A solution of the alcohol (464 mg, 1.62 mmol) and Et$_3$N (0.27 mL, 1.9 mmol) in CH$_2$Cl$_2$ (8 mL) was stirred at −78° C. under nitrogen atmosphere while methanesulfonyl chloride (0.14 mL, 1.8 mmol) was added. The cold bath was removed, and stirring was continued at room temperature for 20 minutes and the solution was concentrated in vacuo. Ethyl acetate (20 mL) was added, and the mixture was washed with saturated NaHCO$_3$(aq) (15 mL) and brine (15 mL). The organic phase was dried (MgSO$_4$) and concentrated in vacuo to give the mesylate as a yellow oil (725 mg). This was used without further purification in the next step.

A solution of the crude mesylate in benzene (6 mL) was stirred at room temperature while a solution of 85% KOH (530 mg, 8.0 mmol) in H$_2$O (2.5 mL) was added. The mixture was stirred for 45 minutes, and benzene (20 mL) was added to the mixture. The organic phase was separated and washed with brine (10 mL), then dried (MgSO$_4$) and concentrated in vacuo. The residue was purified by chromatography on silica gel (25% EtOAc/hexanes) to give the desired aziridine as yellow crystals (293 mg, 67% over 2 steps).

A solution of the aziridine from above (138 mg, 0.514 mmol), N-(2-nitrobenzenesulfonyl)-N-(2-pyridinylmethyl)-N'-(5,6,7,8-tetrahydro-8-quinolinyl)-1,4-benzenedimethanamine (340 mg, 0.625 mmol), and Et$_3$N (0.04 mL, 0.29 mmol) in THF (1.7 mL) was heated at 60° C. under nitrogen atmosphere for 48 hours. The solution was diluted with EtOAc (15 mL) and washed with brine (10 mL). The aqueous phase was extracted with EtOAc (2×10 mL). The combined organic extracts were dried (MgSO$_4$) and concentrated in vacuo. The residue was purified by column chromatography on silica gel (50% THF/hexanes) to give a yellow solid (203 mg, 49%).

Using general procedures C and D: the solid (186 mg, 0.229 mmol) was reacted with thiophenol (0.14 mL, 1.4 mmol) and K$_2$CO$_3$ (253 mg, 1.83 mmol) with stirring in CH$_3$CN (4.6 mL) under nitrogen atmosphere at 40° C. for 20 hours. Brine (10 mL) was added, and the mixture was extracted with CH$_2$Cl$_2$ (3×10 mL). The combined organic extracts were dried (MgSO$_4$) and concentrated in vacuo. The residue was purified by column chromatography on neutral alumina (CH$_2$Cl$_2$ then 10% MeOH/CH$_2$Cl$_2$) to give the free base of the title compound (91 mg, 90%) as a yellow oil. Conversion of the free base (87 mg, 0.20 mmol) to the hydrobromide salt followed by re-precipitation of the crude material from methanol/ether gave AMD8839 (108 mg, 66%) as a light yellow solid. $^1$H NMR (D$_2$O): mixture of diastereomers: δ 1.54–2.52 (m, 20H), 2.88 (m, 4H), 3.23–3.92 (m, 8H), 4.21 (s, 2H), 4.34 (s, 2H), 4.37 (m, 1H), 4.46 (s, 2H), 4.53 (s, 2H), 7.21 (m, 4H), 7.43 (m, 8H), 7.71–7.83 (m, 5H), 7.99 (m, 1H), 8.23 (m, 2H), 8.46 (d, 1H), 8.70 (d, 1H, J=6.0 Hz); $^{13}$C NMR (D$_2$O) δ 20.72, 20.93, 22.04, 22.12, 22.71, 23.96, 26.18, 27.58, 27.67, 28.41, 28.75, 47.32, 48.88, 51.09, 51.33, 52.24, 54.43, 55.93, 56.88, 62.44, 66.92, 72.46, 124.89, 125.53, 126.77, 129.45, 130.11, 130.60, 130.81, 130.90, 138.40, 139.00, 139.26, 139.60, 140.05, 140.34, 143.65, 143.81, 146.56, 146.89, 147.40, 147.63, 151.93, 152.93. ES-MS m/z 442 (M+H). Anal. Calcd. for C$_{28}$H$_{35}$N$_5$.4.3HBr.2.3H$_2$O: C, 40.47; H, 5.32; N, 8.43; Br, 41.35. Found: C, 40.66; H, 5.22; N, 8.27; Br, 41.13.

Example 72

AMD8726: Preparation of N-[[4-[[(2-pyridinylmethyl)amino]methyl]phenyl]methyl]-N-(5,6,7,8-tetrahydro-8-quinolinyl)-glycinamide (hydrobromide salt)

To a stirred solution of N-(2-nitrobenzenesulfonyl)-N-(2-pyridinylmethyl)-N'-(5,6,7,8-tetrahydro-8-quinolinyl)-1,4-benzenedimethanamine (218 mg, 0.40 mmol) in dry CH$_2$Cl$_2$ (5 mL) was added N-(tert-butoxycarbonyl)glycine (85 mg, 0.49 mmol), N,N-diisopropylethylamine (0.23 mL, 1.32 mmol), 1-hydroxybenzotriazole hydrate (73 mg, 0.54 mmol) and 1-(3-dimethylaminopropyl)-3-ethyl carbodiimide HCl (EDC) (105 mg, 0.55 mmol) and the mixture was stirred at room temperature for 17 h. The reaction mixture was diluted with $CH_2Cl_2$ (10 mL) and brine (15 mL) and the aqueous layer was separated and extracted with $CH_2Cl_2$ (2×10 mL). The combined organic phases were dried ($MgSO_4$), filtered and evaporated in vacuo to give the crude product as an orange oil. Purification by column chromatography on silica gel ($CH_2Cl_2$/MeOH, 95:5) gave the intermediate amide (185 mg, 66%) as a yellow foam.

To a stirred solution of the amide from above (185 mg, 0.26 mmol) in dry $CH_3CN$ (5 mL) was added thiolphenol (0.12 mL, 1.2 mmol) and powdered potassium carbonate (196 mg, 1.42 mmol) and the mixture was stirred at room temperature for 16 h. The reaction mixture was concentrated in vacuo and partitioned between $CH_2Cl_2$ (15 mL) and water (15 mL). The aqueous layer was separated and extracted with $CH_2Cl_2$ (2×10 mL) and the combined organic phases were dried ($MgSO_4$), filtered and evaporated in vacuo to give the crude product as a yellow oil. Purification by column chromatography on silica gel ($CH_2Cl_2$/MeOH, 95:5 followed by 9:1) afforded the desired amine (85 mg, 62%) as a pale yellow oil.

To a stirred solution of the free base (58 mg, 0.11 mmol) in glacial acetic acid (1 mL) was added a saturated solution of HBr in acetic acid (1 mL) and the mixture was stirred at room temperature for 1 h. Diethyl ether (20 mL) was added resulting in the formation of a white precipitate. The solid was allowed to settle to the bottom of the flask and the supernatant solution was decanted off. The solid was washed by decantation with ether (4×10 mL) and the remaining traces of solvent removed by evaporation under reduced pressure followed by drying in vacuo overnight to give AMD 8726 as an off-white solid (87 mg, 94%). $^1$H NMR ($D_2O$) mixture of rotational isomers δ 1.64-2.20 (m) and 2.36-2.52 (m) (total 4H), 2.89-3.10 (m, 2H), 4.18 (d, J=16.5 Hz) and 4.30–4.58 (m) (total 7H), 4.70–4.85 (m, overlap with HOD) and 5.46–5.51 (m) (total 2H), 7.17 (d, J=8.1 Hz) and 7.36 (d, J=8.1 Hz) and 7.46 (d, J=8.1 Hz) and 7.53 (d, J=8.1 Hz) (total 4H), 7.82–7.85 (m) and 8.28–8.33 (m) and 8.45 (d, J=5.7 Hz) and 8.75 (d, J=5.7 Hz) (total 7H); $^{13}$C NMR ($D_2O$) mixture of rotational isomers δ 20.55, 20.84, 26.49, 27.53, 27.67, 41.38, 41.52, 47.58, 48.97, 49.14, 51.25, 51.38, 55.43, 56.03, 125.63, 126.62, 126.74, 128.26, 128.91, 129.70, 130.80, 131.16, 136.96, 138.66, 139.56, 139.78, 140.26, 141.13, 143.41, 143.67, 146.72, 146.91, 147.92, 147.99, 148.51, 149.53, 168.40, 168.86. ES-MS m/z 416 (M+H). Anal. Calcd. for $C_{25}H_{29}N_5O.4.0HBr.2.1H_2O.1.2CH_3CO_2H$: C, 38.60; H, 4.98; N, 8.20; Br, 37.78. Found: C, 38.59; H, 4.88; N, 8.22; Br, 37.77.

Example 73

AMD8738: Preparation of N-[[4-[[(2-pyridinylmethyl)amino]methyl]phenyl]methyl]-N-(5,6,7,8-tetrahydro-8-quinolinyl)-(L)-alaninamide (hydrobromide salt)

To a solution of N-(2-nitrobenzenesulfonyl)-N-(2-pyridinylmethyl)-N'-(5,6,7,8-tetrahydro-8-quinolinyl)-1,4-benzenedimethanamine (251 mg, 0.46 mmol) and N-(tert-butoxycarbonyl)-L-alanine (97 mg, 0.51 mmol) in $CH_2Cl_2$ (5 mL) was added N,N-diisopropylethylamine (0.24 mL, 1.38 mmol), 1-hydroxybenzotriazole hydrate (81 mg, 0.60 mmol) and 1-(3-dimethylaminopropyl)-3-ethyl carbodiimide HCl (EDC) (116 mg, 0.61 mmol) and the mixture was stirred at room temperature for 15 hours. The reaction was worked-up as described above to give the crude amide as a mixture of diastereomers. Purification and separation of the diastereomers was accomplished by column chromatography on silica gel (EtOAc) to afford a low polarity diastereomer (78 mg, 24%) and a high polarity diastereomer (48 mg, 15%).

Using procedures C and D: the less polar diastereomer (78 mg, 0.11 mmol) was reacted with thiophenol (50 μL, 0.49 mmol) and potassium carbonate (83 mg, 0.60 mmol) in $CH_3CN$ (5 mL) for 2 hours. The crude material was purified by column chromatography on silica gel ($CH_2Cl_2$/MeOH, 95:5 to 9:1) to give the corresponding free base of AMD8738 (33 mg, 57%) as a clear oil. The oil was converted to the hydrobromide salt to give AMD8738 (49 mg, 89%) as a pale yellow solid. $^1$H NMR ($D_2O$) single diastereomer, mixture of rotational isomers δ 1.61 (d, J=7.1 Hz) and 1.69 (d, J=7.1 Hz) (total 3H), 1.90–2.13 (m) and 2.34–2.48 (m) (total 4H), 2.88–2.91 (m) and 2.97–3.00 (m) (total 2H), 4.27–4.49 (m) and 4.67–5.02 (m, overlap with HOD) (total 7H), 5.02–5.08 (m) and 5.64–5.67 (m) (total 1H), 7.14 (d, J=8.1 Hz) and 7.37 (d, J=8.1 Hz) and 7.50 (br s) (total 4H), 7.71–7.86 (m) and 8.14–8.17 (m) and 8.26 (d, J=8.1 Hz) and 8.35 (d, J=8.1 Hz) and 8.42 (t, J=5.1 Hz) and 8.66 (br s) (total 7H); $^{13}$C NMR ($D_2O$) single diastereomer, mixture of rotational isomers δ 16.75, 16.82, 20.39, 20.49, 26.34, 27.54, 27.62, 28.01, 47.61, 48.43, 48.55, 49.13, 49.36, 51.14, 51.18, 52.77, 56.01, 56.42, 125.38, 126.30, 126.38, 126.46, 126.60, 127.65, 129.67, 130.86, 131.13, 136.46, 138.50, 139.39, 139.48, 140.66, 141.25, 142.77, 143.08, 147.04, 147.26, 147.57, 147.84, 148.06, 148.22, 148.49, 149.87, 171.35, 172.63. ES-MS m/z 430 (M+H). Anal. Calcd. for $C_{26}H_{31}N_5O.4.3HBr.1.9H_2O.1.2CH_3CO_2H$: C, 38.60; H, 5.01; N, 7.92; Br, 38.88. Found: C, 38.45; H, 4.88; N, 7.91; Br, 39.10.

Example 74

AMD8749: Preparation of N-[[4-[[(2-pyridinylmethyl)amino]methyl]phenyl]methyl]-N-(5,6,7,8-tetrahydro-8-quinolinyl)-(L)-aspartamide (hydrobromide salt)

A solution of N-(tert-butoxycarbonyl)-L-aspartic acid β-t-butyl ester dicyclohexylammonium salt (500 mg, 1.06 mmol) in EtOAc (25 mL) was washed with a 10% aqueous citric acid solution (2×25 mL) and brine (1×25 mL). The organic phase was dried ($MgSO_4$), filtered and concentrated to give the corresponding free acid (305 mg) as a clear oil.

To a solution of N-(t-butyloxycarbonyl)-N-(2-pyridinylmethyl)-N'-(5,6,7,8-tetrahydro-8-quinolinyl)-1,4-benzenedimethanamine (420 mg, 0.92 mmol) and N -(tert-butoxycarbonyl)-L-aspartic acid β-t-butyl ester (305 mg, 1.06 mmol) in 1,2-dichloroethane (6 mL) was added N,N-diisopropylethylamine (0.50 mL, 2.88 mmol), 1-hydroxybenzotriazole hydrate (175 mg, 1.30 mmol) and 1-(3-dimethylaminopropyl)-3-ethyl carbodiimide HCl (EDC) (250 mg, 1.30 mmol) and the reaction mixture was stirred at room temperature for 18 hours. The reaction was worked-up as described above and the crude material was purified by column chromatography on silica gel ($CH_2Cl_2$/MeOH, 98:2) to give the desired amide (145 mg, 23%) as a mixture of diastereomers.

Using general procedure D: the intermediate from above (47 mg, 0.08 mmol) was converted to the hydrobromide salt to give AMD8749 (73 mg, 89%) as a light brown solid. $^1$H NMR (D$_2$O) mixture of diastereomers, mixture of rotational isomers: δ 1.69–1.84 (br m) and 1.98–2.04 (br m) and 2.10–2.20 (br m) and 2.45–2.49 (br m) (total 4H), 2.96–3.01 (m) and 3.00 (d, J=6.6 Hz) and 3.08 (d, J=4.2 Hz) and 3.13–3.18 (m) (total 4H), 4.37 (s) and 4.42 (s) and 4.51 (s) and 4.52 (s) and 4.69–4.72 (m) and 4.79–4.88 (m, overlap with HOD) and 4.92–5.01 (m) and 5.07–5.14 (m) and 5.18–5.22 (m) and 5.30–5.38 (m) and 5.71–5.77 (m) (total 8H), 7.19 (d, J=7.8 Hz) and 7.41 (d, J=7.8 Hz) and 7.50–7.58 (m) (total 5H), 7.67–7.73 (m) and 7.79–7.89 (m) and 8.13–8.19 (m) and 8.30–8.39 (m) and 8.44 (t, J=5.7 Hz) and 8.50 (d, J=6.0 Hz) and 8.70 (d, J=4.6 Hz) (total 6H); $^{13}$C NMR (D$_2$O) mixture of diastereomers, mixture of rotational isomers: δ 20.38, 20.56, 20.66, 20.88, 26.37, 26.75, 27.64, 29.42, 34.87, 35.34, 35.49, 48.21, 48.58, 48.81, 51.36, 52.88, 53.02, 56.28, 56.68, 56.96, 125.62, 126.75, 127.00, 127.13, 127.22, 127.92, 129.43, 129.62, 130.93, 131.12, 131.28, 131.36, 136.71, 138.48, 139.51, 139.64, 140.04, 140.75, 141.39, 144.39, 144.45, 144.71, 146.06, 146.24, 146.31, 147.20, 147.31, 147.86, 148.04, 148.62, 149.54, 149.64, 169.30, 169.63, 172.62, 172.90. ES-MS m/z 474 (M+H). Anal. Calcd. for C$_{27}$H$_{31}$N$_5$O$_3$.4.1HBr.1.8H$_2$O.1.8CH$_3$CO$_2$H: C, 38.86; H, 4.89; N, 7.40; Br, 34.64. Found: C, 38.99; H, 4.77; N, 7.47; Br, 34.52.

Example 75

AMD8750: Preparation of N-[[4-[[(2-pyridinylmethyl)amino]methyl]phenyl]methyl]-N-(5,6,7,8-tetrahydro-8-quinolinyl)-pyrazinamide (hydrobromide salt)

To a stirred solution of N-(t-butyloxycarbonyl)-N-(2-pyridinylmethyl)-N'-(5,6,7,8-tetrahydro-8-quinolinyl)-1,4-benzenedimethanamine (183 mg, 0.40 mmol) in dry CH$_2$Cl$_2$ (5 mL) was added 2-pyrazinecarboxylic acid (68 mg, 0.55 mmol), N,N-diisopropylethylamine (0.21 mL, 1.21 mmol), 1-hydroxybenzotriazole hydrate (81 mg, 0.60 mmol) and 1-(3-dimethylaminopropyl)-3-ethyl carbodiimide HCl (EDC) (115 mg, 0.60 mmol) and the mixture was stirred at room temperature for 20 hours. Following standard work-up procedures, the crude material was purified by column chromatography on silica gel (CH$_2$Cl$_2$/MeOH, 98:2 followed by 95:5) to give the desired amide (131 mg, 58%) as a colorless oil.

Using general procedure D: the oil from above (105 mg, 0.19 mmol) was converted to the hydrobromide salt with simultaneous deprotection of the BOC group to give AMD8750 (127 mg, 87%) as a light yellow solid. $^1$H NMR (D$_2$O) mixture of rotational isomers δ 1.71–1.88 (br m, 1H), 2.00–2.19 (br m, 2H), 2.28–2.40 (br m, 1H), 2.95–2.97 (br m) and 3.02–3.04 (m) (total 2H), 4.39 (s) and 4.43 (s) and 4.56–4.67 (m) and 4.62 (s) and 4.66 (s) and 4.76–5.05 (m, overlap with HOD) and 5.59–5.71 (m) and 5.75–5.84 (m) (total 7H), 7.31–7.46 (m, 4H), 7.84–7.90 (m) and 7.94–7.98 (m) and 8.01 (d, J=8.1 Hz) and 8.36 (t, J=7.8 Hz) and 8.47 (t, J=8.1 Hz) and 8.51–8.55 (m) and 8.68–8.71 (m) and 8.73 (s) and 8.80 (br s) and 9.13 (s) (total 10H); $^{13}$C NMR (D$_2$O) mixture of rotational isomers δ 20.43, 20.59, 26.71, 27.57, 27.75, 28.05, 48.12, 48.21, 51.45, 51.59, 53.70, 56.43, 58.13, 125.74, 126.40, 127.53, 127.71, 127.74, 128.13, 129.39, 129.49, 130.43, 130.83, 131.00, 138.21, 138.58, 139.77, 140.14, 140.23, 141.21, 143.99, 144.30, 145.29, 145.44, 145.65, 145.82, 146.37, 146.59, 146.92, 148.07, 148.18, 148.41, 149.48, 169.00, 170.05. ES-MS m/z 465 (M+H). Anal. Calcd. for C$_{28}$H$_{28}$N$_6$O.4.0HBr.1.7H$_2$O.1.5CH$_3$CO$_2$H: C, 40.97; H, 4.59; N, 9.25; Br, 35.16. Found: C, 40.97; H, 4.62; N, 9.27; Br, 35.23.

Example 76

AMD8740: Preparation of N-[[4-[[(2-pyridinylmethyl)amino]methyl]phenyl]methyl]-N-(5,6,7,8-tetrahydro-8-quinolinyl)-(L)-prolinamide (hydrobromide salt)

To a solution of N-(t-butyloxycarbonyl)-N-(2-pyridinylmethyl)-N'-(5,6,7,8-tetrahydro-8-quinolinyl)-1,4-benzenedimethanamine (195 mg, 0.426 mmol) and Boc-(L)-proline (110 mg, 0.511 mmol) in DMF (6 mL) was added diisopropylethylamine (0.22 mL, 1.3 mmol), HOBT (86 mg, 0.639 mmol) and EDC (123 mg, 0.639 mmol) and the mixture was allowed to stir at room temperature overnight. Following standard work-up procedures described above, the crude material was purified by column chromatography on silica gel (5% methanol in dichloromethane) to give an inseparable mixture of two diastereomeric products (117 mg, 42%).

Using general procedure D: the intermediate from above was converted to the hydrobromide salt with simultaneous deprotection of the BOC group to afford AMD8740 (84 mg). $^1$H NMR (D$_2$O) δ (mixture of diastereomers, mixture of rotational isomers) 1.64 (m), 1.90–2.18 (m) total of 16H, 2.44 (m), 2.79 (m) (total of 2H), 2.88 (m, 2H), 2.97 (m, 2H), 3.38 (dd, 2H, J=10.2, 7.1 Hz), 3.47 (dd, 2H, J=10.4, 7.2 Hz), 4.37 (s), 4.40 (s), 4.43 (s) (total of 6H), 4.60 (m, 4H), 4.99 (m, 2H), 5.51 (dd, 1H, J=10.2, 7.1 Hz), 5.81 (dd, 1H, J=10.4, 7.2 Hz), 7.14 (d, 2H, J=8.1 Hz), 7.36 (d, 2H, J=8.1 Hz), 7.45 (d, 2H, J=4.2 Hz), 7.52 (d, 2H, J=1.8 Hz), 7.75 (m, 1H), 7.83 (dd, 1H, J=8.1, 5.3 Hz), 7.96 (m, 2H), 8.04 (d, 2H, J=8.1 Hz), 8.21 (m, 1H), 8.24 (m, 1H), 8.34 (dd, 2H, J=4.5, 3.9 Hz), 8.49 (t, 2H, J=8.1 Hz), 8.81 (m, 2H); $^{13}$C NMR (D$_2$O) δ (both isomers, mixture of rotational isomers) 20.46, 20.60, 24.47, 24.59, 24.94, 24.94, 26.21, 27.60, 27.83, 29.52, 29.93, 46.98, 47.22, 47.79, 47.98, 51.60, 55.44, 55.91, 56.64, 59.67, 59.81, 127.81, 128.00, 129.44, 129.66, 129.91, 131.00, 131.14, 131.28, 136.22, 136.69, 138.61, 140.54, 141.28, 144.70, 144.87, 146.00, 146.05, 146.43, 146.60, 147.91, 148.60, 171.23, 172.25, 172.91. ES-MS m/z 456 (M+H). Anal. Calcd. for C$_{28}$H$_{33}$N$_5$O.4.2HBr.1.6H$_2$O.1.2AcOH: C, 40.74; H, 5.08; N, 7.81; Br 37.44. Found: C, 40.71; H, 5.09; N, 7.36; Br, 37.50.

Example 77

AMD8741: Preparation of N-[[4-[[(2-pyridinylmethyl)amino]methyl]phenyl]methyl]-N-(5,6,7,8-tetrahydro-8-quinolinyl)-(L)-lysinamide (hydrobromide salt)

To a solution of N,N'-Di-(t-butoxycarbonyl)-(L)-lysine (1.05 g, 2 mmol) in ethyl acetate (15 mL) was added DCC (824 mg, 4.0 mmol) and pentafluorophenol (368 mg, 2.0 mmol). The reaction mixture was stirred at room temperature for 60 minutes then filtered through celite and the filtrates were concentrated to afford the pentafluorophenol ester in quantitative yield as a white solid. This was used without further purification in the next step.

To a solution of N-(t-butyloxycarbonyl)-N-(2-pyridinylmethyl)-N'-(5,6,7,8-tetrahydro-8-quinolinyl)-1,4-benzenedimethanamine (125 mg, 0.273 mmol) in dichloroethane (10 mL) was added the pentafluorophenol ester from above (180 mg, 0.355 mmol) and the reaction mixture was heated to 55° C. for 24 hours. The solvents were evaporated and the residue was purified by column chromatography on silica gel (5% methanol in dichloromethane) to afford a mixture of two inseparable diastereomeric amides (80 mg, 37%).

Using general procedure D: the intermediate from above was converted to the hydrobromide salt with simultaneous deprotection of the BOC groups to afford AMD8741 (66 mg). $^1$H NMR (D$_2$O) δ (mixture of diastereomers, mixture of rotational isomers) 1.17–1.83 (m, 20H), 2.01 (m, 2H), 2.95–3.08 (m, 8H), 4.38 (s), 4.41 (s), 4.45 (s), total of 4H, 4.54 (s, 4H), 4.56 (m, 2H), 5.00 (m, 2H), 5.45 (dd, 1H, J=8.1, 4.3 Hz), 5.81 (dd, 1H, J=8.3, 3.6 Hz), 7.20 (d, 2H, J=8.1 Hz), 7.41 (d, 2H J=8.4 Hz), 7.50 (m, 4H), 7.75 (m, 6H), 8.20 (m, 2H), 8.31 (m, 1H), 8.37 (d, 2H, J=8.1 Hz), 8.37 (d, 1H, J=5.8 Hz), 8.71 (d, 2H, J=8.1 Hz); $^{13}$C NMR (D$_2$O) δ (mixture of diastereomers, mixture of rotational isomers) 20.58, 21.77, 26.38, 26.74, 27.66, 30.17, 30.75, 39.48, 47.84, 49.50, 49.67, 51.16, 52.05, 52.27, 53.20, 55.82, 56.86, 126.08, 126.23, 126.65, 128.15, 129.58, 129.80, 130.92, 131.12, 131.33, 136.61, 138.62, 139.37, 141.24, 142.25, 147.49, 147.74, 147.85, 148.37, 148.58, 170.63, 172.22. ES-MS m/z 487 (M+H). Anal. Calcd. for C$_{29}$H$_{38}$N$_6$O.5HBr.3H$_2$O: C, 36.85; H, 5.22; N, 8.89; Br 42.29. Found: C, 37.04; H, 5.03; N, 8.76; Br, 42.20.

Example 78

AMD8724: Preparation of N-[[4-[[(2-pyridinylmethyl)amino]methyl]phenyl]methyl]-N-(5,6,7,8-tetrahydro-8-quinolinyl)-benzamide (hydrobromide salt)

To a pre-cooled (ice bath) solution of N-(2-nitrobenzenesulfonyl)-N-(2-pyridinylmethyl)-N'-(5,6,7,8-tetrahydro-8-quinolinyl)-1,4-benzenedimethanamine (201 mg, 0.37 mmol) and triethylamine (80 μl, 0.55 mmol) in anhydrous CH$_2$Cl$_2$ (4 mL) was added a solution of benzoylchloride (54 μl, 0.46 mmol) in anhydrous CH$_2$Cl$_2$ (0.5 mL) and the reaction mixture was allowed to stir at room temperature for 18 hours and then concentrated. The residue was diluted with ethylacetate (300 mL), washed with sat. aqueous NaHCO$_3$ then brine, dried (Na$_2$SO$_4$) and evaporated. The residue was purified by column chromatography on silica gel (1.5×20 cm, 50:50 EtOAc/CH$_2$Cl$_2$) to give the desired amide (203 mg, 85%) as a yellow oil.

Using general procedures C and D: the amide (203 mg, 0.31 mmol) was reacted with K$_2$CO$_3$ (433 mg, 3.13 mmol) and thiophenol (0.15 mL, 1.46 mmol) in DMF (3 mL). Purification of the crude material by radial chromatography on silica gel (1 mm plate, 3:3:94 MeOH/NH$_4$OH/CH$_2$Cl$_2$) gave the free base (112 mg, 78%) as light yellow oil. Conversion to the hydrobromide salt gave AMD8724 (90 mg). $^1$H NMR (CD$_3$OD) δ 1.64–1.74 (m, 2H), 1.97–2.02 (m, 1H), 2.26–2.38 (m, 1H), 2.99–3.00 (m, 2H), 4.44 (s, 2H), 4.63 (s, 2H), 4.93 (overlapped with MeOH, 2H), 5.12–5.24 (m, 1H), 7.43–7.45 (m, 2H), 7.52 (d, 4H, J=1.8 Hz), 7.63–7.70 (m, 2H), 7.71–7.73 (m, 2H), 7.83–7.90 (m, 1H), 7.95–8.00 (m, 1H), 8.35–8.42 (m, 2H), 8.62–8.66 (m, 1H), 8.88–8.90 (b, 1H); $^{13}$C NMR (CD$_3$OD) δ 22.41, 28.41, 29.26, 52.53, 56.78, 58.07, 67.32, 126.26, 127.69 (b), 128.80, 130.33, 130.82, 132.05, 132.47, 132.74, 136.56, 139.83, 140.61, 140.94, 144.53 (b), 147.66 (b), 148.43, 149.70 (b), 153.47, 174.09; ES-MS m/z 463.2 (M+H); Anal. Calcd. for C$_{30}$H$_{30}$N$_4$O.2.8HBr.2.3H$_2$O: C, 49.32; H, 5.16; N, 7.67; Br, 30.62. Found: C, 49.35; H, 5.06; N, 7.43; Br, 30.53.

Example 79

AMD8725: Preparation of N-[[4-[[(2-pyridinylmethyl)amino]methyl]phenyl]methyl]-N-(5,6,7,8-tetrahydro-8-quinolinyl)-picolinamide (hydrobromide salt)

To a stirred solution of N-(2-nitrobenzenesulfonyl)-N-(2-pyridinylmethyl)-N'-(5,6,7,8-tetrahydro-8-quinolinyl)-1,4-benzenedimethanamine (209 mg, 0.39 mmol) in dry DMF (1 mL) was added N-methylmorpholine (0.5 mL, 4.45 mmol), picolinic acid (64 mg, 0.52 mmol), 1-hydroxybenzotriazole (57 mg, 0.42 mmol), and 1-(3-dimethylaminopropyl)-3-ethylcarbodiimide (85 mg, 0.44 mmol). The reaction mixture was allowed to stir at room temperature for further 18 hours and then concentrated. The residue was diluted with ethylacetate (300 mL) and washed with saturated aqueous NaHCO$_3$, then brine, dried (Na$_2$SO$_4$) and evaporated. Purification of the crude material by column chromatography on silica gel (1.5×20 cm, 50:50 EtOAc/CH$_2$Cl$_2$) gave the desired amide (237 mg, 94%) as a yellow oil.

Using general procedures C and D: the amide (235 mg, 0.36 mmol) was reacted with K$_2$CO$_3$ (300 mg, 2.17 mmol) and thiophenol (0.15 mL, 1.46 mmol) in DMF (3 mL). Purification of the crude product by radial chromatography on silica gel (1 mm plate, 3:3:94 MeOH/NH$_4$OH/CH$_2$Cl$_2$) gave the free base (98 mg, 59%) as a light yellow oil. Conversion of the free base (98 mg, 0.22 mmol) to the hydrobromide salt gave AMD8725 (90 mg). $^1$H NMR (CD$_3$OD) δ 1.79–2.01 (m, 2H), 2.05–2.11 (m, 1H), 2.30–2.41 (m, 1H), 3.03 (s, 2H), 4.47 (s, 2H), 4.70 (s, 2H), 4.96 (overlapped with MeOH, 2H), 5.24–5.50 (m, 1H), 7.40–7.42 (m, 1H), 7.54 (d, 2H, J=7.7 Hz), 7.64 (d, 2H, J=7.7 Hz), 7.88–7.93 (m, 3H), 8.07–8.13 (m, 1H), 8.23 (b, 1H), 8.34–8.47 (m, 3H), 8.66–8.68 (m, 1H), 8.81–8.90 (m, 1H); $^{13}$C NMR (CD$_3$OD) δ 22.25, 28.18, 29.17, 52.66, 56.20, 58.64, 126.56, 127.02, 128.17, 128.90 (b), 129.93 (b), 130.98, 132.00 (b), 132.58, 132.60, 139.45, 140.96, 144.80 (b), 145.10 (b), 145.68 (b), 146.83 (b), 147.57, 148.79 (b). ES-MS m/z 464.2 (M+H). Anal. Calcd. for C$_{29}$H$_{29}$N$_5$O.4.0HBr.2.4H$_2$O: C, 41.94; H, 4.59; N, 8.43; Br, 38.49. Found: C, 41.87; H, 4.58; N, 8.06; Br, 38.61.

Example 80

AMD8713: Preparation of N'-Benzyl-N-[[4-[[(2-pyridinylmethyl) amino]methyl]phenyl]methyl]-N-(5,6,7,8-tetrahydro-8-quinolinyl)-urea To a stirred solution of N-(2-nitrobenzenesulfonyl)-N-(2-pyridinylmethyl)-N'-[5,6,7,8-tetrahydro-8-quinolinyl]-1,4-benzenedimethanamine (140 mg, 0.257 mmol) in dichloromethane (5 ml) cooled to 0° C. was added dropwise, benzyl isocyanate (0.035 mL, 0.284 mmol). The reaction mixture was then allowed to stir at room temperature for two hours. The mixture was evaporated and the residue was purified by column chromatography on silica gel (3% methanol in dichloromethane as eluent) to afford the desired urea in an 81% yield.

Using general procedures C and D: the intermediate from above was reacted with thiophenol and K$_2$CO$_3$ in acetonitrile, and the corresponding free base was converted to the hydrobromide salt to give AMD8713 (61%). $^1$H NMR (D₂O) δ 1.77 (m, 2H), 1.99 (m, 3H), 2.91 (m, 2H), 4.25 (d, 1H, J=15.3 Hz), 4.34 (d, 1H, J=15.3 Hz), 4.44 (s, 2H), 4.62 (dd, 2H, J=14.8 Hz, 8.3 Hz), 4.66 (s, 2H), 5.33 (t, 1H, J=8.3 Hz (NH)), 7.18 (d, 2H, J=6.9 Hz), 7.23 (m, 5H), 7.47 (d, 2H, J=8.1 Hz), 7.77 (dd, 1H, J=8.4, 5.3 Hz), 8.11 (m, 2H), 8.26 (d, 1H, J=7.8 Hz), 8.41 (d, 1H, J=5.8 Hz), 8.55 (dd, 1H, J=8.1, 5.4 Hz), 8.81 (d, 1H, J=5.3 Hz); $^{13}$C NMR (D₂O) δ 20.83, 20.89, 27.59, 27.73, 44.52, 47.39, 50.79, 51.82, 56.83, 66.46, 125.39, 127.57, 127.66, 128.27, 128.56, 129.07, 129.53, 130.95, 139.14, 139.26, 139.60, 139.74, 144.14, 145.45, 147.61, 147.73, 151.52, 159.20. ES-MS m/z 492 (M+H). Anal. Calcd. for $C_{31}H_{33}N_5O\cdot3HBr\cdot3.2H_2O$: C, 47.01; H, 5.40; N, 8.84; Br, 30.27. Found: C, 46.85; H, 5.22; N, 8.58; Br, 30.50.

Example 81

AMD8712: Preparation of N'-phenyl-N-[[4-[[(2-pyridinylmethyl) amino]methyl]phenyl]methyl]-N-(5,6,7,8-tetrahydro-8-quinolinyl)-urea Using phenyl isocyanate in the above procedure followed by deprotection and salt formation according to general procedures C and D, afforded AMD8712. $^1$H NMR (D₂O) δ 1.79 (m, 1H), 1.99–2.10 (m, 4H), 2.93 (m, 2H), 4.46 (s, 2H), 4.70 (s, 2H), 4.80 (m, 2H), 5.44 (br s, 1H (NH)), 7.20 (m, 3H), 7.32 (d, 2H, J=7.5 Hz), 7.46 (d, 2H, J=5.7 Hz), 7.54 (d, 2H, J=5.1 Hz), 7.79 (dd, 1H, J=8.1, 5.3 Hz), 7.99 (dd, 1H, J=8.1, 8.4 Hz), 8.04 (dd, 1H, J=8.4, 5.7 Hz), 8.12 (m, 1H), 8.28 (m, 1H), 8.45 (t, 1H, J=8.1 Hz), 8.82 (d, 1H, J=5.4 Hz); $^{13}$C NMR (D₂O) δ 20.81, 20.91, 27.52, 27.59, 45.22, 50.79, 51.87, 56.75, 66.46, 124.07, 125.50, 125.77, 128.23, 128.81, 129.51, 131.06, 137.67, 139.18, 139.43, 139.80, 143.75, 145.33, 147.88, 151.07, 158.00. ES-MS m/z 478 (M+H). Anal. Calcd. for $C_{30}H_{31}N_5O\cdot3HBr\cdot3.8H_2O$: C, 45.68; H, 5.32; N, 8.88; Br, 30.39. Found: C, 45.58; H, 5.27; N, 8.64; Br, 30.54.

Example 82

AMD8716: Preparation of N-(6,7,8,9-tetrahydro-5H-cyclohepta[b]pyridin-9-yl)-4-[[(2-pyridinylmethyl)amino]methyl]benzamide (hydrobromide salt)

A 1 L glass Fisher-Porter bottle was charged with 9-amino-6,7,8,9-tetrahydro-5H-cyclohepta[b]pyridine (0.583 g, 3.60 mmol), DMF (18 mL), methyl 4-bromobenzoate (0.852 g, 3.96 mmol), dichlorobis(triphenylphosphine)-palladium(II) (0.048 g, 0.07 mmol) and triethylamine (1.0 mL, 7.17 mmol). Carbon monoxide was bubbled through the mixture for 10 minutes. The bottle was capped with a pressure gauge and the mixture was heated to 80° C. under an atmosphere of carbon monoxide (45 psi) for 60 hours. The reaction mixture was cooled to room temperature, filtered through celite and the cake was washed with CH₂Cl₂. The filtrate was concentrated and the residue was purified by column chromatography on silica gel (100:1 CH₂Cl₂—CH₃OH) to afford 0.198 g of the amide-ester as a light yellow oil.

To a cold (−78° C.), stirred solution of amide-ester from above (0.198 g, 0.61 mmol) in CH₂Cl₂ (5.0 mL) was added DIBAL-H (3.5 mL, 3.5 mmol, 1.0 M in CH₂Cl₂). The cooling bath was removed and the reaction mixture was warmed to room temperature. After 2 hours, the mixture was treated with saturated aqueous sodium/potassium tartrate (40 mL) and diluted with CH₂Cl₂ (20 mL). The resultant emulsion was vigorously stirred open to the air until the emulsion became a biphasic mixture. The phases were separated and the aqueous phase was extracted with CH₂Cl₂ (4×20 mL). The combined organic extracts were dried (Na₂SO₄) and concentrated. The crude material was purified by column chromatography on silica gel (20:1 CH₂Cl₂—CH₃OH), to provide 0.120 g of the alcohol as a yellow oil.

To a stirred solution of the alcohol (0.120 g, 0.43 mmol) in dry THF (20 mL) was added 2-(N-(2-nitrobenzenesulfonyl)aminomethyl)pyridine (0.185 g, 0.63 mmol) and triphenylphosphine (0.175 g, 0.67 mmol) followed by dropwise addition of diethylazodicarboxylate (0.10 mL, 0.64 mmol). The resultant mixture was stirred at room temperature for 3 hours. The mixture was concentrated and the residual oil was purified by column chromatography on silica gel (1:1 hexanes-ethyl acetate followed by 50:1 CH₃OH-ethyl acetate) to give 0.235 g of the amide as a yellow solid.

Using general procedures C and D: the amide (0.235 g, 0.411 mmol) was reacted with thiophenol (0.20 mL, 1.95 mmol) and K₂CO₃ (0.316 g, 2.28 mmol) in CH₃CN (8 mL). Purification of the crude material by column chromatography on silica gel (10:1 CH₂Cl₂—CH₃OH) provided 0.075 g of the free base of the title compound as a colorless oil. Conversion of the free base to a hydrobromide salt gave AMD8716 (0.141 g) as an off-white solid. $^1$H NMR (D₂O) δ 1.44–1.56 (m, 1H), 2.00–2.30 (m, 5H), 3.14–3.17 (m, 2H), 4.49 (s, 2H), 4.58 (s, 2H), 5.52 (d, 1H, J=8.1 Hz). 7.65 (d, 2H, J=8.4 Hz), 7.72–7.08 (m, 2H), 7.85 (dd, 1H, J=6.0, 7.8 Hz), 7.96 (d, 2H, J=8.4 Hz), 8.22 (td, 1H, J=7.8, 1.5 Hz), 8.40 (d, 1H, J=7.8 Hz), 8.44 (d, 1H, J=5.4 Hz), 8.71 (d, 1H, J=5.4 Hz); $^{13}$C NMR (D₂O) δ 25.51, 28.52, 31.03, 33.33, 49.49, 51.12, 54.36, 126.07, 126.37, 126.44, 129.09 (2 carbons), 130.72 (2 carbons), 134.17, 135.09, 138.06, 142.31, 142.84, 147.27, 147.91, 148.14, 155.48, 171.02. ES-MS m/z 387 (M+H). Anal. Calcd. for $C_{24}H_{26}N_4O\cdot3.1HBr\cdot2.5H_2O\cdot2.4dioxane$: C, 45.15; H, 6.01; N, 6.27; Br, 27.71. Found: C, 45.05; H, 6.03; N, 6.29; Br, 27.90.

Example 83

AMD8717: Preparation of N-(5,6,7,8-tetrahydro-8-quinolinyl)-4-[[(2-pyridinylmethyl)amino]methyl] benzamide (hydrobromide salt)

In a similar manner to that described above: 8-amino-5,6,7,8-tetrahydroquinoline gave AMD8717. $^1$H NMR (D₂O) δ 1.90–2.16 (m, 3H), 2.20–2.32 (m, 1H), 3.02–3.04 (m, 2H), 4.47 (s, 2H), 4.60 (m, 2H), 5.46 (t, 1H, J=6.9 Hz), 7.61 (d, 2H J=8.4 Hz), 7.78–7.87 (m, 5H), 8.29 (t, 1H, J=7.8 Hz), 8.37 (d, 1H, J=7.5 Hz), 8.51 (d, 1H, J=5.4 Hz), 8.72 (dt, 1H, J=5.4, 0.9 Hz); $^{13}$C NMR (D₂O) δ 19.30, 27.54, 28.35, 47.78, 49.00, 51.23, 125.87, 126.87, 126.91, 128.75 (2 carbons), 130.80 (2 carbons), 134.57, 134.81, 139.77 (2 carbons), 144.00, 146.48, 147.46, 148.12, 150.08, 170.42. ES-MS m/z 373 (M+H). Anal. Calcd. for $C_{23}H_{24}N_4O\cdot3.0HBr\cdot5.2H_2O\cdot1.2dioxane$: C, 40.99; H, 5.82; N, 6.88; Br, 29.43. Found: C, 40.97; H, 5.52; N, 6.84; Br, 29.40.

Example 84

AMD8634: Preparation of N,N'-bis(2-pyridinylmethyl)-N'-(5,6,7,8-tetrahydro-8-quinolinyl)-1,4-benzenedimethanamine (hydrobromide salt)

8-amino-5,6,7,8-tetrahydroquinoline (0.169 g, 1.14 mmol) was condensed with pyridine-2-carboxaldehyde (0.12 mL, 1.26 mmol) in methanol (6 mL) overnight. Hydrogenation (30 psi, room temperature) of the resulting imine over palladium on activated carbon, (10%, 18 mg) for 6 hours provided 0.232 g of a brown oil. The oil was dissolved in CH$_3$CN (20 mL), treated with N-[1-methylene-4-chloromethylenephenylene]-N-(diethylphosphoryl)-2-(aminomethyl)pyridine (0.38 g, 0.99 mmol) and K$_2$CO$_3$ (0.358 g, 2,59 mmol) and heated to reflux for 24 hours. The mixture was cooled to room temperature, concentrated, and partitioned between CH$_2$Cl$_2$ (40 mL) and water (20 mL). The phases were separated and the aqueous phase was extracted with CH$_2$Cl$_2$ (3×20 mL). The combined organic extracts were dried (Na$_2$SO$_4$) and concentrated. Purification of the crude material by column chromatography on basic alumina (20:1 CH$_2$Cl$_2$—CH$_3$OH) provided 0.440 g of a yellow oil.

Using general procedure D: the diethylphosphoryl group of the oil from above was deprotected with HBr/acetic acid to give 0.517 g of a tan solid. The solid was partitioned between CH$_2$Cl$_2$ (20 mL) and a 10 M aqueous solution of NaOH (20 mL). The phases were separated and the aqueous phase was extracted with CH$_2$Cl$_2$ (4×20 mL). The combined organic extracts were dried (Na$_2$SO$_4$) and concentrated. Purification of the crude material by radial chromatography on silica gel (2 mm plate, 20:1:1 CH$_2$Cl$_2$—CH$_3$OH—NH$_4$OH) provided the free base of the title compound (0.079 g) as a colorless oil. Using general procedure D: the oil was converted to a hydrobromide salt giving AMD8634 (0.106 g) as a white solid. $^1$H NMR (D$_2$O) δ 1.83–1.86 (m, 1H), 2.17–2.44 (m, 2H); 3.00 (br s, 2H), 3.79 (s, 2H), 4.22 (s, 2H), 4.39 (d, 1H, J=16.5 Hz), 4.49 (s, 2H), 4.52 (d, 1H, J=16.5 Hz), 4.64 (dd, 1H, J=10.2, 6.3 Hz), 7.19–7.26 (m, 4H), 7.71–7.78 (m, 3H), 7.84 (dd, 1H, J=6, 7.8 Hz), 7.92 (d, 1H, J=8.1 Hz), 8.22 (td, 1H, J=7.8, 1.8 Hz), 8.32 (d, 2H, J=8.4 Hz), 8.37 (dd, 1H, J=7.8, 1.5 Hz), 8.47 (d, 1H, J=5.4 Hz), 8.64 (d, 1H, J=4.8 Hz), 8.68 (d, 1H, J=5.1 Hz); $^{13}$C NMR (D$_2$O) δ 20.46, 20.57, 27.90, 49.04, 51.02, 55.65, 55.79, 61.92, 125.91, 126.16, 126.47, 126.56, 127.40, 130.13, 130.67 (2 carbons), 131.16 (2 carbons), 138.55, 139.61, 140.89, 141.03, 143.26, 146.90, 147.33, 147.85, 148.10, 150.92, 153.78. ES-MS m/z 450 (M+H). Anal. Calcd. for C$_{29}$H$_{31}$N$_5$.4.2HBr.1.8H$_2$O: C, 42.38; H, 4.76; N, 8.52; Br, 40.83. Found: C, 42.31; H, 4.79; N, 8.25; Br, 41.03.

Example 85

AMD8774: Preparation of N,N'-bis(2-pyridinylmethyl)-N'-(6,7,8,9-tetrahydro-5H-cyclohepta[b]pyridin-9-yl)-1,4-benzenedimethanamine (hydrobromide salt)

9-Amino-6,7,8,9-tetrahydro-5H-cyclohepta[b]pyridine (0.104 g, 0.64 mmol) was condensed with pyridine-2-carboxaldehyde (65 μL, 0.68 mmol) in methanol (6 mL) for 2 hours. Hydrogenation (1 atm, room temperature) of the resultant imine over palladium on activated carbon, (10%, 38 mg) for 5 hours provided 0.162 g of a yellow oil. The oil was dissolved in CH$_3$CN (13 mL), treated with N-[1-methylene-4-chloromethylenephenylene]-N-(2-nitrobenzenesulfonyl)-2-(aminomethyl)pyridine (0.263 g, 0.61 mmol) and K$_2$CO$_3$ (0.191 g, 1.38 mmol) and heated to reflux for 24 hours. The mixture was cooled to room temperature, concentrated, and partitioned between CH$_2$Cl$_2$ (25 mL) and water (10 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (4 mm plate, 40:1 CH$_2$Cl$_2$—CH$_3$OH containing 1% NH$_4$OH) provided 0.232 g of a yellow oil.

Using general procedures C and D: the oil from above was reacted with thiophenol (0.20 mL, 1.95 mmol) and K$_2$CO$_3$ (0.498 g, 3.61 mmol) in CH$_3$CN (7 mL). Purification of the crude material by radial chromatography on silica gel (2 mm plate, 20:1:1 CH$_2$Cl$_2$—CH$_3$OH—NH$_4$OH) provided the free base of the title compound (0.136 g) as a yellow oil. Conversion of the free base to a hydrobromide salt gave AMD8774 (0.191 g) as a white solid. $^1$H NMR (D$_2$O) δ 1.72–1.92 (m, 4H), 1.98–2.08 (m, 1H), 2.18–2.25 (m, 1H), 2.88 (dd, 1H, J=15.3, 5.1 Hz), 3.23–3.31 (m, 1H), 3.82 (d, 1H, J=13.5 Hz), 3.92 (d, 1H, J=13.5 Hz), 4.24 (s, 2H), 4.32 (d, 1H, J=16.2 Hz), 4.45–4.56 (m, 4H), 7.25 (s, 4H), 7.71–7.81 (m, 4H), 7.98 (br d, 1H, J=8.1 Hz), 8.18–8.24 (m, 2H), 8.38 (td, 1H, J=8.1, 1.5 Hz), 8.53 (br d, 1H, J=6.0 Hz), 8.60 (dd, 1H, J=6.0, 1.2 Hz), 8.68 (br d, 1H, J=5.1 Hz); $^{13}$C NMR (D$_2$O) δ 24.68, 24.79, 25.21, 32.09, 49.07, 51.06, 54.54, 57.09, 66.14, 126.27, 126.28, 126.47, 126.54, 127.64, 130.16, 130.66 (2 carbons), 130.88 (2 carbons), 138.27, 138.77, 141.55, 142.93, 143.22, 146.95, 147.18, 147.90, 148.47, 153.73, 154.56. ES-MS m/z 464 (M+H). Anal. Calcd. for C$_{30}$H$_{33}$N$_5$.4.0HBr.2.9H$_2$O: C, 42.92; H, 5.14; N, 8.34; Br, 38.07. Found: C, 42.86; H, 5.14; N, 8.20; Br, 38.17.

Example 86

AMD8775: Preparation of N,N'-bis(2-pyridinylmethyl)-N'-(6,7-dihydro-5H-cyclopenta[b]pyridin-7-yl)-1,4-benzenedimethanamine (hydrobromide salt)

In a similar manner to that described above: 7-amino-6,7-dihydro-5H-cyclopenta[b]pyridine and N-[1-methylene-4-chloromethylenephenylene]-N-(2-nitrobenzenesulfonyl)-2-(aminomethyl)pyridine gave AMD8775 as an orange solid. $^1$H NMR (D$_2$O) δ 2.53–2.64 (m, 2H), 3.12–3.20 (m, 1H), 3.26–3.35 (m, 1H), 3.73 (d, 1H, J=12.9 Hz), 3.85 (d, 1H, J=12.9 Hz), 4.21 (d, 1H, J=16.8 Hz), 4.24 (s, 2H), 4.39 (d, 1H, J=16.8 Hz), 4.47 (s, 2H), 5.14 (dd, 1H, J=8.4, 7.2 Hz), 7.25 (d, 2H, J=8.1 Hz), 7.30 (d, 2H, J=8.1 Hz), 7.73–7.80 (m, 3H), 7.84 (dd, 1H, J=7.8, 6.0 Hz), 7.91 (d, 1H J=8.1 Hz), 8.24 (td, 1H, J=7.8, 1.5 Hz), 8.35 (dd, 1H, J=7.8, 1.5 Hz), 8.40 (d, 1H, J=7.2 Hz), 8.52–8.57 (m, 2H), 8.69 (br d, 1H, J=5.1 Hz); $^{13}$C NMR (D$_2$O) δ 22.49, 28.77, 48.91, 51.13, 54.64, 55.89, 67.47, 126.19, 126.64 (2 carbons), 126.85, 127.22, 130.06, 130.67 (2 carbons), 130.96 (2 carbons), 138.85, 139.82, 140.93, 143.58, 144.46, 144.96, 146.70, 147.32, 147.69, 154.19, 156.49. ES-MS m/z 436 (M+H). Anal. Calcd. for C$_{28}$H$_{29}$N$_5$.4.0HBr.2.7H$_2$O: C, 41.63; H, 4.79; N, 8.67; Br, 39.56. Found: C, 41.59; H, 4.72; N, 8.43; Br, 39.59.

Example 87

AMD8819: Preparation of N,N'-bis(2-pyridinylmethyl)-N'-(1,2,3,4-tetrahydro-1-naphthalenyl)-1,4-benzenedimethanamine (hydrobromide salt)

In a similar manner to that described above: 1-amino-1,2,3,4-tetrahydronapthalene and N-[1-methylene-4-chloromethylenephenylene]-N-(2-nitrobenzenesulfonyl)-2-(aminomethyl)pyridine gave AMD8819 as a white solid. $^1$H NMR (D$_2$O) δ 1.62–1.68 (m, 1H), 2.05–2.19 (m, 2H), 2.39–2.44 (m, 1H), 2.69–2.81 (m, 2H), 4.30–4.84 (m, 6H), 4.52 (s, 2H), 4.76–4.79 (m, 1H, overlaps with HOD), 7.16–7.26 (m, 3H), 7.37–7.50 (m, 6H), 7.67 (dd, 1H, J=6.0, 3.3 Hz), 7.79–7.93 (m, 3H), 8.32 (td, 1H, J=7.8, 1.5 Hz), 8.47 (dd, 1H, J=5.7, 1.5 Hz), 8.71 (br d, 1H J=5.7 Hz); $^{13}$C NMR (D$_2$O) δ 21.01, 22.84, 29.19, 48.12, 51.37, 53.29, 56.11, 62.74, 125.36, 125.47, 127.17, 127.47, 127.63, 128.58, 129.27, 130.28, 131.03 (2 carbons), 131.32, 131.49, 131.58 (2 carbons), 134.17, 141.15, 142.17, 145.29, 145.66, 145.86, 146.47, 150.58. ES-MS m/z 449 (M+H). Anal. Calcd. for C$_{30}$H$_{32}$N$_4$.4.0HBr.2.0H$_2$O: C, 44.58; H, 4.99; N, 6.93; Br, 39.54. Found: C, 44.82; H, 5.02; N, 6.86; Br, 39.30.

Example 88

AMD8768: Preparation of N,N'-bis(2-pyridinylmethyl)-N'-[(5,6,7,8-tetrahydro-8-quinolinyl)methyl]-1,4-benzenedimethanamine (hydrobromide salt)

8-carboxymethyl-5,6,7,8-tetrahydroquinoline

To a cold (−78° C.), stirred solution of 5,6,7,8-tetrahydroquinoline (0.713 g, 5.35 mmol) in dry THF (50 mL) was added tert-butyllithium (1.7 M in pentane, 4.5 mL, 7.65 mmol). The initially colorless solution turned deep red. After one hour, CO$_2$ gas was bubbled through the reaction mixture for 15 minutes. The red color faded and the solution became cloudy and colorless. The reaction mixture was warmed to room temperature, treated with water (30 mL), and diluted with diethyl ether (30 mL). The phases were separated and the aqueous phase was extracted with ether (3×30 mL). The aqueous phase was concentrated under reduced pressure to provide a white solid. Methanol (50 mL) was added to the solid followed by the dropwise addition of concentrated H$_2$SO$_4$ (~1 mL) until the mixture became homogenous. The resultant solution was heated to reflux overnight and then was cooled to room temperature. The solution was concentrated and the residue was dissolved in saturated aqueous Na$_2$CO$_3$ (30 mL) and CH$_2$Cl$_2$ (30 mL). The phases were separated and the aqueous phase was extracted with CH$_2$Cl$_2$ (3×30 mL). The combined organic extracts were dried (Na$_2$SO$_4$) and concentrated. Purification of the crude material by radial chromatography on silica gel (4 mm plate, 20:1 CH$_2$Cl$_2$—CH$_3$OH) provided 8-carbomethoxy-5,6,7,8-tetrahydroquinoline (0.724 g, 72%) as a pale yellow oil. $^1$H NMR (CDCl$_3$) δ 1.72–1.82 (m, 1H), 1.92–2.03 (m, 1H), 2.12–2.24 (m, 2H), 2.71–2.91 (m, 2H), 3.74 (s, 3H), 3.98 (dd, 1H, J=6.6, 6.6 Hz), 7.09 (dd, 1H, J=7.8, 4.8 Hz), 7.40 (dd, 1H, J=7.5, 0.9 Hz), 8.40 (d, 1H, J=4.8 Hz); $^{13}$C NMR (CDCl$_3$) δ 20.68, 27.31, 28.70, 48.55, 52.40, 122.39, 132.83, 137.48, 147.60, 154.13, 175.13. ES-MS m/z 192(M+H).

8-hydroxymethyl-5,6,7,8-tetrahydroquinoline

To a cold (−78° C.), stirred solution of 8-carboxymethyl-5,6,7,8-tetrahydroquinoline (0.820 g, 4.29 mmol) in CH$_2$Cl$_2$ (21 mL, 0.2M) was added DIBAL-H (15.0 mL, 15.0 mmol, 1.0 M in CH$_2$Cl$_2$) over. 10 minutes. The cooling bath was removed and the reaction mixture was warmed to room temperature. After 3.5 hours, the mixture was treated with saturated aqueous sodium/potassium tartrate (100 mL) and diluted with CH$_2$Cl$_2$ (21 mL). The resultant emulsion was vigorously stirred open to the air until the emulsion became a biphasic mixture. The phases were separated and the aqueous phase was extracted with CH$_2$Cl$_2$ (4×25 mL). The combined organic extracts were dried (Na$_2$SO$_4$) and concentrated. The crude material was purified by radial chromatography on silica gel (4 mm plate, 20:1 CH$_2$Cl$_2$-CH$_3$OH), to provide 8-hydroxymethyl-5,6,7,8-tetrahydroquinoline (0.573 g) as a yellow oil.

8-(aminomethyl)-5,6,7,8-tetrahydroquinoline

To a stirred solution of 8-hydroxymethyl-5,6,7,8-tetrahydroquinoline (0.573 g, 3.51 mmol) in dry THF (35 mL) was added phthalimide (0.795 g, 5.40 mmol) and triphenylphosphine (1.452 g, 5.53 mmol) followed by the dropwise addition of diethylazodicarboxylate (0.90 mL, 5.72 mmol). The resultant mixture was stirred at room temperature overnight. The mixture was concentrated and filtered (2:1 hexanes-ethyl acetate) through a short pad of silica gel (50 g). The appropriate fractions were combined and concentrated. Purification of the residual oil by radial chromatography on silica gel (4 mm plate, 3:1 hexanes-ethyl acetate) provided 0.711 g of a yellow semi-solid. The yellow semi-solid was dissolved in ethanol (25 mL), treated with hydrazine (1.2 mL, 24.7 mmol), and stirred at room temperature overnight. A voluminous, white precipitate formed. The reaction mixture was diluted with ether, filtered, and the filtrates concentrated to provide a yellow oil. Purification of the crude material by column chromatography on silica gel (20:1:1 CH$_2$Cl$_2$—CH$_3$OH—NH$_4$OH) provided 0.217 g of 8-(aminomethyl)-5,6,7,8-tetrahydroquinoline as a yellow oil. $^1$H NMR (CDCl$_3$) δ 1.59–2.01 (m, 6H), 2.73 (t, 2H, J=5.4 Hz), 2.82–2.29 (m, 1H), 2.99 (dd, 1H, J=12.6, 6.6 Hz), 3.11 (dd, 1H, J=12.6, 5.4 Hz), 7.00 (dd, 1H, J=7.2, 4.8 Hz), 7.32 (d, 1H, J=7.2 Hz), 8.36 (d, 1H, J=4.8 Hz).

Preparation of AMD8768.

8-(aminomethyl)-5,6,7,8-tetrahydroquinoline (0.283 g, 1.74 mmol) was condensed with pyridine-2-carboxaldehyde (0.19 mL, 2.00 mmol) in methanol (17 mL) overnight. Hydrogenation (1 atm, room temperature) of the resulting imine over palladium on activated carbon, (10%, 54 mg) for 5 hours provided 0.452 g of a yellow oil. The oil was dissolved in CH$_3$CN (35 mL), treated with N-[1-methylene-4-chloromethylenephenylene]-N-(2-nitrobenzenesulfonyl)-2-(aminomethyl)pyridine (0.8168 g, 1.89 mmol) and K$_2$CO$_3$ (0.546 g, 3.95 mmol) and heated to reflux for 24 hours. The mixture was cooled to room temperature, concentrated, and partitioned between CH$_2$Cl$_2$ (40 mL) and water (20 mL). The phases were separated and the aqueous phase was extracted with CH$_2$Cl$_2$ (3×20 mL). The combined organic extracts were dried (Na$_2$SO$_4$) and concentrated. Purification of the crude material by column chromatography on silica gel (10:1 CH$_2$Cl$_2$-CH$_3$OH) provided 0.90 g of a yellow solid.

Using general procedures C and D: the yellow solid from above (0.90 g, 1.39 mmol) was reacted with thiophenol (0.85 mL, 8.28 mmol) and K$_2$CO$_3$ (1.949 g, 14.10 mmol) in CH$_3$CN (25 mL). Purification of the crude material by radial chromatography on silica gel (4 mm plate, 20:1:1 CH$_2$Cl$_2$—CH$_3$OH—NH$_4$OH) provided the free base of the title compound (0.67 g) as a yellow oil. Conversion of the free base to a hydrobromide salt gave AMD8768 (0.89 g) as a white solid. $^1$H NMR (D$_2$O) δ 1.55–1.60 (m, 1H), 1.70–1.77 (m, 1H), 1.93–1.98 (m, 1H), 2.05–2.11 (m, 1H), 2.81–2.85 (m, 2H), 2.95–3.09 (m, 2H), 3.49–3.57 (m, 1H), 3.86 (d, 1H, J=13.2 Hz), 3.98 (d, 1H, J=13.2 Hz), 4.31 (d, 2H, J=5.1 Hz), 4.38 (s, 2H), 4.62 (s, 2H), 7.42 (s, 4H), 7.72 (dd, 1H, J=8.1, 6.0 Hz), 7.85–8.04 (m, 4H), 8.18 (br d, 1H, J=8.1 Hz), 8.42–8.48 (m, 3H), 8.64 (dd, 1H, J=5.7, 0.9 Hz), 8.78 (br d, 1H, J=5.7 Hz); $^{13}$C NMR (D$_2$O) δ 17.61, 24.02, 27.39, 34.64, 48.06, 51.54, 56.11, 58.04, 58.94, 124.84, 126.43, 127.54, 127.73, 127.88, 136.08, 130.81 (2 carbons), 131.19 (2 carbons), 138.42, 138.93, 139.12, 142.10, 145.19, 145.85, 146.42, 146.91, 147.41, 153.19, 153.37. ES-MS m/z 464

(M+H). Anal. Calcd. for C$_{30}$H$_{33}$N$_5$.4.7HBr.3.2H$_2$O: C, 39.97; H, 4.93; N, 7.77; Br, 41.66. Found: C, 40.04; H, 4.98; N, 7.63; Br, 41.69.

Example 89

AMD8767: Preparation of N,N'-bis(2-pyridinylmethyl)-N'[(6,7-dihydro-5H-cyclopenta[b]pyridin-7-yl)methyl]-1,4-benzenedimethanamine (hydrobromide salt)

Using similar procedures to those described above: Cyclopentenopyridine gave 7-(aminomethyl)-6,7-dihydro-5H-cyclopenta[b]pyridine. $^1$H NMR (CDCl$_3$) δ 1.50 (br s, 2H, NH$_2$), 1.81–1.93 (m, 1H), 2.26–2.38 (m, 1H), 2.82–3.12 (m, 4H), 3.22 (quintet, 1H, J=7.2 Hz), 7.04 (dd, 1H, J=7.2, 4.8 Hz), 7.49 (d, 1H, J=7.2 Hz), 8.36 (d, 1H, J=4.8 Hz).

Reaction of 7-(aminomethyl)-6,7-dihydro-5H-cyclopenta[b]pyridine, pyridine -2 carboxaldehyde and N-[1-methylene-4-chloromethylenephenylene]-N-(2-nitrobenzenesulfonyl)-2-(aminomethyl)pyridine using similar procedures to those described above gave AMD8767 as a white solid. $^1$H NMR (D$_2$O) δ 2.14–2.22 (m, 1H), 2.50–2.59 (m, 1H), 2.99–3.07 (m, 3H), 3.25 (dd, 1H, J=13.2, 6.0 Hz), 3.89–3.99 (m, 2H), 4.04 (d, 1H, J=9.9 Hz), 4.32 (d, 2H, J=3 Hz), 4.34 (s, 2H), 4.58 (s, 2H), 7.37–7.44 (m, 4H), 7.72–7.81 (m, 2H), 7.82–7.94 (m, 3H), 8.28–8.44 (m, 4H), 8.61 (dd, 1H, J=5.1, 1.2 Hz), 8.75 (dd, 1H, J=5.1, 1.2 Hz); $^{13}$C NMR (D$_2$O) δ 33.64,33.82, 46.86, 53.12, 56.25, 61.12, 62.10, 63.99, 130.47, 131.02, 132.10, 132.25, 132.27, 135.06, 135.57 (2 carbons), 136.06 (2 carbons), 142.65, 143.27, 147.36, 148.13, 149.85,150.01,150.44, 151.01,151.61, 158.11, 164.21; ES-MS m/z 450 (M+H). Anal. Calcd. for C$_{29}$H$_{31}$N$_5$.4.7HBr.3.3H$_2$O: C, 39.17; H, 4.79; N, 7.87; Br, 42.23. Found: C, 39.07; H, 4.58; N, 7.66; Br, 42.46.

Example 90

AMD8838: Preparation of N-(2-pyridinylmethyl)-N-(2-methoxyethyl)-N'-(5,6,7,8-tetrahydro-8-quinolinyl)-1,4-benzenedimethanamine (hydrobromide salt)

To a stirred solution of N-(diethoxyphosphoryl)-N-(2-pyridinylmethyl)-N'-(5,6,7,8-tetrahydro-8-quinolinyl)-1,4-benzenedimethanamine (328 mg, 0.66 mmol) in dry CH$_2$Cl$_2$ (5 mL) was added methoxyacetic acid (0.15 mL, 1.95 mmol), N,N -diisopropylethylamine (0.35 mL, 2.01 mmol), 1-hydroxybenzotriazole hydrate (135 mg, 1.00 mmol) and 1-(3-dimethylaminopropyl)-3-ethyl carbodiimide HCl (EDC) (191 mg, 1.00 mmol) and the mixture was stirred at room temperature for 18 h. The reaction mixture was partitioned between CH$_2$Cl$_2$ (20 mL) and saturated aqueous sodium bicarbonate (30 mL) and the organic phase dried (MgSO$_4$), filtered and evaporated in vacuo. Purification by column chromatography on silica gel (CH$_2$Cl$_2$/MeOH, 95:5) gave the intermediate amide (345 mg, 92%) as a pale yellow foam.

To a stirred solution of the amide from above (345 mg, 0.61 mmol) in dry toluene (5 mL) was added a 70% w/w solution of sodium bis(2-methoxyethoxy)aluminium hydride in toluene (0.59 mL, 2.04 mmol) and the mixture stirred for 40 min. The reaction mixture was quenched with 1 N HCl (5 mL) and stirred for 30 min. The mixture was partitioned between 1 N NaOH (25 mL) and CH$_2$Cl$_2$ (25 mL) and the aqueous layer washed with CH$_2$Cl$_2$ (2×15 mL). The combined organic extracts were dried (MgSO$_4$), filtered and concentrated in vacuo. Purification of the crude product by column chromatography on silica gel (CH$_2$Cl$_2$/MeOH/NH$_4$OH, 95:5:0 followed by 95:4:1) afforded the reduced tertiary amine (166 mg, 49%) as a clear oil.

To a stirred solution of the tertiary amine (116 mg, 0.21 mmol) in glacial acetic acid (1 mL) was added an HBr saturated solution of acetic acid (1 mL) and the mixture was stirred at room temperature for 17 h. Diethyl ether (20 mL) was added resulting in the formation of a white precipitate. The solid was allowed to settle to the bottom of the flask and the supernatant solution was decanted off. The solid was washed by decantation with ether (4×10 mL) and the remaining traces of solvent removed by evaporation under reduced pressure. The HBr salt was then re-dissolved in MeOH (1 mL) and partitioned between CH$_2$Cl$_2$ (25 mL) and 1 N NaOH (30 mL). The aqueous phase was washed with CH$_2$Cl$_2$ (2×15 mL) and the combined organic layers dried (Na$_2$SO$_4$), filtered and concentrated in vacuo to give the crude free amine as a brown oil. Purification of the crude amine by column chromatography on silica gel (CH$_2$Cl$_2$/MeOH, 92:8) gave the free base of the title compound as a colorless oil. Using general procedure D: Conversion of the free base (23 mg, 0.042 mmol) to a hydrobromide salt followed by re-precipitation of the crude material from methanol/ether gave AMD8838 as a white solid (39 mg, quantitative). $^1$H NMR (D$_2$O) δ 1.79–1.83 (br m, 1H), 2.04–2.19 (m, 2H), 2.44–2.48 (m, 1H), 2.86–2.89 (m, 2H), 3.17 (s, 3H), 3.32–3.49 (m, 2H), 3.52–3.57 (m, 1H), 3.77 (td, 1H, J=8.7, 3.0 Hz), 4.21 (d, 1H, J=13.2 Hz), 4.34 (d, 1H, J=13.5 Hz), 4.40 (s, 2H), 4.55 (s, 2H), 4.71–4.73 (m, 1H), 7.44 (dd, 1H, J=8.0, 5.0 Hz), 7.55 (br s, 4H), 7.73–7.81 (m, 3H), 8.24 (td, 1H, J=8.0, 2.0 Hz), 8.49 (d, 1H, J=5.0 Hz), 8.70 (d, 1H, J=5.0 Hz); $^{13}$C NMR (D$_2$O) δ 20.37, 20.79, 27.36, 49.04, 50.22, 51.24, 54.81, 58.59, 61.95, 66.63, 124.96, 126.67 (2 carbons), 131.29 (4 carbons), 131.96, 133.67, 136.52, 140.97, 143.58, 145.61, 146.70, 147.73, 149.14. ES-MS m/z 417 (M+H). Anal. Calcd. for C$_{26}$H$_{32}$N$_4$O.4.0HBr.2.2H$_2$O: C, 40.04; H, 5.22; N, 7.18; Br, 40.98. Found: C, 40.11; H, 5.28; N, 7.08; Br, 40.96.

Example 91

AMD8871: Preparation of N-(2-pyridinylmethyl)-N-[2-(4-methoxyphenyl)ethyl]-N'-(5,6,7,8-tetrahydro-8-quinolinyl)-1,4-benzenedimethanamine (hydrobromide salt)

To a solution of N-(diethoxyphosphoryl)-N-(2-pyridinylmethyl)-N'-(5,6,7,8-tetrahydro-8-quinolinyl)-1,4-benzenedimethanamine (641 mg, 1.30 mmol) and 4-methoxyphenylacetic acid (646 mg, 3.89 mmol) in CH$_2$Cl$_2$ (20 mL) was added N,N-diisopropylethylamine (0.45 mL, 2.59 mmol), 1-hydroxybenzotriazole hydrate (265 mg, 1.96 mmol) and 1-(3-dimethylaminopropyl)-3-ethyl carbodiimide HCl (EDC) (360 mg, 1.88 mmol) and the mixture was stirred at room temperature for 17 hours. Purification of the crude product by column chromatography on silica gel (CH$_2$Cl$_2$/MeOH, 96:4) gave the desired amide (688 mg, 77%) as a yellow foam. Using general procedure D: the diethoxyphosphoryl group was removed with HBr/acetic acid to give the amino-amide (591 mg, 78%) as a yellow foam.

To a stirred solution of the amine (591 mg, 1.17 mmol) in dry CH$_3$CN (5 mL) was added allyl bromide (0.16 mL, 1.9 mmol) and powdered potassium carbonate (378 mg, 2.74 mmol) and the mixture was stirred for 2 h. The reaction was diluted with CH$_2$Cl$_2$ (25 mL) and water (25 mL) and the aqueous layer washed with CH$_2$Cl$_2$ (2×15 mL). The combined organic extracts were dried (MgSO$_4$), filtered and concentrated in vacuo. Purification of the crude product by column chromatography on silica gel (CH$_2$Cl$_2$/MeOH, 96:4) afforded the N-allyl-protected amide (600 mg, 94%) as an orange foam.

To a solution of the N-allyl amide (600 mg, 1.10 mmol) in dry toluene (5 mL) was added a 70% w/w solution of sodium bis(2-methoxyethoxy)aluminum hydride in toluene (0.95 mL, 3.29 mmol) and the mixture stirred for 4.5 h. Purification of the crude product by column chromatography on silica gel (CH$_2$Cl$_2$/MeOH, 95:5 to 9:1) afforded the tertiary amine (222 mg, 38%) as a pale yellow oil.

To a stirred solution of the N-allyl-protected amine in dry CH$_2$Cl$_2$ (5 mL) (150 mg, 0.28 mmol) was added tetrakis (triphenylphosphine)palladium(0) (12 mg, 0.01 mmol) and N,N'-dimethylbarbituric acid (132 mg, 0.85 mmol) and the mixture stirred for 20 hours. The reaction was diluted with CH$_2$Cl$_2$ (20 mL) and saturated aqueous sodium bicarbonate (20 mL) and the aqueous layer washed with CH$_2$Cl$_2$ (2×15 mL). The combined organic extracts were dried (MgSO$_4$), filtered and concentrated in vacuo. Purification of the crude product by column chromatography on silica gel (CH$_2$Cl$_2$/MeOH/NH$_4$OH, 95:5:0 followed by 94:5:1) afforded the free base of the title compound (44 mg, 32%) as an orange oil. Using general procedure D: the free base (44 mg, 0.089 mmol) was converted to a hydrobromide salt. Re-precipitation of the crude material from methanol/ether gave AMD8871 (69 mg, 91%) as a beige solid. $^1$H NMR (D$_2$O) δ 1.80–1.84 (br m, 1H), 2.00–2.19 (m, 2H), 2.47–2.50 (br m, 1H), 2.83–2.94 (br m, 4H), 3.29–3.34 (m, 1H), 3.66–3.69 (br m, 1H), 3.80 (s, 3H), 4.15–4.18 (m, 1H), 4.39 (d, 1H, J=13.2 Hz), 4.45 (d, 1H, J=13.2 Hz), 4.60 (s, 2H), 4.79 (s, 2H, overlap with HOD), 6.81 (d, 2H, J=8.0 Hz), 6.97 (d, 2H, J=8.0 Hz), 7.32–7.35 (br m, 3H), 7.44–7.46 (br m, 2H), 7.68 (d, 1H, J=8.0 Hz), 7.84–7.96 (m, 2H), 8.32–8.40 (br m, 2H), 8.75 (br s, 1H); $^{13}$C NMR (D$_2$O) δ 20.41, 20.98, 27.19, 30.26, 48.31, 51.38, 52.16, 54.61, 55.91, 62.38, 114.98 (2 carbons), 124.78, 127.38, 127.54, 128.08, 130.81 (2 carbons), 131.35 (4 carbons), 131.93, 132.20, 135.60, 139.69, 145.39, 145.50, 146.60, 146.63, 148.28, 158.59. ES-MS m/z 493 (M+H). Anal. Calcd. for C$_{32}$H$_{36}$N$_4$O.3.9HBr.1.6H$_2$O: C, 45.92; H, 5.19; N, 6.69; Br, 37.23. Found: C, 46.13; H, 5.04; N, 6.57; Br, 36.90.

Example 92

AMD8844: Preparation of N,N'-bis(2-pyridinylmethyl)-1,4-(5,6,7,8-tetrahydro-8-quinolinyl)benzenedimethanamine (hydrobromide salt)

To a solution of N-[1-methylene-4-(carboxaldehyde)phenylene]-N -(t-butoxycarbonyl)-2-(aminomethyl)pyridine (1.25 g, 3.8 mmol) in methanol (50 mL) was added 2-aminomethylpyridine (0.400 mL, 3.8 mmol). The reaction mixture was stirred at room temperature for 3 hours and then evaporated to afford the corresponding imine in quantitative yield. $^1$H NMR (CDCl$_3$) δ: 1.44 (s, 9H), 4.47 (m, 2H), 4.60 (m, 2H), 7.15 (m, 1H), 7.40 (m, 2H), 7.61 (dd, 1H, J=7.1, 6.8 Hz), 7.80 (d, 2H, J=7.1 Hz), 8.50 (d, 1H, J=4.8 Hz), 9.98 (s, 1H).

To a cooled (0° C.) solution of 5,6,7,8-tetrahydroquinoline (266 mg, 2.0 mmol) in THF (20 mL) was added nBuLi (1.5 mL of a 1.5M solution in hexanes, 2.5 mmol) over 5 minutes. The resulting bright crimson solution was then stirred at 0° C. for one hour, then a freshly prepared solution of anhydrous cerium trichloride in THF (8 mL of a 0.25M solution, 2 mmol) was added over ten minutes. The solution was stirred at 0° C. for a further 60 minutes, during which time, the reaction turned a brick red colour. A solution of the imine (832 mg, 2.0 mmol) in THF (3 mL) was then added over 10 minutes. The resulting deep violet solution was stirred at 0° C. for three hours. Saturated aqueous ammonium chloride was then added, and the mixture was extracted repeatedly with dichloromethane. The combined organic extracts were dried, filtered and evaporated and the residue was purified by column chromatography on silica gel (5% MeOH in CH$_2$Cl$_2$) to afford the desired product (518 mg, 44%).

Using general procedure D: the intermediate from above was converted to a hydrobromide salt with simultaneous deprotection of the BOC group to afford AMD8844 (81 mg). $^1$H NMR (D$_2$O) δ: 1.44 (m, 4H), 2.77 (m, 2H), 3.67 (m, 1H), 4.11 (dq, 2H, J=15.0, 3.1 Hz), 4.26 (m, 1H), 4.44 (s, 2H), 4.73 (s, 2H), 7.41 (d, 2H, J=7.2 Hz), 7.50 (d, 2H, J=7.2 Hz), 7.65 (t, 1H, J=6.6 Hz), 7.83 (m, 2H), 8.06 (t, 1H, J=6.8 Hz), 8.19 (m, 2H), 8.40 (t, 1H, J=7.8 Hz), 8.59 (m, 3H), 8.81 (d, 1H, J=5.8 Hz); $^{13}$C NMR (D$_2$O) δ 19.20, 24.73, 27.57, 65.76, 125.18, 126.85, 128.06, 128.43, 128.95, 129.26, 130.83, 131.46, 138.90, 139.12, 139.61, 142.01, 143.76, 145.08, 147.39, 148.06, 151.65, 152.45. ES-MS m/z 450 (M+H). Anal. Calcd. for C$_{29}$H$_{31}$N$_5$.4.7HBr.3.0 H$_2$O: C, 39.41; H, 4.75; N, 7.92; Br, 42.49. Found: C, 39.64; H, 4.65; N, 7.59; Br, 42.29.

Example 93

Methods for parallel solution phase combinatorial synthesis of analogs from the following intermediates:

N-(2-nitrobenzenesulfonyl)-N,N'-bis(2-pyridinylmethyl)-1,4-benzenedimethanamine.

N-(2-nitrobenzenesulfonyl)-N,N'-bis(2-pyridinylmethyl)-1,3-benzenedimethanamine.

N-(2-nitrobenzenesulfonyl)-N-(2-pyridinylmethyl)-N'-[2-(2-pyridinyl)ethyl]-1,4-benzenedimethanamine.

N-(2-nitrobenzenesulfonyl)-N-(2-pyridinylmethyl)-N'-[2-(2-pyridinyl)ethyl]-1,3-benzenedimethanamine.

Target compounds were prepared by parallel solution phase combinatorial synthesis via a two-step procedure. (a) Reaction of the intermediate amines from above (0.45 mmol scale) with commercially available aldehydes and ketones and sodium cyanoborohydride in methanol; (b) deprotection of the 2-nitrobenzenesulfonyl group by reaction of the intermediate from step (a) with thiophenol and DBU in DMF; (c) purification.

Step (a): Reductive Amination Procedure (0.45 mmol).

Reaction: 0.5 mmol (1.11 eq.) of aldehyde or ketone was weighed into a 20 mL scintillation vial containing a small amount of activated molecular sieve. 0.5 mL of 0.9M solution (1.0 eq.) of intermediate amine (in MeOH) was added, followed by 1 mL of a 0.6M solution of sodium cyanoborohydride in MeOH (1.33 eq.). The reaction was then diluted to 4 mL with MeOH. Finally, 0.5 mL of 1M acetic acid (in MeOH) was added. The reaction mixture was shaken (on an orbital shaker) for 48 hours.

Work-up: 0.5 mL of 1M sodium borohydride (in MeOH) was added to convert any unreacted carbonyl to the corresponding alcohol. After 15 min., the reaction was quenched with 4 mL of 2N HCl. The reaction mixture was shaken in a fume hood for 15 minutes. 2 mL of 7N NaOH was then added, followed by 5 mL of methylene chloride. After shaking for 20 minutes the organic layer was separated and evaporated (ambient temperature vacuum centrifuge for 4 hours).

Alternative Reductive Amination Procedure.

This procedure was used with all aldehydes that incorporated a pyrrole, indole, benzimidazole or imidazole functionality (0.45 mmol scale).

Reaction: 0.9 mmol (2.0 eq.) of aldehyde was weighed into a 20 mL scintillation vial containing a small amount of activated molecular sieve. 0.5 mL of 0.9M solution (1.0 eq.) of the intermediate amine (in trimethylorthoformate) was added. A further 2.5 mL of triethylorthoformate was added and the mixture was stirred for 30 min. Solid sodium cyanoborohydride was then added (2.25 mmol, 5 eq.) followed by 0.05 mL of acetic acid, and the mixture was shaken for 48 hours.

Work-up: 0.5 mL of 1M sodium borohydride (in MeOH) was added to convert any unreacted carbonyl compound to the corresponding alcohol. After 30 minutes the reaction was quenched by slow addition of 2N HCl (3 mL). The reaction mixture was shaken in a fume hood for 15 minutes. 2 mL of 7N NaOH was added followed by 5 mL of methylene chloride. After shaking for 20 minutes the organic layer was separated and evaporated (ambient temperature vacuum centrifuge for 4 hours).

The reaction products were deprotected without further purification.

Step B: Deprotection of the 2-nitrobenzenesulfonyl Group

Reaction: 1.5 mmol (3.33 eq.) of DBU and 0.75 mmol (1.67 eq.) of thiophenol were dissolved in 2.5 mL DMF were added to each crude reaction product and stirred at room temperature for 14 hours.

Work-up: 2 mL of water and 2 mL of methylene chloride were added to the mixture and shaken for 20 minutes. The organic layer was separated into 4 equal parts in 1 dram vials and evaporated (ambient temperature vacuum centrifuge for 20 hours).

Two methods were used to purify the samples:

Step C: Purification by Parallel Preparative HPLC.

3 of the four 1 dram vials for each sample were purified by high-throughput preparative HPLC parallel purification process using a Biotage Parallex instrument. The crude, de-protected material was dissolved in 1 mL of a mixture of 65:35 DMF/water.

The 1 mL solution was loaded into the injection loop of the HPLC which already contained starting eluent (water/acetonitrile, 90/10). A 100×20 mm YMC C18 120 A column was used and fractions were collected by monitoring at 254 and 307 nm. A gradient of 90/10 $H_2O/CH_3CN$ to 100% $CH_3CN$ over 8 minutes at a flow rate of 35 mL/minute was used. Each run was followed by a 3 minute equilabration/wash with 50/50 $H_2O/CH_3CN$. Each fraction was analyzed by ES FI-MS for the target compound, and the purity of fractions containing the desired products were determined by LC-MS.

Step C: Purification by Traditional Preparative HPLC.

One vial each of the crude products were purified on a Waters 600 Delta Prep instrument. The crude de-protected material was dissolved in 80:20 methylene chloride/MeOH at a concentration of ca. 75 mg/100 µL. The 100 µL sample was injected onto a 100×20 mm YMC C18 120A column, and fractions were collected by UV monitoring at 254 nm and a 8% threshold trigger. Flow rate 10 mL/min; gradient of 80/20 $H_2O/CH_3CN$ to 100% $CH_3CN$ over 20 minutes, isocratic at 100% $CH_3CN$ from 20–30 min, then back to 80/20 from 30–36 minutes. Each fraction was analyzed by ES FI-MS and % purity of fractions containing desired product was further determined by LC-MS.

Products exhibiting a sample purity of greater then 90% by LC-MS were considered suitable for testing.

Example 94

Methods for parallel solution phase combinatorial synthesis of analogs from the following intermediates:

N-(2-nitrobenzenesulfonyl)-N-(2-pyridinylmethyl)-N'-(5,6,7,8-tetrahydro-8-quinolinyl)-1,4-benzenedimethanamine.

N-(2-nitrobenzenesulfonyl)-N-(2-pyridinylmethyl)-N'-(5,6,7,8-tetrahydro-8-quinolinyl)-1,3-benzenedimethanamine.

N-(2-nitrobenzenesulfonyl)-N-(2-pyridinylmethyl)-N'-(6,7,8,9-tetrahydro-5H-cyclohepta[b]pyridin-9-yl)-1,4-benzenedimethanamine.

N-(2-nitrobenzenesulfonyl)-N-(2-pyridinylmethyl)-N'-(6,7,8,9-tetrahydro-5H-cyclohepta[b]pyridin-9-yl)-1,3-benzenedimethanamine.

Target compounds were prepared by parallel solution phase combinatorial synthesis via a two-step procedure. (a) Reaction of the intermediate amines from above (0.5 mmol scale) with commercially available aldehydes and ketones and sodium cyanoborohydride in methanol with a catalytic volume of acetic acid; (b) deprotection of the 2-nitrobenzenesulfonyl group by reaction of the intermediate from step (a) with thiophenol and $K_2CO_3$ in acetonitrile.

Step A:

Reaction: To the pre-weighed amine intermediate from above (0.5 mmol) and the aldehyde or ketone (1.5 equiv.) was added MeOH (5 mL), acetic acid (0.1 mL) and molecular sieves and the reaction vial was shaken for 12 hours. Sodium cyanoborohydride (1.5 equiv.) was then added and the reaction vial was shaken for 96 hours.

Work-up: To the vial is added, 2N NaOH (2 mL) and the solution is extracted with $CH_2Cl_2$ (3×5 mL) with shaking for 30 mins and separation of the organic phases, followed by evaporation of the solvent under reduced pressure (speed vac).

Step B:

The intermediate from above is reacted with thiophenol (5.0 equiv.) and powdered potassium carbonate (8.0 equiv.) in acetonitrile (10 mL) with shaking for 4 hours. The solvent was removed by evaporation under reduced pressure (Savant Speed Vac Plus: SC210A) for 12 hours at room temperature. Dichloromethane (5 mL) and water (5 mL) were then added to the residue, the phases were separated, and the aqueous layer was extracted with $CH_2Cl_2$ (2×5 mL). The combined organic phases were washed with brine (5 mL) and evaporated under reduced pressure (Savant Speed Vac Plus) for 24 hours at room temperature.

The crude reaction products were analyzed by HPLC with multiple post-column detection: positive mode electrospray MS (API 150MCA), UV at 254 nm and evaporative light scattering (ELS). Chromatography conditions were as follows: Column: Monitor C8, 30×4.6 mm id; flow rate 1200 µL/min.; Solvent A: $H_2O$ w/5 mM $NH_4OAc$ and Solvent B: acetonitrile with 5 mM $NH_4OAc$. Gradient (A/B): 90/10 (t=0), 10/90 (t=8 min), 10/90 (t=9.5 min), 90/10 (t=10.25 min), 90/10 (t=11 min).

Compounds exhibiting a molecular ion (MS) for the desired target compound and an ELS purity of greater than 90% were plated for testing. Compounds exhibiting an ELS purity of less than 90% were purified by preparative HPLC using either of the two following conditions:

| Preparative HPLC Purification: Condition 1 | | | | | |
|---|---|---|---|---|---|
| Solvent A | H₂O/NH₄OAc | | Solvent B | CH₃CN | |
| Wash | 50:50 MeOH/CH₃CN | | | | |
| UV1 | 307 nm | | UV2 | 254 nm | |
| Inj. Loop Vol. | 2 mL | | Inj. Vol. | 1 mL | |
| Column | 250 × 20 mm id; C18 | | | | |
| Step No. | Action | Starting B % | Ending B % | Duration (min) | Flow Rate |
| 1 | Equilibration | 15 | 15 | 0.30 | 30 mL/min |
| 2 | Injection | 10 | 10 | 0.27 | 30 mL/min |
| 3 | Gradient | 10 | 100 | 5.30 | 35 mL/min |
| 4 | Gradient | 100 | 100 | 1.30 | 35 mL/min |
| 5 | Gradient | 100 | 10 | 0.10 | 35 mL/min |
| 6 | Gradient | 10 | 10 | 2.00 | 35 mL/min |

| Preparative HPLC Purification: Condition 2 | | | | |
|---|---|---|---|---|
| Solvent A | H₂O | | Solvent B | CH₃CN |
| UV1 | 254 nm | | UV2 | 219 nm |
| Inj. Loop Vol. | 2 mL | | Inj. Vol. | 1 mL |
| Column | 100 × 20 mm id; C18, 120A | | | |
| Time | A % | B % | Flow Rate | |
| 0 | 90 | 10 | 20 mL/min | |
| 21 | 0 | 100 | 20 mL/min | |
| 24 | 0 | 100 | 20 mL/min | |

Peaks corresponding to the molecular ion of the desired compound were collected and evaporated under reduced pressure (Speed Vac) and weighed.

The following compounds (Examples 95–191) were prepared by the procedures described in working Examples 93 and 94. A summary of structures and observed molecular ions (LC-MS analysis) for Examples 95–191 are shown in Table 2.

Example 95

AMD7129: N-[(2,3-dimethoxyphenyl)methyl]-N'-(2-pyridinylmethyl)-N-(5,6,7,8-tetrahydro-8-quinolinyl)-1,4-benzenedimethanamine Example 96

AMD7130: N,N'-bis(2-pyridinylmethyl)-N-[1-(N''-phenyl-N''-methylureido)-4-piperidinyl]-1,3-benzenedimethanamine Example 97

AMD7131: N,N'-bis(2-pyridinylmethyl)-N-[N''-p-toluenesulfonylphenylalanyl)-4-piperidinyl]-1,3-benzenedimethanamine Example 98

AMD7136: N,N'-bis(2-pyridinylmethyl)-N-[1-[3-(2-chlorophenyl)-5-methylisoxazol-4-oyl]-4-piperidinyl]-1,3-benzenedimethanamine Example 99

AMD7138: N-[(2-hydroxyphenyl)methyl]-N'-(2-pyridinylmethyl)-N-(6,7,8,9-tetrahydro-5H-cyclohepta[b]pyridin-9-yl)-1,4-benzenedimethanamine Example 100

AMD7140: N-[(4-cyanophenyl)methyl]-N'-(2-pyridinylmethyl)-N-(6,7,8,9-tetrahydro-5H-cyclohepta[b]pyridin-9-yl)-1,4-benzenedimethanamine Example 101

AMD7141: N-[(4-cyanophenyl)methyl]-N'-(2-pyridinylmethyl)-N-(5,6,7,8-tetrahydro-8-quinolinyl)-1,4-benzenedimethanamine Example 102

AMD7142: N-[(4-acetamidophenyl)methyl]-N'-(2-pyridinylmethyl)-N-(5,6,7,8-tetrahydro-8-quinolinyl)-1,4-benzenedimethanamine Example 103

AMD7145: N-[(4-phenoxyphenyl)methyl]-N'-(2-pyridinylmethyl)-N-(6,7,8,9-tetrahydro-5H-cyclohepta[b]pyridin-9-yl)-1,4-benzenedimethanamine Example 104

AMD7147: N-[(1-methyl-2-carboxamido)ethyl]-N,N'-bis(2-pyridinylmethyl)-1,3-benzenedimethanamine Example 105

AMD7151: N-[(4-benzyloxyphenyl)methyl]-N'-(2-pyridinylmethyl)-N-(6,7,8,9-tetrahydro-5H-cyclohepta[b]pyridin-9-yl)-1,4-benzenedimethanamine Example 106

AMD7155: N-[(thiophene-2-yl)methyl]-N'-(2-pyridinylmethyl)-N-(6,7,8,9-tetrahydro-5H-cyclohepta[b]pyridin-9-yl)-1,4-benzenedimethanamine Example 107

AMD7156: N-[1-(benzyl)-3-pyrrolidinyl]-N,N'-bis(2-pyridinylmethyl)-1,3-benzenedimethanamine Example 108

AMD7159: N-[[1-methyl-3-(pyrazol-3-yl)]propyl]-N,N'-bis(2-pyridinylmethyl)-1,3-benzenedimethanamine Example 109

AMD7160: N-[1-(phenyl)ethyl]-N,N'-bis(2-pyridinylmethyl)-1,3-benzenedimethanamine Example 110

AMD7164: N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine

Example 111

AMD7166: N-[1-benzyl-3-carboxymethyl-4-piperidinyl]-N,N'-bis(2-pyridinylmethyl)-1,3-benzenedimethanamine

Example 112

AMD7167: N-[(3,4-methylenedioxyphenyl)methyl]-N'-(2-pyridinylmethyl)-N-(5,6,7,8-tetrahydro-8-quinolinyl)-1,4-benzenedimethanamine

Example 113

AMD7168: N-(3-pyridinylmethyl)-N'-(2-pyridinylmethyl)-N-(6,7,8,9-tetrahydro-5H-cyclohepta[b]pyridin-9-yl)-1,4-benzenedimethanamine

Example 114

AMD7169: N-[[1-methyl-2-(2-tolyl)carboxamido]ethyl]-N,N'-bis(2-pyridinylmethyl)-1,3-benzenedimethanamine

Example 115

AMD7171: N-[(1,5-dimethyl-2-phenyl-3-pyrazolinone-4-yl)methyl]-N'-(2-pyridinylmethyl)-N-(5,6,7,8-tetrahydro-8-quinolinyl)-1,4-benzenedimethanamine

Example 116

AMD7172: N-[(4-propoxyphenyl)methyl]-N'-(2-pyridinylmethyl)-N-(6,7,8,9-tetrahydro-5H-cyclohepta[b]pyridin-9-yl)-1,4-benzenedimethanamine

Example 117

AMD7175: N-(1-phenyl-3,5-dimethylpyrazolin-4-ylmethyl)-N'-(2-pyridinylmethyl)-N-(5,6,7,8-tetrahydro-8-quinolinyl)-1,4-benzenedimethanamine

Example 118

AMD7177: N-[1H-imidazol-4-ylmethyl]-N,N'-bis(2-pyridinylmethyl)-1,3-benzenedimethanamine

Example 119

AMD7180: N-[(3-methoxy-4,5-methylenedioxyphenyl)methyl]-N'-(2-pyridinylmethyl)-N-(6,7,8,9-tetrahydro-5H-cyclohepta[b]pyridin-9-yl)-1,4-benzenedimethanamine

Example 120

AMD7182: N-[(3-cyanophenyl)methyl]-N'-(2-pyridinylmethyl)-N-(6,7,8,9-tetrahydro-5H-cyclohepta[b]pyridin-9-yl)-1,4-benzenedimethanamine

Example 121

AMD7184: N-[(3-cyanophenyl)methyl]-N'-(2-pyridinylmethyl)-N-(5,6,7,8-tetrahydro-8-quinolinyl)-1,4-benzenedimethanamine

Example 122

AMD7185: N-(5-ethylthiophene-2-ylmethyl)-N'-(2-pyridinylmethyl)-N-(6,7,8,9-tetrahydro-5H-cyclohepta[b]pyridin-9-yl)-1,4-benzenedimethanamine

Example 123

AMD7186: N-(5-ethylthiophene-2-ylmethyl)-N'-(2-pyridinylmethyl)-N-(5,6,7,8-tetrahydro-8-quinolinyl)-1,4-benzenedimethanamine

Example 124

AMD7187: N-[(2,6-difluorophenyl)methyl]-N'-(2-pyridinylmethyl)-N-(6,7,8,9-tetrahydro-5H-cyclohepta[b]pyridin-9-yl)-1,4-benzenedimethanamine

Example 125

AMD7188: N-[(2,6-difluorophenyl)methyl]-N'-(2-pyridinylmethyl)-N-(5,6,7,8-tetrahydro-8-quinolinyl)-1,4-benzenedimethanamine

Example 126

AMD7189: N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine

Example 127

AMD7195: N-(2-difluoromethoxyphenylmethyl)-N'-(2-pyridinylmethyl)-N-(5,6,7,8-tetrahydro-8-quinolinyl)-1,4-benzenedimethanamine

Example 128

AMD7196: N-(1,4-benzodioxan-6-ylmethyl)-N'-(2-pyridinylmethyl)-N-(6,7,8,9-tetrahydro-5H-cyclohepta[b]pyridin-9-yl)-1,4-benzenedimethanamine

Example 129

AMD7197: N,N'-bis(2-pyridinylmethyl)-N-[1-(N''-phenyl-N''-methylureido)-4-piperidinyl]-1,4-benzenedimethanamine

Example 130

AMD7198: N,N'-bis(2-pyridinylmethyl)-N-[N''-p-toluenesulfonylphenylalanyl)-4-piperidinyl]-1,4-benzenedimethanamine

Example 131

AMD7199: N-[1-(3-pyridinecarboxamido)-4-piperidinyl]-N,N'-bis(2-pyridinylmethyl)-1,4-benzenedimethanamine

Example 132

AMD7200: N-[1-(cyclopropylcarboxamido)-4-piperidinyl]-N,N'-bis(2-pyridinylmethyl)-1,4-benzenedimethanamine

Example 133

AMD7201: N-[1-(1-phenylcyclopropylcarboxamido)-4-piperidinyl]-N,N'-bis(2-pyridinylmethyl)-1,4-benzenedimethanamine

Example 134

AMD7202: N-(1,4-benzodioxan-6-ylmethyl)-N'-(2-pyridinylmethyl)-N-(5,6,7,8-tetrahydro-8-quinolinyl)-1,4-benzenedimethanamine

Example 135

AMD7203: N-[1-[3-(2-chlorophenyl)-5-methyl-isoxazol-4-carboxamido]-4-piperidinyl]-N,N'-bis(2-pyridinylmethyl)-1,4-benzenedimethanamine

Example 136

AMD7204: N-[1-(2-thiomethylpyridine-3-carboxamido)-4-piperidinyl]-N,N'-bis(2-pyridinylmethyl)-1,4-benzenedimethanamine

Example 137

AMD7207: N-[(2,4-difluorophenyl)methyl]-N'-(2-pyridinylmethyl)-N-(5,6,7,8-tetrahydro-8-quinolinyl)-1,4-benzenedimethanamine

Example 138

AMD7208: N-(1-methylpyrrol-2-ylmethyl)-N'-(2-pyridinylmethyl)-N-(5,6,7,8-tetrahydro-8-quinolinyl)-1,4-benzenedimethanamine

Example 139

AMD7209: N-[(2-hydroxyphenyl)methyl]-N'-(2-pyridinylmethyl)-N-(5,6,7,8-tetrahydro-8-quinolinyl)-1,4-benzenedimethanamine

Example 140

AMD7212: N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine

Example 141

AMD7216: N-(3-pyridinylmethyl)-N'-(2-pyridinylmethyl)-N-(5,6,7,8-tetrahydro-8-quinolinyl)-1,4-benzenedimethanamine

Example 142

AMD7217: N-[2-(N''-morpholinomethyl)-1-cyclopentyl]-N,N'-bis(2-pyridinylmethyl)-1,4-benzenedimethanamine

Example 143

AMD7220: N-[(1-methyl-3-piperidinyl)propyl]-N,N'-bis(2-pyridinylmethyl)-1,4-benzenedimethanamine

Example 144

AMD7222: N-(1-methylbenzimidazol-2-ylmethyl)-N'-(2-pyridinylmethyl)-N-(5,6,7,8-tetrahydro-8-quinolinyl)-1,4-benzenedimethanamine

Example 145

AMD7223: N-[1-(benzyl)-3-pyrrolidinyl]-N,N'-bis(2-pyridinylmethyl)-1,4-benzenedimethanamine

Example 146

AMD7228: N-[[(1-phenyl-3-(N''-morpholino)]propyl]-N,N'-bis(2-pyridinylmethyl)-1,4-benzenedimethanamine

Example 147

AMD7229: N-[1-(iso-propyl)-4-piperidinyl]-N,N'-bis(2-pyridinylmethyl)-1,4-benzenedimethanamine

Example 148

AMD7230: N-[1-(ethoxycarbonyl)-4-piperidinyl]-N'-(2-pyridinylmethyl)-N-(5,6,7,8-tetrahydro-8-quinolinyl)-1,4-benzenedimethanamine

Example 149

AMD7231: N-[(1-methyl-3-pyrazolyl)propyl]-N'-(2-pyridinylmethyl)-N-(5,6,7,8-tetrahydro-8-quinolinyl)-1,4-benzenedimethanamine

Example 150

AMD7235: N-[1-methyl-2-(N'',N''-diethylcarboxamido)ethyl]-N,N'-bis(2-pyridinylmethyl)-1,4-benzenedimethanamine

Example 151

AMD7236: N-[(1-methyl-2-phenylsulfonyl)ethyl]-N'-(2-pyridinylmethyl)-N-(5,6,7,8-tetrahydro-8-quinolinyl)-1,4-benzenedimethanamine

Example 152

AMD7238: N-[(2-chloro-4,5-methylenedioxyphenyl)methyl]-N'-(2-pyridinylmethyl)-N-(5,6,7,8-tetrahydro-8-quinolinyl)-1,4-benzenedimethanamine

Example 153

AMD7239: N-[1-methyl-2-[N''-(4-chlorophenyl)carboxamido]ethyl]-N'-(2-pyridinylmethyl)-N-(5,6,7,8-tetrahydro-8-quinolinyl)-1,4-benzenedimethanamine

Example 154

AMD7241: N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine

Example 155

AMD7242: N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethanamine

Example 156

AMD7244: N-(3-quinolylmethyl)-N'-(2-pyridinylmethyl)-N-(5,6,7,8-tetrahydro-8-quinolinyl)-1,4-benzenedimethanamine

Example 157

AMD7245: N-[(8-hydroxy)-2-quinolylmethyl]-N'-(2-pyridinylmethyl)-N-(6,7,8,9-tetrahydro-5H-cyclohepta[b]pyridin-9-yl)-1,4-benzenedimethanamine

Example 158

AMD7247: N-(2-quinolylmethyl)-N'-(2-pyridinylmethyl)-N-(6,7,8,9-tetrahydro-5H-cyclohepta[b]pyridin-9-yl)-1,4-benzenedimethanamine

Example 159

AMD7249: N-[(4-acetamidophenyl)methyl]-N'-(2-pyridinylmethyl)-N-(6,7,8,9-tetrahydro-5H-cyclohepta[b]pyridin-9-yl)-1,4-benzenedimethanamine

Example 160

AMD7250: N-[1H-imidazol-2-ylmethyl]-N,N'-bis(2-pyridinylmethyl)-1,4-benzenedimethanamine

Example 161

AMD7251: N-(3-quinolylmethyl)-N'-(2-pyridinylmethyl)-N-(6,7,8,9-tetrahydro-5H-cyclohepta[b]pyridin-9-yl)-1,4-benzenedimethanamine

Example 162

AMD7252: N-(2-thiazolylmethyl)-N'-(2-pyridinylmethyl)-N-(6,7,8,9-tetrahydro-5H-cyclohepta[b]pyridin-9-yl)-1,4-benzenedimethanamine

Example 163

AMD7253: N-(4-pyridinylmethyl)-N'-(2-pyridinylmethyl)-N-(6,7,8,9-tetrahydro-5H-cyclohepta[b]pyridin-9-yl)-1,4-benzenedimethanamine

Example 164

AMD7254: N-[(5-benzyloxy)benzo[b]pyrrol-3-ylmethyl]-N,N'-bis(2-pyridinylmethyl)-1,4-benzenedimethanamine

Example 165

AMD7256: N-(1-methylpyrazol-2-ylmethyl)-N'-(2-pyridinylmethyl)-N-(6,7,8,9-tetrahydro-5H-cyclohepta[b]pyridin-9-yl)-1,4-benzenedimethanamine

Example 166

AMD7257: N-[(4-methyl)-1H-imidazol-5-ylmethyl]-N,N'-bis(2-pyridinylmethyl)-1,4-benzenedimethanamine

Example 167

AMD7259: N-[[(4-dimethylamino)-1-napthalenyl]methyl]-N,N'-bis(2-pyridinylmethyl)-1,4-benzenedimethanamine

Example 168

AMD7260: N-[1,5-dimethyl-2-phenyl-3-pyrazolinone-4-ylmethyl]-N,N'-bis(2-pyridinylmethyl)-1,4-benzenedimethanamine

Example 169

AMD7261: N-[1-[(1-acetyl-2-(R)-prolinyl]-4-piperidinyl]-N-[2-(2-pyridinyl)ethyl]-N'-(2-pyridinylmethyl)-1,3-benzenedimethanamine

Example 170

AMD7262: N-[1-[2-acetamidobenzoyl-4-piperidinyl]-4-piperidinyl]-N-[2-(2-pyridinyl)ethyl]-N'-(2-pyridinylmethyl)-1,3-benzenedimethanamine

Example 171

AMD7270: N-[(2-cyano-2-phenyl)ethyl]-N'-(2-pyridinylmethyl)-N-(6,7,8,9-tetrahydro-5H-cyclohepta[b]pyridin-9-yl)-1,4-benzenedimethanamine

Example 172

AMD7272: N-[(N''-acetyltryptophanyl)-4-piperidinyl]-N-[2-(2-pyridinyl)ethyl]-N'-(2-pyridinylmethyl)-1,3-benzenedimethanamine

Example 173

AMD7273: N-[(N''-benzoylvalinyl)-4-piperidinyl]-N-[2-(2-pyridinyl)ethyl]-N'-(2-pyridinylmethyl)-1,3-benzenedimethanamine

Example 174

AMD7274: N-[(4-dimethylaminophenyl)methyl]-N'-(2-pyridinylmethyl)-N-(6,7,8,9-tetrahydro-5H-cyclohepta[b]pyridin-9-yl)-1,4-benzenedimethanamine

Example 175

AMD7275: N-(4-pyridinylmethyl)-N'-(2-pyridinylmethyl)-N-(5,6,7,8-tetrahydro-8-quinolinyl)-1,4-benzenedimethanamine

Example 176

AMD7276: N-(1-methylbenzimadazol-2-ylmethyl)-N'-(2-pyridinylmethyl)-N-(6,7,8,9-tetrahydro-5H-cyclohepta[b]pyridin-9-yl)-1,4-benzenedimethanamine

Example 177

AMD7277: N-[1-butyl-4-piperidinyl]-N-[2-(2-pyridinyl)ethyl]-N'-(2-pyridinylmethyl)-1,3-benzenedimethanamine

Example 178

AMD7278: N-[1-benzoyl-4-piperidinyl]-N-[2-(2-pyridinyl)ethyl]-N'-(2-pyridinylmethyl)-1,3-benzenedimethanamine

Example 179

AMD7290: N-[1-(benzyl)-3-pyrrolidinyl]-N-[2-(2-pyridinyl)ethyl]-N'-(2-pyridinylmethyl)-1,3-benzenedimethanamine

Example 180

AMD7309: N-[(1-methyl)benzo[b]pyrrol-3-ylmethyl]-N-[2-(2-pyridinyl)ethyl]-N'-(2-pyridinylmethyl)-1,3-benzenedimethanamine

Example 181

AMD7311: N-[1H-imidazol-4-ylmethyl]-N-[2-(2-pyridinyl)ethyl]-N'-(2-pyridinylmethyl)-1,3-benzenedimethanamine

Example 182

AMD7359: N-[1-(benzyl)-4-piperidinyl]-N-[2-(2-pyridinyl)ethyl]-N'-(2

Example 183

AMD7374: N-[1-methylbenzimidazol-2-ylmethyl]-N-[2-(2-pyridinyl)ethyl]-N'-(2-pyridinylmethyl)-1,4-benzenedimethanamine

Example 184

AMD7379: N-[(2-phenyl)benzo[b]pyrrol-3-ylmethyl]-N-[2-(2-pyridinyl)ethyl]-N'-(2-pyridinylmethyl)-1,4-benzenedimethanamine

Example 185

AMD9025: N-[(6-methylpyridin-2-yl)methyl]-N'-(2-pyridinylmethyl)-N-(5,6,7,8-tetrahydro-8-quinolinyl)-1,4-benzenedimethanamine

Example 186

AMD9031: N-(3-methyl-1H-pyrazol-5-ylmethyl)-N'-(2-pyridinylmethyl)-N-(5,6,7,8-tetrahydro-8-quinolinyl)-1,3-benzenedimethanamine

Example 187

AMD9032: N-[(2-methoxyphenyl)methyl]-N'-(2-pyridinylmethyl)-N-(5,6,7,8-tetrahydro-8-quinolinyl)-1,3-benzenedimethanamine

Example 188

AMD9039: N-[(2-ethoxyphenyl)methyl]-N'-(2-pyridinylmethyl)-N-(6,7,8,9-tetrahydro-5H-cyclohepta[b]pyridin-9-yl)-1,3-benzenedimethanamine

Example 189

AMD9045: N-(benzyloxyethyl)-N'-(2-pyridinylmethyl)-N-(5,6,7,8-tetrahydro-8-quinolinyl)-1,3-benzenedimethanamine

Example 190

AMD9052: N-[(2-ethoxy-1-naphthalenyl)methyl]-N'-(2-pyridinylmethyl)-N-(5,6,7,8-tetrahydro-8-quinolinyl)-1,3-benzenedimethanamine

Example 191

AMD9053: N-[(6-methylpyridin-2-yl)methyl]-N'-(2-pyridinylmethyl)-N-(5,6,7,8-tetrahydro-8-quinolinyl)-1,3-benzenedimethanamine

Example 192

96-well plating procedure

Solutions of test compounds (20 µM) were prepared in acetonitrile/methanol (1:1) using a pump dispenser. 5 µmoles of each compound were then dispensed into a single well of a Costar 96-well plate by a Packard Multiprobe II-Ex Robotoc liquid handling system. The solvent was then removed under reduced pressure on a Savant Speed Vac for 12 hours at room temperature.

Example 193

Inhibition of Chemokine Induced Ca Flux Measured on a FLIPR (Molecular Devices)

Reagents:

Loading dye: Fluo-3, AM (Molecular Probes F-1241) is dissolved in anhydrous DMSO and stored frozen in aliquots. To increase the solubility of the dye in the loading medium, 10% (w/v) pluronic acid (Molecular Probes F-127) is added to the Fluo-3 stock solution immediately before use.

Flux Buffer:

HBSS +20 mM Hepes buffer +0.2% BSA, pH 7.4. HBSS 10× [(w/o phenol red and sodium bicarbonate (Gibco 14 065–049)]; Hepes buffer 1M (Gibco 15 630–056), BSA (Sigma A3675). The flux buffer is vacuum-filtered and stored refrigerated for a maximum of 5 days. Before use in the experiment, the buffer is warmed at 37° C. in a water-bath.

Antagonists:

The test compounds were diluted in flux buffer and added to 4 wells of a black microplate (4 parallel measurements per compound). The following control wells were used: 100% response control (no inhibition), flux buffer was added; 100% inhibition control: chemokine was added at 5-times the concentration required to induce a Ca flux.

Preparation of the Agonist (Chemokine) Plate

The chemokines are diluted in flux buffer to concentrations that are 4-fold higher than the desired concentrations required for stimulation of the cells (i.e. 2.5 nM for SDF-1α and 0.6 nM for RANTES). The chemokines were added to untreated 96well Sero well compound plates (International Medical, Sterilin code 611F96). In the negative control well's (baseline monitoring), flux buffer is added instead of chemokine. As a positive control to check for dye loading efficiency, 20 µM digitonin (final concentration) was also included. The agonist plate was incubated in the FLIPR (37° C.) for 15–30 min.

Cell Loading Protocol for Measuring Inhibition of SDF-1α Induced Ca flux in SUP-T1 Cells.

SUP-T1 cells were centrifuged at room temperature (RT) and re-suspended in loading medium (RPMI-1640 containing 2% FBS and 4 µM Fluo-3, AM). The cells were incubate at room temperature for 45 min. then washed twice in flux buffer then incubated in flux buffer at room teperature for 10 min. The cells were centrifuged and re-suspended in flux buffer at a density of 3×10$^6$ cells per mL. A 100 µL aliquot of the cell suspension (3×10⁵ cells) was added to each well of a black microplate (Costar 3603), which already contains 50 μL of a solution of the test compound (at concentrations that are 3-fold higher than the desired final compound concentrations). The microplate is then gently centrifuged at room temperature. Homogeneous spreading of the cells on the bottom of the microplate wells was then confirmed with a microscope and the microplate was incubated in the FLIPR (37° C.) for 10 min. prior to testing.

Fluorescence Measurements as a Function of Time on the FLIPR

The FLIPR settings (camera exposure time and laser power) are adjusted to obtain initial fluorescence values between 8,000 and 10,000 units. After monitoring a 20 second-baseline, the agonist (chemokine) (50 μL) is added by automatic pipettor with black pipette tips. Fluorescence is measured simultaneously in all wells of the microplate every 2 seconds (first 2 min) and thereafter every 6 seconds (additional 2 min). The average ca-flux measured in each set of 4 identical wells (one test compound) was calculated by the FLIPR software.

The compounds of the current invention were tested for inhibition of SDF-1α induced Ca flux in SUP-T1 cells using the method described above. The following compounds inhibited SDF-1α induced Ca flux greater than 20% at 20 μg/mL:

Example numbers: 7, 8, 9, 10, 12, 15, 16, 17, 18, 20, 22, 23 (both isomers), 24, 26, 28, 29, 30, 31, 35, 37, 41, 43, 45, 47, 48, 49, 50, 51, 52, 53, 55, 60, 66, 72, 73, 75, 76, 77, 79, 82, 84, 85, 86, 88, 89, 92, The following compounds inhibited SDF-1α induced Ca flux greater than 20% at 20 μM:

Example numbers: 97, 98, 129, 130, 131, 133, 135, 136, 142, 145, 146, 147, 150, 160, 164, 166, 167, 168, 169, 170, 172, 177, 178, 180, 182, 183, 184.

Example 194

Cell Loading Protocol for Measuring Inhibition of RANTES Induced Ca Flux in U87.CCR5 Cells U87.CCR5 cells were seeded into the black microplates (Costar 3603) on the day before the experiment. The culture medium was removed from the cells and 100 μL of loading medium (DMEM+10% FBS+4 μM Fluo-3, AM) was added to each well and the plate was incubate at 37° C. for 45 min. The loading medium was then removed an the cells were washed twice with flux buffer using the CELLWASH microplate washer (Labsystems) followed by incubation in flux buffer for 10 min. at room temperature (the washing procedure was repeated twice). Finally, the wash buffer was removed from the microplate wells and 150 μL of the test compound, diluted in flux buffer to the desired concentration. The microplate was then incubated in the FLIPR drawer for 10 min. prior to testing. Measurements were performed as described above.

The compounds of the current invention were tested for inhibition of RANTES induced Ca flux in U87.CCR5 cells. The following compounds inhibited RANTES induced Ca flux greater than 20% at 20 μg/mL:

Example numbers: 5, 6, 7, 8, 11, 16, 22, 24, 25, 30, 38, 44, 47, 49, 50, 52, 67, 68, 71, 73, 76, 77.

The following compounds inhibited RANTES induced Ca flux greater than 20% at 20 μM.

Example numbers: 108, 109, 114, 118, 168, 170, 179.

Example 195

Assay for Inhibition of HIV-1 (NL4.3) Replication in MT-4 Cells

Inhibition of HIV-1 NL4.3 (or III$_B$) replication assays were performed as previously described (Bridger et al. J. Med. Chem. 1999, 42, 3971–3981; De Clercq et al. Proc. Natl. Acad. Sci, 1992, 89, 5286–5290; De Clercq et al. Antimicrob. Agents Chemother. 1994, 38, 668–674; Bridger et al. J. Med. Chem. 1995, 38, 366–378). Anti-HIV activity and cytotoxicity measurements were carried out in parallel. They were based on the viability of MT-4 cells that had been infected with HIV in the presence of various concentrations of the test compounds. After the MT-4 cells were allowed to proliferate for 5 days, the number of viable cells was quantified by a tetrazolium-based colorimetric 3-(4,5-dimethylthiazol-2-yl)-2,5-diphenyltetrazolium bromide (MTT) procedure in 96-well microtrays. In all of these assays, viral input (viral multiplicity of infection, MOI) was 0.01, or 100 times the 50% cell culture infective dose (CCID$_{50}$). The EC$_{50}$ was defined as the concentration required to protect 50% of the virus-infected cells against viral cytopathicity.

When compounds of the current invention were tested for inhibition of HIV-1 NL4.3 or III$_B$ replication in MT-4 cells, the following compounds exhibited EC$_{50}$'s of less than 20 μg/mL:

Examples numbers: 1, 2, 3, 4, 6, 7, 8, 11, 12, 13, 14, 15, 16, 17, 18, 19, 20, 21, 23 (both isomers), 24, 28, 29, 30, 32, 33, 34, 35, 36, 37, 38, 39, 40, 41, 42, 43, 44, 45, 47, 48, 49, 50, 51, 52, 53, 55, 58, 61, 66, 67, 68, 69, 70, 71, 84, 85, 86, 88, 89, 91, 92.

When compounds of the current invention were tested for inhibition of HIV-1 NL4.3 or III$_B$ replication in MT-4 cells, the following compounds exhibited EC$_{50}$'s of less than 20 μM:

Example numbers: 95, 96, 101, 102, 103, 105, 112, 113, 115, 116, 119, 121, 123, 124, 125, 126, 137, 138, 139, 140, 141, 144, 151, 153, 157, 158, 166, 170, 171, 176.

Example 196

Assay for Inhibition of HIV-1 (BaL) Replication in PBMC's

When compounds of the current invention were tested for inhibition of HIV-1 BaL (CCR5 using) replication in PHA-stimulated PBMC's (peripheral blood mononuclear cells) using the MTT assay, the following compounds exhibited EC$_{50}$'s of less than 20 μg/mL:

Example numbers: 5, 8, 11, 12, 13, 14, 17, 29, 30, 32, 33, 34, 36, 37, 42, 43, 58, 66, 71, 88, 91.

TABLE 3

| | |
|---|---|
| EXAMPLE 197 AMD7074: | 1-[[4-[[(2- pyridinylmethyl)amino]-methyl]phenyl]methyl]guanidine |
| EXAMPLE 198 AMD7076: | N-(2-pyridinylmethyl)-N-(8-methyl-8-azabicyclo[3.2.1]octan-3-yl)-1,4-benzenedimethanamine |
| EXAMPLE 199 AMD7078: | 1-[[4-[[(2-pyridinylmethyl)amino]-methyl]phenyl]methyl]homopiperazine |
| EXAMPLE 200 AMD7079: | 1-[[3-[[(2-pyridinylmethyl)amino]-methyl]phenyl]methyl]homopiperazine |
| EXAMPLE 201 AMD7103 and 7104: | trans and cis-1-[[4-[[(2-pyridinylmethyl)amino]methyl]phenyl]methyl]-3,5-piperidinediamine |
| EXAMPLE 202 AMD3597: | N,N'-[1,4-Phenylenebis(methylene)]bis-4-(2-pyrimidyl) piperazine |

TABLE 3-continued

| EXAMPLE 203 AMD3602: | 1-[[4-[[(2-pyridinylmethyl)amino]-methyl]phenyl]methyl]-1-(2-pyridinyl)-methylamine |
| --- | --- |
| EXAMPLE 204 AMD3667: | 2-(2-pyridinyl)-5-[[(2-pyridinylmethyl)-amino]methyl]-1,2,3,4-tetrahydroisoquinoline. |
| EXAMPLE 205 AMD7428: | 1-[[4-[[(2-pyridinylmethyl)amino]-methyl]phenyl]methyl]-3,4-diaminopyrrolidine |
| EXAMPLE 206 AMD7485: | 1-[[4-[[(2-pyridinylmethyl)amino]-methyl]phenyl]methyl]-3,4-diacetylaminopyrrolidine |
| EXAMPLE 207 AMD8665: | 8-[[4-[[(2-pyridinylmethyl)amino]-methyl]phenyl]methyl]-2,5,8-triaza-3-oxabicyclo[4.3.0]nonane |
| EXAMPLE 208 AMD8773: | 8-[[4-[[(2-pyridinylmethyl)amino]-methyl]phenyl]methyl]-2,5,8-triazabicyclo-[4.3.0]nonane |

Example 197

AMD7074: Preparation of 1-[[4-[[(2-pyridinylmethyl)amino]methyl]phenyl]methyl]guanidine (hydrobromide salt)

α-Bromo-p-toluamide

α-Bromo-p-toluic acid (8.00 g, 37.2 mmol) was stirred as a suspension in $CCl_4$ (80 mL) while thionyl chloride (6.8 mL, 93 mmol) was added. The mixture was heated at reflux under nitrogen atmosphere for 95 h., then concentrated in vacuo. The residue was dissolved in $CH_2Cl_2$ (150 mL), and $NH_3$(g) was passed through the solution for 10 min, giving a light yellow precipitate. 5% $NaHCO_3$(aq) (70 mL) was added, the mixture was stirred vigorously, and the precipitate was collected by filtration. The precipitate was washed with $H_2O$ and dried at 60° C. under reduced pressure to give a colourless solid (7.35 g, 92%).

N-(Diethoxyphosphoryl)-2-(aminomethyl)pyridine.

A solution of 2-(aminomethyl)pyridine (8.03 g, 74.3 mmol) and $Et_3N$ (13.50 mL, 96.86 mmol) in $CH_2Cl_2$ (60 mL) was stirred at room temperature while a solution of diethyl chlorophosphate (Dep-Cl) (14.09 g, 81.66 mmol) in $CH_2Cl_2$ (30 mL) was added dropwise. The mixture was heated to reflux for 21 h, allowed to cool, then washed with $H_2O$ (50 mL). The aqueous phase was extracted with $CH_2Cl_2$ (20 mL), and the combined organic phases were dried ($MgSO_4$) and concentrated in vacuo. Diethyl ether (100 mL) was added to the residue giving a white precipitate, which was removed by filtration, and the filtrate was then concentrated in vacuo to give the product as an orange oil (18.04 g, 100%).

A solution of N-(diethoxyphosphoryl)-2-(aminomethyl)pyridine (7.45 g, 30.5 mmol) in DMF (70 mL) was treated with 95% NaH (0.96 g, 38 mmol) and stirred under nitrogen atmosphere at room temperature for 10 min. A solution of α-bromo-p-toluamide (6.40 g, 29.9 mmol) in DMF (30 mL) was added in one portion, and the solution was stirred for 1 h. The solution was concentrated in vacuo and the residue was partitioned between 5% aqueous $NaHCO_3$ (25 mL) and EtOAc (100 mL). The organic phase was washed with 5% $NaHCO_3$ (25 mL). The combined aqueous phases were extracted with EtOAc (25 mL). The combined organic phases were washed with brine (5×25 mL), then dried ($MgSO_4$) and concentrated in vacuo to give the amide as a yellow oil (9.71 g, 86%).

1-[4-[[(2-pyridinylmethyl)amino]methyl]phenyl]methylamine

A 1.0 M $BH_3$.THF solution (150 mL, 150 mmol) was added to the amide (8.85 g, 23.5 mmol), and the solution was heated at reflux under nitrogen atmosphere for 3.5 h, then concentrated in vacuo. MeOH (50 mL) was added to the residue, then removed in vacuo (3×). Ethylene diamine (20 mL) was added to the residue, and the solution was stirred at 60° C. for 1 h. The solution was diluted with $CHCl_3$ (150 mL) and washed with $H_2O$ (4×200 mL), then dried ($MgSO_4$) and concentrated in vacuo. The residue was purified by column chromatography on basic alumina (2% MeOH/$CH_2Cl_2$) to give the title amine as a light yellow oil (3.03 g, 36%).

A heterogeneous mixture of the amine (140 mg, 0.385 mmol), 1H-pyrazole-1-carboxanidine hydrochloride (55 mg, 0.38 mmol), and DIEA (0.067 mL, 0.38 mmol) in THF (0.19 mL) was stirred at room temperature under nitrogen atmosphere for 2 hours. Diethyl ether (5 mL) was added to the mixture, then decanted (4×) to give a colourless oil that was dried in vacuo at room temperature to give the corresponding guanidine hydrochloride salt (170 mg, 100%).

Using general procedure D: A solution of the hydrochloride salt (170 mg, 0.38 mmol) was converted to the corresponding hydrobromide salt as a white solid (143 mg, 65% overall yield from the amine): $^1$H NMR ($D_2O$) δ 4.44 (s, 2H), 4.47 (s, 2H), 4.63 (s, 2H), 7.43 (d, 2H, J=8.1), 7.52 (d, 2H, J=8.3), 7.90 (m, 2H), 8.39 (m, 1H), 8.76 (m, 1H). FAB-MS 270 (M+H). Anal. Calcd for $C_{15}H_{19}N_5$.3.0HBr.0.8AcOH.0.8$H_2O$ (574.54): C, 34.70; H, 4.70; N, 12.19; Br, 41.72.

Found: C, 34.66; H, 4.73; N, 12.17; Br, 41.82.

Example 198

AMD7076: Preparation of N-(2-pyridinylmethyl)-N-(8-methyl-8-azabicyclo[3.2.1]octan-3-yl)-1,4-benzenedimethanamine (hydrobromide salt)

Tropinone Oxime

A heterogeneous mixture of tropinone (7.07 g, 50.8 mmol), hydroxylamine hydrochloride (3.53 g, 50.8 mmol), and pyridine (8.20 mL, 101 mmol) in EtOH (100 mL) were heated at reflux for 50 min. The mixture was slightly cooled, treated with $K_2CO_3$ (21.24 g, 153.7 mmol) and $H_2O$ (30 mL), then concentrated in vacuo. The residue was diluted with $H_2O$ (30 mL), then extracted with $CHCl_3$ (3×50 mL). The combined organic extracts were dried ($MgSO_4$) and concentrated in vacuo. The residue was recrystallized from 4:6 EtOAc/petroleum ether to give colourless crystals (5.18 g, 66%).

exo-Tropylamine (beta-tropylamine)

A solution of tropinone oxime (5.17 g, 33.5 mmol) in 1-pentanol (170 mL) was heated at 130° C. under nitrogen atmosphere and a reflux condenser while sodium (5.28 g, 230 mmol) was added portionwise over 1 hours. The solution was allowed to cool to room temperature and stirring was continued for a further 17 hours. The solution was acidified with 6 M HCl (112 mL) and extracted with EtOAc (1×240 mL, 3×120 mL). The aqueous solution was basified to pH 14 using NaOH, then extracted with EtOAc (6×120 mL). The combined organic extracts were dried ($K_2CO_3$) and concentrated in vacuo to give the amine as a yellow oil (3.49 g, 74%).

A solution of exo-tropylamine (596 mg, 4.25 mmol) and N-[1-methylene-4-(carboxaldehyde)phenylene]-N-(2-nitrobenzenesulfonyl)-2-(aminomethyl)pyridine (1.74 g, 4.23 mmol) in MeOH (20 mL) was heated at reflux under nitrogen atmosphere for 2.5 hours. The solution was allowed to cool to 60° C. and NaBH$_3$CN (1.37 g, 21.8 mmol) was added, and the solution was stirred at 60° C. for 24 hours. The solution was concentrated in vacuo, and the residue was partitioned between CH$_2$Cl$_2$ (25 mL) and brine (25 mL). The aqueous phase was extracted with CH$_2$Cl$_2$ (2×25 mL), and the combined organic phases were dried (MgSO$_4$) and concentrated in vacuo to give a yellow solid (2.17 g, 96%).

The solid from above was dissolved in Et$_3$N (2.30 mL, 16.5 mmol) and CH$_2$Cl$_2$ (20 mL) and 2-nitrobenzenesulfonyl chloride (2.68 g, 12.1 mmol) was added in one portion. The mixture was heated to reflux under nitrogen for 21 hours. Further portions of 2-nitrobenzenesulfonyl chloride (2.68 g, 12.1 mmol) and Et$_3$N (2.30 mL, 16.5 mmol) were added to the solution, and heating was continued for an additional 24 hours. The solution was diluted with CH$_2$Cl$_2$ (30 mL) and washed with H$_2$O (50 mL). The aqueous phase was extracted with CH$_2$Cl$_2$ (3×50 mL), and the combined organic phases were washed with brine (4×50 mL), then dried (MgSO$_4$) and concentrated in vacuo. The residue was purified by chromatography on silica gel using 10% MeOH/CH$_2$Cl$_2$ to give a yellow solid (513 mg, 18%).

Using general procedures C and D: the intermediate from above (252 mg, 0.350 mmol) was reacted with thiophenol (0.22 mL, 2.1 mmol) and K$_2$CO$_3$ (390 mg, 2.82 mmol) in CH$_3$CN (3.5 mL) and the mixture was heated at 50° C. under nitrogen atmosphere for 22 hours. The insoluble material was removed by filtration and washed with CH$_2$Cl$_2$. The filtrate was concentrated in vacuo, and the residue was purified by chromatography on basic alumina using CH$_2$Cl$_2$ and 10% MeOH/CH$_2$Cl$_2$ to give a yellow oil (87 mg, 71%). Conversion to the hydrobromide salt using a saturated solution of HBr in methanol followed by drying of the solid at 60° C. under reduced pressure for 87 hours gave AMD7076 as beige solid (99 mg, 58%). $^1$H NMR (D$_2$O) δ 2.06–2.51 (m, 8H), 2.82 (s, 3H), 3.84 (m, 1H), 4.11 (br s, 2H), 4.34 (s, 2H), 4.46 (s, 2H), 4.60 (s, 2H), 7.59 (s, 4H), 7.82 (m, 2H), 8.29 (m, 1H), 8.74 (m, 1H). FAB-MS m/z 351 (M+H). Anal. Calcd for C$_{22}$H$_{30}$N$_4$.4.0HBr.2.1H$_2$O (711.99): C, 37.11; H, 5.41; N, 7.87; Br, 44.89. Found: C, 37.19; H, 5.48; N, 7.79; Br, 44.90.

Example 199

AMD7078: Preparation of 1-[[4-[[(2-pyridinylmethyl)amino]methyl]phenyl]methyl]homopiperazine (hydrobromide salt)

A mixture of K$_2$CO$_3$ (388.4 mg, 2.18 mmol), N-[1-methylene-4-(chloromethylene)phenylene]-N-(2-nitrobenzenesulfonyl)-2-(aminomethyl)pyridine (Bridger et al. U.S. patent application Ser. No. 09/111/895) (404.6 mg, 0.937 mmol) and homopiperazine (281.5 mg, 2.18 mmol) in CH$_3$CN (25 mL) was heated to reflux with stirring overnight. The solvent was evaporated and the residue was partitioned between saturated aqueous NaHCO$_3$ and CH$_2$Cl$_2$. The aqueous phase was separated and extracted with CH$_2$Cl$_2$ and the combined organic extracts were dried (MgSO$_4$) and evaporated. The residue was purified by column chromatography on silica gel (40:2:1 or 20:2:1 CHCl$_3$/MeOH/NH$_4$OH) to give the title compound (352.3 mg, 76%). $^1$H (CDCl$_3$) δ 8.40 (d, 1H, J=6 Hz), 7.98 (d, 1H, J=9 Hz), 7.66 (m, 1H), 7.54 (m, 2H), 7.20 (m, 3H), 7.09 (m, 3H), 4.61 (s, 2H), 4.59 (s, 2H), 3.58 (s, 2H), 2.72–2.68 (m, 2H), 2.51 (s, 2H), 1.70–1.56 (m, 6H).

Using general procedures C and D: the intermediate from above gave AMD7078. $^1$H NMR (D$_2$O) δ 8.75 (d, 1H, J=5 Hz), 8.33 (t, 1H, J=8 Hz), 7.90–7.81 (m, 2H), 7.64–7.61 (m, 4H), 4.63 (s, 2H), 4.54 (s, 2H), 4.49 (s, 2H), 3.79–3.72 (m, 4H), 3.56–3.49 (m, 4H), 2.33–2.29 (m, 2H). $^{13}$C NMR (D$_2$O): δ 147.6, 146.7, 143.9, 132.9, 132.6, 131.5, 130.5, 126.9, 126.8, 61.0, 54.3, 51.3, 50.3, 49.1, 45.1, 41.0, 21.0. ES-MS m/z 311 (M+H). Anal. calcd. for C$_{19}$H$_{26}$N$_4$●4HBr●1.2HOAc●0.7 H$_2$O: C 35.76, H 5.08, N 7.79, Br 44.47; found C 35.71, H 5.40, N 7.74, Br 44.56.

Example 200

AMD7079: Preparation of 1-[[3-[[(2-pyridinylmethyl)amino]methyl]phenyl]methyl]homopiperazine (hydrobromide salt)

Using identical procedures to those described in Example 199, N-[1-methylene-3-(chloromethylene)phenylene]-N-(2-nitrobenzenesulfonyl)-2-(aminomethyl)pyridine gave AMD7079. $^1$H NMR (D$_2$O) δ 8.72 (d, 1H, J=5 Hz), 8.24 (t, 1H, J=8 Hz), 7.83–7.74 (m, 2H), 7.66–7.60 (m, 4H), 4.59 (s, 2H), 4.54 (s, 2H), 4.48 (s, 2H), 3.76–3.69 (m, 4H), 3.61–3.48 (m, 4H), 2.30–2.28 (m, 2H). $^{13}$C NMR (D$_2$O): δ 147.9, 147.0, 142.5, 132.8, 132.7, 132.1, 131.6, 130.6, 126.5, 126.1, 126.0, 60.7, 53.8, 50.9, 49.9, 49.2, 44.7, 40.6, 20.7. ESMS: 311 (M+H). Anal calcd for C$_{19}$H$_{26}$N$_4$●4HBr●1.0C$_4$H$_8$O$_2$●2.3H$_2$O: C 36.18, H 5.62, N 7.34, Br 41.85. Found: C 36.25, H 5.63, N 7.34, Br 41.85.

Example 201

AMD7103 and 7104: Preparation of trans and cis-1-[[4-[[(2-pyridinylmethy)amino]methyl]phenyl]methyl]-3,5-piperidinediamine (hydrobromide salts)

3,5-Diaminopyridine

2-Chloro-3,5-dinitropyridine (4.98 g, 24.46 mmol) was dissolved in ethanol (500 mL) and 5% palladium on carbon (3.74 g, 0.75 g/g substrate) was added. The mixture was hydrogenated at 25° C. under 50 psi of hydrogen for 18 hrs. The mixture was filtered through celite to remove the catalyst and concentrated under reduced pressure. Purification (silica gel, 20:2:1 CHCl$_3$/MeOH/NH$_4$OH, followed by 12:2:1 CHCl$_3$/MeOH/NH$_4$OH) gave 3,5-diaminopyridine (2.27 g, 85%) as a brown solid. $^1$H (CD$_3$OD) δ 7.32 (d, 2H, J=2 Hz), 6.45–6.43 (m, 1H). 3,5-bis(ethoxycarbonylamino)pyridine 3,5-diaminopyridine (381.4 mg, 3.49 mmol) was dissolved in anhydrous 1,4-dioxane (6 mL) and K$_2$CO$_3$ (1.45 g, 10.5 mmol) was added, followed by ethyl chloroformate (1.0 mL, 10.5 mmol). The thick slurry was heated at reflux for 22 hrs. The solvent was removed under reduced pressure, the residue was taken up in methanol and filtered through celite. Purification (silica gel, 9:1 CH$_2$Cl$_2$/MeOH) gave the bis-carbamate (608 mg, 69%) as a light brown solid. $^1$H (CD$_3$OD) δ 8.37 (s, 2H), 8.28–8.27 (m, 1H), 4.22 (q, 4H, J=7 Hz), 1.31 (t, 6H, J=7 Hz). Cis and trans-3,5-bis(ethoxycarbonylamino)piperidine.

The compound from above (5.09 g, 20.1 mmol) was dissolved in glacial acetic acid (200 mL) and concentrated HCl (1.65 mL, 20.1 mmol) was added. After agitation of the solution, Platinum(IV) Oxide (1.60 g, 7.04 mmol) was added and the mixture was hydrogenated at 25° C. under 50 psi of hydrogen for 41 hrs. The solution was then heated to 50° C. and hydrogenated under 50 psi for an additional 20 hrs. An additional batch of the above intermediate (1.10 g, 4.34 mmol) was reduced by hydrogenating at 50° C. under 50 psi of hydrogen pressure for 22 hrs. The two batches were combined, filtered through celite and concentrated. The HCl salt was converted to the free base by stirring with $K_2CO_3$ (500 mg) in MeOH (50 mL). $^1$H NMR analysis of the crude product indicated a ~80:20 trans to cis mixture of piperidines. The two isomers were separated by column chromatography (silica gel, 20:2:1 $CHCl_3$/MeOH/$NH_4OH$) to give the trans product (1.67 g, 26%) and cis product (205.5 mg, 3%).

trans-3,5-bis(ethoxycarbonylamino)piperidine: $^1$H ($CD_3OD$) δ 4.09 (q, 4H, J=7 Hz), 3.58–3.48 (m, 2H), 3.05 (dd, 2H, J=12 Hz, 3 Hz), 2.18 (t, 3H, J=12 Hz), 1.22 (t, 5 H, J=7 Hz).

cis-3,5-bis(ethoxycarbonylamino)piperidine. $^1$H ($CD_3OD$) δ 4.07 (q, 4H, J=7 Hz), 3.73–3.66 (m, 2H), 2.87 (dd, 2H, J=13 Hz, 3 Hz), 2.63–2.56 (m, 2H), 1.79 (t, 2H, J=6 Hz), 1.24 (t, 5 H, J=7 Hz).

The intermediates from above were reacted with the intermediate and conditions described in Example 199. Using general procedures C and D: the nosyl group was deprotected with thiophenol and the corresponding amine intermediate was converted to the hydrobromide salt (HBr/acetic acid, 50° C.) with simultaneous deprotection of the ethoxycarbonyl groups to give the following compounds:

AMD7 103: trans-1-[[4-[[(2-pyridinylmethyl)amino]methyl]phenyl]methyl]-3,5-piperidinediamine (hydrobromide salt). $^1$H NMR ($D_2O$) δ 8.78 (d, 1H, J=5 Hz), 8.38 (t, 1H, J=7 Hz), 7.96–7.86 (m, 2H), 7.65 (s, 4H), 4.65 (s, 2H), 4.56 (s, 2H), 4.50 (s, 2H), 3.85–3.75 (m, 4H), 3.20 (t, 2H, J=10 Hz), 2.69 (d, 1H, J=12 Hz), 1.95 (q, 1H, 12 Hz). $^{13}$C NMR ($D_2O$) δ 147.3, 146.4, 144.5, 132.9, 132.7, 131.5, 130.4, 127.2, 127.2, 61.5, 51.8, 51.4, 49.0, 44.0, 30.9. ES-MS m/z 326 (M+H).

AMD7 104: cis-1-[[4-[[(2-pyridinylmethyl)amino]methyl]phenyl]methyl]-3,5-piperidinediamine (hydrobromide salt). $^1$H NMR ($D_2O$): δ 8.73 (d, 1H, J=5 Hz), 8.27 (t, 1H, J=7 Hz), 7.85–7.63 (m, 2H), 7.52 (s, 4H), 4.79 (s, 2H), 4.56 (s, 2H), 4.43 (s, 2H), 3.83–3.78 (m, 2H), 3.03 (d, 2H, J=11 Hz), 2.81–2.75 (m, 2H), 2.17 (t, 1H, J=6 Hz). $^{13}$C NMR ($D_2O$)δ 150.5, 149.5, 145.8, 140.1, 133.4, 133.3, 133.0, 129.2, 129.1, 63.6, 56.3, 53.9, 51.6, 47.4, 32.6. ES-MS m/z 326 (M+H). Anal. calcd. for $C_{19}H_{27}N_5$•.5.6HBr•0.2$H_2O$: C 29.18, H 4.25, N 8.95, Br 57.21; found C 29.36, H 4.61, N 8.76, Br 57.04.

Example 202

AMD3597: Preparation of N,N'-[1,4-Phenylenebis(methylene)]bis-4-(2-pyrimidyl)piperazine (hydrobromide salt)

Reaction of α,α'-dibromo-p-xylene with 1-(2-pyrimidyl)piperazine dihydrochloride and potassium carbonate in acetonitrile in a similar manner to example 199, followed by conversion to the corresponding hydrobromide salt using general procedure D gave AMD3597. $^1$H NMR ($D_2O$) δ 2.80–3.70 (m, 16H), 4.32 (s, 4H), 6.79 (m, 2H), 7.50 (s, 4H), 8.38 (m, 4H); $^{13}$C NMR ($D_2O$) δ 41.92, 50.57, 60.13, 111.46, 130.29, 132.51, 153.94, 157.36. FAB-MS m/z 431 (M+H). Anal. Calcd for $C_{24}H_{30}N_8$.4HBr.2.5$H_2O$: C, 36.07; H, 4.92; N, 14.02; Br, 39.99. Found C, 36.04; H, 4.80; N, 13.91; Br, 39.94.

Example 203

AMD3602: Preparation of 1-[[4-[[(2-pyridinylmethyl)amino]methyl]phenyl]methyl]-1-(2-pyridinyl)methylamine (hydrochloride salt)

To a stirred solution of p-tolylmagnesium bromide (1.0 M solution in ether, 98 mL, 0.098 mol) cooled to 0° C. was added 2-cyanopyridine (5.1 g, 0.04 mol) in ether (90 mL) and the mixture was heated to reflux for 40 hours. The reaction was allowed to cool to room temperature then quenched with a mixture of concentrated sulfuric acid/water (1:1, 30 mL). The mixture was stirred for twenty minutes and the ether layer was separated. The aqueous phase was made basic with aqueous 10 N NaOH (to pH 8) then extracted with $CH_2Cl_2$. The combined organic extracts were dried (MgSO$_4$) and evaporated to give the crude product as a yellow oil (6.69 g, 69%). This was used without further purification in the next step.

To the ketone from above (2.02 g, 0.01 mol) in a mixture of t-butanol (60 mL) and water (20 mL) was added KMnO4 (16.2 g, 0.1 mol) and the mixture was heated to reflux for 48 hours. The reaction mixture was filtered (hot) through celite, and the celite was washed with hot water and t-butanol. The combined filtrates were concentrated to small volume and extracted with dichloromethane. The aqueous phase was then acidified to pH4 during which time a white solid precipitated. The solid was collected by filtration, washed with water then dried in vacuo to give the corresponding acid (1.69 g, 73%) as a white powder.

To a stirred solution of the acid from above (7.07 g, 0.03 mol) in DMF (80 mL), cooled to 0° C. was added hydroxybenzotriazole (4.21 g, 0.03 mol) and 2-(aminoethyl)pyridine (3.72 mL, 0.03 mol) followed by diisopropylcarbodiimide (4.88 mL, 0.03 mol) and the mixture was stirred at 4° C. for 48 hours. The reaction mixture was evaporated and the residue was suspended in water and acidified to pH1 with aqueous HCl. The aqueous layer was extracted with $CH_2Cl_2$ (6×100 mL) then made basic with 1N NaOH to pH 8. The basic phase was extracted with $CH_2Cl_2$ (6×100 mL) and the combined organic phases were dried (MgSO$_4$) and evaporated to give the crude product as a white solid (5.12 g).

To a solution of the ketone from above (2.55 g, 7.7 mmol) in ethanol (60 mL), water (17 mL) and pyridine (0.03 mol, 2.5 mL) was added hydroxylamine hydrochloride (2.14 g, 0.03 mol) and the mixture was heated to reflux for 2 hours. The reaction mixture was allowed to cool to room temperature during which time a white solid precipitated. The solid was collected by filtration, re-crystallized from ethanol/water and dried in vacuo to give the corresponding oxime (2.12 g).

The oxime (2.0 g, 5.8 mmol) was dissolved in ethanol (140 mL) and methanol (120 mL) containing Pd/C (Aldrich, 10%; 1.0 g) and the mixture was hydrogenated at 50 psi overnight. The mixture was filtered through celite and concentrated to give the amine as a white solid (1.88 g).

The amine (0.5 g, 1.51 mmol) was dissolved in anhydrous THF (15 mL) and a solution of BH$_3$.THF was added (Aldrich, 1.0 M solution in THF, 10 equivalents, 15.05 mL) and the mixture was heated to reflux with stirring overnight. The mixture was allowed to cool to room temperature and evaporated. Anhydrous methanol was added (10 mL) and the mixture was evaporated (repeated 4 times). The residue was dissolved in ethylenediamine (10 mL) and the mixture was heated to 100° C. overnight. Upon cooling, water (10 mL) was added and the solution was extracted with $CH_2Cl_2$ (3×). The combined organic extracts were dried (MgSO$_4$) and evaporated to give an oil (0.205 g).

A portion of the crude product (140 mg) was purified by column chromatography on silica gel (93:7:1, CH$_2$Cl$_2$MeOH/NH$_4$OH) to give a light yellow oil (100 mg). The oil was dissolved in ethanol and HCl(g) was passed through to give a precipitate which was collected by filtration. Trituration of the filtrate with ether gave a second crop of product (30 mg). The solids were combined and dried in vacuo to give AMD3602 as a pink solid (115 mg). $^1$H NMR (D$_2$O) δ 3.20–3.50 (m, 4H), 4.18 (s, 2H), 5.66 (s, 1H), 7.25–7.38 (m, 6H), 7.60–7.80 (m, 3H), 8.35 (m, 1H), 8.44 (m, 1H), 8.53 (m, 1H). FAB-MS m/z 319 (M+H, 100). Anal. Calcd for C$_{20}$H$_{22}$N$_4$.4HCl.0.6EtOH: C, 51.76; H, 6.06; N, 11.39. Found C, 52.16; H, 6.23; N, 11.73.

Example 204

AMD3667: Preparation of 2-(2-pyridinyl)-5-[[(2-pyridinylmethyl)amino]methyl]-1,2,3,4-tetrahydroisoquinoline (hydrobromide salt)

2-(3-hydroxyphenyl)ethylamine hydrochloride

To a stirred solution of 2-(3-methoxyphenyl)ethylamine (10.0 g, 66.2 mmol) in dry CH$_2$Cl$_2$ (100 mL) at −78° C. was added a 1M solution of BBr$_3$ in CH$_2$Cl$_2$ (200 mL, 3 eq.) and the solution was allowed to slowly warm to RT. After stirring for 3 h at RT the resulting precipitate was filtered off, washed with CH$_2$Cl$_2$ (200 mL) and dried. The off-white solid was dissolved in cold H$_2$O (50 mL) and the insoluble material was filtered off. The acidic filtrate (pH 1.2) was made basic (pH 13.0) with 10 N NaOH and the resulting yellow solution was extracted with ether (100 mL) and the organic layer was discarded. The aqueous layer was re-acidified with conc. HCl to pH 1.5 and then made alkaline (pH 9–10) with conc. NH$_4$OH. The aqueous layer was then extracted with n-butanol (2×150 mL), dried (K$_2$CO$_3$) and concentrated to dryness to afford a viscous oil. The oily residue was then dissolved in MeOH (10 mL) and a solution of saturated HCl/MeOH was added. The solution was concentrated to small volume and ether was added to give a precipitate. The ether was decanted off to afford the desired compound as an off white solid (6.5 g, 57%). $^1$H NMR (D$_2$O) 2.79 (t, 2H, J=7.2 Hz), 3.08 (t, 2H, J=7.2 Hz), 6.60–6.78 (m, 3H), 7.11 (t, 1H, J=7.7 Hz).

To a stirred solution of 2-(3-hydroxyphenyl)ethylamine hydrochloride (4.0 g, 23.1 mmol) in ethanol (50 mL) under argon at room temperature was added Et$_3$N (23.2 g, 231 mmol) followed by pyridine-2-carboxaldehyde (2.47 g, 23.1 mmol) and the solution was stirred at 40° C. for 16 h. The mixture was concentrated to dryness and the residue was purified by column chromatography on silica gel (CH$_2$Cl$_2$/MeOH/NH$_4$OH; 90:10:1) to afford the crude product. The crude was re-purified by chromatography on silica gel (CH$_2$Cl$_2$/MeOH/NH$_4$OH; 95:5:0.5) to afford the desired product (580 mg, 11%) as a pale yellow solid. $^1$H NMR (CDCl$_3$) 2.59 (dt, 1H, J=16.5, 4.2 Hz), 2.75–2.89 (m, 1H), 2.94–3.06 (m, 1H), 3.20 (dt, 1H, J=12.4, 5.0 Hz), 5.16 (s, 1H), 6.11 (d, 1H, J=1.9 Hz), 6.60–6.52 (m, 2H), 7.24–7.32 (m, 2H), 7.66–7.74 (m, 1H), 8.06 (d, 1H, J=4.7 Hz).

To a stirred solution of the amine (550 mg, 2.43 mmol) in anhydrous CH$_2$Cl$_2$ (30 mL) was added di-t-butyl dicarbonate (531 mg, 2.43 mmol) and the solution was stirred at room temperature for 16 hours. The reaction mixture was washed with water, dried over MgSO$_4$, and concentrated to afford the product (700 mg, 80%) as a pale yellow solid. $^1$H NMR (CD$_3$OD) 1.42 (br s, 9H), 2.70–2.93 (br m, 2H), 3.78 (br s, 2H), 5.98 (br s, 1H), 6.55–6.61 (m, 2H), 6.99 (d, 1H, J=8.2 Hz), 7.22 (m, 1H), 7.40 (d, 1H, J=7.8 Hz), 7.75 (t, 1H, J=7.4 Hz), 8.44 (d, 1H, J=4.2 Hz).

To a stirred solution of the phenol from above (230 mg, 0.71 mmol) in pyridine (10 mL) cooled to 0° C. was added triflic anhydride (259 mg, 0.92 mmol) and the mixture was stirred for 1 h at 0° C. and then for 16 h at room temperature. The solvent was concentrated and the residue was dissolved in CH$_2$Cl$_2$ (50 mL) and washed with H$_2$O (2×25 mL). The organic layer was dried (MgSO$_4$) and evaporated to give a dark oil (300 mg, 92%). $^1$H NMR (CDCl$_3$) 1.42 (br s, 9H), 2.86–3.03 (m, 2H), 3.62–3.78 (m, 1H), 4.08 (br s, 1H), 6.03–6.38 (m, 1H), 7.01–7.12 (m, 2H), 7.14–7.18 (m, 1H), 7.21–7.30 (m, 1H), 7.38 (br s, 1H), 7.62–7.71 (m, 1H), 8.50 (d, 1H, J=4.5 Hz). This was used without further purification in the next step.

To a stirred solution of the triflate from above (300 mg, 0.66 mmol) in dry THF (5 mL) was added excess 2-aminomethylpyridine (1.0 g, 9.2 mmol), PdCl$_2$ (4.6 mg, 4 mol %) and PPh$_3$ (13.7 mg, 8 mol %). The reaction mixture was the pressurized to 60 psi with CO (g) and stirred for 16 h at 100° C. The reaction mixture was then concentrated and the residue was dissolved in CH$_2$Cl$_2$ (50 mL) and washed with H$_2$O (2×25 mL), brine (25 mL), dried (MgSO$_4$) and concentrated to afford the crude product. Purification by column chromatography on silica gel (CH$_2$Cl$_2$/MeOH; 95:5) afforded the desired compound (190 mg, 66%) as a viscous oil. $^1$H NMR (CDCl$_3$) 1.41 (br s, 9H), 2.97 (br s, 2H), 3.75 (br s, 1H), 4.03 (br s, 1H), 4.72 (d, 2H, J=4.9 Hz), 6.13–6.34 (m, 1H), 7.12–7.32 (m, 4H), 7.38 (s, 1H), 7.61–7.74 (m, 5H), 8.16–8.58 (m, 2H).

To a stirred solution of the amide from above (160 mg, 0.36 mmol) in anhydrous THF (3 mL) was added BH$_3$.THF (1M solution in THF, Aldrich, 3.6 mL, 3.6 mmol) and the resulting mixture was heated to reflux for 18 hours. The mixture was concentrated, MeOH was added to the residue and the solution was evaporated once again. This procedure was repeated 5 times. $^1$H NMR of the crude residue indicated that the product was obtained as a borane adduct. Thus, ethylene diamine (5 mL) was added to the residue and the mixture was stirred at 100° C. for 18 h. The reaction mixture was concentrated, water (5 mL) was added and the pH was adjusted to pH 13 with 10 N NaOH. The aqueous phase was extracted with CH$_2$Cl$_2$ (2×100 mL), dried (MgSO$_4$) and concentrated to afford the crude product. Purification by preparative TLC on a silica gel plate (CH$_2$Cl$_2$/MeOH, 95:5) afforded the desired compound (18.3 mg, 12%) as a viscous oil. $^1$H NMR (CDCl$_3$) 1.37 (br s, 9H), 2.92 (br s, 2H), 3.75 (br s, 1H), 3.80 (s, 2H), 3.93 (s, 2H), 4.01 (br s, 1H), 5.92–6.21 (m, 1H), 7.05–7.21 (m, 5H), 7.30 (d, 1H, J=7.8 Hz), 7.37 (br s, 1H), 7.57–7.68 (m, 2H), 8.48–8.57 (m, 2H).

To a stirred solution of the Boc-amine from above (18.0 mg, 0.04 mmol) in glacial acetic acid (1 mL) was added a solution of freshly prepared HBr/glacial acetic acid (1 mL) and the solution was stirred at room temperature for 18 hours. Ether was then added, resulting in the formation of a white precipitate. The solid was washed with ether by decantation (3×) and dried in vacuo to afford AMD3667 as white solid (22 mg, 80%). $^1$H NMR (D$_2$O) δ 2.97–3.14 (m, 2H), 3.27–3.49 (m, 2H), 4.21 (s, 2H), 4.35 (s, 2H), 5.78 (s, 1H), 6.82 (d, 1H, J=8.2 Hz), 7.14 (d, 1H, J=8.4 Hz), 7.27 (s, 1H), 7.35–7.48 (m, 2H), 7.50–7.58 (m, 2H), 7.85 (td, 1H, J=7.7, 1.7 Hz), 8.01 (td, 1H, J=7.7, 1.7 Hz), 8.41 (dd, 1H, J=5.7, 0.8 Hz), 8.50 (dd, 1H, J=5.7, 0.8 Hz). FAB-MS m/z

Example 205

AMD7428: Preparation of 1-[[4-[[(2-pyridinylmethyl)amino]methyl]phenyl]methyl]-3,4-diaminopyrrolidine (hydrobromide salt)

To a solution of 3-pyrroline (1.0 g, 14.5 mmol) in 0° C. THF (50 mL) and water (20 mL) mixture was added di-tert-butyldicarbonate (4.75 g, 21.8 mmol) over a ten minute period. The resulting solution was then stirred for 3 hours, gradually warming to room temperature. Ethyl acetate (100 mL) was then added to the reaction, and the aqueous and organic layers were separated. Following extraction of the aqueous layer with a second portion of ethyl acetate, the combined organic fractions were washed with 10% citric acid and then brine. The solution was then dried and concentrated to afford N-Boc-3-pyrroline in quantitative yield.

The N-Boc-3-pyrroline (675 mg, 4.0 mmol) was then dissolved in anhydrous THF (8 ml). To this solution was added N-methylmorpholine oxide (468 mg, 4.0 mmol) and a solution of osmium tetroxide in t-butanol (1 mL of a 2.5% w/v solution). The resulting mixture was then stirred at room temperature for four hours. A 5% sodium sulfite solution was then added to the reaction, along with 25 mL of diethyl ether. Following separation of the organic and aqueous layers, the organic layer was washed sequentially with saturated aqueous sodium bicarbonate, then brine, dried ($MgSO_4$) and concentrated. Purification of the residue by column chromatography on silica gel (5% methanol in dichloromethane) afforded the desired diol (418 mg, 51%).

To a cooled (0° C.) solution of N-Boc-3,4-pyrrolidinediol (2.53 g, 12.5 mmol) in dichloromethane (80 mL) was added triethylamine (7 mL, 50 mmol), and methanesulfonyl chloride (2.9 mL, 37.5 mmol). The mixture was then stirred, gradually warming to room temperature, for 90 minutes. The mixture was then washed with saturated ammonium chloride and brine, dried and concentrated to afford the crude mesylate as a white crystalline solid (2.93 g, 68%). $^1$H NMR ($CDCl_3$) δ 1.47 (s, 9H), 3.14 (br s, 3H), 3.66 (m, 2H), 3.77 (m, 2H), 5.16 (m, 2H). This material was used without further purification in the next step.

To a solution of the mesylate (345 mg, 1.0 mmol) in DMF (8 mL) was added sodium azide (163 mg, 2.5 mmol). The mixture was then heated to 120° C. for 4 hours. After cooling the reaction to room temperature, ethyl acetate (50 mL) was added, and the organic layer was extracted repeatedly with water. The organic phase was dried and concentrated and the residue was treated with trifluoroacetic acid (2 mL) in dichloromethane (2 mL) for 2 hours at room temperature. The solvents were then removed under vacuum to afford 3,4-diazidopyrrolidine in a 71% yield (for 2-steps) as the TFA salt. $^1$H NMR ($CDCl_3$) δ 3.14 (dd, 2H, J=13.1, 6.2 Hz), 3.55 (dd, 2H, J=13.1, 6.6 Hz), 3.64 (br s, 1H), 4.27 (m, 2H).

To a solution of N-[1-methylene-4-(chloromethylene)phenylene]-N-(2-nitrobenzenesulfonyl)-2-(aminomethyl)pyridine (692 mg, 2.0 mmol) in acetonitrile (20 mL) was added potassium carbonate (550 mg, 4.0 mmol) and the diazide.TFA salt (2 mmol) from above. The resulting suspension was heated to 60° C. overnight. After cooling to room temperature, water and ethylacetate were added to the reaction. The organic and aqueous layers were separated, and the aqueous layer was extracted twice with ethylacetate. The combined organic layers were dried and concentrated and the residue was purified by column chromatography on silica gel (5% methanol in dichloromethane) afforded the desired product (697 mg, 48%). $^1$H NMR ($CDCl_3$) δ 1.41 (br m, 9H), 2.56 (d, 2H, J=12.2 Hz), 2.90 (d, 2H, J=12.2 Hz), 3.60 (s, 2H), 3.99 (s, 2H), 4.43 (br s, 2H), 4.52 (br s, 2H), 7.15 (m, 2H), 7.21 (s, 4H), 7.61 (t, 1H, J=7.5 Hz), 8.50 (d, 1H, J=4.1 Hz).

1-[[4-[[(N-t-buytoxycarbonyl)(2-pyridinylmethyl)amino]methyl]phenyl]methyl]-3,4-diaminopyrrolidine.

To a solution of the intermediate diazide from above (138 mg, 0.298 mmol) in methanol (10 mL) was added Lindlar's catalyst (5% Pd on $CaCO_3$, 30 mg). The suspension was placed under 1 atm of hydrogen gas, and vigorously stirred for 3 hours. The mixture was then filtered through celite, and the filtrate was concentrated to give the corresponding diamine in quantitative yield (122 mg). $^1$H NMR ($CDCl_3$) δ 1.41 (br m, 9H), 2.30 (dd, 2H, J=9.6, 6.2 Hz), 3.03 (dd, 2H, J=9.6, 6.8), 3.56 (d, 2H, J=6.5 Hz), 3.63 (s, 2H), 4.43 (br s, 2H), 4.52 (br s, 2H), 7.27 (m, 2H), 7.35 (s, 4H), 7.83 (ddd, 1H, J=8.4, 8.1, 0.9 Hz), 8.50 (d, 1H, J=4.2 Hz).

Using general procedure D: Conversion of the amine (48 mg, 0.106 mmol) to the hydrobromide salt with simultaneous deprotection of the BOC group afforded AMD7428 (61 mg). $^1$H NMR ($D_2O$) δ 3.72 (dd, 2H, J=13.2, 6.6 Hz), 4.00 (dd, 2H, J=13.2, 5.7 Hz), 4.39 (s, 2H), 4.41 (m, 2H), 4.58 (s, 2H), 4.65 (s, 2H), 7.51 (br s, 4H), 7.99 (ddd, 1H, J=8.4, 8.1, 0.9 Hz), 8.11 (dd, 1H, J=8.1, 1.5 Hz), 8.54 (ddd, 1H, J=8.4, 5.7, 1.5 Hz), 8.73 (dd, 1H, J=5.7, 1.0 Hz). $^{13}$C NMR ($D_2O$) δ 48.96, 49.52, 51.40, 54.86, 59.56, 127.07, 127.12, 131.57, 131.80, 132.79, 144.37, 146.42, 147.38, 150.96. ES-MS m/z 312 (M+H). Anal. Calcd. for $C_{18}H_{25}N_5$●$.5.2HBr$●$3.0H_2O$: C, 27.50; H, 4.64; N, 8.91; Br, 52.85. Found: C, 27.49; H, 4.30; N, 8.70; Br, 52.84.

Example 206

AND7485: Preparation of 1-[[4-[[(2-pyridinylmethyl)amino]methyl]phenyl]methyl]-3,4-diacetylaminopyrrolidine (hydrobromide salt)

To a solution of 1-[[4-[[(N-t-buytloxycarbonyl)(2-pyridinylmethyl)amino]methyl]phenyl]methyl]-3,4-diaminopyrrolidine (60 mg, 0.146 mmol) in tetrahydrofuran (3 mL) was added 4-dimethylaminopyridine (5 mg, 0.044 mmol), triethylamine (0.13 mL, 0.949 mmol) and acetic anhydride (0.07 mL, 0.73 mmol). The reaction was then stirred at room temperature for 5 hours. After addition of water (5 mL) and ethylacetate (25 mL), the aqueous and organic layers were separated. The aqueous layer was extracted twice with ethylacetate, and the combined organic fractions were dried and concentrated. Purification of the residue by column chromatography on silica gel (10% methanol in dichloromethane) afforded the corresponding diamide (52 mg, 60%).

Using general procedure D: the diamide was converted to the hydrobromide salt with simultaneous deprotection of the BOC group to give AMD7485 (69 mg). $^1$H NMR ($D_2O$) δ 2.00 (s, 6H), 3.53 (br s, 2H), 3.78 (br s, 4H), 4.50 (s, 2H), 4.55 (s, 2H), 4.67 (s, 2H), 7.63 (s, 4H), 7.96 (m, 2H), 8.46 (dd, 1H, J=8.4, 5.3 Hz), 8.83 (d, 1H, J=5.3 Hz). $^{13}$C NMR ($D_2O$) δ 22.28, 47.57, 54.32, 128.46, 128.84, 131.63, 131.71, 131.85, 142.56, 144.09, 145.32, 147.95, 174.98. ES-MS m/z 396 (M+H). Anal. Calcd. for $C_{18}H_{25}N_5$●$.4.0HBr$●$3.0H_2O$●$0.6HOAc$: C, 34.08; H, 5.23; N, 8.54; Br, 39.53. Found: C, 34.46; H, 5.09; N, 8.66; Br, 39.41.

Example 207

AMD8665: Preparation of 8-[[4-[[(2-pyridinylmethyl)amino]methyl]phenyl]methyl]-2,5,8-triaza-3-oxabicyclo[4.3.0]nonane (hydrobromide salt)

To a solution of 1-[[4-[[(N-t-buytloxycarbonyl)(2-pyridinylmethyl)amino]methyl]phenyl]methyl]-3,4-diaminopyrrolidine. (411 mg, 1.0 mmol) in THF (15 mL) was added di-tert-butyldicarbonate (218 mg, 1.0 mmol). The reaction was stirred at room temperature for 1 hour. Ethylacetate (30 mL) was then added, and the mixture was extracted with 10% citric acid (10 mL). Following drying and concentration of the organic fractions, the residue was purified by column chromatography on silica gel (5% methanol in dichloromethane) to give the desired product (one primary amine protected) (315 mg, 62%).

The intermediate from above was dissolved in THF (12 mL) to which potassium carbonate (170 mg, 1.24 mmol) was added. The mixture was then cooled to 0° C., and a solution of bromoacetyl bromide in THF (1 mL of a 1M solution) was added in a dropwise manner over 10 minutes. Following addition, the reaction was stirred at 0° C. for one hour. The reaction was then quenched with water and extracted with ethylacetate. The combined organic fractions were then dried and concentrated.

The residue was then treated with 2 mL of trifluoroacetic acid in 2 mL of dichloromethane for one hour at room temperature. Following removal of the solvent and excess acid by vacuum, the crude reaction product was dissolved in acetonitrile (15 mL) to which potassium carbonate (250 mg, excess) was added. The mixture was stirred at room temperature for two hours. Filtration of the mixture and concentration afforded a yellow residue, which was purified by column chromatography on silica gel (2% aqueous ammonium hydroxide, 8% methanol, 90% chloroform) to yield the desired cyclic amide (115 mg, 43%).

Using general procedure D: the cyclic amide (88 mg, 0.250 mmol) was converted to a hydrobromide salt giving AMD8665 (68 mg). $^1$H NMR (D$_2$O) δ 3.69 (dd, 1H, 12.9, 6.1 Hz), 3.86 (dd, 1H, J=12.6, 2.1 Hz), 3.99–4.07 (br m, 4H), 4.10 (m, 2H), 4.50 (s, 2H), 4.63 (s, 2H), 4.74 (s, 2H), 7.90 (br s, 4H), 7.94 (t, 1H, J=5.7 Hz), 7.99 (d, 1H, J=8.1 Hz), 8.43 (t, 1H, J=8.1 Hz), 8.80 (d, 1H, J=5.7 Hz). $^{13}$C NMR (D$_2$O) δ 41.81, 48.68, 49.68, 50.93, 51.41, 52.55, 57.81, 59.14, 127.31, 127.43, 130.98, 131.55, 132.12, 132.84, 145.02, 145.95, 147.00, 166.28. ES-MS m/z 352 (M+H). Anal. Calcd. for C$_{20}$H$_{25}$N$_5$O●3.9HBr●3.1H$_2$O: C, 33.23; H, 4.89; N, 9.69; Br, 43.11. Found: C, 33.28; H, 4.72; N, 9.31; Br, 43.05.

Example 208

AMD8773: Preparation of 8-[[4-[[(2-pyridinylmethyl)amino]methyl]phenyl]methyl]-2,5,8-triazabicyclo[4.3.0]nonane (hydrobromide salt)

The freebase of AMD8665 from above (18 mg, 0.05 mmol) was dissolved in THF (3 mL). To this mixture, a solution of borane in THF (0.5 mL of a 1M solution) was added. The reaction was then heated to 60° C. for three hours. After cooling to room temperature, 2 mL of methanol was carefully added to the reaction. The mixture was then concentrated under vacuum, and the residue was re-dissolved in 3 mL of ethylenediamine. The reaction was then heated to 75° C. for three hours. After cooling to room temperature, 5 mL of water was added, the aqueous layer was saturated with potassium carbonate, and then extracted repeatedly with dichloromethane. The combined organic fractions were then dried and concentrated to yield a pale yellow oil, which was purified by column chromatography on silica gel (5% aqueous ammonium hydroxide, 15% methanol, 80% dichloromethane) to afford the desired product (11 mg, 64%).

Using general procedure D: the intermediate from above (22 mg, 0.065 mmol) was converted to a hydrobromide salt giving AMD8773 (17 mg). $^1$H NMR (D$_2$O) δ 3.16 (m, 4H), 3.67 (m, 4H), 4.08 (br s, 2H), 4.41 (s, 2H), 4.47 (s, 2H), 4.54 (s, 2H), 7.57 (s, 4H), 7.79 (dd, J=8.4, 5.3 Hz), 8.11 (m, 1H), 8.67 (d, 1H, J=5.8 Hz). $^{13}$C NMR (D$_2$O) δ 39.45, 49.62, 51.07, 51.86, 54.16, 59.43, 126.23, 131.32, 131.73, 131.89, 132,61, 133.38, 146.53, 147.41, 151.22. ES-MS m/z 338 (M+H). Anal. Calcd. for C$_{20}$H$_{27}$N$_5$●.4.8HBr●3.3H$_2$O: C, 30.59; H, 4.93; N, 8.92; Br, 48.84. Found: C, 30.56; H, 4.83; N, 8.56; Br, 49.13.

What is claimed is:

1. A method to treat HIV or rheumatoid arthritis in a subject which method comprises administering to a subject in need of such treatment an effective amount of a compound of formula I

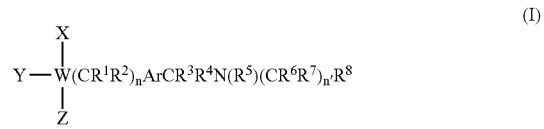

(I)

or pharmaceutically acceptable acid addition salts, and any stereoisomeric forms and mixtures of stereoisomeric forms thereof: and optionally one or more agent useful in the treatment HIV;

wherein, W is a nitrogen atom and Y is void or, W is a carbon atom and Y=H;

$R^1$ to $R^7$ may be the same or different and are independently selected from hydrogen or straight, branched or cyclic $C_{1-6}$ alkyl, where $R^1$ and $R^2$ together may form =O;

$R^8$ is a substituted heterocyclic group or a substituted aromatic group

Ar is an aromatic or heteroaromatic ring each optionally substituted at single or multiple, non-linking positions with electron-donating or withdrawing groups;

n and n' are independently, 0–2;

X is a group of the formula:

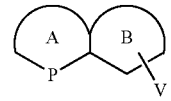

wherein, Ring A is an optionally substituted, saturated or unsaturated 5 or 6-membered ring, and P is an optionally substituted carbon atom, an optionally substituted nitrogen atom, sulfur or oxygen atom;

wherein Ring B is an optionally substituted 5 to 7-membered ring;

wherein Ring A or Ring B are bound to group W from any position through group V;

wherein V is a chemical bond or V is a (CH$_2$)$_{n''}$group, (where n''=0–2) or V is a C=O group; and wherein Z is selected from the group consisting of: a hydrogen atom; an optionally substituted $C_{1-6}$ alkyl group; a $C_{0-6}$ alkyl group substituted with an optionally substituted aromatic or heterocyclic group; an optionally substituted $C_{0-6}$ alkylamino or $C_{3-7}$ cycloalkylamino group; and an optionally substituted carbonyl group or sulfonyl, thereby treating HIV or rheumatoid arthritis in said subject.

2. The method of claim 1, comprising administering the compound of formula I and one or more agents useful in the treatment of HIV.

3. The method of claim 2, wherein said one or more agents are selected from the group consisting of: nucleotide reverse transcriptase inhibitor such as zidovudine, didanosine, lamivudine, zalcitabine, abacavir, stavudine, adefovir, adefovir dipivoxil, fozivudine todoxil; non-nucleotide reverse transcriptase inhibitor such as nevirapine, delavirdine, efavirenz, loviride, immunocal, or oltipraz; and protease inhibitors such as saquinavir, ritonavir, indinavir, nelfinavir, amprenavir, palinavir, and lasinavir.

4. The method of claim 1, wherein said optionally substituted 5 or 6-membered Ring A in said compound of formula 1 is selected from the group consisting of: benzene; pyridine; pyrimidine; pyrazine; pyridazine; triazine; piperidine; piperazine; imidazole; pyrazole; triazole; oxazole; and thiazole, or wherein said optionally substituted Ring B in said compound of formula 1 is selected from the group consisting of: benzene; 5 to 7-membered cycloalkyl ring; furan; dihydrofuran; tetrahydrofuran; thiophene; dihydrothiophene; tetrahydrothiophene (thiolane); pyran; dihydropyran; tetrahydropyran; thiapyran; dihydrothiapyran; tetrahydrothiapyran (pentamethylene sulfide); oxepine; and thiepin.

5. The method of claim 4, wherein said Ring B comprises a 5 to 7-membered cycloalkyl ring selected from the group consisting of: cyclopentyl; cyclohexyl; cycloheptyl; cyclopentenyl; cyclohexenyl; and cycloheptenyl.

6. The method of claim 1, wherein said Ring B in said compound of formula 1 comprises a saturated heterocycloalkane.

7. The method of claim 1, wherein said Ring A and said Ring B in said compound of formula 1 are each 6-membered rings, independently selected from the group consisting of: dihydronaphthalene; tetrahydronaphthalene; dihydroquinoline and tetrahydroquinoline.

8. A method for treating rheumatoid arthritis or HIV in a subject, comprising administering a compound selected from the group consisting of:

AMD7490, N-(2-pyridinylmethyl)-N'-(6,7,8,9-tetrahydro-5H-cyclohepta[b]pyridin-9-yl) -1,4-benzenedimethanamine;

AMD7491, N-(2-pyridinylmethyl)-N'-(5,6,7,8-tetrahydro-8-quinolinyl)-1,4-benzenedimethanamine;

AMD7492, N-(2-pyridinylmethyl)-N'-(6,7dihydro-5H-cyclopenta[b]pyridin-7-y1)-1,4-benzenedimethanamine;

AMD8766, N-(2-pyridinylmethyl)-N'-(1,2,3,4-tetrahydro-1-naphthalenyl)-1,4-benzenedimethanamine;

AMD8789, N-(2-pyridinylmethyl)-N'-(1-naphthalenyl)-1,4-benzenedimethanamine;

AMD8776, N-(2-pyridinylmethyl)-N'-(8-quinolinyl)-14-benzenedimethanamine;

AMD8859, N-(2-pyridinylmethyl)-N'-[2-[(2-pyridinylmethyl)amino]ethyl]-N'-(1-methyl-1,2,3,4-tetrahydro-8-quinolinyl)-1,4-benzenedimethanamine;

AMD8867, N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzene dimethanamine;

AMD8746, N-(2-pyridinylmethyl)-N'-(1,2,3,4-tetrahydro-8-quinolinyl)-1,4-benzenedimethanamine;

AMD8835, N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine;

AMD8833, N-(2-pyridinylmethyl)-N'-(2-phenyl-5,6,7,8-tetrahydro-8-quinolinyl)-1,4-benzenedimethanamine;

AMD8825, N,N'-bis(2-pyridinylmethyl)-N'-(2-phenyl-5,6,7,8-tetrahydro-8-quinolinyl)-1,4-benzenedimethanamine;

AMD8869, N-(2-pyridinylmethyl)-N'-(5,6,7,8-tetrahydro-5-quinolinyl)-1,4-benzenedimethanamine;

AMD8876, N-(2-pyridinylmethyl)-N'-(1H-imidazol-2-ylmethyl)-N'-(5,6,7,8-tetrahydro-5-quinolinyl)-1,4-benzenedimethanamine;

AMD8751, N-(2-pyridinylmethyl)-N'-(1H-imidazol-2-ylmethyl)-N'-(5,6,7,8-tetrahydro-8-quinolinyl)-1,4-benzenedimethanamine;

AMD8777, N-(2-pyridinylmethyl)-N'-[(2-amino-3 -phenyl)propyl]-N'-(5,6,7,8-tetrahydro-8-quinolinyl)-1,4-benzenedimethanamine;

AMD8763, N-(2-pyridinylmethyl)-N'-(1H-imidazol-4-ylmethyl)-N'-(5,6,7,8-tetrahydro-8-quinolinyl)-1,4-benzenedimethanamine;

AMD8771, N-(2-pyridinylmethyl)-N'-(2-quinolinylmethyl)-N'-(5,6,7,8-tetrahydro-8 -quinolinyl)-1,4-benzenedimethanamine;

AMD8778, N-(2-pyridinylmethyl)-N'-(2-(2-naphthoyl)aminoethyl)-N'-(5,6,7,8-tetrahydro -8-quinolinyl)-1,4-benzenedimethanamine;

AMD8781, N-(2-pyridinylmethyl)-N'-[(S)-(2-acetylamino-3 -phenyl)propyl]-N'-(5,6,7,8-tetrahydro-8-quinolinyl)-1,4-benzenedimethanamine;

AMD8782, N-(2-pyridinylmethyl)-N'-[(S)-(2-acetylamino-3 -phenyl)propyl]-N'-(5,6,7,8-tetrahydro-8-quinolinyl)-1,4-benzenedimethanamine;

AMD8788, N-(2-pyridinylmethyl)-N'-[3 -((2-naphthalenylmethyl)amino)propyl]-N'-(5,6,7,8-tetrahydro-8-quinolinyl)-1,4-benzenedimethanamine;

AMD8733 and AMD8734, N-(2-pyridinylmethyl)-N'-[2-(S)-pyrollidinylmethyl]-N'-(5,6,7,8-tetrahydro-8-quinolinyl)-1,4-benzenedimethanamine;

AMD8756, N-(2-pyridinylmethyl)-N'-[2-(R)-pyrollidinylmethyl]-N'-(5,6,7,8-tetrahydro-8-quinolinyl)-1,4-benzenedimethanamine;

AMD8799, N-(2-pyridinylmethyl)-N'-[3 -pyrazolylmethyl]-N'-(5,6,7,8-tetrahydro-8-quinolinyl)-1,4-benzenedimethanamine;

AMD8728, N-(2-pyridinylmethyl)-N'-[2-pyrrolylmethyl]-N'-(5,6,7,8-tetrahydro-8-quinolinyl)-1,4-benzenedimethanamine;

AMD8836, N-(2-pyridinylmethyl)-N'-[2-thiopheneylmethyl]-N'-(5,6,7,8-tetrahydro-8-quinolinyl)-1,4-benzenedimethanamine AMD8841, N-(2-pyridinylmethyl)-N'-[2-thiazolylmethyl]-N'-(5,6,7,8-tetrahydro-8-quinolinyl)-1,4-benzenedimethanamine;

AMD8821, N-(2-pyridinylmethyl)-N'-[2-furanylmethyl]-N'-(5,6,7,8-tetrahydro-8-quinolinyl)-1,4-benzenedimethanamine;

AMD8742, N-(2-pyridinylmethyl)-N'-[2-[(phenylmethyl)amino]ethyl]-N'-(5,6,7,8-tetrahydro-8-quinolinyl)-1,4-benzenedimethanamine;

AMD8743, N-(2-pyridinylmethyl)-N'-(2-aminoethyl)-N'-(5,6,7,8-tetrahydro-8-quinolinyl)-1,4-benzenedimethanamine;

AMD8753, N-(2-pyridinylmethyl)-N'-3-pyrrolidinyl-N'-(5,6,7,8-tetrahydro-8-quinolinyl)-1,4-benzenedimethanamine AMD8754, N-(2-pyridinylmethyl)-N'-4-piperidinyl-N'-(5,6,7,8-tetrahydro-8-quinolinyl)-1,4-benzenedimethanamine;

AMD8784, N-(2-pyridinylmethyl)-N'-[2-[(phenyl)amino]ethyl]-N'-(5,6,7,8-tetrahydro-8-quinolinyl)-1,4-benzenedimethanamine;

AMD8759, N-(2-pyridinylmethyl)-N'-(7-methoxy-1,2,3,4-tetrahydro-2-naphthalenyl)-1,4-benzenedimethanamine;

AMD8762, N-(2-pyridinylmethyl)-N'-(6-methoxy-1,2,3,4-tetrahydro-2-naphthalenyl)-1,4-benzenedimethanamine;

AMD8770, N-(2-pyridinylmethyl)-N'-(1-methyl-1,2,3,4-tetrahydro-2-naphthalenyl)-1,4-benzenedimethanamine;

AMD8790, N-(2-pyridinylmethyl)-N'-(7-methoxy-3,4-dihydronaphthalenyl)-1-(aminomethyl)-4-benzamide;

AMD8805, N-(2-pyridinylmethyl)-N'-(6-methoxy-3,4-dihydronaphthalenyl)-1-(aminomethyl)-4-benzamide;

AMD8902, N-(2-pyridinylmethyl)-N'-(1H-imidazol-2-ylmethyl)-N'-(7-methoxy-1,2,3,4-tetrahydro-2-naphthalenyl)-1,4-benzenedimethanamine;

AMD8863, N-(2-pyridinylmethyl)-N'-(8-hydroxy-1,2,3,4-tetrahydro-2-naphthalenyl)-1,4-benzenedimethanamine;

AMD8886, N-(2-pyridinylmethyl)-N'-(1H-imidazol-2-ylmethyl)-N'-(8-hydroxy-1,2,3,4-tetrahydro-2-naphthalenyl)-1,4-benzenedimethanamine;

AMD8889, N-(2-pyridinylmethyl)-N'-(8-Fluoro-1,2,3,4-tetrahydro-2-naphthalenyl)-1,4-benzenedimethanamine;

AMD8895, N-(2-pyridinylmethyl)-N'-(1H-imidazol-2-ylmethyl)-N'-(8-Fluoro-1,2,3,4-tetrahydro-2-naphthalenyl)-1,4-benzenedimethanamine;

AMD8852, N-(2-pyridinylmethyl)-N'-(5,6,7,8-tetrahydro-7-quinolinyl)-1,4-benzenedimethanamine;

AMD8858, N-(2-pyridinylmethyl)-N'-(1H-imidazol-2-ylmethyl)-N'-(5,6,7,8-tetrahydro-7-quinolinyl)-1,4-benzenedimethanamine;

AMD8785, N-(2-pyridinylmethyl)-N'-[2-[(2-naphthalenylmethyl)amino]ethyl]-N'-(5,6,7,8-tetrahydro-8-quinolinyl)-1,4-benzenedimethanamine;

AMD8820, N-(2-pyridinylmethyl)-N'-[2-(isobutylamino)ethyl]-N'-(5,6,7,8-tetrahydro-8-quinolinyl)-1,4-benzenedimethanamine;

AMD8827, N-(2-pyridinylmethyl)-N'-[2-[(2-pyridinylmethyl)amino]ethyl]-N'-(5,6,7,8-tetrahydro-8-quinolinyl)-1,4-benzenedimethanamine;

AMD8828, N-(2-pyridinylmethyl)-N'-[2-[(2-furanylmethyl)amino]ethyl]-N'-(5,6,7,8-tetrahydro-8-quinolinyl)-1,4-benzenedimethanamine;

AMD8772, N-(2-pyridinylmethyl)-N'-(2-guanidinoethyl)-N'-(5,6,7,8-tetrahydro-8-quinolinyl)-1,4-benzenedimethanamine; and AMD8861, N-(2-pyridinylmethyl)-N'-[2-[bis-[(2-methoxy)phenylmethyl]amino]ethyl]-N'-(5,6,7,8-tetrahydro-8-quinolinyl)-1,4-benzenedimethanamine AMD8862, N-(2-pyridinylmethyl)-N'-[2-[(1H-imidazol-4-ylmethyl)amino]ethyl]-N'-(5,6,7,8-tetrahydro-8-quinolinyl)-1,4-benzene dimethanamine;

AMD8887, N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine;

AMD8816, N-(2-pyridinylmethyl)-N'-[2-(phenylureido)ethyl]-N'-(5,6,7,8-tetrahydro-8-quinolinyl)-1,4-benzenedimethanamine;

AMD8737, N-(2-pyridinylmethyl)-N'-[[N''-(n-butyl)carboxamido]methyl]-N'-(5,6,7,8-tetrahydro-8-quinolinyl)-1,4-benzenedimethanamine;

AMD8739, N-(2-pyridinylmethyl)-N'-(carboxamidomethyl)-N'-(5,6,7,8-tetrahydro-8-quinolinyl)-1,4-benzenedimethanamine;

AMD8752, N-(2-pyridinylmethyl)-N'-[(N''-phenyl)carboxamidomethyl]-N'-(5,6,7,8-tetrahydro-8-quinolinyl)-1,4-benzenedimethanamine;

AMD8765, N-(2-pyridinylmethyl)-N'-(carboxymethyl)-N'-(5,6,7,8-tetrahydro-8-quinolinyl)-1,4-benzenedimethanamine;

AMD8715, N-(2-pyridinylmethyl)-N'-(phenylmethyl)-N'-(5,6,7,8-tetrahydro-8-quinolinyl)-1,4-benzenedimethanamine;

AMD8907, N-(2-pyridinylmethyl)-N'-(1H-benzimidazol-2-ylmethyl)-N'-(5,6,7,8-tetrahydro-8-quinolinyl)-1,4-benzenedimethanamine;

AMD8927, N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine (hydrobromide salt);

AMD8926, N-(2-pyridinylmethyl)-N'-(5-nitro-1H-benzimidazol-2-ylmethyl)-N'-(5,6,7,8-tetrahydro-8-quinolinyl)-1,4-benzenedimethanamine;

AMD8929, N-(2-pyridinylmethyl)-N'-[(1H)-5-azabenzimidazol-2-ylmethyl]-N'-(5,6,7,8-tetrahydro-8-quinolinyl)-1,4-benzenedimethanamine;

AMD8931, N-(2-pyridinylmethyl)-N-(4-phenyl-1H-imidazol-2-ylmethyl)-N'-(5,6,7,8-tetrahydro-8-quinolinyl)-1,4-benzenedimethanamine;

AMD8783, N-(2-pyridinylmethyl)-N'-[2-(2-pyridinyl)ethyl]-N'-(5,6,7,8-tetrahydro-8-quinolinyl)-1,4-benzenedimethanamine;

AMD8764, N-(2-pyridinylmethyl)-N'-(2-benzoxazolyl)-N'-(5,6,7,8-tetrahydro-8-quinolinyl)-1,4-benzenedimethanamine;

AMD8780, N-(2-pyridinylmethyl)-N'-trans-2-aminocyclohexyl)-N'-(5,6,7,8-tetrahydro-8-quinolinyl)-1,4-benzenedimethanamine;

AMD8818, N-(2-pyridinylmethyl)-N'-(2-phenylethyl)-N'-(5,6,7,8-tetrahydro-8-quinolinyl)-1,4-benzenedimethanamine;

AMD8829, N-(2-pyridinylmethyl)-N'-(3-phenylpropyl)-N'-(5,6,7,8-tetrahydro-8-quinolinyl)-1,4-benzenedimethanamine;

AMD8839, N-(2-pyridinylmethyl)-N'-(trans-2-aminocyclopentyl)-N'-(5,6,7,8-tetrahydro-8-quinolinyl)-1,4-benzenedimethanamine;

AMD8726, N-[[4-[[(2-pyridinylmethyl)amino]methyl]phenyl]methyl]-N-(5,6,7,8-tetrahydro-8-quinolinyl)-glycinamide;

AMD8738, N-[[4-[[(2-pyridinylmethyl)amino]methyl]phenyl]methyl]-N-(5,6,7,8-tetrahydro-8-quinolinyl)-(L)-alaninamide;

AMD8749, N-[[4-[[(2-pyridinylmethyl)amino]methyl]phenyl]methyl]-N-(5,6,7,8-tetrahydro-8-quinolinyl)-(L)-aspartamide AMD8750, N-[[4-[[(2-pyridinylmethyl)amino]methyl]phenyl]methyl]-N-(5,6,7,8-tetrahydro-8-quinolinyl)-pyrazinamide;

AMD8740, N-[[4-[[(2-pyridinylmethyl)amino]methyl]phenyl]methyl]-N-(5,6,7,8-tetrahydro-8-quinolinyl)-(L)-prolinamide;

AMD8741, N-[[4-[[(2-pyridinylmethyl)amino]methyl]phenyl]methyl]-N-(5,6,7,8-tetrahydro-8 -quinolinyl)-(L)-lysinamide;

AMD8724, N-[[4-[[(2-pyridinylmethyl)amino]methyl]phenyl]methyl]-N-(5,6,7,8-tetrahydro-8-quinolinyl)-benzamide;

AMD8725, N-[[4-[[(2-pyridinylmethyl)amino]methyl]phenyl]methyl]-N-(5,6,7,8-tetrahydro-8-quinolinyl)-picolinamide;

AMD8713, N'-Benzyl-N-[[4-[[(2-pyridinylmethyl)amino]methyl]phenyl]methyl]-N -(5,6,7,8-tetrahydro-8-quinolinyl)-urea;

AMD8712, N'-phenyl-N-[[4-[[(2-pyridinylmethyl)amino]methyl]phenyl]methyl]-N -(5,6,7,8-tetrahydro-8-quinolinyl)-urea;

AMD8716, N-(6,7,8,9-tetrahydro-5H-cyclohepta[b]pyridin-9-yl)-4-[[(2-pyridinylmethyl)amino]methyl]benzamide;

AMD8717, N-(5,6,7,8-tetrahydro-8-quinolinyl)-4-[[(2-pyridinylmethyl)amino]methyl]benzamide;

AMD8634, N,N'-bis(2-pyridinylmethyl)-N'-(5,6,7,8-tetrahydro-8-quinolinyl)-1,4-benzenedimethanamine;

AMD8774, N,N'-bis(2-pyridinylmethyl)-N'-(6,7,8,9-tetrahydro-5H-cyclohepta[b]pyridin-9-yl)-1 ,4-benzenedimethanamine;

AMD8775, N,N'-bis(2-pyridinylmethyl)-N'-(6,7-dihydro-5H-cyclopenta[b]pyridin-7-yl)  -1,4-benzenedimethanamine;

AMD8819, N,N'-bis(2-pyridinylmethyl)-N'-(1,2,3,4-tetrahydro-1-naphthalenyl)-1,4-benzenedimethanamine;

AMD8768, N,N'-bis(2-pyridinylmethyl)-N'-[(5,6,7,8-tetrahydro-8-quinolinyl)methyl]-1,4-benzenedimethanamine;

AMD8767, N,N'-bis(2-pyridinylmethyl)-N'[(6,7-dihydro-5H-cyclopenta[b]pyridin-7-yl)methyl]-1,4-benzenedimethanamine;

AMD8838, N-(2-pyridinylmethyl)-N-(2-methoxyethyl)-N'-(5,6,7,8-tetrahydro-8-quinolinyl)-1,4-benzenedimethanamine;

AMD8871, N-(2-pyridinylmethyl)-N-[2-(4-methoxyphenyl)ethyl]-N'-(5,6,7,8-tetrahydro-8-quinolinyl)-1,4-benzenedimethanamine;

AMD8844, N,N'-bis(2-pyridinylmethyl)-1,4-(5,6,7, 8-tetrahydro-8-quinolinyl)benzenedimethanamine;

AMD7129, N-[(2,3 -dimethoxyphenyl)methyl]-N'-(2-pyridinylmethyl)-N-(5,6,7,8-tetrahydro-8-quinolinyl)-1,4-benzenedimethanamine;

AMD7138, N-[(2-hydroxyphenyl)methyl]-N'-(2-pyridinylmethyl)-N-(6,7,8,9-tetrahydro -5H-cyclohepta[b]pyridin-9-yl)-1,4-benzenedimethanamine;

AMD7140, N-[(4-cyanophenyl)methyl]-N'-(2-pyridinylmethyl)-N-(6,7, 8,9-tetrahydro-5H -cyclohepta[b]pyridin-9-yl)-1,4-benzenedimethanamine;

AMD7141, N-[(4-cyanophenyl)methyl]-N'-(2-pyridinylmethyl)-N-(5,6,7,8-tetrahydro-8-quinolinyl)-1,4-benzenedimethanamine;

AMD7142, N-[(4-acetamidophenyl)methyl]-N'-(2-pyridinylmethyl)-N-(5,6,7,8-tetrahydro -8-quinolinyl)-1, 4-benzenedimethanamine;

AMD7145, N[(4-phenoxyphenyl)methyl]-N'-(2-pyridinylmethyl)-N-(6,7,8,9-tetrahydro -5H-cyclohepta[b]pyridin-9-yl)-1,4-benzenedimethanamine;

AMD7151, N-[(4-benzyloxyphenyl)methyl]-N'-(2-pyridinylmethyl)-N-(6,7,8,9-tetrahydro -5H-cyclohepta[b]pyridin-9-yl)-1,4-benzenedimethanamine; and AMD7155, N-[(thiophene-2-yl)methyl]-N'-(2-pyridinylmethyl)-N-(6,7,8,9-tetrahydro-5H -cyclohepta[b]pyridin-9-yl)-1,4-benzenedimethanamine.

AMD7164, N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine;

AMD7167, N-[(3,4-methylenedioxyphenyl)methyl]-N'-(2-pyridinylmethyl)-N-(5,6,7,8-tetrahydro-8-quinolinyl)-1,4-benzenedimethanamine;

AMD7168, N-(3 -pyridinylmethyl)-N'-(2-pyridinylmethyl)-N-(6,7,8,9-tetrahydro-5H -cyclohepta[b]pyridin-9-yl)-1,4-benzenedimethanamine;

AMD7171, N-[(1,5-dimethyl-2-phenyl-3-pyrazolinone-4-yl)methyl]-N'-(2-pyridinylmethyl)-N-(5,6,7,8-tetrahydro-8-quinolinyl)-1,4-benzenedimethanamine;

AMD7172, N-[(4-propoxyphenyl)methyl]-N'-(2-pyridinylmethyl)-N-(6,7,8,9-tetrahydro -5H-cyclohepta[b]pyridin-9-yl)-1,4-benzenedimethanamine;

AMD7175, N-(1-phenyl-3,5-dimethylpyrazolin-4-ylmethyl)-N'-(2-pyridinylmethyl)-N -(5,6,7,8-tetrahydro-8-quinolinyl)-1,4-benzenedimethanamine;

AMD7180, N-[(3 -methoxy-4,5 -methylenedioxyphenyl)methyl]-N'-(2-pyridinylmethyl)-N -(6,7,8,9-tetrahydro-5H-cyclohepta[b]pyridin-9-yl)-1,4-benzenedimethanamine;

AMD7182, N-[(3 -cyanophenyl)methyl]-N'-(2-pyridinylmethyl)-N-(6,7,8,9-tetrahydro-5H -cyclohepta[b]pyridin-9-yl)-1,4-benzenedimethanamine;

AMD7184, N-[(3 -cyanophenyl)methyl]-N'-(2-pyridinylmethyl)-N-(5,6,7,8-tetrahydro-8-quinolinyl)-1,4-benzenedimethanamine;

AMD7185, N-(5-ethylthiophene-2-ylmethyl)-N'-(2-pyridinylmethyl)-N-(6,7,8,9-tetrahydro -5H-cyclohepta[b]pyridin-9-yl)-1,4-benzenedimethanamine;

AMD7186, N-(5-ethylthiophene-2-ylmethyl)-N'-(2-pyridinylmethyl)-N-(5,6,7,8-tetrahydro -8-quinolinyl)-1, 4-benzenedimethanamine;

AMD7187, N-[(2,6-difluorophenyl)methyl]-N'-(2-pyridinylmethyl)-N-(6,7,8,9-tetrahydro -5H-cyclohepta[b]pyridin-9-yl)-1,4-benzenedimethanamine;

AMD7188, N-[(2,6-difluorophenyl)methyl]-N'-(2-pyridinylmethyl)-N-(5,6,7,8-tetrahydro -8-quinolinyl)-1,4-benzenedimethanamine;

AMD7189, N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine;

AMD7195, N-(2-difluoromethoxyphenylmethyl)-N'-(2-pyridinylmethyl)-N-(5,6,7,8-tetrahydro-8quinolinyl)-1,4-benzenedimethanamine;

AMD7196, N-(1,4-benzodioxan-6-ylmethyl)-N'-(2-pyridinylmethyl)-N-(6,7,8,9-tetrahydro -5H-cyclohepta[b]pyridin-9-yl)-1,4-benzenedimethanamine;

AMD7202, N-(1,4-benzodioxan-6-ylmethyl)-N'-(2-pyridinylmethyl)-N-(5,6,7,8-tetrahydro -8-quinolinyl)-1, 4-benzenedimethanamine;

AMD7207, N-[(2,4-difluorophenyl)methyl]-N'-(2-pyridinylmethyl)-N-(5,6,7,8-tetrahydro -8-quinolinyl)-1,4-benzenedimethanamine;

AMD7208, N-(1-methylpyrrol-2-ylmethyl)-N'-(2-pyridinylmethyl)-N-(5,6,7,8-tetrahydro-8-quinolinyl)1,4-benzenedimethanamine;

AMD7209, N-[(2-hydroxyphenyl)methyl]-N'-(2-pyridinylmethyl)-N-(5,6,7,8-tetrahydro-8-quinolinyl)1,4-benzenedimethanamine;

AMD7212, N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine;

AMD7216, N-(3-pyridinylmethyl)-N'-(2-pyridinylmethyl)-N-(5,6,7,8-tetrahydro-8-quinolinyl)-1,4-benzenedimethanamine;

AMD7222, N-(1-methylbenzimidazol-2-ylmethyl)-N'-(2-pyridinylmethyl)-N-(5,6,7,8-tetrahydro-8-quinolinyl)-1,4-benzenedimethanamine;

AMD7230, N-[1-(ethoxycarbonyl)-4-piperidinyl]-N'-(2-pyridinylmethyl)-N-(5,6,7,8-tetrahydro-8-quinolinyl)-1,4-benzenedimethanamine;

AMD7231, N-[(1-methyl-3-pyrazolyl)propyl]-N'-(2-pyridinylmethyl)-N-(5,6,7,8-tetrahydro-8-quinolinyl)-1,4-benzenedimethanamine;

AMD7236, N-[(1-methyl-2-phenylsulfonyl)ethyl]-N'-(2-pyridinylmethyl)-N-(5,6,7,8-tetrahydro-8-quinolinyl)-1,4-benzenedimethanamine;

AMD7238, N-[(2-chloro-4,5-methylenedioxyphenyl)methyl]-N'-(2-pyridinylmethyl)-N-(5,6,7,8-tetrahydro-8-quinolinyl)-1,4-benzenedimethanamine;

AMD7239, N-[1-methyl-2-[N''-(4-chlorophenyl)carboxamido]ethyl]-N'-(2-pyridinylmethyl)-N-(5,6,7,8-tetrahydro-8-quinolinyl)-1,4-benzenedimethanamine;

AMD7241, N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine;

AMD7242, N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethanamine;

AMD7244, N-(3-quinolylmethyl)-N'-(2-pyridinylmethyl)-N-(5,6,7,8-tetrahydro-8-quinolinyl)-1,4-benzenedimethanamine;

AMD7245, N-[(8-hydroxy)-2-quinolylmethyl]-N'-(2-pyridinylmethyl)-N-(6,7,8,9-tetrahydro-5H-cyclohepta[b]pyridin-9-yl)-1,4-benzenedimethanamine; and AMD7247, N-(2-quinolylmethyl)-N'-(2-pyridinylmethyl)-N-(6,7,8,9-tetrahydro-5H-cyclohepta[b]pyridin-9-yl)-1,4-benzenedimethanamine;

AMD7249, N-[(4-acetamidophenyl)methyl]-N'-(2-pyridinylmethyl)-N-(6,7,8,9-tetrahydro-5H-cyclohepta[b]pyridin-9-yl)-1,4-benzenedimethanamine;

AMD7251, N-(3-quinolylmethyl)-N'-(2-pyridinylmethyl)-N-(6,7,8,9-tetrahydro-5H-cyclohepta[b]pyridin-9-yl)-1,4-benzenedimethanamine;

AMD7252, N-(2-thiazolylmethyl)-N'-(2-pyridinylmethyl)-N-(6,7,8,9-tetrahydro-5H-cyclohepta[b]pyridin-9-yl)-1,4-benzenedimethanamine;

AMD7253, N-(4-pyridinylmethyl)-N'-(2-pyridinylmethyl)-N-(6,7,8,9-tetrahydro-5H-cyclohepta[b]pyridin-9-yl)-1,4-benzenedimethanamine;

AMD7254, N-[(5-benzyloxy)benzo[b]pyrrol-3-ylmethyl]-N,N'-bis(2-pyridinylmethyl)-1,4-benzenedimethanamine;

AMD7256, N-(1-methylpyrazol-2-ylmethyl)-N'-(2-pyridinylmethyl)-N-(6,7,8,9-tetrahydro-5H-cyclohepta[b]pyridin-9-yl)-1,4-benzenedimethanamine;

AMD7259, N-[[(4-dimethylamino)-1-napthalenyl]methyl]-N,N'-bis(2-pyridinylmethyl)-1,4-benzenedimethanamine;

AMD7270, N-[(2-cyano-2-phenyl)ethyl]-N'-(2-pyridinylmethyl)-N-(6,7,8,9-tetrahydro-5H-cyclohepta[b]pyridin-9-yl)-1,4-benzenedimethanamine;

AMD7274, N-[(4-dimethylaminophenyl)methyl]-N'-(2-pyridinylmethyl)-N-(6,7,8,9-tetrahydro-5H-cyclohepta[b]pyridin-9-yl)-1,4-benzenedimethanamine;

AMD7275, N-(4-pyridinylmethyl)-N'-(2-pyridinylmethyl)-N-(5,6,7,8-tetrahydro-8-quinolinyl)-1,4-benzenedimethanamine;

AMD7276, N-(1-methylbenzimadazol-2-ylmethyl)-N'-(2-pyridinylmethyl)-N-(6,7,8,9-tetrahydro-5H-cyclohepta[b]pyridin-9-yl)-1,4-benzenedimethanamine;

AMD7309, N-[(1-methyl)benzo[b]pyrrol-3-ylmethyl]-N-[2-(2-pyridinyl)ethyl]-N'-(2-pyridinylmethyl)-1,3-benzenedimethanamine;

AMD7374, N-[1-methylbenzimidazol-2-ylmethyl]-N-[2-(2-pyridinyl)ethyl]-N'-(2-pyridinylmethyl)-1,4-benzenedimethanamine;

AMD7379, N-[(2-phenyl)benzo[b]pyrrol-3-ylmethyl]-N-[2-(2-pyridinyl)ethyl]-N'-(2-pyridinylmethyl)-1,4-benzenedimethanamine;

AMD9025, N-[(6-methylpyridin-2-yl)methyl]-N'-(2-pyridinylmethyl)-N-(5,6,7,8-tetrahydro-8-quinolinyl)-1,4-benzenedimethanamine;

AMD9031, N-(3-methyl-1H-pyrazol-5-ylmethyl)-N'-(2-pyridinylmethyl)-N-(5,6,7,8-tetrahydro-8-quinolinyl)-1,3-benzenedimethanamine;

AMD9032, N-[(2-methoxyphenyl)methyl]-N'-(2-pyridinylmethyl)-N-(5,6,7,8-tetrahydro-8-quinolinyl)-13-benzenedimethanamine;

AMD9039, N-[(2-ethoxyphenyl)methyl]-N'-(2-pyridinylmethyl)-N-(6,7,8,9-tetrahydro-5H-cyclohepta[b]pyridin-9-yl)-1,3-benzenedimethanamine;

AMD9045, N-(benzyloxyethyl)-N'-(2-pyridinylmethyl)-N-(5,6,7,8-tetrahydro-8-quinolinyl)-1,3-benzenedimethanamine;

AMD9052, N-[(2-ethoxy-1-naphthalenyl)methyl]-N'-(2-pyridinylmethyl)-N-(5,6,7,8-tetrahydro-8-quinolinyl)-1,3-benzenedimethanamine; and AMD9053, N-[(6-methylpyridin-2-yl)methyl]-N'-(2-pyridinylmethyl)-N-(5,6,7,8-tetrahydro-8-quinolinyl)-1,3-benzenedimethanamine.

9. The method of claim 1, wherein said subject is a mammalian subject.

10. The method of claim 1, comprising administering the compound of formula I in a subject, thereby treating rheumatoid arthritis.

* * * * *